(12) United States Patent
Zhong et al.

(10) Patent No.: US 7,745,484 B2
(45) Date of Patent: Jun. 29, 2010

(54) BETA-SECRETASE MODULATORS AND METHODS OF USE

(75) Inventors: Wenge Zhong, Thousand Oaks, CA (US); Stephen Hitchcock, Westlake Village, CA (US); Brian K. Albrecht, Cambridge, MA (US); Michael D. Bartberger, Sherman Oaks, CA (US); James Brown, Moorpark, CA (US); Ryan Brown, Watertown, MA (US); Stuart C. Chaffee, Philadelphia, PA (US); Yuan Cheng, Newbury Park, CA (US); Michael Croghan, Thousand Oaks, CA (US); Russell Graceffa, Hampton, NH (US); Scott Harried, Woodland Hills, CA (US); Dean Hickman, Moorpark, CA (US); Dan Horne, Thousand Oaks, CA (US); Randall Hungate, San Francisco, CA (US); Ted Judd, Simi Valley, CA (US); Matthew Kaller, Ventura, CA (US); Charles Kreiman, Watertown, MA (US); Daniel La, Brookline, MA (US); Patricia Lopez, West Hills, CA (US); Craig Masse, Cambridge, MA (US); Holger Monenschein, Camarillo, CA (US); Thomas Nguyen, Thousand Oaks, CA (US); Thomas Nixey, Newbury Park, CA (US); Vinod F. Patel, Acton, MA (US); Lewis Pennington, Ventura, CA (US); Matthew Weiss, Boston, MA (US); Qiufen Xue, Newbury Park, CA (US); Bryant Yang, Simi Valley, CA (US)

(73) Assignee: Amgen Inc., Thousand Oaks, CA (US)

( * ) Notice: Subject to any disclaimer, the term of this patent is extended or adjusted under 35 U.S.C. 154(b) by 690 days.

(21) Appl. No.: 11/595,187

(22) Filed: Nov. 10, 2006

(65) Prior Publication Data

US 2007/0185144 A1 Aug. 9, 2007

Related U.S. Application Data

(60) Provisional application No. 60/739,108, filed on Nov. 21, 2005.

(51) Int. Cl.
*A61K 31/352* (2006.01)
*C07D 311/96* (2006.01)
(52) U.S. Cl. .................... 514/454; 549/331
(58) Field of Classification Search ............... 514/454; 549/331
See application file for complete search history.

(56) References Cited

U.S. PATENT DOCUMENTS

| | | | |
|---|---|---|---|
| 5,441,870 A | 8/1995 | Seubert et al. |
| 5,712,130 A | 1/1998 | Hajko et al. |
| 5,942,400 A | 8/1999 | Anderson et al. |
| 6,864,290 B2 | 3/2005 | Schostarez et al. |
| 6,982,264 B2 | 1/2006 | John et al. |
| 6,992,103 B2 | 1/2006 | Faller et al. |
| 7,067,542 B2 | 6/2006 | Schostarez et al. |
| 7,074,799 B2 | 7/2006 | Bakthavatchalam et al. |
| 7,109,217 B2 | 9/2006 | Coburn et al. |
| 7,115,652 B2 | 10/2006 | Yang |
| 7,115,747 B2 | 10/2006 | Reeder et al. |
| 7,132,568 B2 | 11/2006 | Yang et al. |
| 7,176,242 B2 | 2/2007 | John et al. |
| 7,223,774 B2 | 5/2007 | Aquino et al. |
| 7,244,755 B2 | 7/2007 | Fisher et al. |
| 7,253,198 B2 | 8/2007 | Demont et al. |
| 7,291,620 B2 | 11/2007 | Coburn et al. |
| 7,312,360 B2 | 12/2007 | TenBrink et al. |
| 7,348,448 B2 | 3/2008 | Nantermet et al. |
| 7,351,738 B2 | 4/2008 | Pulley et al. |

(Continued)

FOREIGN PATENT DOCUMENTS

WO 00/17369 A2 3/2000

(Continued)

OTHER PUBLICATIONS

Berge, et al., "Pharmaceutical Salts", J. of Pharmaceutical Sciences, 66(1), 1-19 (1977).

(Continued)

*Primary Examiner*—Taofiq A Solola
(74) *Attorney, Agent, or Firm*—G. Prabhakar Reddy

(57) ABSTRACT

The present invention comprises a new class of compounds useful for the modulation of Beta-secretase enzyme activity and for the treatment of Beta-secretase mediated diseases, including Alzheimer's disease (AD) and related conditions. In one embodiment, the compounds have a general Formula I

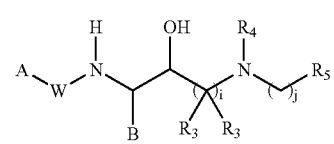

wherein A, B, W, $R^3$, $R^4$, $R^5$, i and j are defined herein. The invention also comprises pharmaceutical compositions including one or more compounds of Formula I, methods of use for these compounds, including treatment of AD and related diseases, by administering the compound(s) of Formula I, or compositions including them, to a subject. The invention also comprises further embodiments of Formulas II and III, intermediates and processes useful for the preparation of compounds of the invention.

15 Claims, No Drawings

U.S. PATENT DOCUMENTS

| | | |
|---|---|---|
| 7,371,853 B2 | 5/2008 | Coburn et al. |
| 2003/0109559 A1 | 6/2003 | Gailunas et al. |
| 2003/0166580 A1 | 9/2003 | Warpehoski et al. |
| 2004/0180939 A1 | 9/2004 | John et al. |
| 2005/0027007 A1 | 2/2005 | Hom |
| 2005/0038019 A1 | 2/2005 | Beck |
| 2005/0054690 A1 | 3/2005 | Aquino et al. |
| 2005/0267199 A1 | 12/2005 | Hom et al. |
| 2006/0211740 A1 | 9/2006 | Demont et al. |
| 2006/0229302 A1 | 10/2006 | Demont et al. |
| 2006/0241133 A1 | 10/2006 | Shearman et al. |
| 2007/0185103 A1 | 8/2007 | Albrecht |

FOREIGN PATENT DOCUMENTS

| | | |
|---|---|---|
| WO | 01/07671 A2 | 9/2001 |
| WO | 02/02505 A2 | 1/2002 |
| WO | 03/002518 A1 | 1/2003 |
| WO | 2004/099376 A2 | 11/2004 |
| WO | WO 2005035535 A1 * | 4/2005 |

OTHER PUBLICATIONS

Citron, M., "β-Secretase Inhibition for the Treatment of Alzheimer's Disease—Promise and Challenge", Trends in Pharmacological Sciences, 25(2), 92-97 (2004).

Corey, et al., "The Application of a Mechanistic Model Leads to the Extension of the Sharpless Asymmetric Dihydroxylation to Allylic 4-Methoxybenzoates and Conformationally Related Aine and Homoallylic Alcohol Derivatives", J. of Am. Chem. Soc., 117, 10805-10816 (1995).

Joachim, et al., "The Seminal Role of β-Amyloid in the Pathogenesis of Alzheimer Disease", Alzheimer Disease and Associated Disorders, 6(1), 7-34 (1992).

Luo, et al., "Mice deficient in BACE1, the Alzheimer's β-secretase, have normal phenotype and abolished β-amyloid generation", Nature Neuroscience, 4(3), 231-232 (2001).

Reynaud, et al., "New Synthesis of the Thiazole Ring", Bulletin de la Societe chimique de France, 1735-1738 (1962).

Sabbagh, et al.,"β-Amyloid and Treatment Opportunities for Alzheimer's Disease", Alzheimer's Disease Review, 3, 1-19 (1998).

Selkoe, D.M., "The Molecular Pathology of Alzheimer's Disease", Neuron, 6, 487-498 (1991).

Seubert, et al., "Isolation and Quantification of Soluble Alzheimer's β-Peptide from Biological Fluids", Nature, 359, 325-327 (1992).

Sinha, et al., "Purification and Cloning of Amyloid Precursor Protein β-Secretase from Human Brain", Nature, 402, 537-540 (1999).

Strangeland, et al., "Use of Thiazoles in the Halogen Dance Reaction: Application to the Total Synthesis of WS75624 B", J. Org, Chem., 69, 2381-2385 (2004).

* cited by examiner

BETA-SECRETASE MODULATORS AND METHODS OF USE

This appln. claims the benefit of 60/739,108 Nov. 21, 2005.

FIELD OF THE INVENTION

The invention relates generally to pharmaceutically active compounds, pharmaceutical compositions and methods of use thereof, to treat Beta-Secretase mediated disorders, including Alzheimer's disease, plaque formation on the brain and related conditions.

BACKGROUND OF THE INVENTION

Alzheimer's disease (AD) is a disease that affects greater than 12 million aging people worldwide. AD accounts for the majority of dementia clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to effectively treat AD upon diagnosis.

AD is caused by two major physiological factors in the brain. The first factor, beta amyloid plaque formation, supports the "amyloid cascade hypothesis" which alleges that AD is caused by the formation of characteristic beta amyloid deposits (commonly referred to as beta amyloid "plaques" or "plaque deposits") in the brain and in cerebral blood vessels (beta amyloid angiopathy). The second factor causing AD is intraneuronal tangles, consisting of an aggregate form of the protein tau. Amyloid plaques are thought to be specific for AD, while intraneuronal tangles are also found in other dementia-inducing disorders. Joachim et al., Alz. Dis. Assoc. Dis., 6:7-34 (1992).

Several lines of evidence indicate that progressive cerebral deposition of beta-amyloid peptide (A-beta) plays a seminal role in the pathogenisis of AD and can precede cognitive symptoms by years or even decades. Selkoe, Neuron, 6:487 (1991). Release of A-beta from neuronal cells grown in culture and the presence of A-beta in cerebrospinal fluid (CSF) of both normal individuals and AD patients has been demonstrated. Seubert et al., Nature, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-Beta formation is a causative precursor or factor in the development of AD. Deposition of A-beta in areas of the brain responsible for cognitive factors is a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide ranging in about 39-42 amino acids. A-beta 42 (42 amino acids long) is thought to be the major component of these plaque deposits. Citron, Trends in Pharmacological Sciences, 25(2):92-97 (2004).

Several aspartyl proteases are thought to be involved in the processing or cleavage of APP, resulting in the formation of A-beta peptide. Beta secretase (BACE, also commonly referred to as memapsin) is thought to first cleave APP to generate two fragments of the A-beta peptide: (1) a first N-terminus fragment and (2) a second C-99 fragment, which is subsequently cleaved by gamma secretase to generate the C-terminus fragment of the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., Nature, 402:537-554 (1999) (p 510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., Alz. Dis. Rev. 3:1-19 (1997). Thus, inhibition of the BACE enzyme activity is desirable for the treatment of AD.

Studies have shown that the inhibition of BACE may be linked to the treatment of AD. BACE I knockout mice fail to produce A-beta, and present a normal phenotype. When crossed with transgenic mice that over express APP, the progeny show reduced amounts of A-beta in brain extracts as compares with control animals (Luo et al., Nature Neuroscience, 4:231-232 (2001)). This evidence further supports the concept that inhibition of beta secretase activity and a corresponding reduction of A-beta in the brain should provide a therapeutic method for treating AD and other beta amyloid or plaque related disorders.

Several approaches have been taken to treat AD and plaque-related disorders. One approach has been to reduce the formation of plaque on the brain. Particularly, a common approach has been to inhibit the activity of beta secretase. For example, each of the following PCT publications:
WO 03/045913, WO 04/043916, WO 03/002122,
WO 03/006021, WO 03/002518, WO 04/024081,
WO 03/040096, WO 04/050619, WO 04/080376,
WO 04/099376, WO 05/004802, WO 04/080459,
WO 04/062625, WO 04/042910, WO 05/004803,
WO 05/005374, WO 03/106405, WO 03/062209,
WO 03/030886, WO 02/002505, WO 01/070671,
WO 03/057721, WO 03/006013, WO 03/037325,
Wo 04/094384, Wo 04/094413, WO 03/006423,
WO 03/050073, WO 03/029169 and WO 04/000821,
describe inhibitors of beta secretase, useful for treating AD and other beta-secretase mediated disorders.

BRIEF DESCRIPTION OF THE INVENTION

The present invention provides a new class of compounds useful for the modulation of beta secretase and, to that end, useful for the regulation or reduction of the formation of A-beta peptide and consequently, the reduction of beta amyloid plaque formation on the brain. Accordingly, the compounds of the invention are useful for the treatment of Alzheimer's disease and other beta secretase mediated disorders.

The compounds provided by the invention, including stereoisomers, tautomers, solvates, pharmaceutically acceptable salts, derivatives or prodrugs thereof, are defined by general Formula I

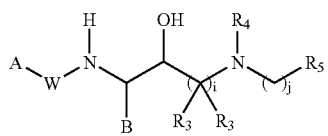

wherein A, B, W, $R^3$, $R^4$, $R^5$, i and j are as described below. The invention also provides procedures for making compounds of Formula I, as well as intermediates useful in such procedures.

The compounds provided by the invention are capable of modulating beta secretase. To this end, the invention further provides for the use of these compounds for therapeutic, prophylactic, acute and/or chronic treatment of beta secretase mediated diseases, such as those described herein. For example, the compounds are useful for the prophylaxis and treatment of AD and other diseases or conditions involving amyloid plaque formation on the brain.

The invention also provides pharmaceutical compositions, which comprise one or more compounds of the invention, methods for the treatment of beta secretase mediated diseases, such as AD, using the compounds and compositions of the invention, and intermediates and processes useful for the preparation of the compounds of the invention. The invention also provides the preparation of a pharmaceutical composition or of a medicament, containing one or more of the compounds, useful to attenuate, alleviate, or treat disorders through inhibition of beta secretase. For example, and in one embodiment, the invention provides a pharmaceutical composition comprising an effective dosage amount of a compound of Formula I in association with at least one pharmaceutically acceptable carrier.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts, derivatives or prodrugs thereof, are defined by

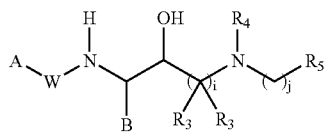

wherein A is $C_{1-10}$-alkyl, $C_{2-10}$-alkenyl, $C_{2-10}$-alkynyl, $R^1$—$C_{1-10}$-alkyl-, $R^1$—$C_{2-10}$-alkenyl- or $R^1$—$C_{2-10}$-alkynyl-, wherein 1, 2 or 3 carbon atoms of (1) said $C_1$-$C_{10}$ alkyl, $C_1$-$C_{10}$ alkenyl, $C_1$-$C_{10}$ alkynyl or (2) said $C_{1-10}$-alkyl, $C_{2-10}$-alkenyl, $C_{2-10}$-alkynyl of $R^1$—$C_{1-10}$-alkyl-, $R^1$—$C_{2-10}$-alkenyl- or $R^1$—$C_{2-10}$-alkynyl-, is optionally replaced with a heteroatom selected from O, S, S(O), S(O)$_2$ and N, and optionally substituted independently with one or more substitutents of $R^9$; and $R^1$ is a fully saturated or a partially or fully unsaturated 4-8 membered monocyclic, 6-12 membered bicyclic, or 7-14 membered tricyclic ring system, said ring system formed of carbon atoms and optionally including 1-3 heteroatoms if monocyclic, 1-6 heteroatoms if bicyclic, or 1-9 heteroatoms if tricyclic, said heteroatoms selected from O, N, or S, wherein said ring system is substituted independently with one or more substitutents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^8$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

W is —C(=O)—, —OC(=O)—, —NHC(=O)—, —S(=O)$_b$— or —NHS(=O)$_b$—, wherein b is 1 or 2;

B is $R^2$—$(CR^{2a}R^{2a})_h$—, $R^2$—O—$(CR^{2a}R^{2a})_h$, $R^2$—S—$(CR^{2a}R^{2a})_h$— or $R^2$—N$(R^{2a})$—$(CR^{2a}R^{2a})_h$—, wherein $R^2$ is $C_1$-$C_{10}$ alkyl, $C_1$-$C_{10}$ haloalkyl, $C_1$-$C_{10}$ alkenyl, $C_1$-$C_{10}$ alkynyl or a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said $C_1$-$C_{10}$ alkyl, $C_1$-$C_{10}$ alkenyl, $C_1$-$C_{10}$ alkynyl is optionally substituted independently with one or more substitutents of $R^9$, and said ring system is optionally substituted independently with one or more substitutents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

each $R^{2a}$, independently, is H, OH, $NO_2$, CN, $NH_2$, $C_1$-$C_{10}$ alkyl, $C_1$-$C_{10}$ alkoxyl or haloalkyl; and h is 0, 1, 2 or 3;

i is 1, 2 or 3;

j is 0, 1 or 2;

each $R^3$, independently, is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substitutents of $R^8$ or $R^9$;

$R^4$ is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substitutents of $R^8$ or $R^9$;

$R^5$ is

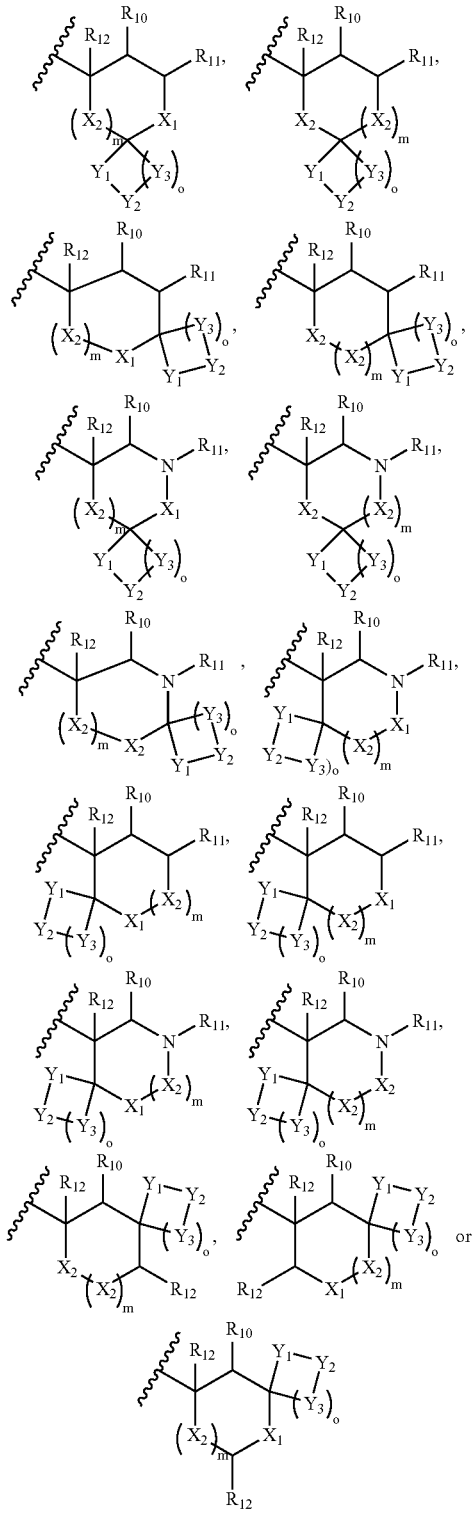

wherein $X^1$ is $CR^{12}$, O, S or $NR^{12}$;
each $X^2$, independently, is $CR^{12}R^{12}$;
each of $Y^1$, $Y^2$ and $Y^3$, independently, is $CR^{12}R^{12}$, O, S or $NR^{12}$;
m is 0, 1 or 2; and
o is 0, 1, 2, 3, 4 or 5;
provided that (a) no more than two of $Y^1$, $Y^2$ and $Y^3$ is O, S or $NR^{12}$ and (b) when o is 0, then each of $Y^1$ and $Y^2$ is $CR^{12}R^{12}$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substitutents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substitutents of $R^9$, oxo, $NR^9R^9$, $OR^9$, $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substitutents of $R^9$;

$R^9$ is H, halo, haloalkyl, CN, OH, $NO_2$, $NH_2$, acetyl, $C_{1-10}$-alkyl, $C_{2-10}$-alkenyl, $C_2$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substitutents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{10}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substitutents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{11}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $Cl_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

alternatively, $R^{10}$ and $R^{11}$ taken together with the carbon or nitrogen atoms to which they are attached form a partially or fully saturated or unsaturated 5-6 membered second ring of carbon atoms optionally including 1-3 heteroatoms selected from O, N, or S, the second ring optionally substituted independently with 1-5 substituents of $R^{12}$, $R^{13}$, $R^{14}$ or $R^{15}$ and optionally fused to a 4-7 membered third ring, the third ring formed of carbon atoms optionally including 1-3 heteroatoms selected from O, N, or S, and optionally substituted independently with 1-5 substituents of $R^2$, $R^{13}$, $R^{14}$ or $R^{15}$;

$R^{12}$ is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl, phenyl or $R^{14}$;

$R^{13}$ is $NR^{14}R^{15}$, $NR^{15}R^{15}$, $OR^{14}$, $SR^{14}$, $OR^{15}$, $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{15}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a partially or fully saturated or unsaturated 3-8 membered or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^{15}$; and $R^{15}$ is H, halo, haloalkyl, CN, OH, $NO_2$, $NH_2$, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl, phenyl, $C_{1-10}$-alkylamino-, $C_{1-10}$-dialkylamino-, $C_{1-10}$-thioalkoxyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl or phenyl.

In another embodiment, the compounds of Formula I include $R^1$—C(=O)— as A, in conjunction with any of the above or below embodiments.

In another embodiment, the compounds of Formula I include $R^1$—OC(=O)— as A, in conjunction with any of the above or below embodiments.

In another embodiment, the compounds of Formula I include $R^1$—NHC(=O)— as A, in conjunction with any of the above or below embodiments.

In another embodiment, the compounds of Formula I include $R^1$—S(=O)$_b$— as A wherein b is 0, 1 or 2, in conjunction with any of the above or below embodiments.

In another embodiment, the compounds of Formula I include or $R^1$—NHS(=O)$_b$— as A wherein b is 0, 1 or 2,in conjunction with any of the above or below embodiments.

In another embodiment, Formula I includes compounds wherein A is $C_{1-6}$alkyl, $C_{2-6}$alkenyl, $C_{2-6}$-alkynyl, $R^1$—O—$C_{1-6}$-alkyl-, $R^1$—S—$C_{1-6}$alkyl-, $R^1$—S(O)$_2$—$C_{1-6}$alkyl-, $R^1$—NH—$C_{1-6}$alkyl-, $R^1$—O—$C_{1-6}$-alkenyl-, $R^1$—S—$C_{2-6}$-alkenyl-, $R^1$—S(O)$_2$—$C_{2-6}$-alkenyl-, $R^1$—NH—$C_{2-6}$-alkenyl-, $R^1$—O—$C_{1-6}$alkynyl-, $R^1$—S—$C_{1-6}$-alkynyl-, $R^1$—S(O)$_2$—$C_{1-6}$-alkynyl-, $R^1$—NH—$C_{1-6}$-alkynyl-, $R^1$—$C_{1-6}$alkyl-O—$C_{1-6}$-alkyl-, $R^1$—$C_{1-6}$alkyl-S—$C_{1-6}$-alkyl-, $R^1$—$C_{1-6}$-alkyl-S(O)$_2$—$C_{1-6}$-alkyl-, $R^1$—$C_{1-6}$-alkyl-NH—$C_{1-4}$-alkyl-, $R^1$—$C_{1-6}$alkyl-O—$C_{1-6}$alkenyl-, $R^1$—$C_{1-4}$-alkyl-S—$C_{2-6}$-alkenyl-, $R^1$—$C_{1-6}$-alkyl-S(O)$_2$—$C_{2-6}$-alkenyl-, $R^1$—$C_{1-6}$-alkyl-NH—$C_{2-6}$-alkenyl-, $R^1$—$C_{1-6}$-alkyl-O—$C_{1-6}$-alkynyl-, $R^1$—$C_{1-6}$alkyl-S—$C_{1-6}$alkynyl-, $R^1$—$C_{1-6}$alkyl-S(O)$_2$—$C_{1-6}$-alkynyl- or $R^1$—$C_{1-6}$-alkyl-NH—$C_{1-6}$alkynyl-, in conjunction with any of the above or below embodiments.

In another embodiment, Formula I includes compounds wherein A is $C_{1-6}$alkyl, $C_{2-6}$alkenyl, $C_{2-6}$-alkynyl, $C_{1-6}$-alkyl-O—$C_{1-3}$-alkyl-, $C_{1-6}$alkyl-S—$C_{1-3}$-alkyl-, $C_{1-6}$-alkyl-S(O)$_2$—$C_{1-3}$-alkyl-, $C_{1-6}$-alkyl-NH—$C_{1-3}$-alkyl, di-($C_{1-6}$-alkyl)-N—$C_{1-3}$-alkyl, $C_{2-6}$-alkenyl-O—$C_{1-3}$-alkyl-, $C_{2-6}$-alkenyl-S—$C_{1-3}$-alkyl-, $C_{2-6}$-alkenyl-S(O)$_2$—$C_{1-3}$-alkyl-, $C_{2-6}$-alkenyl-NH—$C_{1-3}$-alkyl- or $C_{2-6}$-alkynyl-NH—$C_{1-3}$-alkyl-, wherein the alkyl, alkenyl or alkynyl moiety of each is optionally substituted with 1-5 substituents of $R^9$, in conjunction with any of the above or below embodiments.

In another embodiment, the compounds of Formula I include as $R^1$, phenyl, naphthyl, pyridyl, pyrimidyl, pyridazinyl, pyrazinyl, triazinyl, quinolinyl, isoquinolinyl, quinazolinyl, isoquinazolinyl, phthalazinyl, thiophenyl, furyl, pyrrolyl, pyrazolyl, imidazolyl, triazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl, cycloheptyl or a ring system of

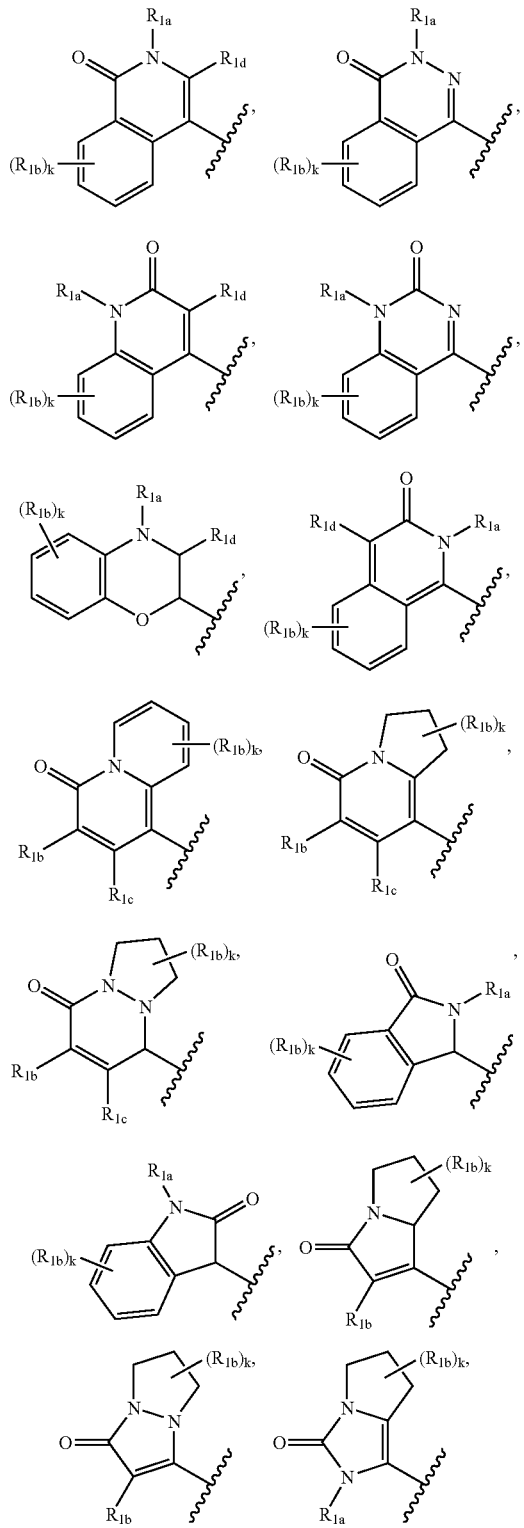

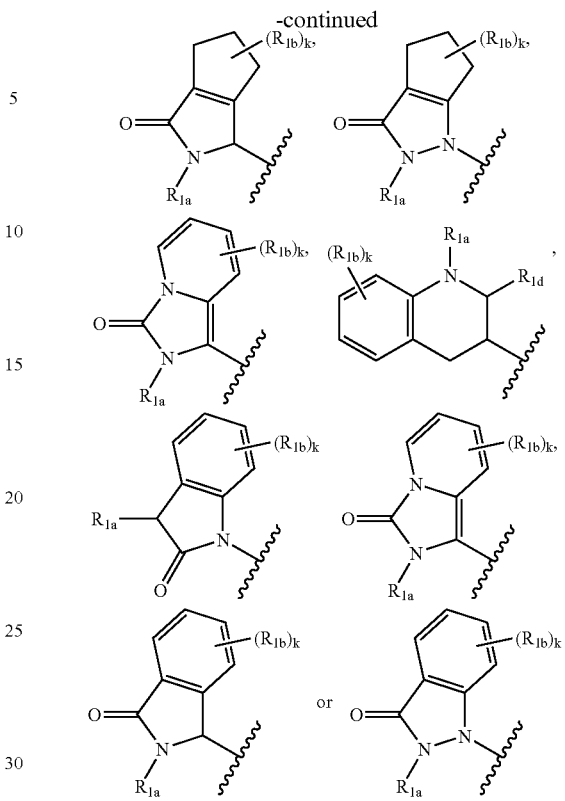

wherein $R^{1a}$ is $R^7$, $R^8$, $R^9$, $C(O)R^7$, $C(O)R^8$, $C(O)NR^7R^7$, $C(S)NR^7R^7$, $C(O)NR^7R^8$, $C(S)NR^7R^8$, $S(O)_2NR^7R^7$, $S(O)_2R^8$, or $S(O)_2NR^7R^8$;

each $R^{1b}$, $R^{1c}$ and $R^{1d}$, independently, is $R^7$, $R^8$, $R^9$, $NR^7R^7$, $NR^7R^8$, $OR^7$, $SR^7$, $OR^8$, $SR^8$, $C(O)R^7$, $COOR^7$, $C(O)R^8$, $COOR^8$, $C(O)NR^7R^7$, $C(S)NR^7R^7$, $NR^7C(O)R^7$, $NR^7C(S)R^7$, $NR^7CC(O)NR^7R^7NR^7C(S)R^7NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$; and k is 0, 1, 2 or 3, in conjunction with any of the above or below embodiments.

In the immediately preceeding embodiment, the compounds of Formula I include $R^7$, $R^8$ or $R^9$, independently, as each of $R^{1a}$, $R^{1b}$, $R^{1c}$ and $R^{1d}$, independently, in conjunction with any of the above or below embodiments.

In another embodiment, the compounds of Formula I include $R^2$—$(CR^{2a}R^{2a})_n$— as B wherein each $R^{2a}$, independently, is H, OH, NO$_2$, CN, NH$_2$, $C_1$-$C_{10}$ alkyl $C_1$-$C_{10}$ alkoxyl or haloalkyl, in conjunction with any of the above or below embodiments.

In another embodiment, the compounds of Formula I include $R^2$—O—$(CR^{2a}R^{2a})_n$— as B wherein each $R^2$, independently, is H, OH, NO$_2$, CN, NH$_2$, $C_1$-$C_{10}$ alkyl $C_1$-$C_{10}$ alkoxyl or haloalkyl, in conjunction with any of the above or below embodiments.

In another embodiment, the compounds of Formula I include $R^2$—S—$(CR^{2a}R^{2a})_n$— as B wherein each $R^{2a}$, independently, is H, OH, NO$_2$, CN, NH$_2$, $C_1$-$C_{10}$ alkyl $C_1$-$C_{10}$ alkoxyl or haloalkyl, in conjunction with any of the above or below embodiments.

In another embodiment, the compounds of Formula I include $R^2$—$NR^{2a}$—$(CR^{2a}R^{2a})_h$— as B wherein each $R^{2a}$, independently, is H, OH, $NO_2$, CN, $NH_2$, $C_1$-$C_{10}$ alkyl $C_1$-$C_{10}$ alkoxyl or haloalkyl, in conjunction with any of the above or below embodiments.

In another embodiment, the compounds of Formula I include $R^2$—$(CR^{2a}R^{2a})_h$— as B wherein $R^{2a}$ is OH, $NO_2$, CN, $NH_2$, $C_1$-$C_{10}$ alkyl, $C_1$-$C_{10}$ alkoxyl or haloalkyl, in conjunction with any of the above or below embodiments.

In another embodiment, the compounds of Formula I include $R^2$—$(CH_2)_h$— as B, in conjunction with any of the above or below embodiments.

In another embodiment, the compounds of Formula I include $R^2$—O—$(CH_2)_h$— as B, in conjunction with any of the above or below embodiments.

In another embodiment, the compounds of Formula I include $R^2$—S—$(CH_2)_h$— as B, in conjunction with any of the above or below embodiments.

In another embodiment, the compounds of Formula I include $R^2$—NH—$(CH_2)_h$— as B, in conjunction with any of the above or below embodiments.

In another embodiment, Formula I includes compounds wherein $R^2$ is a $C_1$-$C_4$alkyl, $C_1$-$C_4$alkenyl, $C_1$-$C_4$alkynyl, $C_1$-$C_{10}$ haloalkyl or an optionally substituted ring system selected from phenyl, naphthyl, pyridyl, pyrimidyl, pyridazinyl, pyrazinyl, triazinyl, quinolinyl, isoquinolinyl, quinazolinyl, isoquinazolinyl, phthalazinyl, thiophenyl, furyl, pyrrolyl, pyrazolyl, imidazolyl, triazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, in conjunction with any of the above or below embodiments.

In another embodiment, the compounds of Formula I include an optionally substituted ring system selected from phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl and benzimidazoly as $R^2$, in conjunction with any of the above or below embodiments.

In another embodiment, the compounds of Formula I include $C_1$-$C_{10}$ alkyl, $C_1$-$C_{10}$ alkenyl or $C_1$-$C_{10}$ alkynyl as $R^2$, in conjunction with any of the above or below embodiments.

In another embodiment, the compounds of Formula I include $C_1$-$C_{10}$ haloalkyl as $R^2$, in conjunction with any of the above or below embodiments.

In another embodiment, the compounds of Formula I include H, haloalkyl, CN, $C_{1-10}$-alkyl, $C_{2-10}$-alkenyl or $C_{2-10}$-alkynyl as $R^3$, in conjunction with any of the above or below embodiments.

In another embodiment, the compounds of Formula I include H as $R^3$, in conjunction with any of the above or below embodiments.

In another embodiment, the compounds of Formula I include $C_{1-10}$-alkyl as $R^3$, in conjunction with any of the above or below embodiments.

In another embodiment, the compounds of Formula I include H, haloalkyl, CN, $C_{1-10}$-alkyl, $C_{2-10}$-alkenyl or $C_{2-10}$-alkynyl as $R^4$, in conjunction with any of the above or below embodiments.

In another embodiment, the compounds of Formula I include H as $R^4$, in conjunction with any of the above or below embodiments.

In another embodiment, the compounds of Formula I include haloalkyl or $C_{1-10}$-alkyl as $R^4$, in conjunction with any of the above or below embodiments.

In another embodiment, the compounds of Formula I include h as 0, 1, 2 or 3, in conjunction with any of the above or below embodiments.

In another embodiment, the compounds of Formula I include h as 1 or 2, in conjunction with any of the above or below embodiments.

In another embodiment, the compounds of Formula I include i as 1, 2 or 3, in conjunction with any of the above or below embodiments.

In another embodiment, the compounds of Formula I include i as I, in conjunction with any of the above or below embodiments.

In another embodiment, the compounds of Formula I include j as 0, 1 or 2, in conjunction with any of the above or below embodiments.

In another embodiment, the compounds of Formula I include j as 0, in conjunction with any of the above or below embodiments.

In another embodiment, the compounds of Formula I include as $R^5$

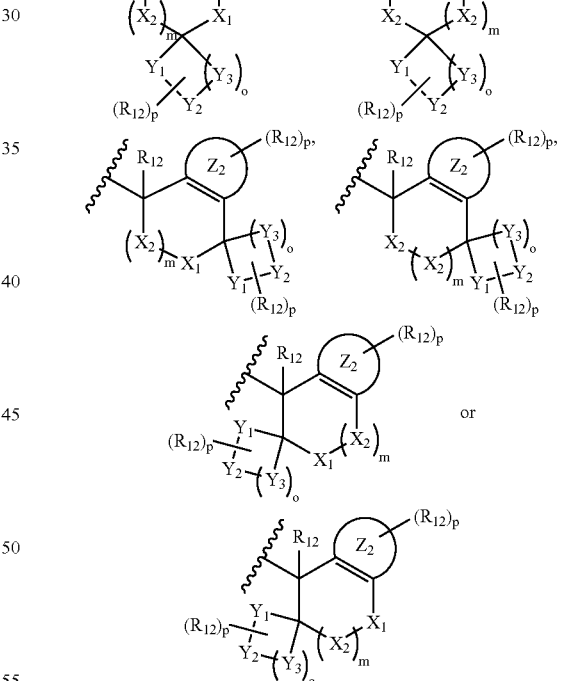

wherein m, o, $R^{12}$, $X^1$, $X^2$, $Y^1$, $Y^2$ and $Y^3$ are as defined hereinabove;

$Z^2$ taken together with the carbon atoms to which it is attached is a partially or fully unsaturated 5-8 membered monocyclic ring, said ring formed of carbon atoms optionally including 1-3 heteroatoms if monocyclic, 1-6 heteroatoms if bicyclic, or 1-9 heteroatoms if tricyclic, said heteroatoms selected from O, N, or S, provided that (a) no more than two of $Y^1$, $Y^2$ and $Y^3$ is O, S or $NR^{12}$ and (b) when o is 0, then each of $Y^1$ and $Y^2$ is $CR^{12}R^{12}$; and p is 0, 1, 2, 3, 4 or 5, in conjunction with any of the above or below embodiments.

In the immediately preceeding embodiment, the compounds of Formula I include $CR^{12}R^{12}$ as $X^1$, in conjunction with any of the above or below embodiments.

In the preceeding embodiment, the compounds of Formula I include $CHR^{12}$ as $X^1$, in conjunction with any of the above or below embodiments.

In the immediately preceeding embodiment, the compounds of Formula I include $C(O)$ as $X^1$, in conjunction with any of the above or below embodiments.

In the preceeding embodiment, the compounds of Formula I include $CH_2$ as $X^1$, in conjunction with any of the above or below embodiments.

In the preceeding embodiment, the compounds of Formula I include O as $X^1$, in conjunction with any of the above or below embodiments.

In the preceeding embodiment, the compounds of Formula I include S as $X^1$, in conjunction with any of the above or below embodiments.

In the preceeding embodiment, the compounds of Formula I include $NR^{12}$ as $X^1$, in conjunction with any of the above or below embodiments.

In the preceeding embodiment, the compounds of Formula I include NH as $X^1$, in conjunction with any of the above or below embodiments.

In the preceeding embodiment, the compounds of Formula I include $CR^{12}R^{12}$ as each $X^2$, independently, in conjunction with any of the above or below embodiments.

In the preceeding embodiment, the compounds of Formula I include $CHR^{12}$ as each $X^2$, independently, in conjunction with any of the above or below embodiments.

In the preceeding embodiment, the compounds of Formula I include $CH_2$ as each $X^2$, independently, in conjunction with any of the above or below embodiments.

In the preceeding embodiment, the compounds of Formula I include $CR^{12}R^{12}$ as each of $Y^1$, $Y^2$ and $Y^3$, independently, in conjunction with any of the above or below embodiments.

In the preceeding embodiment, the compounds of Formula I include $CHR^{12}$ as each of $Y^1$, $Y^2$ and $Y^3$, independently, in conjunction with any of the above or below embodiments.

In the preceeding embodiment, the compounds of Formula I include $CH_2$ as each of $Y^1$, $Y^2$ and $Y^3$, independently, in conjunction with any of the above or below embodiments.

In the preceeding embodiment, the compounds of Formula I include 0 as any one or two of $Y^1$, $Y^2$ and $Y^3$, independently, in conjunction with any of the above or below embodiments.

In the preceeding embodiment, the compounds of Formula I include S as any one or two of $Y^1$, $Y^2$ and $Y^3$, independently, in conjunction with any of the above or below embodiments.

In the preceeding embodiment, the compounds of Formula I include $NR^{12}$ as any one or two of $Y^1$, $Y^2$ and $Y^3$, independently, in conjunction with any of the above or below embodiments.

In the preceeding embodiment, the compounds of Formula I include 0 as $Y^2$ and $CH_2$ as each of $Y^1$ and $Y^3$, in conjunction with any of the above or below embodiments.

In the preceeding embodiment, the compounds of Formula I include S as $Y^2$ and $CH_2$ as each of $Y^1$ and $Y^3$, in conjunction with any of the above or below embodiments.

In the preceeding embodiment, the compounds of Formula I include $NR^{12}$ as $Y^2$ and $CH_2$ as each of $Y^1$ and $Y^3$, in conjunction with any of the above or below embodiments.

In the preceeding embodiment, the compounds of Formula I include an optionally substituted benzene, pyridine, pyrimidine, triazine, pyridazine, pyrazine, pyrrole, imidazole, pyrazole, triazole, thiophene, thiazole, thiadiazole, isothiazole, furan, oxazole, oxadiazole or isoxazole ring as $Z^2$, in conjunction with any of the above or below embodiments.

In the preceeding embodiment, the compounds of Formula I include compounds wherein $R^5$ is

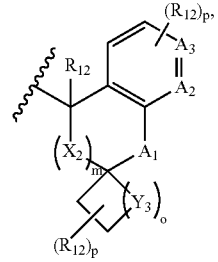

wherein m is 0 or 1;
o is 1 or 2;
p is 0, 1, 2 or 3;
$A^1$ is CH, C(O), O or $NR^{12}$;
each of $A^1$ and $A^2$, independently, is $CR^{12}$ or N, provided that no more than one of $A^1$ and $A^2$ is N;
$X^2$ is CH;
$Y^3$ is $CR^{12}$ or O; and
each $R^{12}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a ring selected from phenyl, pyridyl, pyrimidinyl, triazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, oxazolyl, oxadiazolyl, isoxazolyl, isothiazolyl, oxazolinyl, isoxazolinyl, thiazolinyl, pyrrolidinyl, pyrazolinyl, morpholinyl, piperidinyl, piperazinyl, pyranyl, dioxozinyl, cyclopropyl, cyclobutyl, azetidinyl, cyclopentyl, cyclohexyl and cycloheptyl, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring is optionally substituted independently with 1-5 substitutents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl, in conjunction with any of the above or below embodiments.

In another embodiment, the compounds of Formula I include as $R^5$

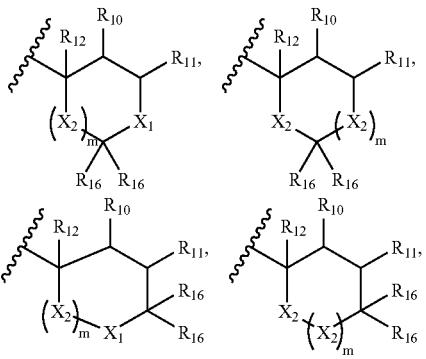

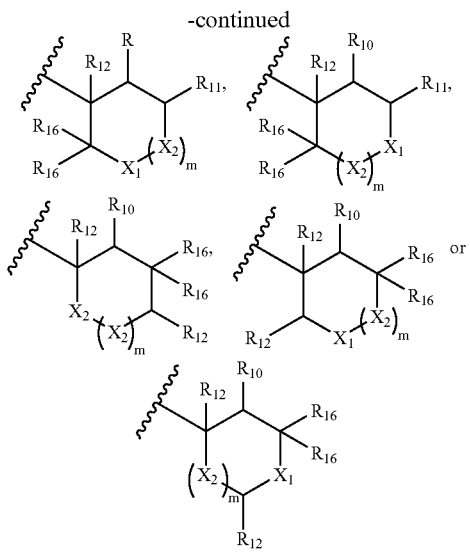

wherein $X^1$ is O, S or $NR^{12}$;

each $X^2$, independently, is $CR^{12}R^{12}$;

m is 0, 1 or 2; and each $R^{16}$, independently, is haloalkyl, methyl, methoxyl, ethyl, ethoxyl, alkoxy-alkyl, alkylamino-alkyl, dialkylamino-alkyl, propyl, propoxyl, isopropyl, isopropoxyl, cyclopropyl, butyl, isobutyl, sec-butyl or tert-butyl, in conjunction with any of the above or below embodiments.

In another embodiment, the compounds of Formula I include as $R^5$

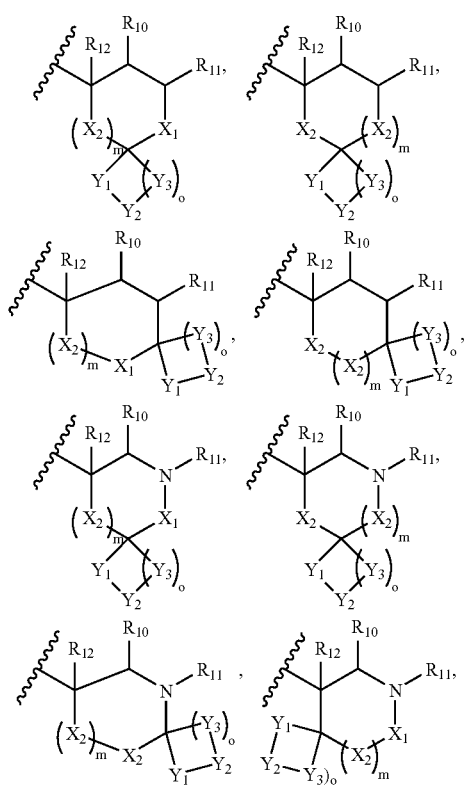

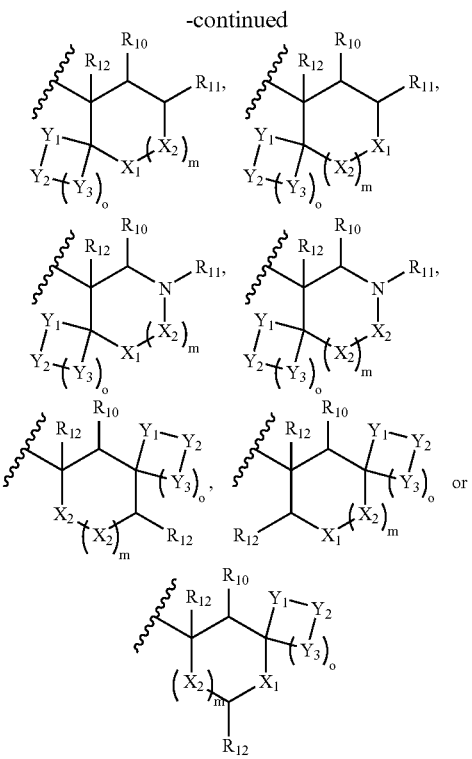

wherein $X^1$ is O, S or $NR^{12}$;

each $X^2$, independently, is $CR^{12}R^{12}$;

each of $Y^1$, $Y^2$ and $Y^3$, independently, is $CR^{12}R^{12}$, O, S or $NR^{12}$;

m is 0, 1 or 2; and o is 0, 1, 2, 3, 4 or 5;

provided that (a) no more than two of $Y^1$, $Y^2$ and $Y^3$ is O, S or $NR^{12}$ and (b) when o is 0, then each of $Y^1$ and $Y^2$ is $CR^{12}R^{12}$, in conjunction with any of the above or below embodiments.

In another embodiment, the invention provides compounds of Formula I, wherein h is 1 or 2;

i is 1;

j is 0;

A is $C_{1-6}$-alkyl, $C_{2-6}$-alkenyl, $R^1$—O—$C_{1-6}$alkyl-, $R^1$—S—$C_{1-6}$-alkyl, $R^1$—S(O)$_2$—$C_{1-6}$-alkyl-, $R^1$—NH—$C_{1-6}$-alkyl-, $R^1$—O—$C_{1-6}$-alkenyl-, $R^1$—S—$C_{2-6}$-alkenyl-, $R^1$—S(O)$_2$—$C_{2-6}$-alkenyl-, $R^1$—NH—$C_{2-6}$-alkenyl-, $R^1$—$C_{1-6}$-alkyl-O—$C_{1-6}$alkyl-, $R^1$—$C_{1-6}$alkyl-S—$C_{1-6}$-alkyl-, $R^1$—$C_{1-6}$-alkyl-S(O)$_2$—$C_{1-6}$-alkyl- or $R^1$—$C_{1-6}$alkyl-NH—$C_{1-4}$-alkyl-, wherein $R^1$ is phenyl, naphthyl, pyridyl, pyrimidyl, pyridazinyl, pyrazinyl, triazinyl, quinolinyl, isoquinolinyl, quinazolinyl, isoquinazolinyl, phthalazinyl, thiophenyl, furyl, pyrrolyl, pyrazolyl, imidazolyl, triazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl or cycloheptyl, each of which is optionally substituted as defined in claim 1;

$R^2$ is an optionally substituted ring system selected from phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzoxazolyl, benzisoxazolyl, benzothiazolyl, benzisothiazolyl, benzotriazolyl and benzimidazolyl;

each $R^3$, independently, is H, haloalkyl, CN, $C_{1-10}$-alkyl, $C_{2-10}$-alkenyl or $C_{2-10}$-alkynyl;

$R^4$ is H, CN or $C_{1-10}$-alkyl;

$R^5$ is

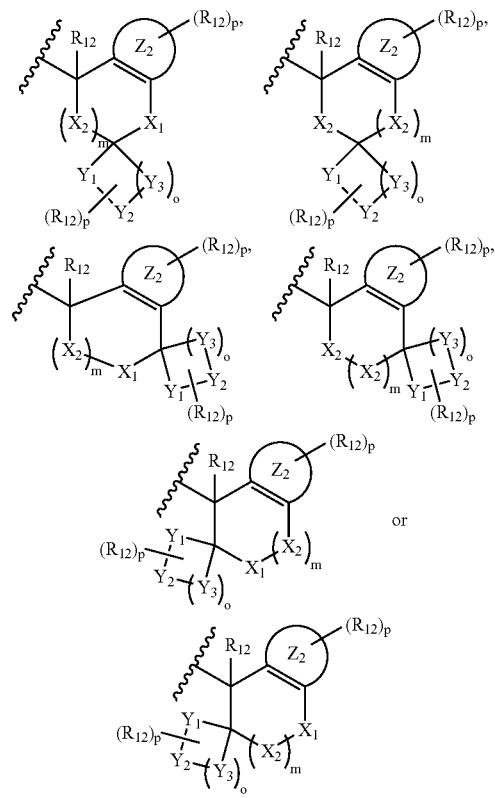

wherein m, o, $R^{12}$, $X^2$, $Y^1$, $Y^2$ and $Y^3$ are as defined in claim 1;

$X^1$ is O, S or $NR^{12}$;

$Z^2$ is an optionally substituted phenyl, pyridine, pyrimidine, triazine, pyridazine, pyrazine, pyrrole, imidazole, pyrazole, triazole, thiophene, thiazole, thiadiazole, isothiazole, furan, oxazole, oxadiazole or isoxazole ring; and p is 0, 1, 2, 3, 4 or 5.

$R^7$ is H, $C_{1-10}$-alkyl or $C_{2-10}$-alkenyl, each of the $C_{1-10}$-alkyl, or $C_{2-10}$-alkenyl optionally substituted with 1-3 substitutents of $R^9$;

$R^8$ is a ring system selected from phenyl, pyridyl, pyrimidinyl, triazinyl, quinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl and cycloheptyl, said ring system optionally substituted independently with 1-3 substituents of $R^9$, oxo, $NR^9R^9$, $OR^9$, $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substitutents of $R^9$;

$R^9$ is H, halo, haloalkyl, CN, OH, $NO_2$, $NH_2$, acetyl, $C_{1-10}$-alkyl, $C_{2-10}$-alkenyl, $C_2$ alkynyl, $C_{3-7}$-cycloalkyl, $C_{4-7}$-cycloalkenyl, $C_{1-10}$-alkylamino-, $C_{1-10}$-dialkylamino-, $C_1$-alkoxyl, $C_{1-10}$-thioalkoxyl; and $R^{12}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substitutents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl.

In another embodiment, the invention provides compounds of Formula II,

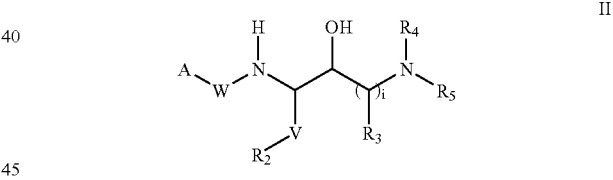

II or stereoisomer, tautomer, solvate, pharmaceutically acceptable salt, derivative or prodrug thereof, wherein A is $C_{1-6}$alkyl, $C_{2-6}$-alkenyl, $C_{2-6}$alkynyl, $R^1$—$C_{1-6}$alkyl-, $R^1$—$C_{2-6}$-alkenyl- or $R^1$—$C_{2-6}$-alkynyl-, wherein 1, 2 or 3 carbon atoms of (1) said $C_1$-$C_6$ alkyl, $C_1$-$C_6$ alkenyl, $C_1$-$C_6$ alkynyl or (2) said $C_{1-6}$alkyl, $C_{2-6}$alkenyl, $C_{2-6}$-alkynyl of $R^1$—$C_{1-6}$alkyl-, $R^1$—$C_{2-6}$-alkenyl- or $R^1$—$C_{2-6}$-alkynyl-, is optionally replaced with a heteroatom selected from O, S, S(O), $S(O)_2$ and NH, and optionally substituted independently with 1-3 substitutents of $R^9$; and $R^1$ is phenyl, naphthyl, pyridyl, pyrimidyl, pyridazinyl, pyrazinyl, triazinyl, quinolinyl, isoquinolinyl, quinazolinyl, isoquinazolinyl, phthalazinyl, thiophenyl, furyl, pyrrolyl, pyrazolyl, imidazolyl, triazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl or cycloheptyl, each of which is optionally substituted 1-3 substitutents of oxo, $R^8$, $R^9$, $N^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, COORS, $C(O)NR^7R^7$, $NR^7C(O)R^7$, $NR^7C(O)NR^7R^7$, $NR^7(COOR^7)$, $OC(O)NR^7R^7$, $C(O)NR^7R^8$, $NR^7C(O)R^8$, $NR^7C(O)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

W is —C(=O)—, —OC(=O)—, —NHC(=O)—, —S(=O)$_b$— or —NHS(=O)$_b$—, wherein b is 1 or 2;

V is —(CR$^{2a}$R$^{2b}$)$_h$—, —O—(CR$^{2a}$R$^{2a}$)$_h$—, —S—(CR$^{2a}$R$^{2a}$)$_h$— or NR$^{2a}$(CR$^{2a}$R$^{2a}$)$_h$—, wherein each $R^{2a}$, independently, is H, $C_1$-$C_{10}$ alkyl or haloalkyl, and h is 0, 1 or 2;

$R^2$ is a $C_1$-$C_{10}$alkyl, $C_1$-$C_{10}$haloalkyl, $C_1$-$C_{10}$alkenyl, $C_1$-$C_{10}$ alkynyl or a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said ring system is optionally substituted independently with one or more substitutents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

$R^3$ is H, haloalkyl, CN, $C_{1-10}$-alkyl, $C_{2-10}$-alkenyl or $C_{2-10}$-alkynyl;

$R^4$ is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substitutents of $R^8$ or $R^9$;

$R^5$ is

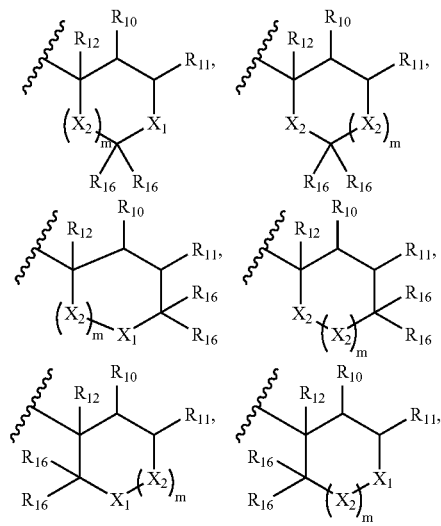

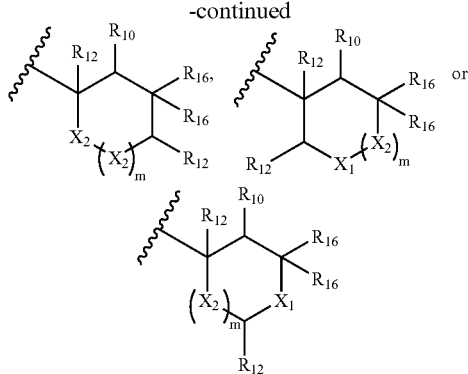

wherein $X^1$ is O, S or $NR^{12}$;
each $X^2$, independently, is $CR^{12}R^{12}$; and
m is 0, 1 or 2;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substitutents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substitutents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substitutents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substitutents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{10}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substitutents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{11}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substitutents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

alternatively, $R^{10}$ and $R^{11}$ taken together with the carbon atoms to which they are attached form a partially or fully saturated or unsaturated 5-6 membered ring of carbon atoms optionally including 1-3 heteroatoms selected from O, N, or S, and the ring optionally substituted independently with 1-5 substitutents of $R^{12}$, $R^{13}$, $R^{14}$ or $R^{15}$;

$R^{12}$ is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substitutents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^5$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a partially or fully saturated or unsaturated 5-8 membered or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substitutents of $R^{15}$;

$R^{15}$ is H, halo, haloalkyl, CN, OH, $NO_2$, $NH_2$, oxo, acetyl, methyl, methoxyl, ethyl, ethoxyl, propyl, propoxyl, isopropyl, cyclopropyl, butyl, isobutyl, tert-butyl, cyclobutyl, $C_{1-10}$-alkylamino-, $C_{1-10}$-dialkylamino-, $C_{1-10}$-thioalkoxyl, benzyl, phenyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substitutents of halo, haloalkyl, CN, $NO_2$, $NH_2$, OH, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, tert-butyl, cyclobutyl, $C_{1-10}$-alkylamino-, $C_{1-10}$-dialkylamino-, $C_{1-10}$-thioalkoxyl, benzyl or phenyl;

each $R^{16}$, independently, is haloalkyl, methyl, methoxyl, ethyl, ethoxyl, alkoxy-alkyl, alkylamino-alkyl, dialkylamino-alkyl, propyl, propoxyl, isopropyl, isopropoxyl, cyclopropyl, butyl, isobutyl, sec-butyl or tert-butyl;

h is 0, 1 or 2; and i is 1, 2 or 3.

In another embodiment, the compounds of Formula II include O as $X^1$, in conjunction with any of the above or below embodiments.

In another embodiment, the compounds of Formula II include S as $X^1$, in conjunction with any of the above or below embodiments.

In another embodiment, the compounds of Formula II include $NR^{12}$ as $X^1$, in conjunction with any of the above or below embodiments.

In another embodiment, the compounds of Formula II include methyl, ethyl, propyl, isopropyl, butyl, isobutyl or sec-butyl as $R^{16}$, independently, in conjunction with any of the above or below embodiments.

In another embodiment, the compounds of Formula II include each independent embodiment, as described herein for variables A, B, $R^1$, $R^{1a}$, $R^{1b}$, $R^{1c}$, $R^{1d}$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, W, V, $X^1$, $X^2$, $Y^1$, $Y^2$, $Y^3$, $Z^1$ and $Z^2$ for compounds of Formula I, independently, in conjunction with any of the above or below embodiments for compounds of Formula II.

In another embodiment, the compounds of Formula I or II include compounds wherein $R^5$ is

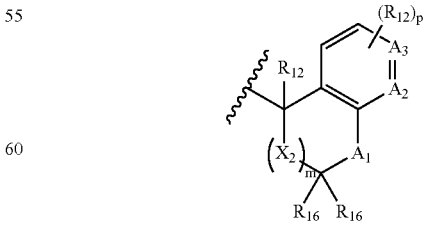

wherein m is 0 or 1;

p is 0, 1, 2 or 3;

$A^1$ is CH, C(O), O or $NR^{12}$;

each of $A^1$ and $A^2$, independently, is $CR^{12}$ or N, provided that no more than one of $A^1$ and $A^2$ is N;

$X^2$ is CH;

$Y^3$ is $CR^{12}$ or O; and each $R^{12}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a ring selected from phenyl, pyridyl, pyrimidinyl, triazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, oxazolyl, oxadiazolyl, isoxazolyl, isothiazolyl, oxazolinyl, isoxazolinyl, thiazolinyl, pyrrolidinyl, pyrazolinyl, morpholinyl, piperidinyl, piperazinyl, pyranyl, dioxozinyl, cyclopropyl, cyclobutyl, azetidinyl, cyclopentyl, cyclohexyl and cycloheptyl, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl, in conjunction with any of the above or below embodiments.

In yet another embodiment, the invention provides compounds generally defined by Formula III,

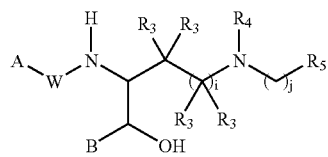

III or stereoisomer, tautomer, solvate, pharmaceutically acceptable salt, derivative or prodrug thereof, wherein A is $C_{1-10}$-alkyl, $C_{2-10}$-alkenyl, $C_{2-10}$-alkynyl, $R^1$—$C_{1-10}$-alkyl-, $R^1$—$C_{2-10}$-alkenyl- or $R^1$—$C_{2-10}$-alkynyl-, wherein 1, 2 or 3 carbon atoms of (1) said $C_1$-$C_{10}$ alkyl, $C_1$-$C_{10}$ alkenyl, $C_1$-$C_{10}$ alkynyl or (2) said $C_{1-10}$-alkyl, $C_{2-10}$-alkenyl, $C_{2-10}$-alkynyl of $R^1$—$C_{1-10}$-alkyl-, $R^1$—$C_{2-10}$-alkenyl- or $R^1$—$C_{2-10}$-alkynyl-, is optionally replaced with a heteroatom selected from O, S, S(O), $S(O)_2$ and NH, and optionally substituted independently with one or more substituents of $R^9$; and $R^1$ is a fully saturated or a partially or fully unsaturated 4-8 membered monocyclic, 6-12 membered bicyclic, or 7-14 membered tricyclic ring system, said ring system formed of carbon atoms and optionally including 1-3 heteroatoms if monocyclic, 1-6 heteroatoms if bicyclic, or 1-9 heteroatoms if tricyclic, said heteroatoms selected from O, N, or S, wherein said ring system is substituted independently with one or more substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

W is —C(=O)—, —OC(=O)—, —NHC(=O)—, —S(=O)$_b$— or —NHS(=O)$_b$—, wherein b is 1 or 2;

B is $R^2$—$(CR^{2a}R^{2a})_h$—, $R^2$—O—$(CR^{2a}R^{2a})_b$—, $R^2$—S—$(CR^{2a}R^{2a})_h$— or $R^2$—$NR^{2a}$—$(CR^{2a}R^{2a})^h$—, wherein $R^2$ is $C_1$-$C_{10}$ alkyl, $C_1$-$C_{10}$ haloalkyl, $C_1$-$C_{10}$ alkenyl, $C_1$-$C_{10}$ alkynyl or a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said $C_1$-$C_{10}$ alkyl, $C_1$-$C_{10}$ alkenyl, $C_1$-$C_{10}$ alkynyl is optionally substituted independently with one or more substituents of $R^9$, and said ring system is optionally substituted independently with one or more substituents of oxo, $R^7$, $R^8$, $R^9$, $NR^7R^7$, $NR^7R^8$, $OR^7SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

each $R^{2a}$, independently, is H, OH, $NO_2$, CN, $NH_2$, $C_1$-$C_{10}$ alkyl, $C_1$-$C_{10}$ alkoxyl or haloalkyl; and h is 0, 1, 2 or 3;

i is 1, 2 or 3;

j is 0, 1 or 2;

each $R^3$, independently, is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^4$ is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^5$ is

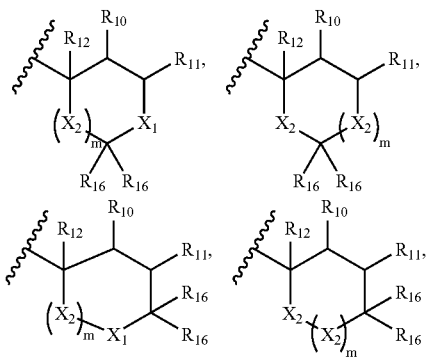

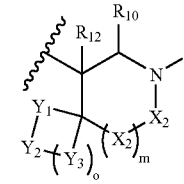

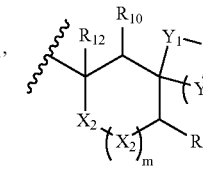

wherein $X^1$ is O, S or $NR^{12}$;
each $X^2$, independently, is $CR^{12}R^{12}$;
each of $Y^1$, $Y^2$ and $Y^3$, independently, is $CR^{12}R^{12}$, O, S or $NR^{12}$;
m is 0, 1 or 2; and
o is 0, 1, 2, 3, 4 or 5;
provided that (a) no more than two of $Y^1$, $Y^2$ and $Y^3$ is O, S or $NR^{12}$ and (b) when
o is 0, then each of $Y^1$ and $Y^2$ is $CR^{12}R^{12}$;
$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substitutents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;
$R^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substitutents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substitutents of $R^9$;
$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substitutents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{10}$ is H, halo, haloalkyl, CN, OH, $NO_2$, $NH_2$, acetyl, $C_{1-10}$-alkyl, $C_{2-10}$-alkenyl, $C_2$-alkynyl, $C_{3-10}$-cycloalkyl, $C_{4-10}$-cycloalkenyl, $C_{1-10}$-alkylamino-, $C_{1-10}$-dialkylamino-, $C_1$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substitutents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{11}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substitutents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

alternatively, $R^{10}$ and $R^{11}$ taken together with the carbon or nitrogen atoms to which they are attached form a partially or fully saturated or unsaturated 5-6 membered second ring of carbon atoms optionally including 1-3 heteroatoms selected from O, N, or S, the second ring optionally substituted independently with 1-5 substitutents of $R^{12}$, $R^{13}$, $R^{14}$ or $R^{15}$ and optionally fused to a 4-7 membered third ring, the third ring formed of carbon atoms optionally including 1-3 heteroatoms selected from O, N, or S, and optionally substituted independently with 1-5 substitutents of $R^{12}$, $R^{13}$, $R^{14}$ or $R^{15}$;

$R^{12}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substitutents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl, phenyl or $R^{14}$;

$R^{13}$ is $NR^{14}R^{15}$, $NR^{15}R^{15}$, $OR^{14}$; $SR^{14}$, $OR^{15}$; $SR^{15}$, C(O) $R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a partially or fully saturated or unsaturated 5-8 membered or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S. and wherein said ring system is optionally substituted independently with 1-5 substitutents of $R^{15}$; and $R^{15}$ is H, halo, haloalkyl, CN, OH, $NO_2$, $NH_2$, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl, phenyl, $C_{1-10}$-alkylamino-, $C_{1-10}$-dialkylamino-, $C_{1-10}$-thioalkoxyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substitutents of halo, haloalkyl, CN, $NO_2$, $NH_2$, OH, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl or phenyl; and each $R^{16}$, independently, is haloalkyl, methyl, methoxyl, ethyl, ethoxyl, alkoxy-alkyl, alkylamino-alkyl, dialkylamino-alkyl, propyl, propoxyl, isopropyl, isopropoxyl, cyclopropyl, butyl, isobutyl, sec-butyl or tert-butyl.

In another embodiment, the compounds of Formula III include each independent embodiment, as described herein for variables A, B, $R^1$, $R^{1a}$, $R^{1b}$, $R^{1c}$, $R^{1d}$, $R^2$, $R^3$, $R^4$, $R^5$, $R^6$, $R^7$, $R^8$, $R^9$, $R^{10}$, $R^{11}$, $R^{12}$, $R^{13}$, $R^4$, $R^5$, W, V, $X^1$, $X^2$, $Y^1$, $Y^2$, $Y^3$, Z and $Z^2$ for compounds of Formula I, independently, in conjunction with any of the above or below embodiments for compounds of Formula III.

In another embodiment, the invention provides each of the Exemplary compounds, and stereoisomers, tautomers, solvates, pharmaceutically acceptable salts, derivatives or prodrugs thereof, and related intermediates, described herein.

Definitions

The following definitions should assist in understanding the invention described herein.

The term "comprising" is meant to be open ended, including the indicated component(s), but not excluding other elements.

The term "H" denotes a single hydrogen atom. This radical may be attached, for example, to an oxygen atom to form a hydroxyl radical.

The term "$C_{\alpha-\beta}$alkyl", when used either alone or within other terms such as "haloalkyl" and "alkylamino", embraces linear or branched radicals having α to β number of carbon atoms (such as $C_1$-$C_{10}$). One or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like. The term "alkylenyl" embraces bridging divalent alkyl radicals such as methylenyl and ethylenyl.

The term "alkenyl", when used alone or in combination, embraces linear or branched radicals having at least one carbon-carbon double bond in a moiety having between two and ten carbon atoms. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, denotes linear or branched radicals having at least one carbon-carbon triple bond and having two to ten carbon atoms. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$-alkoxyl" when used alone or in combination, embraces linear or branched oxygen-containing alkyl radicals each having $\alpha$ to $\beta$ number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy, fluoropropoxy and cyclopropylmethoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substitutents including lower alkyl, hydroxyl, halo, haloalkyl, nitro, cyano, alkoxy and lower alkylamino, and the like. Phenyl substituted with —O—$CH_2$—O— or —O—$CH_2$—$CH_2$—O— forms an aryl benzodioxolyl substitutent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 5-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10—membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—. "Carbonyl" is also used herein synonymously with the term "oxo".

The term "aminocarbonyl" denotes an amide group of the formula —C(=O)$NH_2$.

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio,($CH_3S$—).

The term "haloalkylthio" embraces radicals containing a haloalkyl radical, of one to ten carbon atoms, attached to a divalent sulfur atom. An example of "haloalkylthio" is trifluoromethylthio.

The term "alkylaminoalkyl" embraces alkyl radicals substituted with alkylamino radicals. Examples of alkylaminoalkyl radicals include "lower alkylaminoalkyl" radicals having alkyl radicals of one to six carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. Examples of alkylaminoalkoxy radicals include "lower alkylaminoalkoxy" radicals having alkoxy radicals of one to six carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "Formula I" includes any sub formulas, such as Formula II. Similarly, the term "Formula II" includes any sub formulas and "Formula III" includes any sub formulas.

The term "pharmaceutically-acceptable" when used with reference to a compound of Formulas I-III is intended to refer to a form of the compound that is safe for administration. For example, a salt form, a solvate, a hydrate or derivative form of a compound of Formula I, II or of Formula III, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-III are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-III may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I, II and III include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I-III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, hydrobromic acid, citric acid, sulphuric acid and phosphoric acid and such organic acids as oxalic acid, stearic and, salicylic acid, pamoic acid, gluconic acid, ethanesulfonic acid, methanesulfonic acid, toluenesulfonic acid, tartaric acid, fumaric acid, medronic acid, napsylic acid, maleic acid, succinic acid and citric acid. Other examples include salts with alkali metals or alkaline earth metals such as sodium, potassium, calcium or magnesium, or with organic bases.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate an enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I-III. A "pharmaceutically-acceptable prodrug" as used herein, denotes a prodrug which is pharmaceutically acceptable. Pharmaceutically acceptable modifications to the compounds of Formula I-III are readily appreciated by those of ordinary skill in the art.

The compound(s) of Formulas I-III may be used to treat a subject by administering the compound(s) as a pharmaceutical composition. To this end, the compound(s) can be combined with one or more carriers, diluents or adjuvants to form a suitable composition, which is described in more detail herein.

The term "carrier", as used herein, denotes any pharmaceutically acceptable additive, excipient, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., SCH$_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I, II and III.

The compounds of Formulas I-III can be synthesized according to the procedures described in the following Schemes 1-5, wherein the substituents are as defined for Formulas I, II and III above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:
ACN, MeCN—acetonitrile
Aq.—aqueous
BOP—benzotriazol-1-yl-oxy Hexafluorophosphate
$Cs_2CO_3$—cesium carbonate
$CHCl_3$—chloroform
$CH_2Cl_2$, DCM—dichloromethane, methylene chloride
CuI—copper iodide
DCC—dicyclohexylcarbodiimide
DIC—1,3-diisopropylcarbodiimide
DIEA, DIPEA—diisopropylethylamine
DME—dimethoxyethane
DMF—dimethylformamide
DMAP—4-dimethylaminopyridine
DMS—dimethylsulfide
DMSO—dimethylsulfoxide
EDC, EDCI—1-(3-dimethylaminopropyl)-3-ethylcarbodiimide
$Et_2O$—diethyl ether
EtOAc—ethyl acetate
FBS—fetal bovine serum
G, gm—gram
h, hr—hour
$H_2$—hydrogen
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$— potassium carbonate
KI—potassium iodide
LG—leaving group
LiOH—lithium hydroxide
$MgSO_4$— magnesium sulfate
MS—mass spectrum
MeOH—methanol
$N_2$— nitrogen
$NaCNBH_3$— sodium cyanoborohydride
$Na_2CO_3$— sodium carbonate
$NaHCO_3$— sodium bicarbonate
NaH—sodium hydride
NaBH—sodium borohydride
NaOH—sodium hydroxide
$Na_2SO_4$— sodium sulfate
$NH_4C_1$—ammonium chloride
$NH_4OH$—ammonium hydroxide
$P(t-bu)_3$—tri(tert-butyl)phosphine
PBS—phosphate buffered saline
Pd/C—palladium on carbon
$Pd(PPh_3)_4$— palladium(0)triphenylphosphine tetrakis
$Pd(dppf)Cl_2$—palladium(1,1-bisdiphenylphosphinoferrocene) II chloride
$Pd(PhCN)_2Cl_2$—palladium di-cyanophenyl dichloride
$Pd(OAc)_2$—palladium acetate
$Pd_2(dba)_3$—tris(dibenzylideneacetone) dipalladium
PyBop—benzotriazol-1-yl-oxy-tripyrrolidino-phosphonium hexafluorophosphate
RT, rt—room temperature
RBF, rbf—round bottom flask
TLC, tlc—thin layer chromatography
TBTU—O-benzotriazol-1-yl-N,N,N',N'-tetramethyluronium tetrafluoroborate
TEA, $Et_3N$—triethylamine
TFA—trifluoroacetic acid
THF—tetrahydrofuran
UV—ultraviolet light.

While the synthetic strategy for preparing the compounds of Formulas I, II and III may vary, as appreciated by persons skilled in the art, one strategy for devising a method of making compounds of these formulas is by retro-synthetic disconnection. For example,

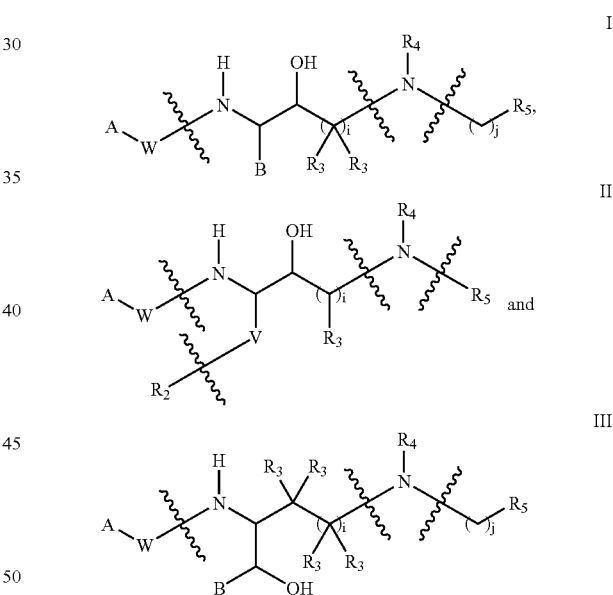

as shown in Formulas I-III above, each squiggly line represents a possible point of bond-construction, whose order is generally dependent upon the particular compound being synthesized. Such bond construction methods are generally described in synthetic Schemes 1-5 below.

Scheme 1

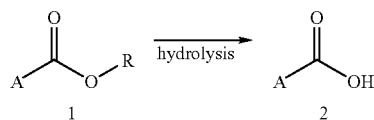

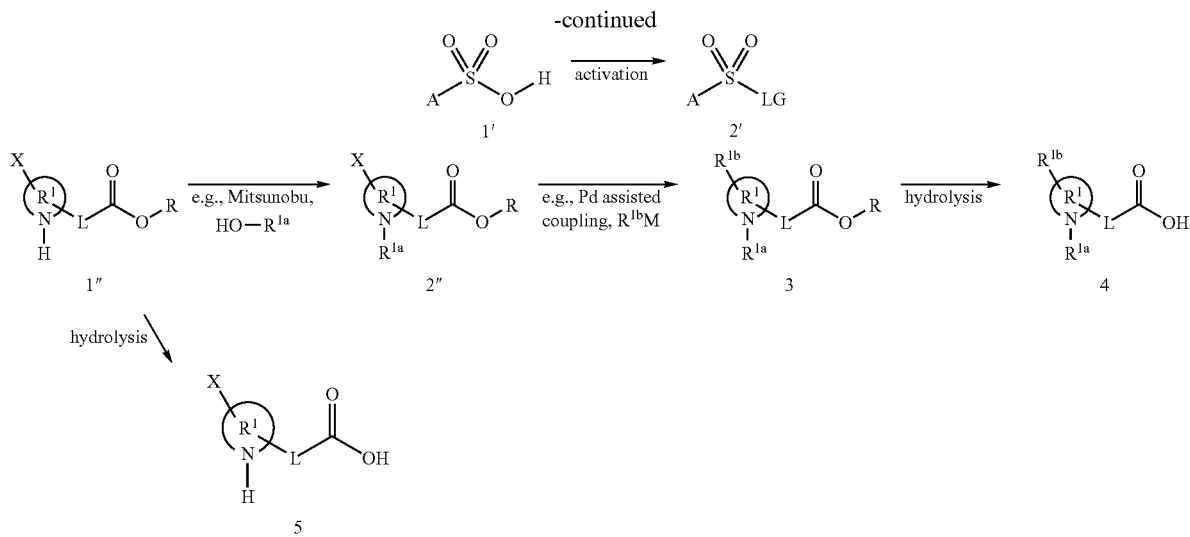

wherein,
R is C1–C4 alkyl, e.g., CH₃, C₂H₅, etc.
and e.g., X = Br, I, Cl, etc.; R$^{1b}$ = R$^{1b}$B(OH)₂, R$^{1b}$SnBu₃, etc.

Scheme 1 describes a few methods for preparing A-W acids, useful for preparing compounds of Formulas I-III (see scheme 2) wherein W is —C(O)— or —S(O)₂— and A is $C_{1-10}$-alkyl, $C_{2-10}$-alkenyl, $C_{2-10}$-alkynyl, $R^1$—$C_{1-10}$-alkyl-, $R^1$—$C_{2-10}$-alkenyl- or $R^1$—$C_{2-10}$-alkynyl- ("L" in scheme 1 corresponds to the $C_{1-10}$-alkyl, $C_{2-10}$-alkenyl or $C_{2-10}$-alkynyl of A defined in A-W above). Desired A-W groups may be commercially available and purchased, or may be made by known, conventional methods. As shown, esters 1 can be hydrolyzed to their corresponding acids 2 using known bases, such as NaOH or LiOH. Acids 2 can then be coupled to an amine (not shown) to prepare compounds of Formula I-III. Similarly, sulfonic acids 1' can be converted to an activated sulfonate 2' by reaction with oxalyl chloride, for example, to prepare the corresponding sulfonyl chloride 2'. The sulfonyl chloride 2' can be reacted with an amine to prepare compounds of Formula I-III.

In a similar manner, a desired ring $R^1$ of compounds 1", where A is a spacer "L" between the $R^1$ ring and W, may first be functionalized prior to coupling to the amino-backbone, as shown in scheme 2. An ester-halo (X=halogen such as Br or I) substituted $R^1$ ring acid 4 or 5, both of which include a substitutable nitrogen in the ring, and which are generally referred to herein as the left-hand portion of the compounds of Formulas I, II and III, can be prepared according to the method generally described in the second half of Scheme 1. As shown, a methyl ester-halo substituted compound 1" can be reacted in a Mitsunobu-type reaction with a desired hydroxyl-substituted $R^{1a}$ compound under suitable conditions, such as in the presence of tri-phenyl phosphine and diethylazodicarboxylate (commonly referred to as DEAD) for a suitable time period to form the ring N—$R^{1a}$ substituted adduct 2". Intermediate 2" may also be formed using a suitable reductive amination method as well utilizing an aldehyde, for example (not shown in scheme 1). Compound 2" can be reacted in a palladium-catalyzed coupling reaction, such as a suzuki-type reaction, in the presence of suitable solvents and accompanying reagents, such as a base, to form the $R^1$—$R^{1b}$ substituted compound 3. Formation of compound 3 may require heat, up to and including reflux temperatures depending on the particular substrate, solvent and reagent(s) concentration, as appreciated by those skilled in the art. Compound 3 can then be hydrolyzed in the presence of a suitable base and solvent to form the corresponding acid-adduct 4. Acid 4 is then utilized as an intermediate to couple, as described in scheme 2 below, with desired intermediates or other building blocks to make compounds of Formulas I-III.

Alternatively, compound 1" can be hydrolyzed directly to the corresponding acid 5. Ester-Halo-substituted compound 5 is a useful intermediate for coupling the backbone core compounds with desired B, $R^3$ and $R^4$ substitutions already in place. Compound 5 can then be modified to include desirable $R^1$ substitutions, including $R^{1a}$, $R^7$, $R^8$ and $R^9$ groups. In this fashion, analogs of a variety of desired left-hand pieces of compounds of Formulas I-III may be readily synthesized (see scheme 3).

By known methods, the acids 1', 2, 4 and 5, may be converted to the corresponding isocyanates and then reacted with an amine (not shown) to make a urea "W" linker or an $R^1$-urea linked A group (where W≡—NHC(O)—).

Scheme 2

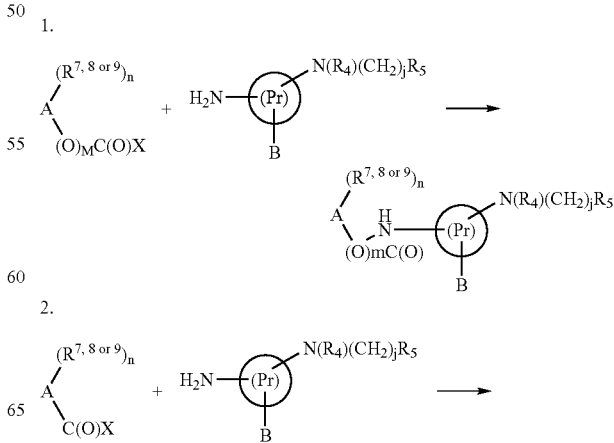

-continued

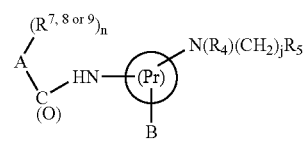

3.

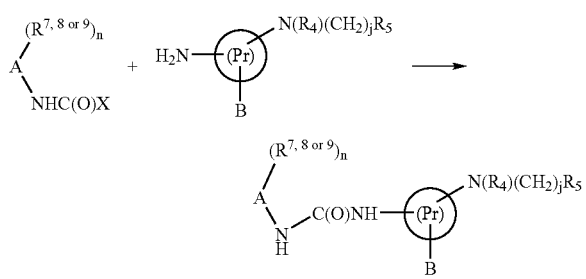

4.

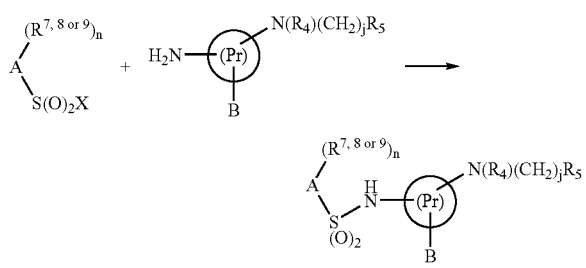

Desires A-W groups, which may be substituted with various substitutions including one or more $R^7$, $R^8$ or $R^9$ groups, can be coupled to the core hydroxyl-propyl, hydroxyl-butyl or hydroxyl-pentyl backbone structure, generally designated in Scheme 2 as "Pr" group, by various coupling methods as described in Scheme 2. In each of the 4 sub-schemes, X refers generally to a "LG" or a "leaving group" such as a halide (bromine, chlorine, iodine or fluorine), alkylsulfonate and other known groups (also see definitions herein) which generally forms an electrophilic species ($E^+$) and m is an integer from 0-1. The $NH_2$ group (primary amine) is a nucleophilic species ($Nu^-$), as is secondary amines, hydroxides, alkoxides, an anionic carbon species and the like, which should be sufficiently strong to the attack the $E^+$ species and displace the leaving group X thereby effecting a coupling of A-W to the Pr backbone. Examples of suitable electrophilic carbonyl species include, without limitation, acid halides, mixed anhydrides, aldehydes, carbamoyl-chlorides, sulfonyl chlorides, acids activated by coupling with activating reagents such as TBTU, HBTU, HATU, HOBT, BOP, PyBOP and carbodiimides (DCC, EDC and the like), and other electrophilic species including halides, isocyanates, daizonium ions and the like.

The coupled adduct of A-W and Pr, shown as products in sub-schemes 1-4, can be brought about using various conventional methods. For example, an amide or a sulfonamide linkage, as shown in sub-schemes 2 and 4, can be made utilizing an amine on the Pr intermediate and an activated electrophilic species, on the A-W group such as the acid chloride or sulfonyl chloride as shown. The reaction proceeds generally in the presence of a suitable solvent and/or base. Suitable solvents include, without limitation, generally non-nucleophilic, anhydrous solvents such as toluene, $CH_2Cl_2$, THF, DMF, DMSO, N,N-dimethylacetamide and the like, including solvent combinations thereof. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH, borohydrides, cyanoborohydrides and the like, alkoxides such as $NaOCH_3$, and the like. The base itself may also serve as a solvent. The reaction may optionally be run neat, i.e., without any base and/or solvent. These coupling reactions are generally fast and conversion occurs typically in ambient conditions. However, depending upon the particular substrate, such reactions may require heat, as appreciated by those skilled in the art.

Similarly, carbamates as illustrated in sub-scheme I and ureas as illustrated in sub-scheme 3 may be made as shown, wherein X has the same definition as above, using the same coupling methods described above for sub-schemes 2 and 4. While the above methods are so described, they are not exhaustive, and other methods for linking A-W groups and desired Pr groups together may be utilized as appreciated by those skilled in the art.

The coupling methods described in sub-schemes 1-4 of scheme 2 are also applicable for coupling desired A-W intermediates to desired Pr intermediates not containing desired $R^5$ groups, although sub-schemes 1-4 as illustrated do contain $R^5$ groups.

Scheme 3

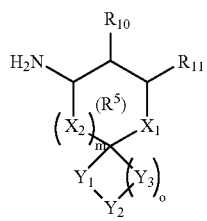

9

-continued

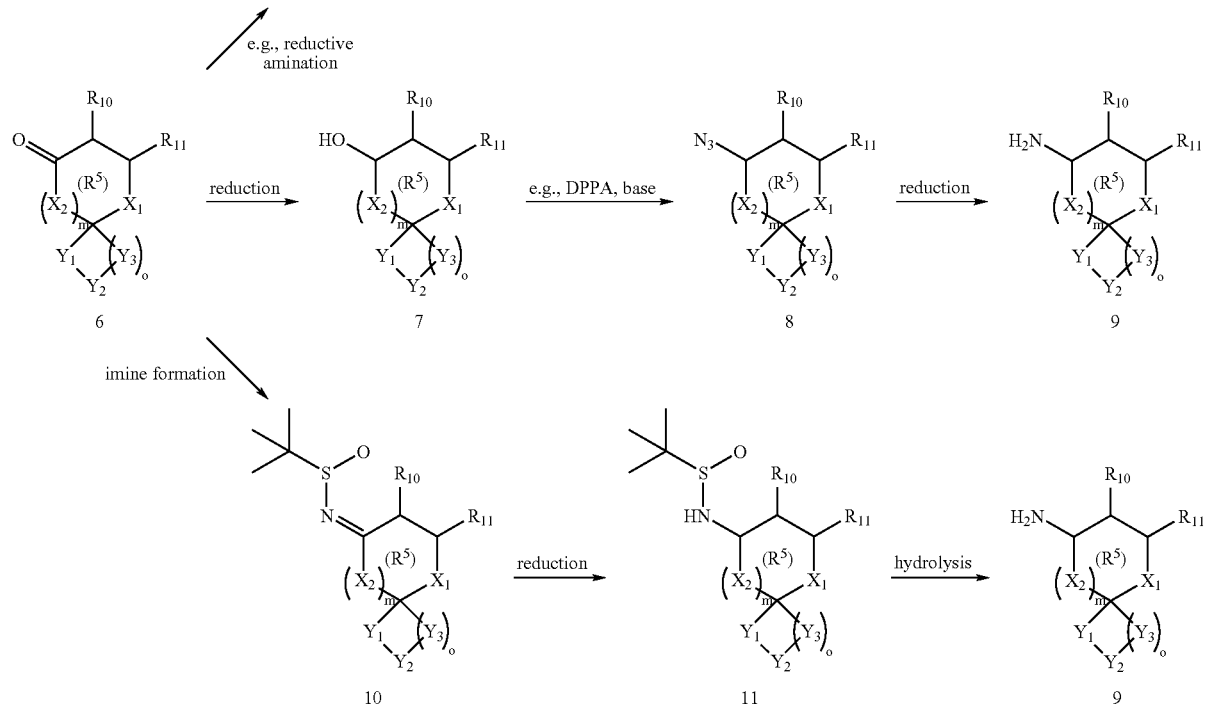

Amine intermediate 9 (j=0) can be prepared according to the method generally described in Scheme 3. As shown, spiro-substituted- or gem-dialky-substituted (not shown) oxo-$R^5$ ring intermediates 6 can be converted directly to the amino-intermediate 9 using known reductive amination methods, such as in the presence of sodium cyanoborohydride and ammonium acetate. Alternatively, the carbonyl of $R^5$ may be reduced to the corresponding alcohol using conventional reducing reagents, and then displaced to form the corresponding azido-intermediate 8 using known reagents, such as DPPA, in the presence of a suitable base as shown. Intermediate 8 may be reduced with a suitable reducing agent or by known methods, including triphenylphosphene, trimethylphosphene or lithium aluminum hydride (LAH), to produce the desired amino adduct 9.

Yet another method of forming the amine adduct 9, can be via an imine formation to form compound 10. The imine double bond of compound 10 may then be successively reduced and hydrolyzed to yield the primary amine product 9. Such steps may be conducted using known, convention methods, as appreciated by those skilled in the art.

Scheme 4

1.

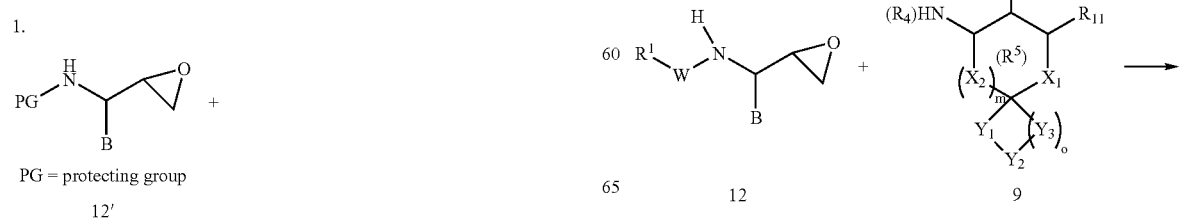

PG = protecting group

12′

-continued

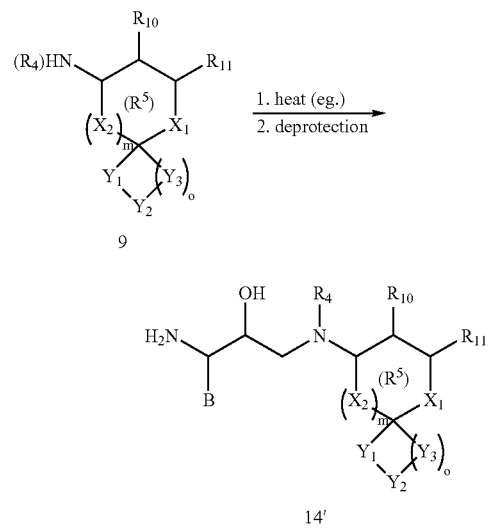

2.

-continued

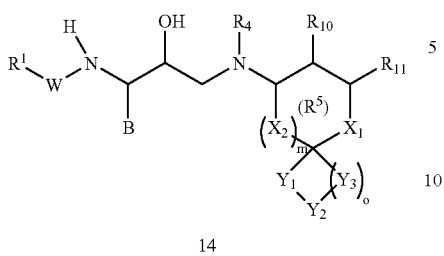

14

3.

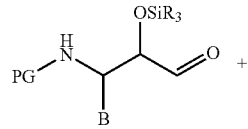

PG = protecting group
13'

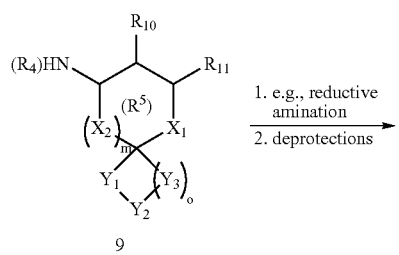

9

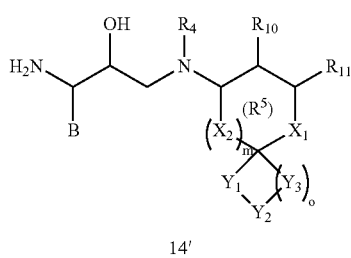

14'

4.

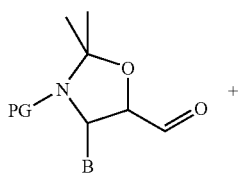

PG = protecting group
13

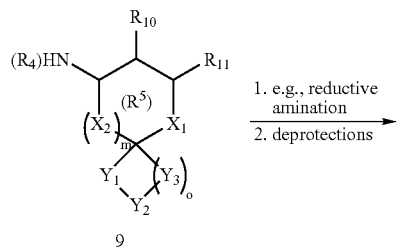

9

-continued

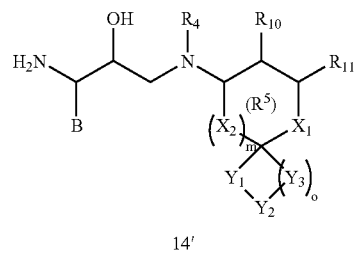

14'

Scheme 4 describes, generally, multiple different methods for constructing the bond between the Pr starting material or intermediate 12' (sub-scheme 1) or 12 (sub-scheme 2) and an $R^5$ ring intermediate 9, thereby synthesizing a desired intermediate 14' or a final compound 14 of Formulas I-III. One method to make this bond is to react an epoxide intermediate 12 or 12' (Note: the epoxide 12 or 12' may be purchased commercially or made via known, published methods such as from the olefin precursor), with an amino-$R^5$ intermediate 9, as shown. The reaction may proceed in the presence of a polar solvent, such as an alcohol or dioxanes, and may require additional reagents, as appreciated by those skilled in the art. Additionally, the reaction may require heat for a period of time. Note that while the scheme described the addition o heat, this is by way of example, and not every reaction would require heat as appreciated by those of ordinary skill in the art. The protecting group may be removed using an acid, such as HCl, such that the bonded adduct 14' is recovered as an HCl salt.

Alternatively, desired intermediates 14' may be synthesized starting with an amine-protected aldehyde intermediate 13' (sub-scheme 3) or 13 (sub-scheme 4) and condensing the aldehyde with a primary or secondary amine 9 to form an imine (not shown, generally formed in-situ and not isolated). The imine can then be reduced using a known reducing agent, such as a hydride or borohydride, the reduced intermediate may be deprotected to provide an intermediate 14' having an amine useful to prepare compounds 14 of Formulas I-III.

Scheme 5

Method A:

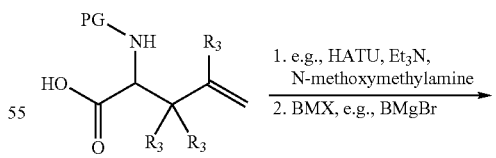

15

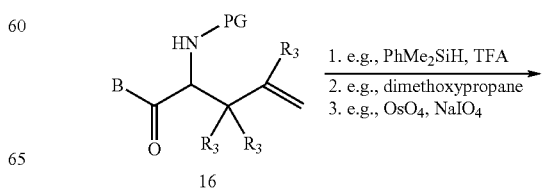

16

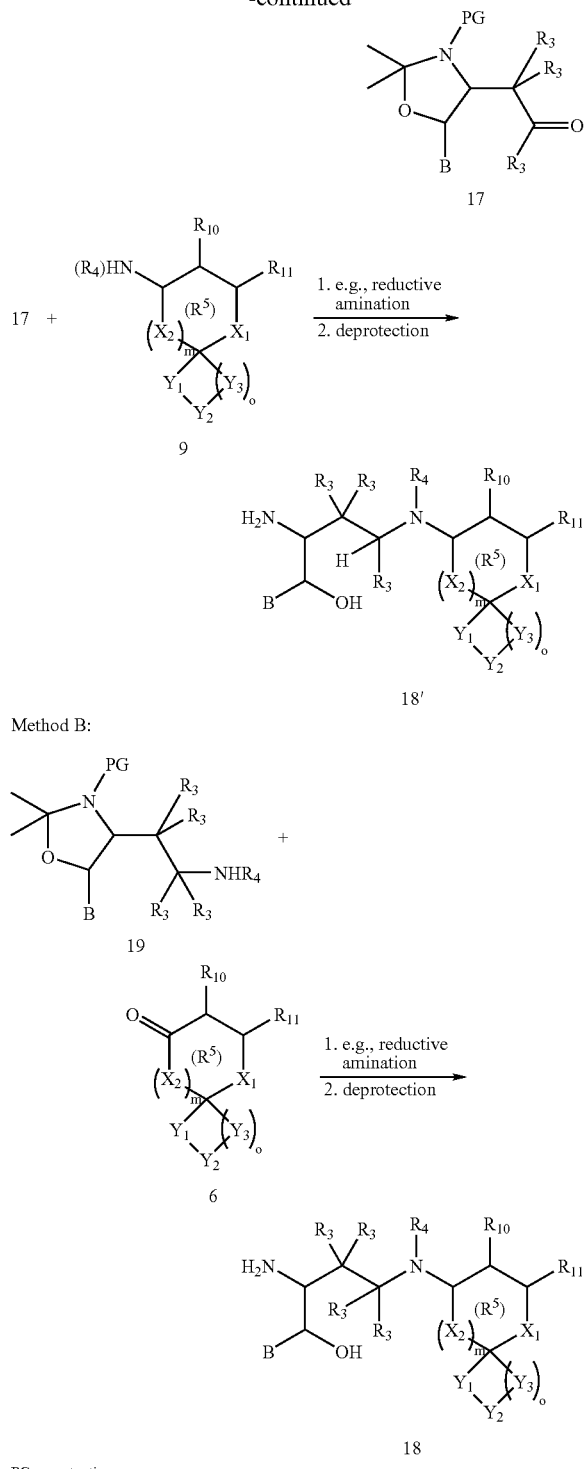

Scheme 5 describes, generally, two different methods (Methods A and B) for constructing intermediates 18' (Method A) or 18 (Method B) which are useful for making compounds of Formula III. As shown in Method A, the acid group of an olefinic amino-acid compound 15 may be modified with a desired B group to form a compound 16, by first activating the acid of 15 with a known activating agent, such as HATU in the presence of a suitable base, and treating activated 15 with a B-substituted grignard reagent or B-ligand metal reagent, which delivers the desired B group to displace the carbonyl activating group and form compound 16. Compound 16 may be oxidized to the corresponding ketone 17 by known methods, such as with sodium periodiate and osmium tetroxide. Ketone 17 may then be reacted with amine 9, via a reductive amination step, to form an amino protected intermediate, which can be deprotected to yield intermediate 18', as shown.

Alternatively, intermediate 18 may be made using a reductive amination step with an amine-protected diamine compound 19 and a ketone 6. Such reductive amination step may be employed with conventional conditions using known reducing reagents in suitable solvents, at suitable temperatures, as appreciated by one of ordinary skill in the art.

Amine compounds 18 and 18' can then be coupled to acids and sulfonic acid compounds 2, 2', 4 and 5, described in scheme 1, to make amides and sulfonamide compounds ("W" groups) of Formulas I-III by methods described in scheme 2.

To enhance the understanding and appreciation of the present invention, the following specific examples (starting reagents, intermediates and compounds of Formulas I-III) are set forth. The following analytical methods were used to purify and/or characterize the compounds, and intermediates, described in the examples below.

Analytical HPLC and LC-MS Methods:

Unless otherwise indicated, all analytical HPLC analyses were run on an Agilent Model 1100 series system LC/MSD SL using one of the two following Columns: (a) Phenomenex Sernegi (4 micron, C18, 50×2 mm) or (b) a Gemini column (5 micron, C18, 100×2 mm). A typical run through the instrument included: eluting at 1 ml/min with an linear gradient of 10% (v/v) to 100% MeCN (0.1% v/v TFA) in water (0.1% TFA) over 10 minutes; conditions may be varied to achieve optimal separation.

Preparative HPLC Method:

Unless otherwise indicated, the compounds described herein were purified via reverse phase HPLC using one of the following instruments: Shimadzu, varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 110% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 1 50EX MS instrument.

Compounds having an isotopic atom, such as bromine and the like, are generally reported according to the detected isotopic pattern, as appreciated by those skilled in the art.

Naming Convention

The compounds disclosed and described herein have been named using the naming convention provided with Chem-Draw Ultra 8.0 software, available in Chem. Office. In some instances, compounds were named with the term "spirocarbocycle" inserted where appropriate. For example, where the chroman is substituted with 2,2-spirocyclobutyl, "2,2-spirocyclobutyl" is added to the Chem-Draw nomenclature in the appropriate place. Chem-Draw utilizes the ISIS Draw software compound naming convention, as appreciated by those skilled in the art.

EXAMPLES

The Examples, described herein below, represent various exemplary starting materials, intermediates and compounds of Formulas I-III, which should assist in a better understanding and appreciation of the scope of the present invention and of the various methods which may be used to synthesize compounds of Formulas I, II and III. It should be appreciated that the general methods above and specific examples below are illustrative only, for purpose of assistance, and should not be construed as limiting the scope of the present invention in any manner.

Example 1

N-((2S,3R)-4-((S)-2,2-spirocyclobutylchroman-4-ylamino)-3-hydroxy-1-phenylbutan-2-yl)acetamide Step 1. 2,2-spirocyclobutylchroman-4-one 1-(2-hydroxyphenyl)ethanone (3.2 ml, 26.6 mmol), cyclobutanone (4 ml, 53.3 mmol), pyrrolidine (2.6 ml, 32 mmol), and diisopropylethyl amine (4.5 ml, 26.6 mmol) were dissolved in 30 ml toluene and refluxed under a Dean Stark trap for 3.5 h. The reaction was terminated (although a large amount of starting material was still present). The cooled reaction mixture was diluted with 100 ml ether, washed with 30 ml HCl (aq., 5M), dried over $MgSO_4$ and evaporated. Column chromatography (3% EtOAc in Hexanes) gave the title compound as a yellow oil 760 mg (4.04 mmol, 15%). MS m/z: 189 (M+1).

Step 2. (R)-2,2-spirocyclobutylchroman-4-ol

A solution of (S)-2 Methyl-CBS-oxazaborolidin (1 M, 200 ul, 0.2 mmol) and borane DMS complex (0.5 ml, 5.25 mmol) in 10 ml toluene was cooled to −20° C. and a solution of 2,2-spirocyclobutylchroman-4-one (17 a, 0.76 g, 4.04 mmol) in 5 ml THF was added slowly over a period of 2.5 h. The reaction mixture was stirred for 0.5 h at the same temperature and was than carefully hydrolyzed with MeOH. The mixture was washed with HCl (1 M, aq.) and $NaHCO_3$ (sat., aq.) and the organic phase was dried over $MgSO_4$ and evaporated. The crude material was used without further purification in the next step.

Step 3. (S)-4-azido-2,2-spirocyclobutylchroman

The crude material from Step 2 was dissolved in 10 ml toluene and dppa (1.17 ml, 5.2 mmol) and dbu (0.776 ml, 5.2 mmol) was added and the mixture was stirred for 12 h. Two phases were observed and the less heavy layer was diluted with ether and washed with HCl (1 M, aq.) and $NaHCO_3$ (sat., aq.), dried over $MgSO_4$ and evaporated. Column chromatography (3% EtOAc in hexanes) gave 0.32 g (1.48 mmol, 35% (over 2 steps)) of the title compound as a yellow oil. MS m/z: 188(40%, $M-N_2$); 173(17%, $M-N_3$).

Step 4.(S)-2,2-spirocyclobutylchroman-4-amine (S)-4-azido-2,2-spirocyclobutylchroman (0.32 g, 1.48 mmol) was dissolved in 10 ml THF and cooled to 3° C. LAH (1M in THF, 4.5 ml, 4.5 mmol) was added and stirring was continued for 2.5 h. The reaction mixture was allowed to warm up to room temperature during this period of time and 10 ml THF and 10 ml $CH_2Cl_2$ were added. 5 g $NaSO_4.10H_2O$ was added carefully, the mixture was stirred 15 min and was filtered. The filtrate was dried over $MgSO_4$ and evaporated and the crude product (MS m/z/z: 173(100%, $M-NH_2$)) was used without further purification in the next step (240 mg, 1.26 mmol, 86% crude).

Step 5. tert-Butyl (2S,3R)-4-((S)-2,2-spirocyclobutylchroman -4-ylamino)-3-hydroxy-1-phenylbutan-2-ylcarbamate (S)-2,2-spirocyclobutylchroman-4-amine (240 mg, 1.26 mmol) was mixed with 1 ml of IPA and tert-butyl (S)-1-((S)-oxiran-2-yl)-2-phenylethylcarbamate (396 mg, 1.5 mmol) and heated in the microwave to 125° C. for 15 min. The mixture was diluted wit 2 ml DMF and purified on the prep HPLC (Gilson) to give the title compound. Yield (white TFA salt): 400 mg (0.88 mmol, 70% over 2 steps, MS m/z: 453 (100%, M+1)).

Step 6. (2R,3S)-3-amino-1-((S)-2,2-spirocyclobutylchroman-4-ylamino)-4-phenylbutan-2-ol tert-Butyl (2S,3R)-4-((S)-2,2-spirocyclobutylchroman-4-ylamino)-3-hydroxy-1-phenylbutan-2-ylcarbamate was dissolved in 2 ml dioxane and 4 ml HCl (4M in dioxane) was added and stirring was continued for 2 h. The reaction mixture was evaporated and the crude product used without further purification in the next step: white HCl salt, MS m/z: 353 (100%, M+1).

Step 7. N-((2S,3R)-4-((S)-2,2-spirocyclobutylchroman-4-ylamino)-3-hydroxy-1-phenylbutan-2-yl)acetamide (2R,3S)-3-amino-1-((S)-2,2-spirocyclobutylchroman-4-ylamino)-4-phenylbutan-2-ol (34 mg, 0.08 mmol) was dissolved in 1 ml DMF and acetic acid (4.5 ul, 0.08 mmol), hatu (30 mg, 0.08 mmol) and diisopropyl-ethyl amine (40 ul, 0.24 mmol) were added. The mixture was stirred for 2 h and 5 drops from a Pasteur pipette of HCl (5 M, aq.) was added. The mixture was purified without further work up procedure on the prep HPLC (Gilson) to give the title compound as its white TFA salt. MS m/z: 395(100%, M+1).

Example 2

N-((2S,3R)-4((S)-6-ethyl-2,2-spirocyclopentylchroman-4-ylamino)-3-hydroxy-1-phenylbutan-2-yl)acetamide.TFA Salt.

To a solution of (2S,3R)-3-amino-1-((S)-6-ethyl-2,2-spirocyclopentylchroman-4-ylamino)-4-phenylbutan-2-ol (25 mg, 0.06 mmol, synthesized using analogous procedures as in Example 1), triethylamine (0.02 mL, 0.14 mmol, Aldrich), and $CH_2Cl_2$ (1 mL) was added N-acetylimidazole (9 mg, 0.08 mmol, Fluka). Stir at room temperature. After 2 h, more N-acetylimidazole (5 mg) was added. After 3 days, the solution was purified by reverse-phase preparative HPLC on a Phenomenex Synergi column (4 micron, MAX-RP, 80 Å, 150×30 mm) eluting at 45 ml/min with an linear gradient of 10% (v/v) to 100% MeCN (0.1% v/v TFA) in water (0.1% TFA) over 10 minutes to give 3.7 mg of the desired product as a colorless solid. MS m/z: 437.4(M+1).

Example 3

N-((2S,3R)-4((S)-6-ethyl-2,2-spirocyclobutylchroman-4-ylamino)-3-hydroxy-1-phenylbutan-2-yl)-2-(pyridin-4-yl)acetamide.TFA Salt The title compound was synthesized by a method analogous to that described in Example 1, using (2S,3R)-3-amino-1-((S)-6-ethyl-2,2-spirocyclobutylchroman-4-ylamino)-4-phenylbutan-2-ol dihydrochloride salt and 2-(pyridin-4-yl)acetic acid hydrochloride (Aldrich) in the presence of DIPEA to obtain the title compound as a colorless solid. MS m/z: 500.3 (M+1).

Example 4

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)-2-(5-methyl-1H-pyrazol-1-yl)acetamide The title compound was prepared via an intermediate obtained by a method analogous to that described in Example 171 of co-pending patent application Ser. No. 60/738,767. The intermediate was finally coupled by a method analogous to that described in Example 1 above using 2-(5-methyl-1H-pyrazol-1-yl)acetic acid to provide the title compound. MS m/z: 546.3 (M+1).

Example 5

Methyl (2S,3R)-3-hydroxy-4-((S)-6-neopentyl-2,2-spirocyclobutyl-3,4-dihydro-2H-pyrano[2,3-b]pyridin-4-ylamino)-1-phenylbutan-2-ylcarbamate The title compound was prepared via an intermediate obtained by a method analogous to that described in Example 171 of co-pending patent application Ser. No. 60/738,767. The intermediate was finally coupled by a method analogous to that described in Example 3 above using methyl chloroformate to provide the title compound. MS m/z: 482.3 (M+1).

Example 6

Ethyl (2S,3R)-4-((S)-6-ethyl-2,2-spirocyclobutyl-chroman-4-ylamino)-3-hydroxy-1-phenylbutan-2-ylcarbamate A mixture of di-succinimidyl carbonate (2.56 g, 1.0 eq), DIPEA (1.29 g, 1.0 eq), and anhydrous EtOH (1.16 mL, 2.0 eq) in dry $CH_2Cl_2$ and $CH_3CN$ was stirred at rt overnight. The solvents were removed and the residue was used directly in the next step. TA portion of the crude residue was mixed with (2R,3S)-3-amino-1-((S)-6-ethyl-2,2-spirocyclobutyl-chroman-4-ylamino)-4-phenylbutan-2-ol hydrochloric acid salt in the presence of 3 drops of DIPEA in anhydrous and the resulting mixture was stirred at rt until the complete consumption of the amine. The title product was obtained as a TFA salt after purification by HPLC. MS m/z: 453 (M+1).

The following examples were prepared by a method analogous to that described in Examples 1-6 above.

| Ex. No. | STRUCTURE | Mass found | MW |
|---|---|---|---|
| 7 | N-((2S,3R)-4-((S)-6-ethyl-2,2-spirocyclobutylchroman-4-ylamino)-3-hydroxy-1-phenylbutan-2-yl)pent-4-ynamide | 461 | 460.614 |
| 8 | 3-cyclopentyl-N-((2S,3R)-4-((S)-6-ethyl-2,2-spirocyclobutylchroman-4-ylamino)-3-hydroxy-1-phenylbutan-2-yl)propanamide | 505 | 504.711 |
| 9 | N-((2S,3R)-4-((S)-6-ethyl-2,2-spirocyclobutylchroman-4-ylamino)-3-hydroxy-1-phenylbutan-2-yl)propionamide | 437 | 436.592 |
| 10 | N-((2S,3R)-4-((S)-6-ethyl-2,2-spirocyclobutylchroman-4-ylamino)-3-hydroxy-1-phenylbutan-2-yl)-2-methoxyacetamide | 453 | 452.591 |
| 11 | N-((2S,3R)-4-((S)-6-bromo-2,2-spirocyclobutylchroman-4-ylamino)-3-hydroxy-1-phenylbutan-2-yl)-2-isopropoxyacetamide | 531, 533 | 531.487 |
| 12 | N-((2S,3R)-4-((S)-6-bromo-2,2-spirocyclobutylchroman-4-ylamino)-3-hydroxy-1-phenylbutan-2-yl)-2-methoxyacetamide | 503, 505 | 503.434 |
| 13 | 2-(allyloxy)-N-((2S,3R)-4-((S)-6-bromo-2,2-spirocyclobutylchroman-4-ylamino)-3-hydroxy-1-phenylbutan-2-yl)acetamide | 529, 531 | 529.472 |
| 14 | N-((1S,2R)-3-(((4S)-6-bromo-3,4-dihydrospiro[chromene-2,1'-cyclobutan]-4-yl)amino)-2-hydroxy-1-(phenylmethyl)propyl)-3-(methyloxy)propanamide | 517, 519 | 517.461 |
| 15 | N-((1S,2R)-3-(((4S)-6-bromo-3,4-dihydrospiro[chromene-2,1'-cyclobutan]-4-yl)amino)-2-hydroxy-1-(phenylmethyl)propyl)-2-(ethyloxy)acetamide | 517, 519 | 517.461 |
| 16 | N-((1S,2R)-3-(((4S)-6-bromo-3,4-dihydrospiro[chromene-2,1'-cyclobutan]-4-yl)amino)-2-hydroxy-1-(phenylmethyl)propyl)-2-((cyclopropylmethyl) oxyacetamide | 543, 545 | 543.498 |
| 17 | N-((1S,2R)-3-(((4S)-6-bromo-3,4-dihydrospiro[chromene-2,1'-cyclobutan]-4-yl)amino)-2-hydroxy-1-(phenylmethyl)propyl)-2-((2,2,2-trifluoroethyl)oxy) acetamide | 571, 573 | 571.431 |
| 18 | 2-((cyclopropylmethyl)oxy)-N-((1S,2R)-3-(((4S)-6-ethyl-3,4-dihydrospiro[chromene-2,1'-cyclobutan]-4-yl)amino)-2-hydroxy-1-(phenylmethyl)propyl)acetamide | 493 | 492.656 |

-continued

| Ex. No. | STRUCTURE | Mass found | MW |
|---|---|---|---|
| 19 | 2-((cyclopropylmethyl)oxy)-N-((1S,2R)-3-(((4S)-6-(2,2-dimethylpropyl)-3,4-dihydrospiro[chromene-2,1'-cyclobutan]-4-yl)amino)-2-hydroxy-1-(phenylmethyl) propyl)acetamide | 535 | 534.736 |
| 20 | N-((1S,2R)-3-(((5R)-3,3-dimethyl-1,3,4,5-tetrahydro-2-benzoxepin-5-yl)amino)-2-hydroxy-1-(phenylmethyl)propyl)acetamide | 397 | 793.056 |
| 21 | N-((1S,2R)-3-(((5R)-3,3-dimethyl-1,3,4,5-tetrahydro-2-benzoxepin-5-yl)amino)-2-hydroxy-1-(phenylmethyl)propyl)-2-(methyloxy)acetamide | 427 | 853.107 |
| 22 | N-((1S,2R)-3-(((5S)-7-ethyl-3,3-dimethyl-1,3,4,5-tetrahydro-2-benzoxepin-5-yl)amino)-2-hydroxy-1-(phenylmethyl)propyl)acetamide | 425 | 424.581 |
| 23 | N-((1S,2R)-3-(((5S)-7-ethyl-3,3-dimethyl-1,3,4,5-tetrahydro-2-benzoxepin-5-yl)amino)-2-hydroxy-1-(phenylmethyl) propyl)-2-(methyloxy)acetamide | 455 | 454.607 |
| 24 | 2-(1,3-benzothiazol-2-yloxy)-N-((1S,2R)-3-(((4S)-6-bromo-3,4-dihydrospiro [chromene-2,1'-cyclobutan]-4-yl)amino)-2-hydroxy-1-(phenylmethyl)propyl)acetamide | 622, 624 | 622.581 |
| 25 | 2-(1,3-benzothiazol-2-yloxy)-N-((1S,2R)-3-(((4S)-6-ethyl-3,4-dihydrospiro [chromene-2,1'-cyclobutan]-4-yl)amino)-2-hydroxy-1-(phenylmethyl)propyl)acetamide | 572 | 571.738 |
| 26 | N-((1S,2R)-3-(((4S)-6-ethyl-3,4-dihydrospiro[chromene-2,1'-cyclobutan]-4-yl)amino)-2-hydroxy-1-(phenylmethyl) propyl)-2-(2-oxo-1,3-oxazolidin-3-yl)acetamide | 508 | 507.627 |
| 27 | N-((1S,2R)-3-(((4S)-6-bromo-3,4-dihydrospiro[chromene-2,1'-cyclobutan]-4-yl)amino)-2-hydroxy-1-(phenylmethyl) propyl)-2-(2-oxo-1,3-oxazolidin-3-yl)acetamide | 558, 560 | 558.47 |
| 28 | 2-(1,3-benzoxazol-2-ylthio)-N-((1S,2R)-3-(((4S)-6-ethyl-3,4-dihydrospiro[chromene-2,1'-cyclobutan]-4-yl)amino)-2-hydroxy-1-(phenylmethyl)propyl)acetamide | 572 | 571.738 |
| 29 | 2-(1,3-benzothiazol-2-ylthio)-N-((1S,2R)-3-(((4S)-6-ethyl-3,4-dihydrospiro [chromene-2,1'-cyclobutan]-4-yl)amino)-2-hydroxy-1-(phenylmethyl)propyl)acetamide | 588 | 587.805 |
| 30 | N-((1S,2R)-3-(((4S)-6-ethyl-3,4-dihydrospiro[chromene-2,1'-cyclobutan]-4-yl)amino)-2-hydroxy-1-(phenylmethyl) propyl)-2-(1H-pyrrolo[2,3-b]pyridin-1-yl)acetamide | 539 | 538.688 |
| 31 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-((5-methyl-3-isoxazolyl)oxy)acetamide | 520 | 519.638 |
| 32 | 2-(1,3-benzoxazol-2-yloxy)-N-((1S,2R)-3-(((4S)-6-ethyl-3,4-dihydrospiro[chromene-2,1'-cyclobutan]-4-yl)amino)-2-hydroxy-1-(phenylmethyl)propyl)acetamide | 556 | 555.671 |
| 33 | N-((1S,2R)-3-(((4S)-6-ethyl-3,4-dihydrospiro[chromene-2,1'-cyclobutan]-4-yl)amino)-2-hydroxy-1-(phenylmethyl) propyl)-2-(1H-pyrazol-1-yl)acetamide | 489 | 488.628 |
| 34 | 2-((1,3-benzothiazol-2-ylmethyl)oxy)-N-((1S,2R)-3-(((4S)-6-ethyl-3,4-dihydrospiro[chromene-2,1'-cyclobutan]-4-yl)amino)-2-hydroxy-1-(phenylmethyl) propyl)acetamide | 586 | 585.765 |
| 35 | N-((1S,2R)-3-(((4S)-6-ethyl-3,4-dihydrospiro[chromene-2,1'-cyclobutan]-4-yl)amino)-2-hydroxy-1-(phenylmethyl) propyl)-2-((3R)-tetrahydro-3-furanyloxy)acetamide | 509 | 508.655 |
| 36 | N-((1S,2R)-3-(((4S)-6-ethyl-3,4-dihydrospiro[chromene-2,1'-cyclobutan]-4-yl)amino)-2-hydroxy-1-(phenylmethyl) propyl)-2-((1,3-oxazol-2-ylmethyl)oxy) acetamide | 520 | 519.638 |
| 37 | N-((1S,2R)-3-(((4S)-6-ethyl-3,4-dihydrospiro[chromene-2,1'-cyclobutan]-4-yl)amino)-2-hydroxy-1-(phenylmethyl) propyl)-2-((3S)-tetrahydro-3-furanyloxy)acetamide | 509 | 508.655 |
| 38 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-(2-oxo-1,3-oxazolidin-3-yl)acetamide | 533 | 532.6374 |
| 39 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-((3S)-tetrahydro-3-furanyloxy)acetamide | 534 | 533.6651 |
| 40 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-((5-methyl-3-isoxazolyl) oxy)acetamide | 545 | 544.6484 |
| 41 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-(1H-pyrrolo[2,3-b]pyridin-1-yl)acetamide | 564 | 563.6983 |
| 42 | N-((1S,2S)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(2-oxo-1,3-oxazolidin-3-yl) acetamide | 551 | 550.6958 |

-continued

| Ex. No. | STRUCTURE | Mass found | MW |
|---|---|---|---|
| 43 | N-((1S,2S)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-((3S)-tetrahydro-3-furanyloxy) acetamide | 552 | 551.7235 |
| 44 | N-((1S,2S)-3-(((4'S)-6'-(2,2-dimethylpropyl)-3',4'-dihydrospiro cyclobutane-1,2'-pyrano[2,3-b]pyridin]-4'-yl)amino)-2-hydroxy-1-(phenylmethyl) propyl)-2-(1H-pyrrolo[2,3-b]pyridin-1-yl)acetamide | 582 | 581.7567 |
| 45 | N-((1S,2S)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-((5-methyl-3-isoxazolyl)oxy) acetamide | 563 | 562.7068 |
| 46 | N-((1S,2R)-3-(((4S)-6-ethyl-2,2-dimethyl-3,4-dihydro-2H-chromen-4-yl)amino)-2-hydroxy-1-(phenylmethyl)propyl)-3-(2-(1-methylethyl)-1H-imidazol-1-yl)propanamide | 533 | 532.7246 |
| 47 | (2E)-N-((1S,2R)-3-(((4S)-6-ethyl-2,2-dimethyl-3,4-dihydro-2H-chromen-4-yl)amino)-2-hydroxy-1-(phenylmethyl) propyl)-3-(1-(2-methylpropyl)-1H-imidazol-4-yl)-2-propenamide | 545 | 544.7356 |
| 48 | N-((1S,2R)-1-((3-bromophenyl)methyl)-3-(((4S)-6-ethyl-3,4-dihydrospiro[chromene-2,1'-cyclobutan]-4-yl)amino)-2-hydroxypropyl)acetamide | 502 | 501.462 |
| 49 | N-((1S,2R)-3-(((4S)-6-cyano-3,4-dihydrospiro[chromene-2,1'-cyclobutan]-4-yl)amino)-2-hydroxy-1-(phenylmethyl) propyl)acetamide | 420 | 419.522 |
| 50 | N-((2S,3R)-4-((S)-6-ethyl-2,2'-spirocyclobutylchroman-4-ylamino)-3-hydroxy-1-(4-phenyl-phenyl)-butan-2-yl) acetamide | 499 | 498.663 |
| 51 | N-((2S,3R)-4-((S)-6-ethyl-2,2'-spirocyclobutylchroman-4-ylamino)-1-(4-fluorophenyl)-3-hydroxybutan-2-yl) acetamide | 441 | 440.556 |
| 52 | N-((2S,3R)-4-((S)-6-ethyl-2,2'-spirocyclobutylchroman-4-ylamino)-1-(4-fluorophenyl)-3-hydroxybutan-2-yl)-2-methoxyacetamide | 471 | 470.582 |
| 53 | N-((1S,2R)-3-(((4S)-6-ethyl-3,4-dihydrospiro[chromene-2,1'-cyclobutan]-4-yl)amino)-2-hydroxy-1-phenylpropyl)-2-(methyloxy)acetamide | 439 | 438.565 |
| 54 | N-((1S,2R)-3-(((4S)-6-ethyl-3,4-dihydrospiro[chromene-2,1'-cyclobutan]-4-yl)amino)-2-hydroxy-1-phenylpropyl) acetamide | 409 | 408.539 |
| 55 | N-((1S,2R)-1-((3-bromophenyl)methyl)-3-(((4S)-6-ethyl-3,4-dihydrospiro[chromene-2,1'-cyclobutan]-4-yl)amino)-2-hydroxypropyl)-2-(methyloxy)acetamide | 532 | 531.487 |
| 56 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-(methyloxy)acetamide | 478 | 477.602 |
| 57 | N-((1S,2R)-3-(((4S)-6-bromo-2,2-dimethyl-3,4-dihydro-2H-chromen-4-yl)amino)-1-((3,5-difluorophenyl)methyl)-2-hydroxypropyl)-2-(3-pyridinyl)acetamide | 575 | 574.463 |
| 58 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)acetamide | 448 | 447.576 |
| 59 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-phenylacetamide | 524 | 523.673 |
| 60 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-(phenyloxy)acetamide | 540 | 539.672 |
| 61 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-(3-thienyl)acetamide | 530 | 529.701 |
| 62 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)tetrahydro-2-furancarboxamide | 504 | 503.639 |
| 63 | (3S)—N-((1S,2R)-1-((3-cyanophenyl) methyl)-3-(((4S)-6-ethyl-3,4-dihydrospiro [chromene-2,1'-cyclobutan]-4-yl)amino)-2-hydroxypropyl)-1-cyclobutyl-5-oxo-3-pyrrolidinecarboxamide | 571 | 570.73 |
| 64 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)propanamide | 462 | 461.603 |
| 65 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-((cyclopropylmethyl)oxy) acetamide | 518 | 517.666 |
| 66 | N-((1S,2R)-3-(((4S)-6-bromo-3,4-dihydrospiro[chromene-2,1'-cyclobutan]-4-yl)amino)-2-hydroxy-1-((3-(trifluoromethyl)phenyl)methyl)propyl)acetamide | 542 | 541.4052 |

| Ex. No. | STRUCTURE | Mass found | MW |
|---|---|---|---|
| 67 | N-((1S,2R)-3-(((4S)-6-bromo-3,4-dihydrospiro[chromene-2,1'-cyclobutan]-4-yl)amino)-2-hydroxy-1-((3-(trifluoromethyl)phenyl)methyl)propyl)-2-(methyloxy)acetamide | 572 | 571.431 |
| 68 | (S)—N-((2S,3R)-4-((S)-6-ethyl-2,2-spirocyclopentylchroman-4-ylamino)-3-hydroxy-1-phenylbutan-2-yl)-2-(1-oxoisoindolin-2-yl)propanamide | 582.3 | 581.753 |
| 69 | N-((2S,3R)-4-((S)-6-ethyl-2,2-spirocyclopentylchroman-4-ylamino)-3-hydroxy-1-phenylbutan-2-yl)-3-(5-fluoro-2-methoxyphenyl)propanamide | 575.3 | 574.733 |
| 70 | (S)—N-((2S,3R)-4-((S)-6-ethyl-2,2-spirocyclopentylchroman-4-ylamino)-3-hydroxy-1-phenylbutan-2-yl)-5-oxopyrrolidine-2-carboxamide | 506.3 | 505.655 |
| 71 | (E)-N-((2S,3R)-4-((S)-6-ethyl-2,2-spirocyclopentylchroman-4-ylamino)-3-hydroxy-1-phenylbutan-2-yl)-3-(5-fluoro-2-methoxyphenyl)acrylamide | 573.3 | 572.717 |
| 72 | N-((1S,2R)-1-((3,5-difluorophenyl)methyl)-3-((6-ethyl-2,2-dimethyl-3,4-dihydro-2H-chromen-4-yl)amino)-2-hydroxypropyl)acetamide | 447.2 | 446.535 |
| 73 | N-((1S,2R)-1-((3,5-difluorophenyl) methyl)-3-(((4S)-6-ethyl-3,4-dihydrospiro[chromene-2,1'-cyclobutan]-4-yl)amino)-2-hydroxypropyl) acetamide | 459.2 | 458.546 |
| 74 | N-((1S,2R)-1-((3,5-difluorophenyl) methyl)-3-(((4S)-6-ethyl-3,4-dihydrospiro [chromene-2,1'-cyclobutan]-4-yl)amino)-2-hydroxypropyl)-2-(methyloxy)acetamide | 489.2 | 488.572 |
| 75 | N-((1S,2R)-3-(((7S)-2-ethyl-5,5-dimethyl-4,5,6,7-tetrahydro-1,3-benzothiazol-7-yl)amino)-2-hydroxy-1-(phenylmethyl)propyl)acetamide | 416.2 | 415.599 |
| 76 | N-((1S,2R)-3-(((1S)-3,3-dimethyl-2,3-dihydro-1H-inden-1-yl)amino)-2-hydroxy-1-(phenylmethyl)propyl)acetamide | 367.2 | 366.502 |
| 77 | N-((1S,2R)-3-(((1S)-3,3-dimethyl-2,3-dihydro-1H-inden-1-yl)amino)-2-hydroxy-1-(phenylmethyl)propyl)-2-(methyloxy)acetamide | 397.2 | 396.528 |
| 78 | N-((1S,2R)-1-((3-cyanophenyl)methyl)-3-(((2S,4S)-6-ethyl-3,4,4',5'-tetrahydrospiro[chromene-2,3'-furan]-4-yl)amino)-2-hydroxypropyl)-2-(methyloxy) acetamide | 494.2 | 987.201 |
| 79 | N-((1S,2R)-1-((3,5-difluorophenyl) methyl)-3-(((2S,4S)-6-ethyl-3,4,4',5'-tetrahydrospiro[chromene-2,3'-furan]-4-yl)amino)-2-hydroxypropyl)acetamide | 475.2 | 949.0896 |
| 80 | N-((1S,2R)-3-(((2R,4S)-6-ethyl-3,4,4',5'-tetrahydrospiro[chromene-2,3'-furan]-4-yl)amino)-2-hydroxy-1-(phenylmethyl) propyl)-2-(1H-1,2,4-triazol-1-yl) acetamide | 506.2 | 1011.231 |
| 81 | N-((1S,2R)-1-((3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 491.3 | 490.6442 |
| 82 | N-((1S,2S)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-phenylacetamide | 542 | 541.7317 |
| 83 | N'—((1S,2S)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-N,N-dimethylbutanediamide | 551 | 550.7394 |
| 84 | N-((1S,2S)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(2-pyrimidinyloxy)acetamide | 560 | 559.7069 |
| 85 | 2-(((1S,2R)-3-(((4'S)-6'-ethyl-3',4'-dihydrospiro[cyclobutane-1,2'-pyrano[2,3-b]pyridin]-4'-yl)amino)-2-hydroxy-1-(phenylmethyl)propyl)amino)-2-oxoethyl dimethylcarbamate | 511 | 510.6312 |
| 86 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(2-thienyl)acetamide | 548 | 547.7599 |
| 87 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl propyl)-4-pentynamide | 504 | 503.6829 |
| 88 | N-((1S,2R)-3-(((1R)-3,3-dimethyl-7-(methyloxy)-4-oxo-1,2,3,4-tetrahydro-1-naphthalenyl)amino)-2-hydroxy-1-(phenylmethyl)propyl)acetamide | 425 | 849.0756 |
| 89 | 2-(((1S,2R)-1-((3-cyanophenyl)methyl)-2-hydroxy-3-(((4S)-6-(4-morpholinyl)-3,4-dihydrospiro[chromene-2,1'-cyclobutan]-4-yl)amino)propyl)amino)-2-oxoethyl dimethylcarbamate | 592 | 591.7049 |

| Ex. No. | STRUCTURE | Mass found | MW |
|---|---|---|---|
| 90 | N-((1S,2R)-1-((3-cyanophenyl)methyl)-2-hydroxy-3-(((4S)-6-(4-morpholinyl)-3,4-dihydrospiro[chromene-2,1'-cyclobutan]-4-yl)amino)propyl)-2-(2-thienyl)acetamide | 587 | 586.7532 |
| 91 | N-((1S,2R)-3-(((4S)-6-ethyl-3,4-dihydro-2H-chromen-4-yl)amino)-2-hydroxy-1-(phenylmethyl)propyl)-2-(9-oxo-10(9H)-acridinyl)acetamide | 576 | 575.705 |
| 92 | N-((1S,2R)-3-(((4S)-6-ethyl-3,4-dihydro-2H-chromen-4-yl)amino)-2-hydroxy-1-(phenylmethyl)propyl)-2-((2-fluorophenyl)thio)acetamide | 509 | 508.655 |
| 93 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(9-oxo-10(9H)-acridinyl)acetamide | 616 | 615.77 |
| 94 | (2Z)-2-(6-bromo-2-oxo-1,2-dihydro-3H-indol-3-ylidene)-N-((1S,2R)-3-(((4S)-6-ethyl-3,4-dihydrospiro[chromene-2,1'-cyclobutan]-4-yl)amino)-2-hydroxy-1-(phenylmethyl)propyl)ethanamide | 632 | 630.579 |
| 95 | 2-((3-chloro-2-methylphenyl)thio)-N-((1S,2R)-3-(((4S)-6-ethyl-3,4-dihydrospiro[chromene-2,1'-cyclobutan]-4-yl)amino)-2-hydroxy-1-(phenylmethyl) propyl)acetamide | 579 | 579.201 |
| 96 | (2S)—N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(1-oxo-1,3-dihydro-2H-isoindol-2-yl)propanamide | 568 | 567.726 |
| 97 | 2-((2-acetylphenyl)oxy)-N-((1S,2R)-3-(((4S)-6-ethyl-3,4-dihydrospiro[chromene-2,1'-cyclobutan]-4-yl)amino)-2-hydroxy-1-(phenylmethyl)propyl)acetamide | 557 | 556.699 |
| 98 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-(1-oxo-1,3-dihydro-2H-isoindol-2-yl)acetamide | 579 | 578.7092 |
| 99 | N-((1S,2R)-3-(((4S)-6-bromo-3,4-dihydrospiro[chromene-2,1'-cyclobutan]-4-yl)amino)-2-hydroxy-1-(phenylmethyl) propyl)-2-(1-oxo-1,3-dihydro-2H-isoindol-2-yl)acetamide | 606 | 604.5416 |
| 100 | N-((2S,3R)-4-((S)-6-ethyl-2,2-spirocyclobutyl-3,4-dihydro-2H-pyrano [2,3-b]pyridin-4-ylamino)-3-hydroxy-1-phenylbutan-2-yl)-2-(1-oxoisoindolin-2-yl)acetamide | 555 | 554.6872 |
| 101 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(1-oxo-1,3-dihydro-2H-isoindol-2-yl)acetamide | 597 | 596.7676 |
| 102 | N-((1S,2R)-3-(((4'S)-6'-(2,2-dimethylpropyl)-3',4,4',5-tetrahydrospiro [furan-3,2'-pyrano[2,3-b]pyridin]-4'-yl) amino)-2-hydroxy-1-(phenylmethyl) propyl)-2-(1-oxo-1,3-dihydro-2H-isoindol-2-yl)acetamide | 613 | 612.7666 |
| 103 | N-((1S,2R)-3-(((3R,4'S)-6'-(2,2-dimethylpropyl)-3',4,4',5-tetrahydrospiro[furan-3,2'-pyrano[2,3-b] pyridin]-4'-yl)amino)-2-hydroxy-1-(phenylmethyl)propyl)acetamide | 482 | 963.2662 |
| 104 | N-((1S,2R)-3-(((3S,4'S)-6'-(2,2-dimethylpropyl)-3',4,4',5-tetrahydrospiro [furan-3,2'-pyrano[2,3-b]pyridin]-4'-yl)amino)-2-hydroxy-1-(phenylmethyl)propyl)-2-(methyloxy)acetamide | 512 | 1023.318 |
| 105 | N-((1S,2R)-3-(((3R,4'S)-6'-(2,2-dimethylpropyl)-3',4,4',5-tetrahydrospiro [furan-3,2'-pyrano[2,3-b]pyridin]-4'-yl)amino)-2-hydroxy-1-(phenylmethyl) propyl)-2-(1H-1,2,4-triazol-1-yl) acetamide | 549 | 1097.368 |
| 106 | N-((1S,2R)-3-(((3R,4'S)-6'-(2,2-dimethylpropyl)-3',4,4',5-tetrahydrospiro [furan-3,2'-pyrano[2,3-b]pyridin]-4'-yl)amino)-2-hydroxy-1-(phenylmethyl) propyl)-2-(2H-1,2,3-triazol-2-yl) acetamide | 549 | 1097.368 |
| 107 | N-((1S,2R)-3-(((4S)-6-chloro-3,4-dihydrospiro[chromene-2,1'-cyclobutan]-4-yl)amino)-2-hydroxy-1-(phenylmethyl) propyl)acetamide | 429 | 428.957 |
| 108 | N-((1S,2R)-3-(((4S)-6-chloro-3,4-dihydrospiro[chromene-2,1'-cyclobutan]-4-yl)amino)-2-hydroxy-1-(phenylmethyl) propyl)-2-(methyloxy)acetamide | 459 | 458.983 |
| 109 | N-((1S)-1-((1R)-2-(((4S)-6-bromo-3,4-dihydrospiro[chromene-2,1'-cyclobutan]-4-yl)amino)-1-hydroxyethyl)-3-methylbutyl)-2-(methyloxy)acetamide | 469 | 938.833 |
| 110 | N-((1S)-1-((1R)-2-(((4S)-6-bromo-3,4-dihydrospiro[chromene-2,1'-cyclobutan]-4-yl)amino)-1-hydroxyethyl)-3-methylbutyl)acetamide | 439 | 878.782 |
| 111 | N-((1S,2S)-3-(((4S)-6-ethyl-3,4-dihydrospiro[chromene-2,1'-cyclobutan]-4-yl)amino)-2-hydroxy-1-(1-naphthalenylmethyl)propyl)acetamide | 473 | 945.251 |

-continued

| Ex. No. | STRUCTURE | Mass found | MW |
|---|---|---|---|
| 112 | N-((1S,2S)-3-(((4S)-6-ethyl-3,4-dihydrospiro[chromene-2,1'-cyclobutan]-4-yl)amino)-2-hydroxy-1-(1-naphthalenylmethyl)propyl)-2-(methyloxy acetamide | 503 | 1005.3 |
| 113 | N-((1S,2S)-3-(((4S)-6-bromo-2,2-dimethyl-3,4-dihydro-2H-chromen-4-yl)amino)-2-hydroxy-1-(1-naphthalenylmethyl) propyl) acetamide | 511 | 1022.91 |
| 114 | N-((1S,2R)-3-(((4S)-6-bromo-2,2-dimethyl-3,4-dihydro-2H-chromen-4-yl)amino)-1-(cyclohexylmethyl)-2-hydroxypropyl) acetamide | 467 | 934.889 |
| 115 | N-((1S,2S)-3-(((4S)-6-bromo-2,2-dimethyl-3,4-dihydro-2H-chromen-4-yl)amino)-2-hydroxy-1-(3-thienylmethyl) propyl) acetamide | 467 | 934.851 |
| 116 | N-((1S,2R)-3-(((4S)-6-bromo-2,2-dimethyl-3,4-dihydro-2H-chromen-4-yl)amino)-2-hydroxy-1-(3-thienylmethyl)propyl)-2-(methyloxy)acetamide | 497 | 994.902 |
| 117 | N-((1S,2R)-1-((3-cyano-5-fluorophenyl) methyl)-3-(((4S)-6-ethyl-3,4-dihydrospiro[chromene-2,1'-cyclobutan]-4-yl)amino)-2-hydroxypropyl)acetamide | 466 | 465.5658 |
| 118 | N-((1S,2R)-3-(((4S)-6-bromo-2,2-dimethyl-3,4-dihydro-2H-chromen-4-yl)amino)-2-hydroxy-1-((3-(3-pyridinyl)phenyl) methyl)propyl)acetamide | 538 | 538.483 |
| 119 | N-((3S,4S)-5-((S)-6-bromo-2,2-dimethylchroman-4-ylamino)-1,1,1-trifluoro-4-hydroxypentan-3-yl)acetamide | 453 | 453.2966 |
| 120 | N-((1S,2R)-3-(((4S)-6-bromo-2,2-dimethyl-3,4-dihydro-2H-chromen-4-yl)amino)-1-((3-ethynylphenyl)methyl)-2-hydroxypropyl)acetamide | 485 | 485.4191 |
| 121 | N-((1S)-1-((1R)-2-(((4'S)-6'-(2,2-dimethylpropyl)-3',4'-dihydrospiro [cyclobutane-1,2'-pyrano[2,3-b]pyridin]-4'-yl)amino)-1-hydroxyethyl)-3,3,3-trifluoropropyl)-2-(methyloxy)acetamide | 488 | 487.5594 |
| 122 | N-((1S,2R)-3-(((4S)-6-ethyl-2,2-dimethyl-1,1-dioxido-3,4-dihydro-2H-1-benzothiopyran-4-yl)amino)-2-hydroxy-1-(phenylmethyl)propyl)acetamide | 459 | 458.6196 |
| 123 | N-((1S,2R)-3-(((4S)-6-ethyl-3,4-dihydrospiro[chromene-2,1'-cyclobutan]-4-yl)amino)-2-hydroxy-1-(1,3-thiazol-4-ylmethyl)propyl)acetamide | 430 | 429.5819 |
| 124 | N-((1S,2R)-3-(((4S)-6-ethyl-3,4-dihydrospiro[chromene-2,1'-cyclobutan]-4-yl)amino)-2-hydroxy-1-(phenylmethyl) propyl)acetamide | 423 | 422.566 |
| 125 | N-((1S,2R)-3-(((4S)-6-ethyl-2,2-dimethyl-3,4-dihydro-2H-chromen-4-yl)amino)-2-hydroxy-1-(phenylmethyl)propyl)-2-phenylacetamide | 487 | 486.652 |
| 126 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-phenylacetamide | 499 | 498.663 |
| 127 | (E)-N-((2S,3R)-4-((S)-6-ethyl-2,2-spirocyclobutylchroman-4-ylamino)-3-hydroxy-1-phenylbutan-2-yl)-3-(3-fluorophenyl)acrylamide | 529 | 528.664 |
| 128 | N-((1S,2R)-2-hydroxy-1-(phenylmethyl)-3-(((4S)-2,6,6-trimethyl-4,5,6,7-tetrahydro-1-benzofuran-4-yl)amino) propyl)acetamide | 385 | 384.517 |
| 129 | N-((1S,2R)-2-hydroxy-1-(phenylmethyl)-3-(((4S)-2,6,6-trimethyl-4,5,6,7-tetrahydro-1-benzothien-4-yl)amino)propyl)acetamide | 402 | 400.584 |
| 130 | N-((1S,2R)-2-hydroxy-1-(phenylmethyl)-3-(((4S)-2,6,6-trimethyl-4,5,6,7-tetrahydro-1-benzothien-4-yl)amino)propyl)-2-(methyloxy)acetamide | 432 | 430.61 |
| 131 | N-((1S,2R)-3-(((4S)-2-ethyl-6,6-dimethyl-4,5,6,7-tetrahydro-1-benzothien-4-yl)amino)-2-hydroxy-1-(phenylmethyl) propyl)-2-(methyloxy)acetamide | 445 | 444.636 |
| 132 | N-((1S,2R)-1-((3,5-difluorophenyl) methyl)-2-hydroxy-3-(((4S)-2,6,6-trimethyl-4,5,6,7-tetrahydro-1-benzothien-4-yl)amino) propyl)-2-(methyloxy)acetamide | 467 | 466.5898 |
| 133 | N-((1S,2R)-1-((3,5-difluorophenyl) methyl)-2-hydroxy-3-(((4S)-2,6,6-trimethyl-4,5,6,7-tetrahydro-1-benzothien-4-yl)amino)propyl)acetamide | 437 | 436.564 |
| 134 | N-((1S,2R)-1-((3-cyanophenyl)methyl)-2-hydroxy-3-(((4S)-2,6,6-trimethyl-4,5,6,7-tetrahydro-1-benzothien-4-yl)amino) propyl)acetamide | 426 | 425.5939 |
| 135 | N-((1S,2R)-1-((3-cyanophenyl)methyl)-2-hydroxy-3-(((4S)-2,6,6-trimethyl-4,5,6,7-tetrahydro-1-benzothien-4-yl)amino) propyl)-2-(methyloxy)acetamide | 456 | 455.6197 |
| 136 | N-((1S,2R)-3-(((4S)-2-ethyl-6,6-dimethyl-4,5,6,7-tetrahydro-1-benzothien-4-yl)amino)-2-hydroxy-1-(phenylmethyl) propyl)-2-(2-oxo-1-pyrrolidinyl)acetamide | 498 | 497.7001 |

-continued

| Ex. No. | STRUCTURE | Mass found | MW |
|---|---|---|---|
| 137 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(3-methyl-5-isoxazolyl) acetamide | 547 | 546.7078 |
| 138 | N-((1S,2R)-3-(((4S)-6-((2R,6S)-2,6-dimethyl-4-morpholinyl)-3,4-dihydrospiro [chromene-2,1'-cyclobutan]-4-yl)amino)-2-hydroxy-1-(phenylmethyl)propyl)acetamide | 508 | 507.6709 |
| 139 | N-((1S,2R)-2-hydroxy-3-(((4S)-6-((3S)-3-methyl-4-morpholinyl)-3,4-dihydrospiro [chromene-2,1'-cyclobutan]-4-yl)amino)-1-(phenylmethyl)propyl)acetamide | 494 | 493.6441 |
| 140 | N-((1S,2R)-3-(((4'R)-6'-bromo-3',4'-dihydrospiro[cyclobutane-1,2'-pyrano[2,3-b]pyridin]-4'-yl)amino)-2-hydroxy-1-(phenylmethyl)propyl)acetamide | 476 | 474.3962 |
| 141 | N-((1S,2R)-3-(((4'S)-6'-bromo-3',4'-dihydrospiro[cyclobutane-1,2'-pyrano[2,3-b]pyridin]-4'-yl)amino)-2-hydroxy-1-(phenylmethyl)propyl)acetamide | 476 | 474.3962 |
| 142 | N-((1S,2R)-1-((3,5-difluorophenyl) methyl)-2-hydroxy-3-(((4'S)-6'-(4-morpholinyl)-3',4'-dihydrospiro [cyclobutane-1,2'-pyrano[2,3-b]pyridin]-4'-yl)amino)propyl)acetamide | 517 | 516.5856 |
| 143 | N-((1S,2R)-1-((3,5-difluorophenyl) methyl)-2-hydroxy-3-(((4'R)-6'-(4-morpholinyl)-3',4'-dihydrospiro [cyclobutane-1,2'-pyrano[2,3-b]pyridin]-4'-yl)amino)propyl)acetamide | 517 | 516.5856 |
| 144 | N-((1S,2R)-2-hydroxy-1-(phenylmethyl)-3-(((4S)-6-((trifluoromethyl)oxy)-3,4-dihydrospiro-2,2-spirocyclobutyl [chromene-2,1'-cyclobutan]-4-yl)amino)propyl)-2-(methyloxy)acetamide | 509 | 508.534 |
| 145 | N-((1S,2R)-2-hydroxy-1-(phenylmethyl)-3-(((4S)-6-((trifluoromethyl)oxy)-3,4-dihydrospiro-2,2-spirocyclobutyl [chromene-2,1'-cyclobutan]-4-yl)amino)propyl)propanamide | 493 | 492.535 |
| 146 | N-((1S,2R)-2-hydroxy-1-(phenylmethyl)-3-(((4S)-6-((trifluoromethyl)oxy)-3,4-dihydrospiro-2,2-spirocyclobutyl [chromene-2,1'-cyclobutan]-4-yl)amino)propyl)acetamide | 479 | 478.508 |
| 147 | N-((1S,2R)-2-hydroxy-1-(phenylmethyl)-3-(((4S)-6-((trifluoromethyl)oxy)-3,4-dihydrospiro-2,2-spirocyclobutyl [chromene-2,1'-cyclobutan]-4-yl) amino)propyl)-2-(3-thienyl)acetamide | 561 | 560.634 |
| 148 | N-((1S,2R)-2-hydroxy-1-(phenylmethyl)-3-(((4S)-6-((trifluoromethyl)oxy)-3,4-dihydrospiro-2,2-spirocyclobutyl [chromene-2,1'-cyclobutan]-4-yl) amino)propyl)-2-phenylacetamide | 555 | 554.606 |
| 149 | N-((1S,2R)-2-hydroxy-1-(phenylmethyl)-3-(((4S)-6-((trifluoromethyl)oxy)-3,4-dihydrospiro-2,2-spirocyclobutyl [chromene-2,1'-cyclobutan]-4-yl)amino) propyl)-2-(3-methyl-5-isoxazolyl) acetamide | 560 | 559.582 |
| 150 | N-((1S,2R)-3-(((4S)-6-ethyl-7-fluoro-3,4-dihydrospiro-2,2-spirocyclobutyl [chromene-2,1'-cyclobutan]-4-yl)amino)-2-hydroxy-1-(phenylmethyl)propyl)acetamide | 441 | 440.556 |
| 151 | N-((1S,2R)-3-(((4S)-6-ethyl-7-fluoro-3,4-dihydrospiro-2,2-spirocyclobutyl [chromene-2,1'-cyclobutan]-4-yl)amino)-2-hydroxy-1-(phenylmethyl)propyl) propanamide | 455 | 454.582 |
| 152 | N-((1S,2R)-3-(((4S)-6-ethyl-7-fluoro-3,4-dihydrospiro-2,2-spirocyclobutyl [chromene-2,1'-cyclobutan]-4-yl)amino)-2-hydroxy-1-(phenylmethyl)propyl)-2-(methyloxy)acetamide | 471 | 470.582 |
| 153 | N-((1S,2R)-3-(((4S)-6-ethyl-7-fluoro-3,4-dihydrospiro-2,2-spirocyclobutyl [chromene-2,1'-cyclobutan]-4-yl)amino)-2-hydroxy-1-(phenylmethyl)propyl)-2-(3-methyl-5-isoxazolyl)acetamide | 522 | 521.629 |
| 154 | N-((1S,2R)-3-(((4S)-6-ethyl-7-fluoro-3,4-dihydrospiro-2,2-spirocyclobutyl [chromene-2,1'-cyclobutan]-4-yl)amino)-2-hydroxy-1-(phenylmethyl)propyl)-2-phenylacetamide | 517 | 516.653 |
| 155 | N-((1S,2R)-3-(((4S)-6-ethyl-7-fluoro-3,4-dihydrospiro-2,2-spirocyclobutyl [chromene-2,1'-cyclobutan]-4-yl)amino)-2-hydroxy-1-(phenylmethyl)propyl)-2-(2-oxo-1-pyrrolidinyl)acetamide | 524 | 523.645 |
| 156 | N-((1S,2R)-3-(((4S)-6-ethyl-7-fluoro-3,4-dihydrospiro-2,2-spirocyclobutyl [chromene-2,1'-cyclobutan]-4-yl)amino)-2-hydroxy-1-(phenylmethyl)propyl)-2-(2-oxo-1,3-oxazolidin-3-yl)acetamide | 526 | 525.617 |
| 157 | N-((1S,2R)-2-hydroxy-1-(phenylmethyl)-3-(((4S)-6-((trifluoromethyl)oxy)-3,4-dihydrospiro-2,2-spirocyclobutyl [chromene-2,1'-cyclobutan]-4-yl)amino) propyl)-2-(2-oxo-1,3-oxazolidin-3-yl) acetamide | 564 | 563.57 |
| 158 | N-((1S,2R)-2-hydroxy-1-(phenylmethyl)-3-(((4S)-6-((trifluoromethyl)oxy)-3,4-dihydrospiro-2,2-spirocyclobutyl [chromene-2,1'-cyclobutan]-4-yl)amino) propyl)-2-(2-oxo-1-pyrrolidinyl)acetamide | 562 | 561.598 |

| Ex. No. | STRUCTURE | Mass found | MW |
|---|---|---|---|
| 159 | N-((1S,2R)-3-(((4S)-6-ethyl-3,4-dihydrospiro-2,2-spirocyclobutyl [chromene-2,1'-cyclobutan]-4-yl)amino)-2-hydroxy-1-(phenylmethyl)propyl)-2-(2-pyrazinyloxy)acetamide | 517 | 516.6384 |
| 160 | N'—((1S,2R)-3-(((4S)-6-ethyl-3,4-dihydrospiro-2,2-spirocyclobutyl [chromene-2,1'-cyclobutan]-4-yl)amino)-2-hydroxy-1-(phenylmethyl)propyl)-N,N-dimethylbutanediamide | 508 | 507.6709 |
| 161 | N-((1S,2R)-3-(((4S)-6-ethyl-2,2-dimethyl-3,4-dihydro-2H-chromen-4-yl)amino)-2-hydroxy-1-(phenylmethyl)propyl)-2-(2-pyrimidinyloxy)acetamide | 505 | 504.6274 |
| 162 | N'—((1S,2R)-3-(((4S)-6-ethyl-2,2-dimethyl-3,4-dihydro-2H-chromen-4-yl) amino)-2-hydroxy-1-(phenylmethyl)propyl)-N,N-dimethylbutanediamide | 496 | 495.6599 |
| 163 | N'—((1S,2R)-3-(((4S)-6-ethyl-7-fluoro-3,4-dihydrospiro-2,2-spirocyclobutyl [chromene-2,1'-cyclobutan]-4-yl)amino)-2-hydroxy-1-(phenylmethyl)propyl)-N,N-dimethylbutanediamide | 526 | 525.661 |
| 164 | N'—((1S,2R)-2-hydroxy-1-(phenylmethyl)-3-(((4S)-6-((trifluoromethyl)oxy)-3,4-dihydrospiro-2,2-spirocyclobutyl [chromene-2,1'-cyclobutan]-4-yl) amino)propyl)-N,N-dimethylbutanediamide | 564 | 563.6134 |
| 165 | N-((1S,2R)-3-(((4S)-6-acetyl-3,4-dihydrospiro-2,2-spirocyclobutyl [chromene-2,1'-cyclobutan]-4-yl)amino)-2-hydroxy-1-(phenylmethyl)propyl)acetamide | 437 | 436.5488 |
| 166 | N-((1S,2R)-3-(((4S)-6-ethyl-3,4-dihydrospiro-2,2-spirocyclobutyl [chromene-2,1'-cyclobutan]-4-yl)amino)-2-hydroxy-1-(phenylmethyl)propyl)-2-(2-pyrimidinyloxy)acetamide | 517 | 516.6384 |
| 167 | N-((1S,2R)-1-((3-cyanophenyl)methyl)-3-(((4S)-6-ethyl-3,4-dihydrospiro-2,2-spirocyclobutyl[chromene-2,1'-cyclobutan]-4-yl)amino)-2-hydroxypropyl)-2-(2-pyrimidinyloxy)acetamide | 542 | 541.6485 |
| 168 | N-((1S,2R)-3-(((4S)-6-ethyl-7-fluoro-3,4-dihydrospiro-2,2-spirocyclobutyl [chromene-2,1'-cyclobutan]-4-yl)amino)-2-hydroxy-1-(phenylmethyl)propyl)-2-(2-pyrimidinyloxy)acetamide | 535 | 534.6285 |
| 169 | N-((1S,2R)-2-hydroxy-1-(phenylmethyl)-3-(((4S)-6-((trifluoromethyl)oxy)-3,4-dihydrospiro-2,2-spirocyclobutyl [chromene-2,1'-cyclobutan]-4-yl) amino) propyl)-2-(2-pyrimidinyloxy) acetamide | 573 | 572.5809 |
| 170 | N'—((1S,2R)-1-((3-cyanophenyl)methyl)-3-(((4S)-6-ethyl-3,4-dihydrospiro-2,2-spirocyclobutyl[chromene-2,1'-cyclobutan]-4-yl)amino)-2-hydroxypropyl)-N,N-dimethylbutanediamide | 533 | 532.681 |
| 171 | N-((1S,2R)-2-hydroxy-1-(phenylmethyl)-3-(((4S)-6-((trifluoromethyl)oxy)-3,4-dihydrospiro-2,2-spirocyclobutyl [chromene-2,1'-cyclobutan]-4-yl) amino) propyl)-2-(2-pyrazinyloxy)acetamide | 542 | 541.6485 |
| 172 | N-((1S,2R)-3-(((3R,4S)-6-bromo-3-hydroxy-2,2-dimethyl-3,4-dihydro-2H-chromen-4-yl) amino)-2-hydroxy-1-(phenylmethyl)propyl)-2-(methyloxy)acetamide | 508 | 1014.844 |
| 173 | N-((1S,2R)-1-((3-cyanophenyl)methyl)-2-hydroxy-3-(((4S)-6-(4-morpholinyl)-3,4-dihydrospiro-2,2-spirocyclobutyl [chromene-2,1'-cyclobutan]-4-yl)amino) propyl)-2-(methyloxy)acetamide | 535 | 534.6532 |
| 174 | N-((1S,2R)-1-((3-cyanophenyl)methyl)-2-hydroxy-3-(((4S)-6-(4-morpholinyl)-3,4-dihydrospiro-2,2-spirocyclobutyl [chromene-2,1'-cyclobutan]-4-yl)amino) propyl)acetamide | 505 | 504.6274 |
| 175 | N-((1S,2R)-3-(((4S)-6-ethyl-3,4-dihydrospiro[chromene-2,1'-cyclopentan]-4-yl)amino)-2-hydroxy-1-(phenylmethyl) propyl)-2-(((5R)-2-(3-methylbutyl)-2,3,4,5-tetrahydro-1H-2-benzazepin-5-yl) acetamide | 652 | 651.93 |
| 176 | N-((1S,2R)-3-(((4S)-6-ethyl-3,4-dihydrospiro[chromene-2,1'-cyclobutan]-4-yl)amino)-2-hydroxy-1-((3-methylphenyl) methyl)propyl)-2-(methyloxy)acetamide | 467 | 466.618 |
| 177 | N-((1S,2R)-3-(((4S)-6-cyano-2,2-dimethyl-3,4-dihydro-2H-chromen-4-yl)amino)-1-((3,5-difluorophenyl)methyl)-2-hydroxypropyl)acetamide | 444 | 443.491 |
| 178 | N-((1S,2R)-3-(((4S)-6-bromo-2,2-dimethyl-3,4-dihydro-2H-chromen-4-yl)amino)-1-((2-chlorophenyl)methyl)-2-hydroxypropyl)-2-(methyloxy)acetamide | 525 | 525.868 |
| 179 | N-((1S,2S)-3-(((4S)-6-bromo-2,2-dimethyl-3,4-dihydro-2H-chromen-4-yl)amino)-1-((2-chlorophenyl)methyl)-2-hydroxypropyl) acetamide | 495 | 495.842 |

-continued

| Ex. No. | STRUCTURE | Mass found | MW |
|---|---|---|---|
| 180 | N-((1S,2R)-3-(((4S)-6-bromo-2,2-dimethyl-3,4-dihydro-2H-chromen-4-yl)amino)-1-((3-chlorophenyl)methyl)-2-hydroxypropyl)-2-(methyloxy)acetamide | 525 | 525.868 |
| 181 | N-((1S,2R)-3-(((4S)-6-bromo-2,2-dimethyl-3,4-dihydro-2H-chromen-4-yl)amino)-1-((2-chlorophenyl)methyl)-2-hydroxypropyl) acetamide | 495 | 495.842 |
| 182 | N-((1S,2R)-3-(((4S)-6-bromo-2,2-dimethyl-3,4-dihydro-2H-chromen-4-yl)amino)-1-((3-chlorophenyl)methyl)-2-hydroxypropyl) acetamide | 496 | 495.842 |
| 183 | N-((1S)-1-((1R)-2-(((4S)-6-bromo-2,2-dimethyl-3,4-dihydro-2H-chromen-4-yl)amino)-1-hydroxyethyl)-3-butyn-1-yl)-2-(methyloxy)acetamide | 439 | 439.347 |
| 184 | N-((1S)-1-((1R)-2-(((4S)-6-bromo-2,2-dimethyl-3,4-dihydro-2H-chromen-4-yl) amino)-1-hydroxyethyl)-3-butyn-1-yl) acetamide | 409 | 409.322 |
| 185 | N-((1S,2R)-3-(((4S)-6-ethyl-3,4-dihydrospiro[chromene-2,1'-cyclobutan]-4-yl)amino)-2-hydroxy-1-((1-(phenylmethyl)-1H-1,2,3-triazol-4-yl)methyl)propyl)-2-(methyloxy)acetamide | 534 | 533.669 |
| 186 | N-((1S,2R)-3-(((4S)-6-ethyl-3,4-dihydrospiro[chromene-2,1'-cyclobutan]-4-yl)amino)-2-hydroxy-1-((1-(phenylmethyl)-1H-1,2,3-triazol-4-yl)methyl)propyl) acetamide | 504 | 503.643 |
| 187 | N-((1S)-1-((1R)-2-(((4S)-6-ethyl-3,4-dihydrospiro[chromene-2,1'-cyclobutan]-4-yl)amino)-1-hydroxyethyl)-3-butyn-1-yl)-2-(methyloxy)acetamide | 401 | 400.516 |
| 188 | N-((1S,2R)-3-(((4S)-6-bromo-2,2-dimethyl-3,4-dihydro-2H-chromen-4-yl)amino)-2-hydroxy-1-(2-phenylethyl)propyl)-2-(methyloxy)acetamide | 506 | 505.45 |
| 189 | N-((1S,2R)-3-(((4S)-6-bromo-2,2-dimethyl-3,4-dihydro-2H-chromen-4-yl)amino)-2-hydroxy-1-(2-phenylethyl)propyl)acetamide | 475 | 475.424 |
| 190 | N-((1S,2R)-3-(((4S)-6-bromo-2,2-dimethyl-3,4-dihydro-2H-chromen-4-yl)amino)-2-hydroxy-1-((3-(methyloxy)phenyl)methyl) propyl)acetamide | 491 | 491.4229 |
| 191 | N-((1S,2R)-3-(((4S)-6-bromo-2,2-dimethyl-3,4-dihydro-2H-chromen-4-yl)amino)-2-hydroxy-1-((3-(methyloxy)phenyl)methyl) propyl)-2-(methyloxy)acetamide | 521 | 521.4487 |
| 192 | N-((1S)-1-((1R)-2-(((4S)-6-bromo-2,2-dimethyl-3,4-dihydro-2H-chromen-4-yl) amino)-1-hydroxyethyl)-3-buten-1-yl) acetamide | 411 | 411.3373 |
| 193 | N-((1S,2R)-3-(((4S)-6-cyano-2,2-dimethyl-3,4-dihydro-2H-chromen-4-yl)amino)-1-((3,5-difluorophenyl)methyl)-2-hydroxypropyl)-2-(methyloxy)acetamide | 474 | 473.5171 |
| 194 | N-((1S,2R)-3-(((4S)-6-bromo-3,4-dihydrospiro[chromene-2,1'-cyclobutan]-4-yl)amino)-2-hydroxy-1-(phenylmethyl) propyl)-3-butynamide | 497 | 497.4301 |
| 195 | N-((1S,2R)-3-(((4S)-6-bromo-3,4-dihydrospiro[chromene-2,1'-cyclobutan]-4-yl)amino)-2-hydroxy-1-(phenylmethyl) propyl)-2-(1-(phenylmethyl)-1H-1,2,3-triazol-5-yl)acetamide | 630 | 630.5834 |
| 196 | N-((1S,2R)-3-(((4S)-6-bromo-3,4-dihydrospiro[chromene-2,1'-cyclobutan]-4-yl)amino)-2-hydroxy-1-(phenylmethyl) propyl)-2-(1H-1,2,3-triazol-4-yl) acetamide | 540 | 540.459 |
| 197 | 2-(4-(1,1-dimethylethyl)-1H-1,2,3-triazol-1-yl)-N-((1S,2R)-3-(((4S)-6-ethyl-3,4-dihydrospiro[chromene-2,1'-cyclobutan]-4-yl)amino)-2-hydroxy-1-(phenylmethyl)propyl)acetamide | 546 | 545.7237 |
| 198 | N-((1S,2R)-3-(((4S)-6-ethyl-3,4-dihydrospiro[chromene-2,1'-cyclobutan]-4-yl)amino)-2-hydroxy-1-(phenylmethyl) propyl)-2-(4-propyl-1H-1,2,3-triazol-1-yl)acetamide | 532 | 531.6969 |
| 199 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(3-(trifluoromethyl)-1H-pyrazol-1-yl)acetamide | 600 | 599.694 |
| 200 | 2-(4-chloro-3-methyl-1H-pyrazol-1-yl)-N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)acetamide | 580 | 580.1688 |
| 201 | 2-(4-chloro-3,5-dimethyl-1H-pyrazol-1-yl)-N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)acetamide | 594 | 594.1956 |
| 202 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(3-methyl-5-(trifluoromethyl)-1H-pyrazol-1-yl)acetamide | 614 | 613.7208 |
| 203 | methyl (4S)-4-(((2R,3S)-4-(3,5-difluorophenyl)-2-hydroxy-3-(((methyloxy) acetyl)amino)butyl)amino)-3,4-dihydrospiro[chromene-2,1'-cyclobutane]-6-carboxylate | 519 | 518.5538 |

-continued

| Ex. No. | STRUCTURE | Mass found | MW |
|---|---|---|---|
| 204 | methyl (4S)-4-(((2R,3S)-4-(3-bromophenyl)-2-hydroxy-3-(((methyloxy) acetyl)amino)butyl)amino)-3,4-dihydrospiro[chromene-2,1'-cyclobutane]-6-carboxylate | 561 | 561.4697 |
| 205 | (4S)-4-(((2R,3S)-4-(3,5-difluorophenyl)-2-hydroxy-3-(((methyloxy)acetyl)amino) butyl)amino)-3,4-dihydrospiro[chromene-2,1'-cyclobutane]-6-carboxylic acid | 505 | 504.527 |
| 206 | (E)-N-((2S,3R)-4-((S)-6-ethyl-2,2-spirocycloheptylchroman-4-ylamino)-3-hydroxy-1-phenylbutan-2-yl)-3-(5-fluoro-2-methoxyphenyl)acrylamide | 601.3 | 600.771 |
| 207 | (E)-N-((2S,3R)-4-((S)-6-ethyl-2,2-spirocyclohexylchroman-4-ylamino)-3-hydroxy-1-phenylbutan-2-yl)-3-(5-fluoro-2-methoxyphenyl)acrylamide | 587.3 | 586.744 |
| 208 | (E)-N-((2S,3R)-4-((S)-6-ethyl-2,2-spirocyclopentylchroman-4-ylamino)-3-hydroxy-1-phenylbutan-2-yl)-3-(5-fluoro-2-methoxyphenyl)acrylamide | 559.2 | 558.69 |
| 209 | (E)-N-((2S,3R)-4-((S)-2,2-spirocyclopentyl-6-(trifluoromethoxy) chroman-4-ylamino)-3-hydroxy-1-phenylbutan-2-yl)-3-(5-fluoro-2-methoxyphenyl)acrylamide | 629.2 | 628.659 |
| 210 | (E)-3-(5-fluoro-2-methoxyphenyl)-N-((2S,3R)-3-hydroxy-4-((S)-6-isopropyl-2,2-spirocyclopentylchroman-4-ylamino)-1-phenylbutan-2-yl)acrylamide | 587.2 | 586.744 |
| 211 | (E)-N-((2S,3R)-4-((S)-6-ethyl-2,2-(2-methyl)-spirocyclopentylchroman-4-ylamino)-3-hydroxy-1-phenylbutan-2-yl)-3-(5-fluoro-2-methoxyphenyl)acrylamide | 587.3 | 2346.97 |
| 212 | N-((1S,2R)-3-(((4R)-6-ethyl-4-methyl-3,4-dihydrospiro[chromene-2,1'-cyclobutan]-4-yl)amino)-2-hydroxy-1-(phenylmethyl) propyl)acetamide | 437.2 | 873.185 |
| 213 | N-((1S,2R)-3-(((4S)-6-bromo-3,4-dihydrospiro[chromene-2,1'-cyclobutan]-4-yl)amino)-2-hydroxy-1-(phenylmethyl) propyl)acetamide | 473.1; 475.1 | 473.408 |
| 214 | N-((1S,2R)-3-((4'S)-3',4'-dihydrospiro[cyclobutane-1,2'-pyrano[2,3-b]pyridin]-4'-ylamino)-2-hydroxy-1-(phenylmethyl)propyl)acetamide | 396.2 | 395.5 |
| 215 | N-((1S,2R)-3-((4'R)-3',4'-dihydrospiro [cyclobutane-1,2'-pyrano[2,3-c]pyridin]-4'-ylamino)-2-hydroxy-1-(phenylmethyl) propyl)acetamide | 396.2 | 395.5 |
| 216 | N-((1S,2R)-3-((4'S)-3',4'-dihydrospiro [cyclobutane-1,2'-pyrano[2,3-c]pyridin]-4'-ylamino)-2-hydroxy-1-(phenylmethyl) propyl)acetamide | 396.2 | 395.5 |
| 217 | N-((1S,2R)-3-((4'S)-3',4'-dihydrospiro [cyclobutane-1,2'-pyrano[2,3-c]pyridin]-4'-ylamino)-2-hydroxy-1-(phenylmethyl) propyl)-2-(methyloxy)acetamide | 426.2 | 425.526 |
| 218 | N-((1S,2R)-2-hydroxy-1-(phenylmethyl)-3-(((4'S)-6'-(trifluoromethyl)-3',4'-dihydrospiro[cyclobutane-1,2'-pyrano[2,3-b]pyridin]-4'-yl)amino)propyl)acetamide | 464.2 | 463.497 |
| 219 | N-((1S,2R)-2-hydroxy-1-(phenylmethyl)-3-(((4'S)-6'-(trifluoromethyl)-3',4'-dihydrospiro[cyclobutane-1,2'-pyrano[2,3-b]pyridin]-4'-yl)amino)propyl)-2-(methyloxy)acetamide | 494.1 | 493.523 |
| 220 | N-((2S,3R)-4-((S)-6-chloro-2,2-spirocyclobutyl-3,4-dihydro-2H-pyrano[2,3-b]pyridin-4-ylamino)-3-hydroxy-1-phenylbutan-2-yl)acetamide | 430.1 | 429.945 |
| 221 | N-((2S,3R)-4-((S)-6-chloro-2,2-spirocyclobutyl-3,4-dihydro-2H-pyrano[2,3-b]pyridin-4-ylamino)-3-hydroxy-1-phenylbutan-2-yl)-2-methoxyacetamide | 460.1 | 459.971 |
| 222 | N-((2S,3R)-4-((R)-6-chloro-2,2-spirocyclobutyl-3,4-dihydro-2H-pyrano[2,3-b]pyridin-4-ylamino)-3-hydroxy-1-phenylbutan-2-yl)acetamide | 430.1 | 429.945 |
| 223 | N-((1S,2R)-1-((3-cyanophenyl)methyl)-3-(((4'S)-6'-ethyl-3',4'-dihydrospiro [cyclobutane-1,2'-pyrano[2,3-b]pyridin]-4'-yl)amino)-2-hydroxypropyl)acetamide | 449.2 | 448.564 |
| 224 | N-((1S,2R)-3-(((4'S)-6'-ethyl-3',4'-dihydrospiro[cyclobutane-1,2'-pyrano[2,3-b]pyridin]-4'-yl)amino)-2-hydroxy-1-(phenylmethyl)propyl)-2-(methyloxy) acetamide | 454.3 | 453.579 |
| 225 | N-((1S,2R)-1-((3-cyanophenyl)methyl)-3-(((4'S)-6'-ethyl-3',4'-dihydrospiro [cyclobutane-1,2'-pyrano[2,3-b]pyridin]-4'-yl)amino)-2-hydroxypropyl)-2-(methyloxy)acetamide | NMR only | 478.5896 |
| 226 | N-((1S,2R)-2-hydroxy-3-(((4'S)-6'-(3-methylbutyl)-3',4'-dihydrospiro [cyclobutane-1,2'-pyrano[2,3-b]pyridin]-4'-yl)amino)-1-(phenylmethyl)propyl)-2-(methyloxy)acetamide | 496.2 | 495.6599 |
| 227 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(2-methyl-1,3-thiazol-4-yl) acetamide | 563.2 | 562.7748 |

-continued

| Ex. No. | STRUCTURE | Mass found | MW |
|---|---|---|---|
| 228 | 2-(3,5-dimethyl-4-isoxazolyl)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)acetamide | 561.3 | 560.7346 |
| 229 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(1H-1,2,4-triazol-1-yl) acetamide | 533.3 | 532.685 |
| 230 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(2H-1,2,3-triazol-2-yl) acetamide | 533.3 | 532.685 |
| 231 | N-((1S,2R)-3-(((4'S)-6'-ethyl-3',4'-dihydrospiro[cyclobutane-1,2'-pyrano[2,3-b]pyridin]-4'-yl)amino)-2-hydroxy-1-(phenylmethyl)propyl)-2-(2H-1,2,3-triazol-2-yl)acetamide | 491.2 | 490.6046 |
| 232 | N-((1S,2R)-3-(((4'S)-6'-ethyl-3',4'-dihydrospiro[cyclobutane-1,2'-pyrano[2,3-b]pyridin]-4'-yl)amino)-2-hydroxy-1-(phenylmethyl)propyl)-2-(1H-1,2,4-triazol-1-yl)acetamide | 491.2 | 490.6046 |
| 233 | 2-(4-chloro-3-cyclopropyl-1H-pyrazol-1-yl)-N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)acetamide | 606.3 | 606.2066 |
| 234 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(3,5-dimethyl-1H-pyrazol-1-yl) acetamide | 560.3 | 559.7505 |
| 235 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(3-methyl-1H-pyrazol-1-yl) acetamide | 546.3 | 545.7237 |
| 236 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(4-methyl-1H-pyrazol-1-yl) acetamide | 546.3 | 545.7237 |
| 237 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(4H-1,2,4-triazol-4-yl) acetamide | 533.2 | 532.685 |
| 238 | N-((1S,2R)-3-((8-bromo-6-chloro-3,4-dihydrospiro[chromene-2,1'-cyclobutan]-4-yl)amino)-2-hydroxy-1-(phenylmethyl) propyl)acetamide | 507.0; 509.0 | 507.8532 |
| 239 | N-((1S,2R)-3-(((4S)-8-bromo-6-chloro-3,4-dihydrospiro[chromene-2,1'-cyclobutan]-4-yl)amino)-1-((3,5-difluorophenyl)methyl)-2-hydroxypropyl)acetamide | 543.0; 545.0 | 543.8334 |
| 240 | —(1S,2R)-3-(((4R)-8-bromo-6-chloro-3,4-dihydrospiro[chromene-2,1'-cyclobutan]-4-yl)amino)-1-((3,5-difluorophenyl)methyl)-2-hydroxypropyl)acetamide | 543.0; 545.0 | 543.8334 |
| 241 | N-((1S,2R)-3-(((4S)-8-bromo-6-chloro-3,4-dihydrospiro[chromene-2,1'-cyclobutan]-4-yl)amino)-1-((3-cyanophenyl)methyl)-2-hydroxypropyl)acetamide | 532.0; 534.0 | 532.8633 |
| 242 | N-((1S,2R)-3-(((4S)-6-chloro-8-(4-morpholinyl)-3,4-dihydrospiro[chromene-2,1'-cyclobutan]-4-yl)amino)-2-hydroxy-1-(phenylmethyl)propyl)acetamide | 514.1 | 514.0624 |
| 243 | N-((1S,2R)-3-(((4S)-6,8-di-4-morpholinyl-3,4-dihydrospiro[chromene-2,1'-cyclobutan]-4-yl)amino)-2-hydroxy-1-(phenylmethyl)propyl)acetamide | 565.1 | 564.7226 |
| 244 | N-((1S,2R)-3-(((4S)-6-chloro-8-(4-morpholinyl)-3,4-dihydrospiro[chromene-2,1'-cyclobutan]-4-yl)amino)-1-((3,5-difluorophenyl)methyl)-2-hydroxypropyl) acetamide | 550.1 | 550.0426 |
| 245 | N-((1S,2R)-3-(((4S)-6-chloro-8-(4-morpholinyl)-3,4-dihydrospiro[chromene-2,1'-cyclobutan]-4-yl)amino)-1-((3-cyanophenyl)methyl)-2-hydroxypropyl) acetamide | 539.1 | 539.0725 |
| 246 | N-((1S,2R)-3-(((2S,4S)-6-chloro-8-(4-morpholinyl)-3,4,4',5'-tetrahydrospiro [chromene-2,3'-furan]-4-yl)amino)-1-((3,5-difluorophenyl)methyl)-2-hydroxypropyl)acetamide | 566.1 | 1132.083 |
| 247 | N-((1S,2R)-3-(((2S,4S)-8-bromo-6-chloro-3,4,4',5'-tetrahydrospiro[chromene-2,3'-furan]-4-yl)amino)-2-hydroxy-1-(phenylmethyl)propyl)acetamide | 523.0; 525.0 | 1047.704 |
| 248 | N-((1S,2R)-3-(((2S,4R)-8-bromo-6-chloro-3,4,4',5'-tetrahydrospiro[chromene-2,3'-furan]-4-yl)amino)-2-hydroxy-1-(phenylmethyl)propyl)acetamide | 523.0; 523.0 | 1047.704 |
| 249 | N-((1S,2R)-3-(((2S,4S)-8-bromo-6-chloro-3,4,4',5'-tetrahydrospiro[chromene-2,3'-furan]-4-yl)amino)-1-((3,5-difluorophenyl)methyl)-2-hydroxypropyl) acetamide | 559.0; 561.0 | 1119.665 |

-continued

| Ex. No. | STRUCTURE | Mass found | MW |
|---|---|---|---|
| 250 | N-((1S,2R)-3-(((2S,4R)-8-bromo-6-chloro-3,4,4',5'-tetrahydrospiro[chromene-2,3'-furan]-4-yl)amino)-1-((3,5-difluorophenyl)methyl)-2-hydroxypropyl) acetamide | 559.0; 561.0 | 1119.665 |
| 251 | N-((1S,2R)-3-(((2S,4S)-6-chloro-8-(4-morpholinyl)-3,4,4',5'-tetrahydrospiro [chromene-2,3'-furan]-4-yl)amino)-2-hydroxy-1-(phenylmethyl)propyl)acetamide | 530.0; 532.0 | 530.0614 |
| 252 | N-((1S,2R)-3-(((2R,4S)-6-chloro-8-(4-morpholinyl)-3,4,4',5'-tetrahydrospiro [chromene-2,3'-furan]-4-yl)amino)-2-hydroxy-1-(phenylmethyl)propyl)acetamide | 530.0; 532.0 | 530.0614 |
| 253 | (E)-N-((2S,3R)-4-((S)-6,8-difluoro-3,4-dihydrospiro[chromen-2,1'-cyclopentan]-4-ylamino)-3-hydroxy-1-phenylbutan-2-yl)-3-(5-fluoro-2-methoxyphenyl)acrylamide | 581 | 580.643 |
| 254 | (E)-N-((2S,3R)-4-((S)-6-fluoro-3,4-dihydrospiro[chromen-2,1'-cyclopentan]-4-ylamino)-3-hydroxy-1-phenylbutan-2-yl)-3-(5-fluoro-2-methoxyphenyl)acrylamide | 563 | 562.653 |
| 255 | (E)-N-((2S,3R)-4-((S)-6-ethyl-3,4-dihydrospiro[chromen-2,1'-cyclopentan]-4-ylamino)-3-hydroxy-1-phenylbutan-2-yl)-3-(5-fluoro-2-methoxyphenyl)acrylamide | 559 | 558.69 |
| 256 | N-((1S,2R)-3-(((4S)-6-neopentyl-3,4-dihydrospiro[chromene-2,1'-cyclopentyl]-4-yl)amino)-2-hydroxy-1-(phenylmethyl) propyl)acetamide | 479 | 478.673 |
| 257 | N-((1S,2R)-3-(((4S)-6-fluoro-3,4-dihydrospiro[chromene-2,1'-cyclobutan]-4-yl)amino)-2-hydroxy-1-(phenylmethyl) propyl)acetamide | 413 | 412.502 |
| 258 | N-((1S,2R)-3-(((4S)-6-(2,2-dimethylpropyl)-3,4-dihydrospiro [chromene-2,1'-cyclobutan]-4-yl)amino)-2-hydroxy-1-(phenylmethyl)propyl)acetamide | 465 | 464.646 |
| 259 | N-((1S,2R)-3-(((4S)-6-(2,2-dimethylpropyl)-3,4-dihydrospiro [chromene-2,1'-cyclobutan]-4-yl)amino)-2-hydroxy-1-(phenylmethyl)propyl)-2-(methyloxy)acetamide | 495 | 494.672 |
| 260 | N-((1S,2R)-2-hydroxy-1-(phenylmethyl)-3-(((4S)-6-(trifluoromethyl)-3,4-dihydrospiro[chromene-2,1'-cyclobutan]-4-yl)amino)propyl)acetamide | 463 | 462.509 |
| 261 | N-((1S,2R)-2-hydroxy-1-(phenylmethyl)-3-(((4S)-6-(trifluoromethyl)-3,4-dihydrospiro[chromene-2,1'-cyclobutan]-4-yl)amino)propyl)-2-(methyloxy)acetamide | 493 | 492.535 |
| 262 | N-((1S,2R)-2-hydroxy-3-(((4S)-6-(4-morpholinyl)-3,4-dihydrospiro[chromene-2,1'-cyclobutan]-4-yl)amino)-1-(phenylmethyl)propyl)acetamide | 480 | 479.617 |
| 263 | N-((1S,2R)-2-hydroxy-3-(((4S)-6-(4-methyl-1-piperazinyl)-3,4-dihydrospiro [chromene-2,1'-cyclobutan]-4-yl)amino)-1-(phenylmethyl)propyl)acetamide | 493 | 492.66 |
| 264 | N-((1S,2R)-2-hydroxy-1-(phenylmethyl)-3-(((4S)-6-(1-pyrrolidinyl)-3,4-dihydrospiro[chromene-2,1'-cyclobutan]-4-yl)amino)propyl)acetamide | 464 | 463.618 |
| 265 | N-((1S,2R)-3-(((4S)-6-((2,2-dimethylpropyl)amino)-3,4-dihydrospiro [chromene-2,1'-cyclobutan]-4-yl)amino)-2-hydroxy-1-(phenylmethyl)propyl)acetamide | 480 | 479.661 |
| 266 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)acetamide | 466 | 465.634 |
| 267 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(methyloxy)acetamide | 496 | 495.66 |
| 268 | N-((1S,2R)-3-(((4S)-6-chloro-7-(4-morpholinylmethyl)-3,4-dihydrospiro [chromene-2,1'-cyclobutan]-4-yl)amino)-2-hydroxy-1-(phenylmethyl)propyl)-2-(methyloxy)acetamide | 559 | 558.115 |
| 269 | 2-cyano-N-((1S,2R)-1-((3,5-difluorophenyl)methyl)-3-(((4'S)-6'-(2,2-dimethylpropyl)-3',4'-dihydrospiro [cyclobutane-1,2'-pyrano[2,3-b]pyridin]-4'-yl)amino)-2-hydroxypropyl)acetamide | 527 | 526.6244 |
| 270 | N-((1S,2R)-1-((3,5-difluorophenyl) methyl)-3-(((4'S)-6'-(2,2-dimethylpropyl)-3',4'-dihydrospiro [cyclobutane-1,2'-pyrano[2,3-b]pyridin]-4'-yl)amino)-2-hydroxypropyl)acetamide | 502 | 501.6143 |
| 271 | N-((1S,2R)-1-((3,5-difluorophenyl) methyl)-3-(((4'S)-6'-(2,2-dimethylpropyl)-3',4'-dihydrospiro [cyclobutane-1,2'-pyrano[2,3-b]pyridin]-4'-yl)amino)-2-hydroxypropyl)-2-methoxyacetamide | 532 | 531.6401 |
| 272 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(1H-tetrazol-5-yl)acetamide | 534 | 533.6731 |

-continued

| Ex. No. | STRUCTURE | Mass found | MW |
|---|---|---|---|
| 273 | N-((1S,2R)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(1-methyl-1H-pyrrol-2-yl) acetamide | 545 | 544.7356 |
| 274 | N-((1S,2R)-3-(((4S)-6-chloro-7-(1-piperidinylmethyl)-3,4-dihydrospiro [chromene-2,1'-cyclobutan]-4-yl)amino)-2-hydroxy-1-(phenylmethyl)propyl)-2-(methyloxy)acetamide | 557 | 556.1428 |
| 275 | N-((1S,2R)-1-((3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide | 521 | 520.67 |
| 276 | N-((1S,2R)-1-((3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(1H-1,2,4-triazol-1-yl)acetamide | 558 | 557.6951 |
| 277 | N-((1S,2R)-3-(((4S)-6-((2-(dimethylamino) ethyl)(methyl)amino)-3,4-dihydrospiro [chromene-2,1'-cyclobutan]-4-yl)amino)-2-hydroxy-1-(phenylmethyl) propyl)acetamide | 495 | 494.6758 |
| 278 | N-((1S,2R)-2-hydroxy-3-(((4S)-6-(methyl (2-(methyloxy)ethyl)amino)-3,4-dihydrospiro[chromene-2,1'-cyclobutan]-4-yl)amino)-1-(phenylmethyl)propyl) acetamide | 482 | 481.6331 |
| 279 | N-((1S,2R)-2-hydroxy-3-(((4S)-6-(1H-imidazol-1-yl)-3,4-dihydrospiro[chromene-2,1'-cyclobutan]-4-yl)amino)-1-(phenylmethyl)propyl)acetamide | 461 | 460.5748 |
| 280 | N-((1S,2R)-2-hydroxy-1-(phenylmethyl)-3-(((4S)-6-(1H-pyrazol-1-yl)-3,4-dihydrospiro[chromene-2,1'-cyclobutan]-4-yl)amino)propyl)acetamide | 461 | 460.5748 |
| 281 | N-((2S,3R)-4-((S)-6-ethyl-2,2-spirocyclopentylchroman-4-ylamino)-3-hydroxy-1-phenylbutan-2-yl)-2-(3-fluorophenoxy)acetamide | 547 | 546.679 |
| 282 | (E)-N-((2S,3R)-4-((S)-6-ethyl-2,2-spirocyclopentylchroman-4-ylamino)-3-hydroxy-1-phenylbutan-2-yl)-3-(furan-2-yl)acrylamide | 515 | 514.662 |
| 283 | (E)-3-(2,4-dimethoxypyrimidin-5-yl)-N-((2S,3R)-4-((S)-6-ethyl-2,2-spirocyclopentylchroman-4-ylamino)-3-hydroxy-1-phenylbutan-2-yl)acrylamide | 587 | 586.729 |
| 284 | (E)-N-((2S,3R)-4-((S)-6-ethyl-2,2-spirocyclopentylchroman-4-ylamino)-3-hydroxy-1-phenylbutan-2-yl)-3-(furan-3-yl)acrylamide | 515 | 514.662 |
| 285 | (E)-3-(benzo[d][1,3]dioxol-5-yl)-N-((2S,3R)-4-((S)-6-ethyl-2,2-spirocyclopentylchroman-4-ylamino)-3-hydroxy-1-phenylbutan-2-yl)acrylamide | 569 | 568.71 |
| 286 | (E)-N-((2S,3R)-4-((S)-6-ethyl-2,2-spirocyclopentylchroman-4-ylamino)-3-hydroxy-1-phenylbutan-2-yl)-3-(thiophen-2-yl)acrylamide | 531 | 530.729 |
| 287 | (E)-N-((2S,3R)-4-((S)-6-ethyl-2,2-spirocyclopentylchroman-4-ylamino)-3-hydroxy-1-phenylbutan-2-yl)-3-(1H-indol-3-yl)acrylamide | 564 | 563.738 |
| 288 | (E)-N-((2S,3R)-4-((S)-6-ethyl-2,2-spirocyclopentylchroman-4-ylamino)-3-hydroxy-1-phenylbutan-2-yl)-3-(pyridin-4-yl)acrylamide | 526 | 525.689 |
| 289 | (E)-N-((2S,3R)-4-((S)-6-ethyl-2,2-spirocyclopentylchroman-4-ylamino)-3-hydroxy-1-phenylbutan-2-yl)-3-(pyridin-3-yl)acrylamide | 526 | 525.689 |
| 290 | (E)-N-((2S,3R)-4-((S)-6-ethyl-2,2-spirocyclopentylchroman-4-ylamino)-3-hydroxy-1-phenylbutan-2-yl)-3-(pyridin-2-yl)acrylamide | 526 | 525.689 |
| 291 | N-((1S,2R)-3-(((4S)-6-ethyl-2,2-dimethyl-3,4-dihydro-2H-chromen-4-yl)amino)-2-hydroxy-1-(phenylmethyl)propyl)acetamide | 411 | 410.555 |
| 292 | N-((1S,2R)-3-(((4S)-6-ethyl-2,2-dimethyl-3,4-dihydro-2H-chromen-4-yl)amino)-2-hydroxy-1-(phenylmethyl)propyl)-2-(phenyloxy)acetamide | 503 | 502.651 |
| 293 | N-((1S,2R)-3-(((4S)-6-ethyl-2,2-dimethyl-3,4-dihydro-2H-chromen-4-yl)amino)-2-hydroxy-1-(phenylmethyl)propyl)-2-(methyloxy)acetamide | 441 | 440.58 |
| 294 | N-((1S,2R)-3-(((4S)-6-ethyl-2,2-dimethyl-3,4-dihydro-2H-chromen-4-yl)amino)-2-hydroxy-1-(phenylmethyl)propyl)-2-((3-fluorophenyl)oxy)acetamide | 521 | 520.641 |
| 295 | (2S)—N-((1S,2R)-3-(((4S)-6-ethyl-2,2-dimethyl-3,4-dihydro-2H-chromen-4-yl) amino)-2-hydroxy-1-(phenylmethyl)propyl)-2-((3-fluorophenyl)oxy)propanamide and '(2R)—N-((1S,2R)-3-(((4S)-6-ethyl-2,2-dimethyl-3,4-dihydro-2H-chromen-4-yl) amino)-2-hydroxy-1-(phenylmethyl)propyl)-2-((3-fluorophenyl)oxy)propanamide | 535 | 1069.34 |

-continued

| Ex. No. | STRUCTURE | Mass found | MW |
|---|---|---|---|
| 296 | N-((1S,2R)-3-(((4S)-6-ethyl-2,2-dimethyl-3,4-dihydro-2H-chromen-4-yl)amino)-2-hydroxy-1-(phenylmethyl)propyl)-2-(3-methyl-5-isoxazolyl)acetamide | 492 | 491.628 |
| 297 | N-((1S,2R)-3-(((4S)-6-ethyl-2,2-dimethyl-3,4-dihydro-2H-chromen-4-yl)amino)-2-hydroxy-1-(phenylmethyl)propyl)-2-((3-(methyloxy)phenyl)oxy)acetamide | 533 | 532.677 |
| 298 | N-((1S,2R)-3-(((4S)-6-ethyl-2,2-dimethyl-3,4-dihydro-2H-chromen-4-yl)amino)-2-hydroxy-1-(phenylmethyl)propyl)-3-phenylpropanamide | 501 | 500.679 |
| 299 | N-((1S,2R)-3-(((4S)-6-ethyl-2,2-dimethyl-3,4-dihydro-2H-chromen-4-yl)amino)-2-hydroxy-1-(phenylmethyl)propyl)-2-(ethyloxy)acetamide | 455 | 454.607 |
| 300 | N-((1S,2R)-3-(((4S)-6-ethyl-2,2-dimethyl-3,4-dihydro-2H-chromen-4-yl)amino)-2-hydroxy-1-(phenylmethyl)propyl)-2-(((1R,2S,5R)-5-methyl-2-(1-methylethyl)cyclohexyl)oxy)acetamide | 565 | 564.806 |
| 301 | N-((1S,2R)-3-(((4S)-6-ethyl-2,2-dimethyl-3,4-dihydro-2H-chromen-4-yl)amino)-2-hydroxy-1-(phenylmethyl)propyl)-2-((2-methylphenyl)oxy)acetamide | 517 | 516.678 |
| 302 | N-((1S,2R)-3-(((4S)-6-ethyl-2,2-dimethyl-3,4-dihydro-2H-chromen-4-yl)amino)-2-hydroxy-1-(phenylmethyl)propyl)-2-((2-(methyloxy)phenyl)oxy)acetamide | 533 | 532.677 |
| 303 | N-((1S,2R)-3-(((4S)-6-ethyl-2,2-dimethyl-3,4-dihydro-2H-chromen-4-yl)amino)-2-hydroxy-1-(phenylmethyl)propyl)-2-((2-methylpropyl)oxy)acetamide | 483 | 482.661 |
| 304 | N-((1S,2R)-3-(((4S)-6-ethyl-2,2-dimethyl-3,4-dihydro-2H-chromen-4-yl)amino)-2-hydroxy-1-(phenylmethyl)propyl)-2-(3-pyridinyloxy)acetamide | 504 | 503.639 |
| 305 | N-((1S,2R)-3-(((4S)-6-ethyl-2,2-dimethyl-3,4-dihydro-2H-chromen-4-yl)amino)-2-hydroxy-1-(phenylmethyl)propyl) propanamide | 425 | 424.581 |
| 306 | N-((1S,2R)-3-(((4S)-6-ethyl-2,2-dimethyl-3,4-dihydro-2H-chromen-4-yl)amino)-2-hydroxy-1-(phenylmethyl)propyl)-2-methylpropanamide | 439 | 438.608 |
| 307 | N-((1S,2R)-3-(((2R,4S)-6-ethyl-2-methyl-2-((methyloxy)methyl)-3,4-dihydro-2H-chromen-4-yl)amino)-2-hydroxy-1-(phenylmethyl)propyl)-2-(methyloxy) acetamide and 'N-((1S,2R)-3-(((2S,4S)-6-ethyl-2-methyl-2-((methyloxy)methyl)-3,4-dihydro-2H-chromen-4-yl)amino)-2-hydroxy-1-(phenylmethyl)propyl)-2-(methyloxy) acetamide | 471 | 941.212 |
| 308 | N-((1S,2R)-3-(((2R,4S)-6-ethyl-2-methyl-2-((methyloxy)methyl)-3,4-dihydro-2H-chromen-4-yl)amino)-2-hydroxy-1-(phenylmethyl)propyl)propanamide and 'N-((1S,2R)-3-(((2S,4S)-6-ethyl-2-methyl-2-((methyloxy)methyl)-3,4-dihydro-2H-chromen-4-yl)amino)-2-hydroxy-1-(phenylmethyl)propyl)propanamide | 455 | 909.214 |
| 309 | N-((1S,2R)-3-(((4'S)-6'-ethyl-3',4'-dihydrospiro[cyclobutane-1,2'-pyrano[2,3-b]pyridin]-4'-yl)amino)-2-hydroxy-1-(phenylmethyl)propyl)acetamide | 424 | 423.554 |
| 310 | N-((1S,2R)-3-(((4S)-6-ethyl-2,2-dimethyl-3,4-dihydro-2H-chromen-4-yl)amino)-2-hydroxy-1-(phenylmethyl)propyl)-2-(tetrahydro-2H-pyran-4-yl)acetamide | 495 | 494.6718 |
| 311 | N-((1S,2R)-3-(((4S)-6-ethyl-2,2-dimethyl-3,4-dihydro-2H-chromen-4-yl)amino)-2-hydroxy-1-(phenylmethyl)propyl)-2-((2R)-tetrahydro-2-furanyl)acetamide and 'N-((1S,2R)-3-(((4S)-6-ethyl-2,2-dimethyl-3,4-dihydro-2H-chromen-4-yl)amino)-2-hydroxy-1-(phenylmethyl)propyl)-2-((2S)-tetrahydro-2-furanyl)acetamide | 481 | 961.29 |
| 312 | N-((1S,2R)-3-(((4S)-6-ethyl-2,2-dimethyl-3,4-dihydro-2H-chromen-4-yl)amino)-2-hydroxy-1-(phenylmethyl)propyl)-2-(tetrahydro-2H-pyran-4-yloxy)acetamide | 511 | 510.6708 |
| 313 | N-((1S,2R)-3-(((4S)-6-ethyl-2,2-dimethyl-3,4-dihydro-2H-chromen-4-yl)amino)-2-hydroxy-1-(phenylmethyl)propyl)-2-((3R)-tetrahydro-2H-pyran-3-yloxy)acetamide and 'N-((1S,2R)-3-(((4S)-6-ethyl-2,2-dimethyl-3,4-dihydro-2H-chromen-4-yl) amino)-2-hydroxy-1-(phenylmethyl)propyl)-2-((3S)-tetrahydro-2H-pyran-3-yloxy) acetamide | 511 | 1021.342 |
| 314 | N-((1S,2R)-3-(((4S)-6-ethyl-3,4-dihydrospiro[chromene-2,1'-cyclobutan]-4-yl)amino)-2-hydroxy-1-(phenylmethyl) propyl)-2-(4-morpholinyl)acetamide | 508.3 | 507.671 |
| 315 | N-((1S,2R)-3-(((4S)-6-ethyl-3,4-dihydrospiro[chromene-2,1'-cyclobutan]-4-yl)amino)-2-hydroxy-1-((3-(2-propen-1-yl)phenyl)methyl)propyl)-6-heptenamide | 531.3 | 530.748 |
| 316 | N-((1S,2R)-3-(((2S,4S)-6-ethyl-3,4,4',5'-tetrahydrospiro[chromene-2,3'-furan]-4-yl)amino)-2-hydroxy-1-(phenylmethyl) propyl)acetamide | 439.3 | 877.129 |

-continued

| Ex. No. | STRUCTURE | Mass found | MW |
|---|---|---|---|
| 317 | N-((1S,2R)-3-(((2S,4S)-6-ethyl-3,4,4',5'-tetrahydrospiro[chromene-2,3'-furan]-4-yl)amino)-2-hydroxy-1-(phenylmethyl) propyl)-2-(methyloxy)acetamide | 469.2 | 937.181 |
| 318 | N-((1S,2R)-3-(((4S)-2-cyclopropyl-6,6-dimethyl-4,5,6,7-tetrahydro-1,3-benzoxazol-4-yl)amino)-2-hydroxy-1-(phenylmethyl)propyl)acetamide | 412.2 | 411.543 |
| 319 | N-((1S,2R)-3-(((4S)-2-cyclopropyl-6,6-dimethyl-4,5,6,7-tetrahydro-1,3-benzoxazol-4-yl)amino)-2-hydroxy-1-(phenylmethyl)propyl)-2-(methyloxy) acetamide | 442.3 | 441.569 |
| 320 | N-((1S,2R)-3-(((4S)-6-ethyl-3,4-dihydrospiro[chromene-2,1'-cyclobutan]-4-yl)amino)-2-hydroxy-1-(phenylmethyl) propyl)-3-(4-morpholinyl)propanamide | 522.3 | 521.698 |
| 321 | N-((1S,2R)-2-hydroxy-1-(phenylmethyl)-3-(((5S)-3,7,7-trimethyl-5,6,7,8-tetrahydro-5-quinolinyl)amino) propyl)acetamide | 396.2 | 395.544 |
| 322 | N-((1S,2R)-3-(((2R,4S)-6-ethyl-3,4,4',5'-tetrahydrospiro[chromene-2,3'-furan]-4-yl)amino)-2-hydroxy-1-(phenylmethyl) propyl)-2-(methyloxy)acetamide | 469.2 | 468.59 |
| 323 | N-((1S,2R)-3-(((2S,4S)-6-ethyl-3,4,4',5'-tetrahydrospiro[chromene-2,3'-furan]-4-yl)amino)-2-hydroxy-1-(phenylmethyl) propyl)-2-(methyloxy)acetamide | 469.2 | 468.59 |
| 324 | N-((1S,2R)-3-(((2R,4S)-6-ethyl-3,4,4',5'-tetrahydrospiro[chromene-2,3'-furan]-4-yl)amino)-2-hydroxy-1-(phenylmethyl) propyl)acetamide | 439.2 | 438.565 |
| 325 | N-((1S,2R)-3-(((2S,4S)-6-ethyl-3,4,4',5'-tetrahydrospiro[chromene-2,3'-furan]-4-yl)amino)-2-hydroxy-1-(phenylmethyl) propyl)acetamide | 439.2 | 438.565 |
| 326 | N-((1S,2R)-3-(((4S)-6-ethyl-2',3,3',4,5',6'-hexahydrospiro[chromene-2,4'-pyran]-4-yl)amino)-2-hydroxy-1-(phenylmethyl)propyl)acetamide | 453.3 | 452.591 |
| 327 | N-((1S,2R)-3-(((4S)-6-ethyl-2',3,3',4,5',6'-hexahydrospiro[chromene-2,4'-pyran]-4-yl)amino)-2-hydroxy-1-(phenylmethyl)propyl)-2-(methyloxy) acetamide | 483.3 | 482.617 |
| 328 | N-((1S,2R)-2-hydroxy-3-(((5'S)-3'-methyl-5',8'-dihydro-6'H-spiro[cyclobutane-1,7'-quinolin]-5'-yl)amino)-1-(phenylmethyl) propyl)-2-(methyloxy)acetamide | 438.3 | 437.5805 |
| 329 | N-((1S,2R)-1-((3,5-difluorophenyl) methyl)-2-hydroxy-3-(((5'S)-3'-methyl-5',8'-dihydro-6'H-spiro[cyclobutane-1,7'-quinolin]-5'-yl)amino)propyl)-2-(methyloxy)acetamide | 474.2 | 473.5607 |
| 330 | N-((1S,2R)-2-hydroxy-3-(((5'S)-3'-methyl-5',8'-dihydro-6'H-spiro[cyclobutane-1,7'-quinolin]-5'-yl)amino)-1-(phenylmethyl) propyl)-2-(1H-1,2,4-triazol-1-yl) acetamide | 475.2 | 474.6056 |
| 331 | N-((1S,2R)-1-((3,5-difluorophenyl) methyl)-2-hydroxy-3-(((5'S)-3'-methyl-5',8'-dihydro-6'H-spiro[cyclobutane-1,7'-quinolin]-5'-yl)amino)propyl)-2-(1H-1,2,4-triazol-1-yl)acetamide | 511.2 | 510.5858 |
| 332 | N-((1S,2R)-3-(((4S)-6-ethyl-3,4-dihydrospiro[chromene-2,1'-cyclobutan]-4-yl)amino)-2-hydroxy-1-((3-(2-propen-1-yl)phenyl)methyl)propyl)-2-propenamide | 475.3 | 474.6412 |
| 333 | N-((1S,2R)-3-(((4S)-6-ethyl-3,4-dihydrospiro[chromene-2,1'-cyclobutan]-4-yl)amino)-2-hydroxy-1-((3-(2-propen-1-yl)phenyl)methyl)propyl)-3-butenamide | 489.3 | 488.668 |
| 334 | N-((1S,2R)-3-(((4S)-6-ethyl-3,4-dihydrospiro[chromene-2,1'-cyclobutan]-4-yl)amino)-2-hydroxy-1-((3-(2-propen-1-yl)phenyl)methyl)propyl)-4-pentenamide | 503.3 | 502.6948 |
| 335 | N-((1S,2R)-3-(((4S)-6-ethyl-3,4-dihydrospiro[chromene-2,1'-cyclobutan]-4-yl)amino)-2-hydroxy-1-((3-(2-propen-1-yl)phenyl)methyl)propyl)-5-hexenamide | 517.3 | 516.7216 |
| 336 | 1,1-dimethylethyl (7-(((1S,2R)-1-((3-bromophenyl)methyl)-3-(((4S)-6-ethyl-3,4-dihydrospiro[chromene-2,1'-cyclobutan]-4-yl)amino)-2-hydroxypropyl)amino)-7-oxoheptyl)carbamate | 686, 688 | 686.7268 |
| 337 | phenylmethyl (7-(((1S,2R)-1-((3-bromophenyl)methyl)-3-(((4S)-6-ethyl-3,4-dihydrospiro[chromene-2,1'-cyclobutan]-4-yl)amino)-2-hydroxypropyl)amino)-7-oxoheptyl)carbamate | 720, 722 | 720.744 |
| 338 | N-((2S,3R)-4-((S)-6-ethyl-2,2-spirocyclobutylchroman-4-ylamino)-3-hydroxy-1-phenylbutan-2-yl)pentanamide | 465.2 | 464.646 |
| 339 | N-((2S,3R)-4-((S)-6-ethyl-2,2-spirocyclobutylchroman-4-ylamino)-3-hydroxy-1-phenylbutan-2-yl)-3-methylbutanamide | 465.2 | 464.646 |
| 340 | N-((2S,3R)-4-((S)-6-ethyl-2,2-spirocyclobutylchroman-4-ylamino)-3-hydroxy-1-phenylbutan-2-yl)-2-methylbutanamide | 465.2 | 929.292 |
| 341 | 2-(dimethylamino)-N-((2S,3R)-4-((S)-6-ethyl-2,2-spirocyclobutylchroman-4-ylamino)-3-hydroxy-1-phenylbutan-2-yl) acetamide | 466.1 | 465.634 |
| 342 | N-((2S,3R)-4-((S)-6-ethyl-2,2-spirocyclobutylchroman-4-ylamino)-3-hydroxy-1-phenylbutan-2-yl)-2-(pyridin-2-yl)acetamide | 500.2 | 499.651 |

-continued

| Ex. No. | STRUCTURE | Mass found | MW |
|---|---|---|---|
| 343 | 2-cyclopropyl-N-((2S,3R)-4-((S)-6-ethyl-2,2-spirocyclobutylchroman-4-ylamino)-3-hydroxy-1-phenylbutan-2-yl)acetamide | 463.1 | 462.63 |
| 344 | N-((2S,3R)-4-((S)-6-ethyl-2,2-spirocyclobutylchroman-4-ylamino)-3-hydroxy-1-phenylbutan-2-yl)-2-(thiophen-2-yl)acetamide | 505.1 | 504.691 |
| 345 | N-((2S,3R)-4-((S)-6-ethyl-2,2-spirocyclobutylchroman-4-ylamino)-3-hydroxy-1-phenylbutan-2-yl)-2-(3-methylisoxazol-5-yl)acetamide | 504.2 | 503.639 |
| 346 | N-((2S,3R)-4-((S)-6-ethyl-2,2-spirocyclobutylchroman-4-ylamino)-3-hydroxy-1-phenylbutan-2-yl)heptanamide | 493.2 | 492.7 |
| 347 | 2-cyclopentyl-N-((2S,3R)-4-((S)-6-ethyl-2,2-spirocyclobutylchroman-4-ylamino)-3-hydroxy-1-phenylbutan-2-yl)acetamide | 491.2 | 490.684 |
| 348 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(3-thienyl)acetamide | 505.1 | 504.691 |
| 349 | N-((1S,2R)-3-(((4S)-6-bromo-3,4-dihydrospiro[chromene-2,1'-cyclobutan]-4-yl)amino)-2-hydroxy-1-(phenylmethyl)propyl)-2-(3-thienyl)acetamide | 555.1 | 555.534 |
| 350 | 2-(1-benzothien-3-yl)-N-((1S,2R)-3-(((4S)-6-bromo-3,4-dihydrospiro[chromene-2,1'-cyclobutan]-4-yl)amino)-2-hydroxy-1-(phenylmethyl)propyl)acetamide | 605.1 | 605.594 |
| 351 | N-((1S,2R)-3-(((4S)-6-bromo-3,4-dihydrospiro[chromene-2,1'-cyclobutan]-4-yl)amino)-2-hydroxy-1-(phenylmethyl)propyl)-2-(2-methyl-3-thienyl)acetamide | 569.1 | 569.561 |
| 352 | N-((1S,2R)-3-(((4S)-6-bromo-3,4-dihydrospiro[chromene-2,1'-cyclobutan]-4-yl)amino)-2-hydroxy-1-(phenylmethyl)propyl)-2-(2,5-dimethyl-1,3-thiazol-4-yl)acetamide | 584.1 | 584.576 |
| 353 | N-((1S,2R)-3-(((4S)-6-bromo-3,4-dihydrospiro[chromene-2,1'-cyclobutan]-4-yl)amino)-2-hydroxy-1-(phenylmethyl)propyl)-2-(1-methyl-1H-imidazol-4-yl)acetamide | 553.2 | 553.498 |
| 354 | N-((1S,2R)-3-(((4S)-6-bromo-3,4-dihydrospiro[chromene-2,1'-cyclobutan]-4-yl)amino)-2-hydroxy-1-(phenylmethyl)propyl)-2-(1H-imidazol-1-yl)acetamide | 539.1 | 539.471 |
| 355 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(1-methyl-1H-imidazol-4-yl)acetamide | 503.3 | 502.655 |
| 356 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(1H-imidazol-1-yl)acetamide | 489.3 | 488.628 |
| 357 | N-((1S,2R)-1-((1-acetyl-3-piperidinyl) methyl)-3-(((4S)-6-ethyl-3,4-dihydrospiro [chromene-2,1'-cyclobutan]-4-yl)amino)-2-hydroxypropyl)acetamide | 472.2 | 471.638 |
| 358 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(2-oxo-1-pyrrolidinyl)acetamide | 506.2 | 505.655 |
| 359 | N-((1S,2R)-3-(((4S)-6-bromo-3,4-dihydrospiro[chromene-2,1'-cyclobutan]-4-yl)amino)-2-hydroxy-1-(phenylmethyl)propyl)-2-(2-oxo-1-pyrrolidinyl)acetamide | 556.1 | 556.498 |
| 360 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(1-oxo-1,3-dihydro-2H-isoindol-2-yl)acetamide | 554.2 | 553.699 |
| 361 | (2R)—N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(2-oxo-1-pyrrolidinyl) propanamide | 520.3 | 1039.36 |
| 362 | (2R)—N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(2-oxo-1-pyrrolidinyl) propanamide | 520.3 | 519.682 |
| 363 | (2S)—N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(2-oxo-1-pyrrolidinyl) propanamide | 520.3 | 519.682 |
| 364 | N~2~-acetyl-N~1~-((1S,2R)-3-(((4S)-6-ethyl-3,4-dihydrospiro[chromene-2,1'-cyclobutan]-4-yl)amino)-2-hydroxy-1-(phenylmethyl)propyl)glycinamide | 480.2 | 479.617 |
| 365 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-((1R)-2-oxocyclopentyl) acetamide | 505.3 | 1009.33 |
| 366 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-((3R)-3-methyl-2-oxo-1-pyrrolidinyl)acetamide | 520.3 | 1039.36 |
| 367 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-((3R)-3-methyl-2-oxo-1-pyrrolidinyl)acetamide | 520.3 | 519.682 |

-continued

| Ex. No. | STRUCTURE | Mass found | MW |
|---|---|---|---|
| 368 | N-((1S,2R)-3-(((4S)-6-ethyl-3,4-dihydrospiro[chromene-2,1'-cyclobutan]-4-yl)amino)-2-hydroxy-1-(phenylmethyl) propyl)-2-((3S)-3-methyl-2-oxo-1-pyrrolidinyl)acetamide | 520.3 | 519.682 |
| 369 | 2-(2-cyano-1H-pyrrol-1-yl)-N-((1S,2R)-3-(((4S)-6-ethyl-3,4-dihydrospiro[chromene-2,1'-cyclobutan]-4-yl)amino)-2-hydroxy-1-(phenylmethyl)propyl)acetamide | 513.3 | 512.65 |
| 370 | N-((1S,2R)-3-(((4S)-6-ethyl-2,2-dimethyl-3,4-dihydro-2H-chromen-4-yl)amino)-2-hydroxy-1-(phenylmethyl)propyl)-2-(2-oxo-1-pyrrolidinyl)acetamide | 494.2 | 493.644 |
| 371 | 2-cyano-N-((1S,2R)-3-(((4S)-6-ethyl-2,2-dimethyl-3,4-dihydro-2H-chromen-4-yl) amino)-2-hydroxy-1-(phenylmethyl) propyl) acetamide | 436.1 | 435.565 |
| 372 | N-((1S,2R)-2-hydroxy-1-(phenylmethyl)-3-(((8R)-2,6,6-trimethyl-3-oxo-2,3,5,6,7,8-hexahydro-8-isoquinolinyl)amino)propyl)-2-methoxyacetamide | 442.1 | 883.137 |
| 373 | N-((1S,2R)-2-hydroxy-1-(phenylmethyl)-3-(((8R)-2,6,6-trimethyl-3-oxo-2,3,5,6,7,8-hexahydro-8-isoquinolinyl)amino) propyl) acetamide | 412.1 | 823.0854 |
| 374 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-(2-oxo-1-pyrrolidinyl)acetamide | 531.2 | 530.6652 |
| 375 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-(3-methyl-2-oxo-1-pyrrolidinyl)acetamide | 545.2 | 544.692 |
| 376 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-(3-methyl-5-isoxazolyl) acetamide | 529.2 | 528.6494 |
| 377 | N-((1S,2S)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(2-oxo-1-pyrrolidinyl)acetamide | 549.3 | 548.7236 |
| 378 | N-((1S,2S)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(3-methyl-2-oxo-1-pyrrolidinyl) acetamide | 563.3 | 562.7504 |
| 379 | N-((1S,2S)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(3-methyl-5-isoxazolyl) acetamide | 547.3 | 546.7078 |
| 380 | N-((1S,2S)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-((1R)-2-oxocyclopentyl)acetamide | 548.3 | 1095.471 |
| 381 | N-((1S,2S)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-(2-oxo-1(2H)-pyridinyl) acetamide | 559.3 | 558.7188 |
| 382 | N-((1S,2S)-3-(((4'S)-6'-(2,2-dimethylpropyl)-3',4'-dihydrospiro [cyclobutane-1,2'-pyrano[2,3-b]pyridin]-4'-yl)amino)-2-hydroxy-1-(phenylmethyl) propyl)-2-((1S,2E)-2-((methyloxy) imino)cyclopentyl)acetamide | 577.3 | 1153.554 |
| 383 | N-((1S,2R)-2-hydroxy-3-(((4'S)-6'-(4-morpholinyl)-3',4'-dihydrospiro [cyclobutane-1,2'-pyrano[2,3-b]pyridin]-4'-yl)amino)-1-(phenylmethyl)propyl) acetamide | 481.1 | 480.6054 |
| 384 | N-((1S,2R)-2-hydroxy-3-(((4'S)-6'-(tetrahydrofuran-2-yl)-3',4'-dihydrospiro [cyclobutane-1,2'-pyrano[2,3-b]pyridin]-4'-yl)amino)-1-(phenylmethyl)propyl) acetamide | 466.1 | 931.181 |
| 385 | N-((2S,3R)-3-hydroxy-1-phenyl-4-((R)-2,7,7-trimethyl-5,6,7,8-tetrahydroquinazolin-5-ylamino)butan-2-yl)acetamide | 397.3 | 793.064 |
| 386 | N-((1S,2R)-2-hydroxy-1-(phenylmethyl)-3-((2S,4S)-3,4,4',5'-tetrahydrospiro [chromene-2,3'-furan]-4-ylamino)propyl) acetamide | 411.3 | 821.022 |
| 387 | N-((1S,2R)-3-(((2R,4S)-6-bromo-3,4,4',5'-tetrahydrospiro[chromene-2,3'-furan]-4-yl)amino)-2-hydroxy-1-(phenylmethyl) propyl)acetamide | 489.1 | 978.8142 |
| 388 | N-((1S,2R)-2-hydroxy-3-(((4S)-6-((1S,4S)-2-oxa-5-azabicyclo[2.2.1]hept-5-yl)-3,4-dihydrospiro[chromene-2,1'-cyclobutan]-4-yl)amino)-1-(phenylmethyl)propyl) acetamide | 492.3 | 491.6283 |
| 389 | N-((1S,2R)-3-(((4S)-6-((2R,6S)-2,6-dimethyl-4-morpholinyl)-3,4-dihydrospiro [chromene-2,1'-cyclobutan]-4-yl)amino)-2-hydroxy-1-(phenylmethyl)propyl)acetamide | 507.9 | 1015.342 |
| 390 | N-((1S,2R)-3-(((4S)-6-((2S,5S)-2,5-dimethyl-4-morpholinyl)-3,4-dihydrospiro [chromene-2,1'-cyclobutan]-4-yl)amino)-2-hydroxy-1-(phenylmethyl)propyl)acetamide | 508.3 | 507.6709 |

-continued

| Ex. No. | STRUCTURE | Mass found | MW |
|---|---|---|---|
| 391 | (3S)-tetrahydro-3-furanyl ((1S,2R)-3-(((4S)-6-ethyl-3,4-dihydrospiro[chromene-2,1'-cyclopentan]-4-yl)amino)-2-hydroxy-1-(phenylmethyl)propyl)carbamate | 509 | 508.655 |
| 392 | (3S)-tetrahydro-3-furanyl ((1S,2R)-3-(((4S)-6-ethyl-3,4-dihydrospiro[chromene-2,1'-cyclobutan]-4-yl)amino)-2-hydroxy-1-(phenylmethyl)propyl)carbamate | 495 | 494.628 |
| 393 | methyl ((1S,2R)-1-((3,5-difluorophenyl) methyl)-3-(((4S)-6-ethyl-2,2-dimethyl-3,4-dihydro-2H-chromen-4-yl)amino)-2-hydroxypropyl)carbamate | 463 | 462.534 |
| 394 | methyl (2S,3R)-4-((S)-6-ethyl-2,2-spirocyclobutyl-chroman-4-ylamino)-3-hydroxy-1-phenylbutan-2-ylcarbamate | 439 | 438.565 |
| 395 | 2-(methyloxy)ethyl((1S,2R)-3-(((4S)-6-ethyl-3,4-dihydrospiro[chromene-2,1'-cyclobutan]-4-yl)amino)-2-hydroxy-1-(phenylmethyl)propyl)carbamate | 483 | 482.617 |
| 396 | N-((1S,2R)-3-(((4S)-2-ethyl-6,6-dimethyl-4,5,6,7-tetrahydro-1-benzothien-4-yl)amino)-2-hydroxy-1-(phenylmethyl)propyl)acetamide | 415 | 414.611 |
| 397 | (2E)-N-((1S,2R)-3-(((4S)-6-ethyl-3,4-dihydrospiro[chromene-2,1'-cyclobutan]-4-yl)amino)-2-hydroxy-1-(phenylmethyl)propyl)-3-(3-pyridinyl)-2-propenamide | 512 | 511.6623 |
| 398 | (2E)-N-((1S,2R)-3-(((4S)-6-ethyl-3,4-dihydrospiro[chromene-2,1'-cyclobutan]-4-yl)amino)-2-hydroxy-1-(phenylmethyl)propyl)-3-(3-fluoro-4-hydroxyphenyl)-2-propenamide | 545 | 544.6633 |
| 399 | 3-(1H-benzimidazol-1-yl)-N-((1S,2R)-3-(((4S)-6-ethyl-3,4-dihydrospiro[chromene-2,1'-cyclobutan]-4-yl)amino)-2-hydroxy-1-(phenylmethyl)propyl)-2-methylpropanamide | 567 | 566.7418 |
| 400 | (2E)-3-(4-bromo-2-furanyl)-N-((1S,2R)-3-(((4S)-6-ethyl-3,4-dihydrospiro[chromene-2,1'-cyclobutan]-4-yl)amino)-2-hydroxy-1-(phenylmethyl)propyl)-2-propenamide | 579 | 579.5315 |
| 401 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(4-quinazolinylthio)acetamide | 583 | 582.7652 |
| 402 | (2E)-3-(5-bromo-3-pyridinyl)-N-((1S,2R)-3-(((4S)-6-ethyl-3,4-dihydrospiro [chromene-2,1'-cyclobutan]-4-yl)amino)-2-hydroxy-1-(phenylmethyl)propyl)-2-propenamide | 590 | 590.5584 |
| 403 | (2E)-N-((1S,2R)-3-(((4S)-6-ethyl-3,4-dihydrospiro[chromene-2,1'-cyclobutan]-4-yl)amino)-2-hydroxy-1-(phenylmethyl)propyl)-3-(5-fluoro-2-(trifluoromethyl) phenyl)-2-propenamide | 597 | 596.6614 |
| 404 | N-((1S,2R)-3-(((4S)-6-ethyl-3,4-dihydrospiro[chromene-2,1'-cyclobutan]-4-yl)amino)-2-hydroxy-1-(phenylmethyl)propyl)-3-(3-pyridinyl)propanamide | 514 | 513.6781 |
| 405 | N-((1S,2R)-3-(((4S)-6-ethyl-3,4-dihydrospiro[chromene-2,1'-cyclobutan]-4-yl)amino)-2-hydroxy-1-(phenylmethyl)propyl)-3-(1H-imidazol-1-yl)butanamide | 517 | 516.682 |
| 406 | N-((1S,2R)-3-(((4S)-6-ethyl-3,4-dihydrospiro[chromene-2,1'-cyclobutan]-4-yl)amino)-2-hydroxy-1-(phenylmethyl)propyl)-3-(2-thienyl)propanamide | 519 | 518.7182 |
| 407 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(4-pyridinylthio)acetamide | 532 | 531.7173 |
| 408 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-((4-methyl-1,3-thiazol-2-yl) thio)acetamide | 552 | 551.7723 |
| 409 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(5-fluoro-1H-indol-3-yl) acetamide | 556 | 555.6902 |
| 410 | (2E)-N-((1S,2R)-3-(((4S)-6-ethyl-3,4-dihydrospiro[chromene-2,1'-cyclobutan]-4-yl)amino)-2-hydroxy-1-(phenylmethyl)propyl)-3-(3-quinolinyl)-2-propenamide | 562 | 561.7221 |
| 411 | (2E)-N-((1S,2R)-3-(((4S)-6-ethyl-3,4-dihydrospiro[chromene-2,1'-cyclobutan]-4-yl)amino)-2-hydroxy-1-(phenylmethyl)propyl)-3-(3,4,5-trifluorophenyl)-2-propenamide | 565 | 564.6445 |
| 412 | N-((1S,2R)-3-(((4S)-6-ethyl-3,4-dihydrospiro[chromene-2,1'-cyclobutan]-4-yl)amino)-2-hydroxy-1-(phenylmethyl)propyl)-4-(3-fluoro-4-methylphenyl)-4-oxobutanamide | 573 | 572.7169 |
| 413 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(2-(3-pyridinyl)phenyl) acetamide | 576 | 575.7489 |
| 414 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(1-phthalazinylthio)acetamide | 583 | 582.7652 |

-continued

| Ex. No. | STRUCTURE | Mass found | MW |
|---|---|---|---|
| 415 | (2E)-3-(2,2-difluoro-1,3-benzodioxol-4-yl)-N-((1S,2R)-3-(((4S)-6-ethyl-3,4-dihydrospiro[chromene-2,1'-cyclobutan]-4-yl)amino)-2-hydroxy-1-(phenylmethyl) propyl)-2-propenamide | 591 | 590.6634 |
| 416 | N~1~-((1S,2R)-3-(((4S)-6-ethyl-3,4-dihydrospiro[chromene-2,1'-cyclobutan]-4-yl)amino)-2-hydroxy-1-(phenylmethyl) propyl)-N~2~-(2-fluorophenyl)-N~2~-(methylsulfonyl)glycinamide | 610 | 609.759 |
| 417 | (3R)-3-(1H-1,2,3-benzotriazol-1-yl)-N-((1S,2R)-3-(((4S)-6-ethyl-3,4-dihydrospiro[chromene-2,1'-cyclobutan]-4-yl)amino)-2-hydroxy-1-(phenylmethyl) propyl)butanamide | 568 | 567.7299 |
| 418 | N-((1S,2R)-3-(((4S)-6-ethyl-3,4-dihydrospiro[chromene-2,1'-cyclobutan]-4-yl)amino)-2-hydroxy-1-(phenylmethyl) propyl)-2-(2-thienylthio)propanamide | 551 | 550.7842 |

The following compounds in Tables 1 and 2 are additional representative examples of Formulas I-III, as provided by the present invention.

TABLE 1

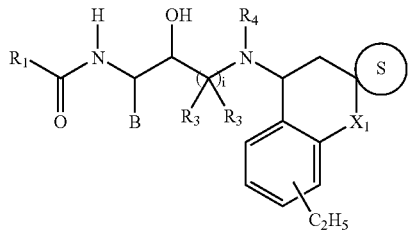

| Ex. No. | $R^1$ | B | $R^3$ and $R^4$ | $X^1$ | S |
|---|---|---|---|---|---|
| 419 | 1-morpholinyl-$CH_2$— | benzyl-O— | H | NH | cyclobutyl |
| 420 | 1-piperazinyl-$CH_2$— | benzyl-S— | H | S | cyclobutyl |
| 421 | 1-piperidinyl-$CH_2$— | benzyl-NH— | H | O | cyclobutyl |
| 422 | 3-oxo-1-pyrrolidinyl-$CH_2$— | benzyl-O— | H | NH | cyclopentyl |
| 423 | 1-morpholinyl-CH=CH— | benzyl-S— | H | S | cyclopentyl |
| 424 | 1-piperazinyl-CH=CH— | benzyl-NH— | H | O | cyclopentyl |
| 425 | oxo-pyrrolidinyl-CH=CH— | Benzyl-$CH_2$— | H | $SO_2$ | cyclopropyl |
| 426 | oxazolidinyl-CH=CH— | benzyl-O— | H | NH | cyclopropyl |
| 427 | isoxazolidinyl-$CH_2$— | benzyl-S— | H | S | cyclopropyl |
| 428 | indolinyl-$CH_2$— | benzyl-NH— | H | O | cyclohexyl |
| 429 | 1-morpholinyl-$CH_2$— | benzyl-$CH_2$— | H | $SO_2$ | cyclohexyl |
| 430 | 1-piperazinyl-$CH_2$— | benzyl-O— | H | NH | cyclohexyl |
| 431 | 1-piperidinyl-$CH_2$— | benzyl-S— | H | S | cyclobutyl |
| 432 | 3-oxo-1-pyrrolidinyl-$CH_2$— | benzyl-NH— | H | O | cyclobutyl |
| 433 | 1-morpholinyl-CH=CH— | benzyl-$CH_2$— | H | $SO_2$ | cyclobutyl |
| 434 | 1-piperazinyl-CH=CH— | benzyl-O— | H | NH | cyclopentyl |
| 435 | oxo-pyrrolidinyl-CH=CH— | benzyl-S— | H | S | cyclopentyl |
| 436 | oxazolidinyl-CH=CH— | benzyl-NH— | H | O | cyclopentyl |
| 437 | isoxazolidinyl-$CH_2$— | benzyl-$CH_2$— | H | $SO_2$ | cyclohexyl |
| 438 | indolinyl-$CH_2$— | 4-$CH_3$-phenyl | H | NH | cyclohexyl |
| 439 | $CH_3$— | phenyl | H | S | cyclohexyl |

TABLE 2

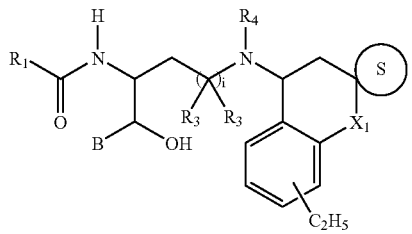

| Ex. No. | R¹ | B | R³ and R⁴ | X¹ | S |
|---|---|---|---|---|---|
| 440 | 1-morpholinyl-CH$_2$— | 4-CH$_3$-phenyl | H | NH | cyclobutyl |
| 441 | 1-piperazinyl-CH$_2$— | 4-CH$_3$-phenyl | H | S | cyclobutyl |
| 442 | 1-piperidinyl-CH$_2$— | 4-CH$_3$-pyridyl | H | O | cyclobutyl |
| 443 | 3-oxo-1-pyrrolidinyl-CH$_2$— | 4-CH$_3$-phenyl | H | NH | cyclopentyl |
| 444 | 1-morpholinyl-CH=CH— | 3-CH$_3$-phenyl | H | S | cyclopentyl |
| 445 | 1-piperazinyl-CH=CH— | 3-CH$_3$-phenyl | H | O | cyclopentyl |
| 446 | oxo-pyrrolidinyl-CH=CH— | 3-CH$_3$-phenyl | H | SO$_2$ | cyclopropyl |
| 447 | oxazolidinyl-CH=CH— | 3-CH$_3$-phenyl | H | NH | cyclopropyl |
| 448 | isoxazolidinyl-CH$_2$— | phenyl | H | S | cyclopropyl |
| 449 | indolinyl-CH$_2$— | phenyl | H | O | cyclohexyl |
| 450 | 1-morpholinyl-CH$_2$— | phenyl | H | SO$_2$ | cyclohexyl |
| 451 | 1-piperazinyl-CH$_2$— | phenyl | H | NH | cyclohexyl |
| 452 | 1-piperidinyl-CH$_2$— | pyridyl | H | S | cyclobutyl |
| 453 | 3-oxo-1-pyrrolidinyl-CH$_2$— | phenyl | H | O | cyclobutyl |
| 454 | 1-morpholinyl-CH=CH— | 3-F-phenyl | H | SO$_2$ | cyclobutyl |
| 455 | 1-piperazinyl-CH=CH— | 3-Cl-phenyl | H | NH | cyclopentyl |
| 456 | oxo-pyrrolidinyl-CH=CH— | 3-CN-phenyl | H | S | cyclopentyl |
| 457 | oxazolidinyl-CH=CH— | 3-NH$_2$-phenyl | H | O | cyclopentyl |
| 458 | isoxazolidinyl-CH$_2$— | 2-F-phenyl | H | SO$_2$ | cyclohexyl |
| 459 | indolinyl-CH$_2$— | 4-CH$_3$-phenyl | H | NH | cyclohexyl |
| 460 | CH$_3$— | phenyl | H | S | cyclohexyl |

The following examples provide a further understanding and appreciation of compounds of the present invention.

Example 461

N-((1S,2R)-3-(((4S)-6-(2-fluoro-2-methylpropyl)-3,4-dihydrospiro[chromene-2,1'-cyclobutanyl-]4-yl)amino)-2-hydroxy-1-(phenylmethyl)propyl)acetamide Step 1: (S)-tert-butyl 6-(2-oxopropyl)-2,2-spirocyclobutyl-3,4-dihydro-2H-chromen-4-ylcarbamate Pd$_2$(dba)$_3$ (15 mg, 0.017 mmol), (S)-tert-butyl 6-bromo-2,2-spirocyclobutyl-3,4-dihydro-2H-chromen-4-ylcarbamate (15 mg, 0.041 mmol), 2-(dicyclohexylphosphino)-2'-methylbiphenyl (80 mg, 0.170 mmol), potassium phosphate (179 mg, 0.845 mmol), and acetone (2.5 ml, 33.8 mmol) were dissolved in 1 ml THF in a sealed tube. The tube was sealed and heated to 70° C. for 8 hours. The cooled reaction mixture was diluted with DCM (10 mL) and poured into saturated sodium bicarbonate (25 mL). The layers were separated and the aqueous layer was extracted with DCM 2×25 mL.

The combined organic layers were washed with water and brine, dried over MgSO$_4$ and evaporated to provide the title compound as a yellow oil (75 mg; 0.166 mmol, 99%). MS m/z: 368.2 (M+Na).

Step 2: (S)-6-(2-fluoro-2-methylpropyl)-2,2-spirocyclobutyl-3,4-dihydro-2H-chromen-4-amine To pulverized cerium chloride (428 mg, 1.74 mmol) suspended in 10 mL of THF at 0° C. was added methylmagnesium bromide (3.0 M in diethyl ether, 0.60 mL, 1.79 mmol). After stirring for 20 min a solution of (S)-tert-butyl 6-(2-oxopropyl)-2,2-spirocyclobutyl-chroman-4-ylcarbamate (200 mg, 0.579 mmol) in 3 mL of THF was added and the resulting mixture was stirred at 0° C. for 30 minutes. The reaction was quenched with saturated ammonium chloride (10 mL) and the aqueous layer was extracted with EtOAc 3×20 mL. The combined organic layers were washed with brine, dried over sodium sulfate and concentrated to provide the corresponding alcohol (209 mg, 99%) as a yellow oil. The derived alcohol (209 mg, 0.578 mmol) was taken up in 1 mL of DCM cooled to –78° C. and treated with DAST (0.153 mL, 1.16 mmol). After stirring for 45 minutes the reaction was warmed to 0° C. and quenched with saturated potassium carbonate (10 mL). The layers were separated and the aqueous layer was extracted with dichloromethane 3×10 mL. The combined organic layers were washed with brine, dried over sodium sulfate, filtered and concentrated. The residue was purified by column chromatography (0-25% EtOAc in hexanes) to provide the amine as a yellow oil. The derived amine was taken up in 5 mL of DCM and treated with 2 mL of TFA. After stirring for 1 hour, the reaction was diluted with mL of DCM and poured into 10% aqueous potassium carbonate (50 mL). The layers were separated and the aqueous layer was extracted with DCM 3×20 mL. The combined organic layers were washed with water and brine, dried over sodium sulfate and concentrated to provide the title compound as a yellow oil (113 mg, 74%). MS m/z: 386.2 (M+Na).

Step 3: N-((1S,2R)-3-(((4S)-6-(2-fluoro-2-methylpropyl)-3,4-dihydrospiro[chromene-2,1'-cyclobutan]-4-yl)amino)-2-hydroxy-1-(phenylmethyl)propyl)acetamide The amine from step 2 was carried on by methods analogous to those described in Example 464, Steps 8-10 herein to afford the title compound. MS found: m/z: 469 (M+1).

Example 462

N-((1S,2R)-3-(((4'S)-6'-(2-fluoro-2-methylpropyl)-3',4'-dihydrospirocyclobutane-1,2'-pyrano[2,3-b]pyridin]-4'-yl)amino)-2-hydroxy-1-(phenylmethyl)propyl)acetamide Step 1: (S)-tert-butyl 6-(2-oxopropyl)-2,2-spirocyclobutyl-3,4-dihydro-2H-pyrano[2,3-b]pyridin-4-ylcarbamate Pd$_2$(dba)$_3$ (409 mg, 0.447 mmol) and 2-(dicyclohexylphosphino)-2'-methylbiphenyl (391 mg, 1.07 mmol) were combined in a 250 mL sealable tube. THF (15 mL) was added and the mixture was purged with nitrogen for 5 minutes before the introduction of (S)-tert-butyl 6-bromo-2,2-spirocyclobutyl-3,4-dihydro-2H-pyrano[2,3-b]pyridin-4-ylcarbamate (3.30 mg, 8.94 mmol, potassium phosphate (4.74 g, 22.3 mmol), and acetone (51.9 g, 894 mmol). The tube was sealed and heated to 70° C. for 8 hours. The cooled reaction mixture was concentrated and purified by silica gel chromatography (0-100% ethyl acetate in hexanes) to provide the title compound as a yellow oil (2.15 g, 69%). MS m/z: 347.2 (M+1).

Step 2: (S)-6-(2-fluoro-2-methylpropyl)-2,2-spirocyclobutyl-3,4-dihydro-2H-pyrano[2,3-b]pyridin-4-amine To pulverized cerium chloride (12.0 g, 51 mmol) suspended in 25 mL of THF at 0° C. was added methylmagnesium bromide (3.0 M in diethyl ether, 17.0 mL, 51 mmol). After stirring for twenty minutes a solution of (S)-tert-butyl-6-(2-oxopropyl)-2,2-spirocyclobutyl-3,4-dihydro-2H-pyrano[2,3-b]pyridin-4-ylcarbamate (3.50 g, 10 mmol) in 50 mL of THF was added over the course of thirty minutes. After stirring at 0° C. for 30 minutes the reaction was quenched with saturated ammonium chloride (100 mL) and the aqueous layer was extracted with ethyl acetate 3×100 mL. The combined organic layers were washed with brine, dried over sodium sulfate and concentrated to provide the corresponding alcohol as a yellow oil. The derived alcohol was taken up in 100 mL of DCM and cooled to −78° C. at which point DAST (7.0 mL, 51 mmol) was added. After stirring for 45 minutes the reaction was quenched with saturated sodium bicarbonate (150 mL). The layers were separated and the aqueous layer was extracted with DCM 3×100 mL. The combined organic layers were washed with brine, dried over sodium sulfate, filtered and concentrated. The residue was purified by column chromatography (0-35% EtOAc in hexanes) to provide the fluoride as a yellow foam. The derived amine was taken up in 50 mL of DCM and treated with 20 mL of TFA. After stirring for 1 hour, the reaction was concentrated, taken up in 50 mL of DCM and poured into 10% aqueous potassium carbonate (200 mL). The layers were separated and the aqueous layer was extracted with DCM 3×100 mL. The combined organic layers were washed with water and brine, dried over sodium sulfate and concentrated to provide the title compound as a brown oil (1.15 g, 43%). MS m/z/z: 365.2 (M+1).

Step 3: N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxy-1-(phenylmethyl)propyl)acetamide The amine from step 2 was carried on by methods analogous to those described in Example 464, Steps 8-10 herein to afford the title compound. MS found m/z: 470 (M+1).

Example 463

N-((1S,2R)-3-(((4'S)-6'-(2,2-dimethylpropyl)-3',4'-dihydrospiro[cyclopent-3-ene-1,2'-pyrano[2,3-b]pyridin]-4'-yl)amino)-1-((4-fluorophenyl)methyl)-2-hydroxypropyl)acetamide Step 1: 4-(2,2-dimethoxyethyl)hepta-1,6-dien-4-ol In a 2 liter round bottom flask equipped with a stir bar, methyl 3,3-dimethoxypropanoate (24 g, 162 mmol) was dissolved in THF (1L). Under nitrogen, the solution was chilled to −78° C. Allyl Magnesium bromide, 1.0 M solution in diethyl ether (405 mL, 405 mmol) was added dropwise in such a way that the internal temperature remained lower than −75° C. After addition, the reaction was allowed to stir for 3 hours at −78° C. before being quenched with saturated ammonium chloride solution (300 mL). The ice bath was removed and the reaction allowed to come to RT. Water was added (200 mL) and the reaction was concentrated on a rotary evaporator to remove as much THF as possible. The product was extracted from the resulting aqueous with diethyl ether (3×200 mL). The organics were then washed with brine (100 mL), dried over magnesium sulfate, filtered and concentrated to afford the product.

Step 2: 1-(2,2-dimethoxyethylcyclopent-3-enol

A solution of 4-(2,2-dimethoxyethyl)hepta-1,6-dien-4-ol (28 g, 140 mmol) in DCM (2L) was charged to a 3 L RB flask. Dry argon was bubbled through the solution for 30 minutes. Grubbs second generation catalyst (5.9 g, 7.0 mmol) was added and the reaction was allowed to stir under argon for 15 hours. The reaction was quenched with a solution of tetrakis-(hydroxymethyl)phosphonium chloride (27 g, 140 mmol) in isopropanol (200 mL) and 10 N NaOH (14 mL), and stirred for 15 hours. The reaction was diluted with water (1 L) and poured into a seperatory funnel. The DCM layer was separated and the aqueous was extracted with DCM (3×100 mL). The combined organics were concentrated to a dark oil which was purified by flash chromatography on a 330 g ISCO column eluting by gradient hexanes to 20% EtOAc/ hexanes over a 50 minute period. Product fractions were combined to afford the title compound.

Step 3: 2-(1-(tert-butyldimethylsilyloxy)cyclopent-3-enyl)acetaldehyde 1-(2,2-dimethoxyethyl)cyclopent-3-enol (13.5 g, 78 mmol) was dissolved in DCM (250 mL). This was chilled to 0° C. under nitrogen and 2,4,6-trimethylpyridine (42 mL, 314 mmol) was added dropwise over 10 minutes. Tert-butyldimethylsilyl trifluoromethanesulfonate (18 mL, 78 mmol) was added dropwise via syringe very slowly over 20 minutes keeping the internal temperature below 5° C. The reaction was allowed to come to RT. By TLC (20% EtOAc/hexanes; KMnO4 stain), the starting material was completely consumed (~2 hours). The reaction was then chilled back to 0° C. and triethylsilyl trifluoromethanesulfonate (35 mL, 157 mmol) was added in dropwise over a 10 minute period. This was allowed to stir at 0° C. for 1 hour before adding water (250 mL). The ice bath was removed and this mixture was stirred vigorously for ~18 hours. The reaction was poured into a seperatory funnel and the DCM layer was separated. The organic was washed with dilute aqueous HCl, brine, dried over sodium sulfate, filtered and concentrated to afford a yellow oil which was flashed on silica by gradient eluting with hexanes to 20% EtOAc/hexanes over a 40 minute period. Product fractions were combined to afford the title compound.

Step 4: (Z)-N-(2-(1-(tert-butyldimethylsilyloxy)cyclopent-3-enyl)ethylidene-2-methylpropane-2-sulfinamide 2-(1-(tert-butyldimethylsilyloxy)cyclopent-3-enyl)acetaldehyde (22 g, 92 mmol) was dissolved in DCM (500 mL). To this was added 2(R)-methylpropane-2-sulfinamide (13 g, 110 mmol), followed by anhydrous cupric sulfate (128 mmol). This was allowed to stir at RT for 72 hours. The reaction was filtered and the resulting mother liquor was concentrated to a yellow oil which was purified by flash chromatography eluting with hexanes to 20% EtOAc/hexanes over a 40 minute period. Product fractions were combined and concentrated to afford the product as a colorless oil.

Step 5: (2S)—N-(2-(1-(tertbutyldimethylsilyloxy)cyclopent-3-enyl)-1-(2-fluoro-5-neopentylpyridi-3-yl)ethyl)-2-methylpropane-2-sulfinamide In a flame dried flask, 2,2,6,6-tetramethyl piperidine (6.3 mL, 37.1 mmol) was added to THF (20 mL). Chilled to −78° C. under nitrogen. To this was added dropwise n-butyllithium (1.6M in hexanes, 12 mL, 30.3 mmol). After stirring an additional 5 minutes at −78° C., the reaction was removed from the ice bath and allowed to warm to 0° C. and then recooled to −78° C. 2-fluoro-5-neopentyl pyridine (4.5 g, 27 mmol) was added dropwise over a 5 minute period. This was allowed to stir for 30 minutes before adding dropwise (Z)-N-(2-(1-(tert-butyldimethylsilyloxy)cyclopent-3-enyl)ethylidene-2-methylpropane-2-sulfinamide (11.6 g, 33.7 mmol) over a 5 minute period. This was allowed to stir for 3 hours before being quenched with saturated bicarbonate solution (100 mL) and the ice bath was removed. Product was extracted with EtOAc (3×75 mL), washed with brine, and concentrated to give a yellow oil which was purified by column chromatography (20% EtOAc/hexanes). The desired compound is the faster running spot at Rf=0.2, which is UV active. These product fractions were combined and concentrated to afford the product.

Step 6: 3',4'-dihydrospiro[cyclopent-3-ene-1 2'-pyrano[2,3-b]pyridin]-4'-yl)amine 2(S)—N-(2-(1-(tertbutyldimethylsilyloxy)cyclopent-3-enyl)-1-(2-fluoro-5-neopentylpyridi-3-yl)ethyl)-2-methylpropane-2-sulfinamide (600 mg, 1.2 mmol) was dissolved in DMSO (10 mL) under nitrogen. To this was added granulated cesium fluoride (535 mg, 3.5 mmol). The mixture was heated at 130° C. under nitrogen for 8 hours, then cooled to Rt and poured onto 200 mL of saturated sodium bicarbonate. The product was extracted with EtOAc (3×75 mL). Washed with brine, dried over sodium sulfate, filtered and concentrated to give a yellow oil which was dissolved in methanol (10 mL). To this was added 4N HCl in dioxane (20 mL). This was allowed to stir at RT for 1 hour, and concentrated to a yellowish residue. The crude salt was free based with 10% sodium carbonate, dried and concentrated to afford the free amine product. MS m/z: 273.2 (M+1)

Step 7: N-((1S,2R)-3-(((4'S)-6'-(2,2-dimethylpropyl)-3' 4'-dihydrospiro[cyclopent-3-ene-1,2'-pyrano[2,3-b]pyridin]-4'-yl)amino)-1-((4-fluorophenyl)methyl)-2-hydroxypropyl)acetamide The title compound was obtained using 3',4'-dihydrospiro[cyclopent-3-ene-1,2'-pyrano[2,3-b]pyridin]-4'-yl)amine in a method analogous to that described in Example 464 below, Steps 8-10. MS found: m/z: 496 (M+1).

Example 464

N-((1S,2R)-1-((3-chloro-5-fluorophenyl)methyl)-3-(((4'S)-6'-ethyl-3',4'-dihydrospiro[cyclobutane-1,2'-pyrano[2,3-b]pyridin]-4'-yl)amino)-2-hydroxypropyl)acetamide Step 1. (S)-2,3-bis(tert-butyldimethylsilyloxy)propyl 4-methoxybenzoate To a 1.0 L RB flask containing (R)-2,3-dihydroxypropyl 4-methoxybenzoate (4.800 g, 21.2 mmol; according to the procedure described in Corey, E. J.; Guzman-Perez, A.; and Noe, M. C. J. Am. Chem. Soc. 1995, 117, 10805-10816) was added DCM (100 mL ) and the mixture was allowed to stir at 0° C. for 5 minutes. At this time, TEA (8.87 ml, 63.7 mmol) was added and the reaction was allowed to stir for 5 min before the dropwise addition of tert-butyldimethylsilyl triflate (10.2 ml, 44.6 mmol) via syringe. The reaction was allowed to stir for 1 h and then quenched by pouring into HCl (0.1 N, 100 mL). The aqueous layer was extracted with DCM (2×75 mL). The combined organics were washed with HCl (0.1 N, 2×150 mL), sodium bicarbonate (1×150 mL, sat), brine, dried sodium sulfate. The concentrated solution was passed through a plug of silica gel to and concentrated to give the title compound as a colorless oil.

Step 2: (S)-2,3-bis(tert-butyldimethylsilyloxy)propan-1-ol To a 1.0 L RB flask containing (S)-2,3-bis(tert-butyldimethylsilyloxy)propyl 4-methoxybenzoate (9.200 g, 20 mmol) was added DCM (100 mL ) and the mixture was allowed to stir at −78° C. for 5 minutes. At this time, DIBAL-H (1.0 M, hexanes) (61 ml, 61 mmol) was added via a syringe. The reaction was allowed to stir for 30 min and then quenched with MeOH (4.1 ml, 101 mmol). Sodium potassium tartate (sat, 200 mL) and DCM (100 mL) was added and the solution was allowed to warm to 23° C. and stirred for 3 h. The aq. layer was extracted with DCM (3 100 mL). The combined organics were washed with brine and dried with sodium sulfate and concentrated to give a residue.

Step 3: (R)-2,3-bis(tert-butyldimethylsilyloxy)propanaldehyde

To a 500 mL RB flask containing (S)-2,3-bis(tert-butyldimethylsilyloxy)propan-1-ol (4.70 g, 14.7 mmol) was added DCM (100 mL ) and the mixture was allowed to stir at 23° C. for 2 minutes. At this time, SODIUM BICARBONATE (3.69 g, 44.0 mmol) and Dess-MartinPeriodinane (7.46 g, 17.6 mmol) were added in one portion and the reaction was allowed to stir for 1.5 h. The reaction was quenched by the addition of SODIUM THIOSULFATE (6.95 g, 44.0 mmol) in one portion followed by sodium bicarbonate (sat, 250 mL) and diethyl ether (250 mL). The quenched reaction was allowed to stir for 45 min and then the clear layers were separated. The organic layer was washed with sodium bicarbonate (2×250 mL), water (1×250 mL) and brine (1×100 mL). The organic layer was dried with magnesium sulfate, filtered and concentrated to give 5.00 g of a colorless oil. Rf=0.80 in 20% EtOac in hexanes, not UV, stains pink/orange to anisaldehyde. The aq. layers were back extracted with ether (2×125 mL). The combined back extractions were washed with brine, dried with magnesium sulfate, filtered and concentrated to give less than 200 mg of oil.

Step 4: (S,E)-N-((S)-2,3-bis(tert-butyldimethylsilyloxy)propylidene)-2-methylpropane-2-sulfinamide To a 500 mL RB flask containing (R)-2,3-bis(tert-butyldimethylsilyloxy)propanal (4.670 g, 14.7 mmol) was added DCM (100 mL) and the mixture was allowed to stir at 23° C. for 2 minutes. At this time, (S)-2-methylpropane-2-sulfinamide (2.13 g, 17.6 mmol) and COPPER(II) SULFATE (5.85 g, 36.6 mmol) (100 g Fluka bottle) were added and the reaction was allowed to stir for 3 days. At this time tlc showed that all of the aldehyde was consumed. The crude reaction mixture was filtered through a plug of celite in order to remove the solid copper salt. The organic layer was concentrated to give 7.50 g of oil, which was subjected to a 330 g Isco column 10-35% EtOAc in hexanes to give the title compound as a white solid. rf=0.50 in 20% EtOAc in hexanes, UV active and stains yellow to anisaldehyde.

Step 5: (S)—N-((2S,3S)-3,4-bis(tert-butyldimethylsilyloxy)-1-(3-chloro-5-fluorophenyl)butan-2-yl)-2-methylpropane-2-sulfinamide A 500 mL RB flask containing (3-chloro-5-fluorobenzyl)magnesium chloride, 0.25 M in diethyl ether (13040 µl, 3260 µmol) was allowed to stir at −78° C. for 5 minutes. At this time, TMEDA (492 µl, 3260 µmol) was added via a syringe and then THF (10 mL) was added via a syringe and the mixture was allowed to stir for 15 min before the addition of (S,E)-N-((S)-2,3-bis(tert-butyldimethylsilyloxy)propylidene)-2-methylpropane-2-sulfinamide (550.00 mg, 1304 µmol) (14 mL THF) via a syringe. The reaction was allowed to stir for 30 min and then quenched with ammonium chloride (sat, 100 mL). The aq. layer was extracted with EtOAc (3×100 mL). The combined organics were washed with brine and dried with sodium sulfate. The dried solution was filtered and concentrated to give 1.30 g of a crude oil that was purified on a 120 g ISCO column to give the title compound. Rf=0.40 in 20% EtOAc in hexanes.

Step 6: (S)—N-((2S,3S)-3-(tert-butyldimethylsilyloxy)-1-(3-chloro-5-fluorophenyl)-4-hydroxybutan-2-yl)-2-methylpropane-2-sulfinamide To a 50 mL polypropylene bottle containing (S)—N-((2S,3S)-3,4-bis(tert-butyldimethylsilyloxy)-1-(3-chloro-5-fluorophenyl)butan-2-yl)-2-methylpropane-2-sulfinamide (350.00 mg, 618 µmol) was added THF (10 mL) and the mixture was allowed to stir at 0° C. for 5 minutes. At this time, PYRIDINE (2699 µl, 33371 µmol) was added via syringe before the addition of HF-Pyridine, 70% HF 30% pyr (1782 µl, 19775 µmol) via a syringe. The reaction was allowed to stir at this temp for 2 h and then quenched by pouring into sodium bicarbonate (sat 150 ml). The aq. layer was extracted with EtOAc 94×75 mL). The combined organics were washed with HCl (0.1 N, 3×100 mL), bicarbonate (sat, 100 mL), brine and dried with sodium sulfate. The dried solution was filtered and concentrated to give a yellow oil which was purified on a 40 g ISCO column to give the title compound.

Step 7: (S)—N-((2S,3S)-3-(tert-butyldimethylsilyloxy)-1-(3-chloro-5-fluorophenyl)-4-oxobutan-2-yl)-2-methylpropane-2-sulfinamide To a 250 ml rbf was added (S)—N-((2S,3S)-3-(tert-butyldimethylsilyloxy)-1-(3-chloro-5-fluorophenyl)-4-hydroxybutan-2-yl)-2-methylpropane-2-sulfinamide (160.00 mg) and DCM (10 ml) followed by SODIUM BICARBONATE (148.7 mg, 5 eq) and Dess-MartinPeriodinane (195.1 mg, 1.30 eq). The reaction was allowed to stir for 2 h and then quenched with sodium bicarbonate (sat, 100 mL) and added SODIUM THIOSULFATE (391.7 mg, 2477 µmol) along with diethyl ether (100 ml). The quenched reaction was allowed to stir for 2 h and then the aq. layer was extracted with ether (3×75 mL). The combined organics were washed with brine and dried with magnesium sulfate, filtered and concentrated to give 1280 mg of a solid/oil mixture, which was purified on a silica gel column (20% EtOAc in hexanes) to give the title compound as a colorless oil.

Step 8: (S)—N-((2S,3R)-3-(tert-butyldimethylsilyloxy)-1-(3-chloro-5-fluorophenyl)-4-((S)-6-ethyl-2,2-spirocyclobutyl-3,4-dihydro-2H-pyrano[2,3-b]pyridin-4-ylamino)butan-2-yl)-2-methylpropane-2-sulfinamide To a 150 mL rbf containing (S)—N-((2S,3S)-3-(tert-butyldimethylsilyloxy)-1-(3-chloro-5-fluorophenyl)-4-oxobutan-2-yl)-2-methylpropane-2-sulfinamide (75.00 mg, 167 µmol) was added DCE (3 mL) and the mixture was allowed to stir at 23° C. for 2 minutes. At this time, 6-ethyl-2,2-spirocyclobutyl-8-azachromanyl-4-amine (36 mg, 167 µmol) was added in DCE (5 mL) and TRIMETHYL ORTHOFORMATE (276 µl, 2500 µmol) was added via a syringe. The reaction was allowed to stir for 20 min when FIA/MS indicated that imine had formed. At this time, SODIUM TRIACETOXYBOROHYDRIDE (141 mg, 667 µmol) was added in one portion and the reaction was allowed to stir for 12 h. The reaction was quenched by the addition of sodium carbonate (10%, 30 mL) and diluted with DCM (50 mL). The aq. layer was extracted with DCM (3×50 mL). The combined organics were washed with brine and dried with sodium sulfate. The dried solution was passed through a plug of silica gel and eluted with EtOAc, concentrated and placed on a high vacuum to give the title compound as a colorless oil.

Step 9: (2R,3S)-3-amino-4-(3-chloro-5-fluorophenyl)-1-((S)-6-ethyl-2,2-spirocyclobutyl-3,4-dihydro-2H-pyrano[2,3-b]pyridin-4-ylamino)butan-2-ol To a 100 mL rbf was added MeOH (1 0 mL) and the mixture was allowed to stir at 0° C. for 5 minutes. At this time, ACETYL CHLORIDE (2518 µl, 35409 µmol) was added via syringe and the reaction was allowed to stir for 20 min before it was added to a flask containing Reactant 1 (105.00 mg, 161 µmol). The reaction was allowed to stir at 23° C. for 24 h and checked by LC/MS. The reaction was allowed to stir an additional 2 days and then the solvents were removed by rotary evaporator. The residue was placed on a high vacuum for 3 h. Note that acetyl chloride reacts with anhydrous MeOH, generating methylacetate and HCl. In the described procedure above, HCl is the reactive reagent for the removal of sulfinyl or other protecting groups involved in the synthesis of this compound or analogs. Alternatively, commercially available reagent HCl (e.g., 4.0 M in dioxane) can be used directly.

Step 10: N-((1S,2R)-1-((3-chloro-5-fluorophenyl)methyl)-3-(((4'S)-6'-ethyl-3',4'-dihydrospiro[cyclobutane-1 2'-pyrano[2,3-b]pyridin]-4'-yl)amino)-2-hydroxypropyl)acetamide The title compound was prepared using 1-(1H-imidazol-1-yl)ethanone (18 mg, 159 µmol) and (2R,3S)-3-amino-4-(3-chloro-5-fluorophenyl)-1-((S)-6-ethyl-2,2-spirocyclobutyl-3,4-dihydro-2H-pyrano[2,3-b]pyridin-4-ylamino)butan-2-ol in DMF. The crude reaction was injected into a reverse phase HPLC and the clean fractions were collected and extracted after adding sodium carbonate (3×EtOAc). The combined organics were washed with brine, dried with sodium sulfate and concentrated to give the title compound as a white solid. MS Found: m/z: 476 (M+1).

Example 465

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)acetamide Step 1: (S)—N-((2S,3S)-3,4-bis(tert-butyldimethylsilyloxy)-1-(3-fluorophenyl)butan-2-yl)-2-methylpropane-2-sulfinamide The title compound was prepared by the method described in Example 464, Step 5 using 3-fluorobenzyl)magnesium chloride (0.25 M in diethyl ether) (139 ml, 35 mmol), TMEDA (5.2 ml, 35 mmol) and (S,E)-N-((S)-2,3-bis(tert-butyldimethylsilyloxy)propylidene)-2-methylpropane-2-sulfinamide (4.890 g, 12 mmol).

Step 2: tert-Butyl (2S,3S)-3-(tert-butyldimethylsilyloxy)-1-(3-fluorophenyl)-4-hydroxybutan-2-ylcarbamate To a 500 mL RBF containing (S)—N-((2S,3S)-3,4-bis(tert-butyldimethylsilyloxy)-1-(3-fluorophenyl)butan-2-yl)-2-methylpropane-2-sulfinamide (2.600 g, 4.9 mmol) was added EtOH (25 ml) and the mixture was allowed to stir at 0° C. for 15 min. At this time, HCl (4N in dioxane) (3.7 ml, 15 mmol) was added via syringe. The reaction was monitored at 1 h by LC/MS 76877-2-1 and tlc (100% EtOAC amino bis TBS; Rf=0.80 UV active stains orange to anisaldehyde amine with primary alcohol deprotected Rf=0.45 to 0.1 streak, UV active and stains white to anisaldehyde). The reaction was allowed to stir for 3 h at 0° C. and then TEA (4.1 ml, 29 mmol) was added fast dropwise and a white solid formed. An LC/Ms was obtained to confirm that the secondary TBS ether was not removed during the TEA neutralization process. Approximately 15 mL of EtOH were removed by rotary evaporator and then DCM (10 mL) was added and the solid went into solution. At this time, (BOC)$_2$O (2.3 ml, 9.8 mmol) was added in one portion and the reaction was allowed to stir for 1 h and then poured into diethyl ether (300 ml). The organic layer was washed with ammonium chloride (3×150 mL, sat) and brine. The organic layer was dried with magnesium sulfate, filtered and concentrated to give a colorless crude oil. The desired product has an Rf=0.40 in 35% EtOAc in hexanes, UV active, stains white to anisaldehyde and purple to moly stain. The crude oil was purified on a 120 g Isco column (10 to 35% EtOAc in hexanes) to give the title compound as a colorless oil.

Step 3: Tert-Butyl (2S,3 S)-3-(tert-butyldimethylsilyloxy)-1-(3-fluorophenyl)-4-oxobutan-2-ylcarbamate To a 150 mL RBF containing tert-butyl (2S,3S)-3-(tert-butyldimethylsilyloxy)-1-(3-fluorophenyl)-4-hydroxybutan-2-ylcarbamate (170.00 mg, 411 µmol) was added DCM (10 mL) and the mixture was allowed to stir at 23° C. for 2 minutes. At this time, pyridine (299 µl, 3699 µmol) was added via syringe before the addition of Dess-MartinPeriodinane (262 mg, 617 µmol) in one portion. The reaction stayed a clear solution and was allowed to stir 1 h before loading directly to a silica gel column (20% EtOAc). The purified product was concentrated to give the title compound as a colorless oil.

Step 4: N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)acetamide The title compound was prepared using the methods described in Example 464, steps 8-herein. The final product was purified by reverse phase HPLC and the pure fraction was lyophilized to give the title compound as a white solid. MS Found m/z: 484(M+1).

Example 466

N-((2S,3R)-4-((S)-2,2-spirocyclopropyl-6-neopentyl-3,4-dihydro-2H-pyrano[2,3-b]pyridin-4-ylamino)-1-(4-fluorophenyl)-3-hydroxybutan-2-yl)acetamide Step 1: 1-(2,2-dimethoxyethyl)cyclopropanol To a 1.0 L RBF containing methyl 3,3-dimethoxypropanoate (17.6500 g, 119 mmol) was added THF (150 ml) and diethyl ether (150 ml), and the mixture was allowed to stir at 0° C. for 15 min. At this time, tetra-isopropoxy titanium (6.98 ml, 23.8 mmol) was added in one portion before the dropwise addition of ethylmagnesium bromide (99.3 ml, 298 mmol) via syringe. The reaction was allowed to warm to 23° C. and stir for 14 hours before being re-chilled to 0° C. After 5 min at this temp, water (15 ml) was added and a solid formed. Diethyl ether (200 ml) was added and the quenched reaction was stirred for 10 min before filtering through a plug of magnesium sulfate. The filtrate was dried with additional magnesium sulfate, filtered and concentrated to give a colorless oil. The crude material was used directly in the next reaction.

Step 2: 2-(1-(tert-butyldimethylsilyloxy)cyclopropyl)acetaldehyde

To a 2.0 L RBF containing 1-(2,2-dimethoxyethyl)cyclopropanol (17.400 g, 119 mmol) was added DCM (550 ml) and the mixture was allowed to stir at 0° C. for 15 min. 2,4,6-Colliding (63.1 ml, 476 mmol) was added and the reaction was allowed to chill for 5 min before the addition of tert-butyldimethylsilyl triflate (27.3 ml, 119 mmol) over 10 min. The reaction was allowed to stir for 20 min and then analyzed by tlc which showed that all of the tertiary alcohol had been protected as its TBS ether. So, triethylsilyl trifluoromethanesulfonate (53.8 ml, 238 mmol) was added via syringe over 10 min. After 20 min, tic showed all of the material was converted to a baseline Rf material (mixed acetal) and then water (300 mL) was added and the reaction was allowed to stir overnight. The layers were separated. The DCM was washed with dilute HCl to remove the 2,4,6-collidine. The aq. layer was back extracted with DCM. The combined organics were washed with sodium bicarbonate, brine, dried with sodium sulfate and filtered though a plug of silica gel. Desired fractions were collected to give the product.

Step 3: (R,E)-N-(2-(1-(tert-butyldimethylsilyloxy)cyclopropyl)ethylidene)-2-methylpropane-2-sulfinamide To a 1.0 L round bottom flask containing 2-(1-(tert-butyldimethylsilyloxy)cyclopropyl)acetaldehyde (5.00 g, 23.3 mmol) (crude 10.5 g with TESOH, 1H NMR showed about 50/50 sm to impurity) was added DCM (200 mL) and the mixture was allowed to stir at 23° C. for 5 min. At this time, (R)-2-methylpropane-2-sulfinamide (2.83 g, 23.3 mmol) and cupric sulfate anhydrous (2.58 ml, 58.3 mmol) were added and the reaction was allowed to stir for 40 h. The copper salts were removed by celite filtration. The filtrate was concentrated to give a yellow oil that was purified on a 330 g Isco column (5 to 20% EtOAc in hexanes)to afford the title compound as a colorless oil.

Step 4: (26R)-N-(2-(1-(tert-butyldimethylsilyloxy)cyclopropyl)-1-(2-fluoro-5-neopentylpyridin-3-yl)ethyl)-2-methylpropane-2-sulfinamide Prepared following the procedure described for Example 272, Step 7 utilizing 2,2,6,6-tetramethylpiperidine (2.21 ml, 13.0 mmol), butyllithium (4.62 ml, 11.6 mmol), 2-fluoro-5-neopentylpyridine (1.610 g, 9.63 mmol), and (R,E)-N-(2-(1-(tert-butyldimethylsilyloxy)cyclopropyl)ethylidene)-2-methylpropane-2-sulfinamide (3.97 g, 12.5 mmol). The desired product is the stereoisomer with higher Rf (approx 3:1 ratio) (Rf=0.45 in 35% EtOAc in hexanes).

Step 5: (S)-1-(2-amino-2-(2-fluoro-5-neopentylpyridin-3-yl)ethyl)cyclopropanol

To a 500 mL RBF containing (26R)-N-(2-(1-(tert-butyldimethylsilyloxy)cyclopropyl)-1-(2-fluoro-5-neopentylpyridin-3-yl)ethyl)-2-methylpropane-2-sulfinamide (1.03 g, 2.12 mmol) was added THF (13 ml) and the mixture was allowed to stir at 23° C. for 5 min. At this time, TBAF (1.00 M in THF) (2.12 ml, 2.12 mmol) was added and tlc showed that the TBS group was removed in the first 5 min. After 30 min, tlc showed that a rearrangement started to occur at 23° C. (higher Rf spot=0.80 in 35% EtOAc in hexanes, UV active, stains pink to anisaldehyse). So, EtOH (5 ml) and HCl (4 N in dioxane, 5 ml) were added and the reaction was allowed to stir for 1 h. The solution was poured into sodium bicarbonate and extracted with EtOAc. The combined organics were washed with brine, dried with sodium sulfate, filtered and concentrated to give the title compound as a crude, colorless oil.

Step 6: (S)-2,2-spirocyclopropyl-6-neopentyl-3,4-dihydro-2H-pyrano[2,3-b]pyridin-4-amine To a 500 mL RBF containing 1-(2-amino-2-(2-fluoro-5-neopentylpyridin-3-yl)ethyl)cyclopropanol (crude) (750.00 mg, 2816 µmol) was added THF (200 mL) and the mixture was allowed to stir at 23° C. for 5 min. At this time, KHMDS (0.5 M in toluene) (5632 µl, 2816 µmol) was added via syringe over 2 min. TLC at 10 min showed all of the starting material was consumed and converted to slightly lower Rf compound. The reaction was poured into sodium carbonate (10%, 100 ml) and extracted with EtOac (2×100 ml). The combined EtOAc were washed with brine, dried with sodium sulfate, filtered and concentrated. The aq. layers were combined and then back extracted with DCM. The combined organics was concentrated and the resulting residue purified through a short silica gel column (EtOAc to 10% MeOH (2 M in NH$_3$) in EtOAc to give the title compound as a yellow oil.

Step 7: N-((2S,3R)-4-((S)-2,2-spirocyclopropyl-6-neopentyl-3,4-dihydro-2H-pyrano[2,3-b]pyridin-4-ylamino)-1-(4-fluorophenyl)-3-hydroxybutan-2-yl)acetamide The title compound was prepared by a method analogous to that described in Example 464, steps 8-10, and the title compound was purified by reverse phase HPLC and isolated as a white solid. MS Found: m/z: 470 (M+1).

Example 467

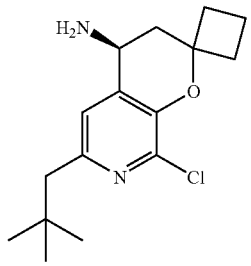

Synthesis of (S)-8-chloro-2,2-spirocyclobutyl-6-neopentyl-3,4-dihydro-2H-pyrano[2,3-c]pyridin-4-amine Step 1: 2-bromo-5-(methoxymethoxy)pyridine To a solution of 6-bromopyridin-3-ol (25 g, 144 mmol) in DMF (300 mL) at 0° C. under N$_2$ is added portionwise NaH (5.7 g, 144 mmol) over 5 min. The reaction was stirred 1 h, then chloro(methoxy)methane (12 g, 144 mmol) was added and the reaction stirred an additional 1 h at 0° C. Saturated sodium bicarbonate (500 mL) was added slowly and the suspension stirred 30 min and warmed to rt. The solution was extracted with EtOAc (3×400 mL), the combined organic layers washed with H$_2$O (500 mL), saturated NaCl (500 mL), dried (Na$_2$SO$_4$), and concentrated in vacuo to give the title compound as a brown oil.

Step 2: 5-(methoxymethoxy)-2-neopentylpyridine

To a solution of 2-bromo-5-(methoxymethoxy)pyridine (30.5 g, 140 mmol) in THF (5 mL) at 0° C. under N$_2$ is added dichloro-((bis-diphenylphosphino)ferrocenyl)-palladium(II) (4.88 g, 5.5 mmol) followed by dropwise addition of neopentylmagnesium chloride (155 mL, 155 mmol) over 2 min. After addition, the cooling bath was removed and the reaction stirred 3 h at rt. The reaction was cooled to 0° C. and saturated NH$_4$Cl (500 mL) was added, and the aqueous layers extracted with EtOAc (3×200 mL). The combined organic layers were washed with saturated NaCl, dried (Na$_2$SO$_4$) and concentrated to give a red oil. Purification by vacuum filtration through a silica plug (9×7 cm, dry load, 10-20%% EtOAc/Hexanes) gives 5-(methoxymethoxy)-2-neopentylpyridine as a light yellow oil.

Step 3: 1-(5-(methoxymethoxy)-2-neopentylpyridin-4-yl)ethanol

To a solution of 5-(methoxymethoxy)-2-neopentylpyridine (16.5 g, 79 mmol) and in THF (200 mL) −78° C. is added tert-butyllithium (46 ml, 79 mmol) (1.7 M in pentane ) over 2 min via cannula. The reaction was stirred at −78° C. 30 min, and acetaldehyde (11 ml, 197 mmol) was added. The reaction was stirred at −78° C. 10 min, then the reaction was warmed to rt and stirred 3 h. The reaction was quenched by addition of saturated aqueous NH$_4$Cl (400 mL), extracted with EtOAc (3×200 mL), the combined organic layers washed with saturated NaCl (10 mL), dried (Na$_2$SO$_4$), and concentrated to give a orange oil, which was purified by chromatography on an ISCO (330 g SiO$_2$, 10%-50% EtOAc/Hexane) gives 1-(5-(methoxymethoxy)-2-neopentylpyridin-4-yl)ethanol as a clear, light yellow oil.

Step 4: 1-(5-(methoxymethoxy)-2-neopentylpyridin-4-yl)ethanone

To a solution of 1-(5-(methoxymethoxy)-2-neopentylpyridin-4-yl)ethanol (24.4 g, 96.3 mmol) and sodium bicarbonate (32.4 g, 385 mmol) in CHCl$_3$ (500 mL) at 0° C. was added Dess-Martin Periodinane (53.1 g, 125 mmol). The reaction was stirred 5 h, quenched with saturated aqueous Na$_2$SO$_3$ (300 mL), extracted with CH$_2$Cl$_2$ (3×250 mL), the combined organic layers washed with saturated NaCl (300 mL), dried (Na$_2$SO$_4$), and concentrated to give a yellow oil. Purification by ISCO (330 g SiO$_2$, 20% EtOAc/Hexane) gives 1-(5-(methoxymethoxy)-2-neopentylpyridin-4-yl)ethanone as a clear, colorless oil.

Step 5: 1-(5-hydroxy-2-neopentylpyridin-4-yl)ethanone

A solution of 1-(5-(methoxymethoxy)-2-neopentylpyridin-4-yl)ethanone (21.6 g, 86 mmol) in (2:1:1) 5 M HCl: i-PrOH : THF (800 mL) was stirred 4 h at rt. The mixture was concentrated to remove the THF and i-PrOH. The resulting solution consisting of the product in aqueous HCl was quenched by slow addition to a solution of saturated aqueous NaHCO$_3$ (500 mL) containing excess solid NaHCO$_3$ (50 g). The aqueous layer was extracted with CH$_2$Cl$_2$ (3×250 mL), the organic layers combined and washed with saturated aqueous NaCl (250 mL), dried (MgSO$_4$), and concentrated to give 1-(5-hydroxy-2-neopentylpyridin-4-yl)ethanone as a brown oil.

Step 6: 2,2-spirocyclobutyl-6-neopentyl-2,3-dihydropyrano[2,3-c]pyridin-4-one

A mixture of 1-(5-hydroxy-2-neopentylpyridin-4-yl)ethanone (14.8 g, 71 mmol) (76894-11), Hünig's base (12 ml, 71 mmol),pyrrolidine (8.9 ml, 107 mmol), and cyclobutanone (13 ml, 179 mmol) in toluene (300 mL) with a Dean-Stark trap was heated in a 140° C. oil bath for 2 h. The mixture was cooled to rt, then diluted with EtOAc (25 mL), washed with $H_2O$, saturated aqueous $NH_4Cl$, saturated aqueous NaCl, dried ($MgSO_4$), and concentrated. Purification by ISCO (120 g $SiO_2$, 10-20% EtOAc/Hexane) gives the title compound as a yellow solid.

Step 7: 2,2-spirocyclobutyl-6-neopentyl-7-oxo-2,3-dihydropyrano[2,3-c]pyridin-4-one 2,2-spirocyclobutyl-6-neopentyl-2,3-dihydropyrano[2,3-c]pyridin-4-one (5.00 g, 19 mmol) was dissolved in 100 ml $CHCl_3$ and cooled to 0° C., mCPBA (10.0 g, 58 mmol) was added portionwise and the reaction was stirred under $N_2$ and allowed to warm slowly to rt; stirring was continued for 17 h. The mixture was then cooled to 0° C., 1M NaOH (100 mL) was added, and stirring was continued vigorously for 10 min. The mixture was extracted with $CH_2Cl_2$ (3×100 mL), the combined organic layers washed with saturated sodium chloride (100 mL), dried ($Na_2SO_4$) and evaporated to give the title compound as a white solid.

Step 8: 8-chloro-2,2-spirocyclobutyl-6-neopentyl-2,3-dihydro pyrano[2,3-c]pyridin-4-one 2,2-spirocyclobutyl-6-neopentyl-7-oxo-2,3-dihydropyrano[2,3-c]pyridin-4-one. (5.3 g, 19 mmol) was taken up in phosphoryl trichloride (20 mL, 218 mmol) and the mixture was heated to 80° C. for 2 h under $N_2$. The reaction mixture was quenched by slow addition to vigorously stirred cold 10% aqueous $NaCO_3$ (300 mL), extracted with EtOAc (3×200 mL), the combined organic layers were washed with saturated NaCl (200 mL), dried ($Na_2SO_4$), and concentrated to give a brown oil. Purification by ISCO (120 g $SiO_2$, 10% EtOAc/Hexane) gives the title compound as a light yellow solid.

Step 9: (R)-8-chloro-2,2-spirocyclobutyl-6-neopentyl-3,4-dihydro-2H-pyrano[2,3-c]pyridin-4-ol To a stirred solution of (s)-2-methyl-cbs-oxazaborolidine (1.7 ml, 1.7 mmol) in THF (20 mL) at 0° C. is added borane-methyl sulfide complex (14 ml, 28 mmol) followed by a solution of 8-chloro-2,2-spirocyclobutyl-6-neopentyl-2,3-dihydropyrano[2,3-c]pyridin-4-one (4.90 g, 17 mmol) in THF (40 mL) dropwise via syringe pump over 2.8 h. The reaction was stirred an additional 30 min, then was quenched by dropwise addition (1 drop/10 sec) of 5 M HCl (25 mL) at 0° C., after 15 mL HCl was added, bubbling had ceased and the addition rate was increased as the ice bath was removed. The reaction was stirred an additional 2 h at rt. The reaction was recooled to 0° C. and neutralized with 5 M NaOH (27 mL). The mixture was then extracted with EtOAc (2×150 mL), washed with saturated aqueous NaCl (200 mL), dried ($MgSO_4$), and concentrated in vacuo. Purification by ISCO (120 g $SiO_2$, 20% EtOAc/Hexane) gives the title compound as a white foam.

Step 10: (S)-4-azido-8-chloro-2,2-spirocyclobutyl-6-neopentyl-3,4-dihydro-2H-pyrano[2,3-c]pyridine To a solution of (R)-8-chloro-2,2-spirocyclobutyl-6-neopentyl-3,4-dihydro-2H-pyrano[2,3-c]pyridin-4-ol (2.33 g, 7.9 mmol) in toluene (43 mL) is added diphenylphosphoryl azide (2.4 ml, 11 mmol) then 1,8-diazabicyclo(5.4.0)-7-undecene (1.6 ml, 11 mmol). The reaction was stirred under $N_2$ at rt 4 days. The clear, light yellow solution first turned into a yellow cloudy/opaque solution after 10 min. Water (100 mL) was added and the reaction mixture extracted with EtOAc (3×100 mL). The combined organic layers were washed with saturated NaCl (150 mL), dried ($MgSO_4$), and concentrated to give the title compound as a brown oil which was used in the next step without purification.

Step 11: (S)-8-chloro-2,2-spirocyclobutyl-6-neopentyl-3,4-dihydro-2H-pyrano[2,3-c]pyridin-4-amine To a solution of (S)-4-azido-8-chloro-2,2-spirocyclobutyl-6-neopentyl-3,4-dihydro-2H-pyrano[2,3-c]pyridine (2.21 g, 6.9 mmol) in 10: I $THF/H_2O$ (44 mL) at 0° C. is added NaOH (3.0 ml, 15 mmol) (5 N). After 5 min, trimethylphosphine (2.4 ml, 28 mmol) was added dropwise over 4 min. The reaction went from brown to pink to purple as $N_2$ evolution occurred. The ice bath was allowed to melt as the reaction warmed to rt and stirred a total of 15 h. The mixture was re-cooled to 0° C. and 5 N HCl (25 mL) was added. The resulting mixture was extracted with EtOAc (3×50 mL), the combined organic layers were washed with 2.5 N HCl (2×25 mL). The combined aqueous layers were cooled to 0° C. and basified to pH 14 with 5 N NaOH (100 mL). The aqueous layer was extracted with EtOAc (3×50 mL) the combined organic layers dried ($Na_2SO_4$), and concentrated to give the crude product as a viscous yellow oil. The combined organic layers were combined with the crude product from above and concentrated to give a crude yellow oil. Purification of the crude oil by flash chromatography (5×15 cm $SiO_2$, 0-10% $MeOH/CH_2Cl_2$ gradient elution) gave the title compound as a yellow oil.

Example 468

N-((1S,2R)-3-(((4'S)-8'-chloro-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide

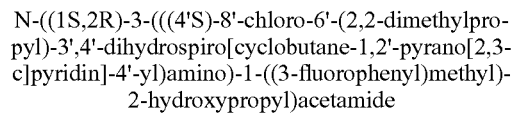

The title compound was synthesized in manner analogous to that of Example 466, using (S)-8-chloro-2,2-spirocyclobutyl-6-neopentyl-3,4-dihydro-2H-pyrano[2,3-c]pyridin-4-amine and N-((2S,3S)-3-(tert-butyldimethylsilyloxy)-1-(3-fluorophenyl)-4-oxobutan-2-yl)acetamide to obtain the title compound as a colorless solid. MS m/z: 518.2(M+1).

Example 469

N-((2S,3R)-4-((S)-2,2-spirocyclobutyl-8-(methylamino)-6-neopentyl-3,4-dihydro-2H-pyrano[2,3-c]pyridin-4-ylamino)-1-(3-fluorophenyl)-3-hydroxybutan-2-yl)acetamide

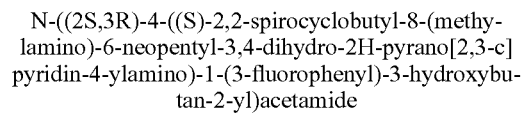

To a flame-dried microwave vial under argon is added N-((1S,2R)-3-(((4'S)-8'-chloro-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide (60 mg, 95 μmol), Pd2 dba3 (17 mg, 19 μmol), and DavePhos (16 mg, 42 μmol). The vial was purged with $N_2$ 5×, then methanamine (949 1l, 1898 μmol) and LiHMDS (475 1l, 475 μmol, 1.0 M in THF) were added. The vial was sealed and heated in a microwave at 110° C. for 10 min. The reaction mixture was directly purified by reverse phase HPLC on a Phenomenex Synergi column (5 micron, MAX-RP, 80 Å, 150×30 mm) eluting at 45 ml/min with an linear gradient of 10% (v/v) to 100% MeCN (0.1% v/v TFA) in water (0.1% TFA) over 30 minutes to give the title compound as a white amorphous solid. MS m/z/z: 513.2(M+1).

Example 470

N-((1S,2R)-3-(((4'S)-6'-(2,2-dimethylpropyl)-8'-(methyloxy)-3',4'-dihydrospiro[cyclobutane-1,2'-pyrano[2,3-c]pyridin]-4'-yl)amino)-1-((3-fluorophenyl)methyl)-2-hydroxypropyl)acetamide To a 2 mL microwave vial is added cesium carbonate (283 mg, 869 μmol), di-tert-butyl(2-(2-isopropylnaphthalen-1-yl)-3,4,5,6-tetramethylphenyl)phosphine (71 mg, 159 μmol), palladium(II) acetate (33 mg, 145 μmol), and N-((1S,2R)-3-(((4'S)-8'-chloro-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide (75 mg, 145 μmol) were added and the vial was flushed with $N_2$ 5×, then methanol (160 μl, 3619 μmol) and toluene (1 mL) were added simultaneously. The reaction was heated in the microwave at 110° C. for 30 min. LCMS shows 100% conversion. The reaction mixture was filtered through a small plug of silica gel, and the residue purified by reverse phase HPLC on a Phenomenex Synergi column (5 micron, MAX-RP, 80 Å, 150×30 mm) eluting at 45 mL/min with an linear gradient of 10% (v/v) to 100% MeCN (0.1% v/v TFA) in water (0.1% TFA) over 30 minutes to give the title compound as a tan amorphous solid. MS m/z: 514.2(M+1).

Example 471

General Procedure for the Synthesis of Examples 634-650 and 652, Various B and V—$R^2$ Groups of Formulas I and II

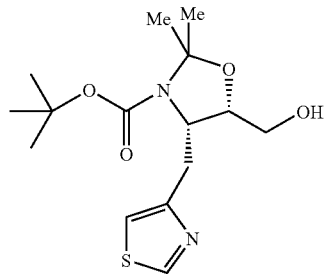

(4S,5S)-tert-butyl 5-(hydroxymethyl)-2,2-dimethyl-4-(thiazol-4-ylmethyl)oxazolidine-3-carboxylate This compound was prepared according to a method described in Example 472, from (S)-2-(tert-butoxycarbonyl)-3-(thiazol-4-yl)propanoic acid.

Example 472

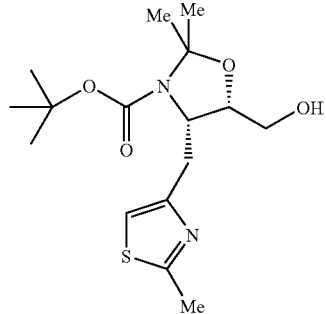

Synthesis of (4S,5S)-tert-butyl 5-(hydroxymethyl)-2,2-dimethyl-4-((2-methylthiazol-4-yl)methyl)oxazolidine-3-carboxylate Step 1: (4S,5S)-tert-butyl 5-((tert-butyldimethylsilyloxy)methyl)-2,2-dimethyl-4-(thiazol-4-ylmethyl)oxazolidine-3-carboxylate (4S,5S)-Tert-butyl 5-(hydroxymethyl)-2,2-dimethyl-4-(thiazol-4-ylmethyl)oxazolidine-3-carboxylate (0.096 g, 0.29 mmol) was dissolved in DMF (1 mL) with 1H-imidazole (0.026 g, 0.38 mmol) and tert-butylchlorodimethylsilane (0.053 g, 0.35 mmol). The reaction was stirred 2 hrs, diluted with diethyl ether and washed twice with water and once with brine. The organic layer was dried over magnesium sulfate and concentrated to furnish the title compound, which was used for the next step without purification.

Step 2: (4S,5S)-tert-butyl 5-((tert-butyldimethylsilyloxy)methyl)-2,2-dimethyl-4-((2-methylthiazol-4-yl)methyl)oxazolidine-3-carboxylate (4S,5S)-Tert-butyl 5-((tert-butyldimethylsilyloxy)methyl)-2,2-dimethyl-4-(thiazol-4-ylmethyl)oxazolidine-3-carboxylate (0.100 g, 0.23 mmol) was dissolved in THF (2.5 mL) and cooled to −78° C. n-Butyllithium (0.12 ml, 0.29 mmol) was added and the reaction was stirred at −50° C. for 40 minutes followed by the addition of iodomethane (0.018 ml, 0.29 mmol). After stirring 40 minutes the reaction was quenched with saturated ammonium chloride and extracted with ethyl acetate. The combined organic layers were washed with water, brine, and dried over sodium sulfate to afford the title compound. MS m/z: 457.3 (M+1).

Step 3: (4S,5S)-tert-butyl 5-(hydroxymethyl)-2,2-dimethyl-4-((2-methylthiazol-4-yl)methyl)oxazolidine-3-carboxylate (4S,5S)-Tert-butyl 5-((tert-butyldimethylsilyloxy)methyl)-2,2-dimethyl-4-((2-methylthiazol-4-yl)methyl)oxazolidine-3-carboxylate (0.100 g, 0.219 mmol) was dissolved in THF (4 mL) and cooled to 0° C. Next, TBAF (0.547 ml, 0.547 mmol) was added dropwise and the reaction was stirred 1 hr. and then quenched with saturated ammonium chloride and diluted with EtOAc. The layers were separated and the aqueous layer was extracted with ethyl acetate. The combined organic layers were washed with water, brine, dried over sodium sulfate, and concentrated. Purification by column chromatography (2.5:1 Hexanes/EtOAc) afforded the title compound.

Example 473

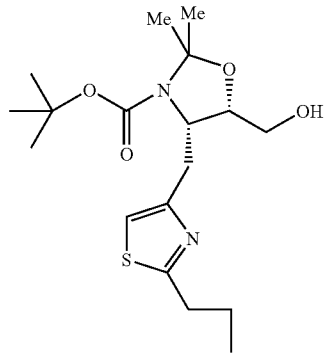

(4S,5S)-tert-butyl 5-(hydroxymethyl)-2,2-dimethyl-4-((2-propylthiazol-4-yl)methyl)oxazolidine-3-carboxylate The title compound was prepared in a manner analogous to that described in Example 472. MS m/z: 371.3 (M+1).

Example 474

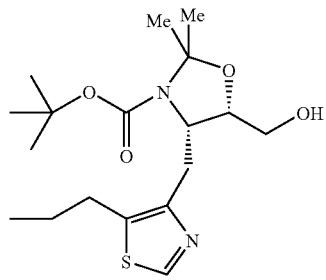

(4S,5S)-tert-butyl 5-(hydroxymethyl)-2,2-dimethyl-4-((5-propylthiazol-4-yl)methyl)oxazolidine-3-carboxylate Step 1: (4S,5S)-tert-butyl 4-((2-(tert-butyldimethylsilyl)thiazol-4-yl)methyl)-5-((tert-butyldimethylsilyloxy)methyl)-2,2-dimethyloxazolidine-3-carboxylate (4S,5S)-Tert-butyl 5-((tert-butyldimethylsilyloxy)methyl)-2,2-dimethyl-4-(thiazol-4-ylmethyl)oxazolidine-3-carboxylate (0.148 g, 0.334 mmol) in THF (3 mL) was cooled to −78° C. when n-butyllithium (2.5 M in hexanes)(0.160 ml, 0.401 mmol) was added dropwise. The solution was warmed to −50° C. for 40 minutes and then cooled to −78° C. TBS-Cl (0.0605 g, 0.401 mmol) in THF (2 mL) was added dropwise and the solution was allowed to slowly warm to 0° C. when it was quenched with saturated ammonium chloride. The layers were separated and the aqueous layer was extracted with EtOAc. The combined organic layers were washed with water, brine and dried over sodium sulfate to afford the title compound, which was used without further purification.

Step 2: (4S,5S)-tert-butyl 4-((2-(tert-butyldimethylsilyl)-5-propylthiazol-4-yl)methyl)-5-((tert-butyldimethylsilyloxy)methyl)-2,2-dimethyloxazolidine-3-carboxylate (4S,5S)-Tert-butyl 4-((2-(tert-butyldimethylsilyl)thiazol-4-yl)methyl)-5-((tert-butyldimethylsilyloxy)methyl)-2,2-dimethyloxazolidine-3-carboxylate (0.150 g, 0.269 mmol) in THF (3 mL) was cooled to −78° C. when N-BUTYL-LITHIUM (2.5 M in hexanes) (0.1 19 ml, 0.296 mmol) was added dropwise. The solution was warmed to −50° C. for 40 minutes and then cooled to −78° C. 1-Iodopropane (0.0549 g, 0.323 mmol) was added dropwise and the solution was allowed to slowly warm to −50° C. and stirred for 1 hr. The reaction was quenched with saturated ammonium chloride. The layers were separated and the aqueous layer was extracted with ethyl acetate. The combined organic layers were washed with water, brine and dried over sodium sulfate to afford the title compound, which was used without further purification for the next step.

Step 3: (4S,5S)-tert-butyl 5-(hydroxymethyl)-2,2-dimethyl-4-((5-propylthiazol-4-yl)methyl)oxazolidine-3-carboxylate (4S,5S)-Tert-butyl 4-((2-(tert-butyldimethylsilyl)-5-propylthiazol-4-yl)methyl)-5-((tert-butyldimethylsilyloxy)methyl)-2,2-dimethyloxazolidine-3-carboxylate was dissolved in THF (3 mL) and cooled to 0° C. when TBAF (0.808 ml, 0.808 mmol) was added. The reaction was stirred one hour before being quenched with saturated ammonium chloride. The layers were separated and the aqueous layer was extracted with EtOAc. The combined organic layers were washed with water, brine and dried over sodium sulfate to afford the title compound.

Example 475

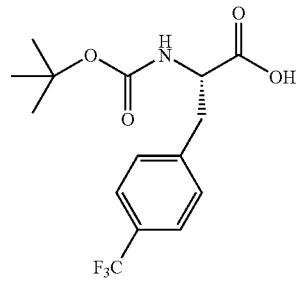

Step 1: (S)-methyl 2-(tert-butoxycarbonyl)-3-(4-(trifluoromethyl)phenyl)propanoate Iodine (0.0140 g, 0.0553 mmol) was added to zinc (0.542 g, 8.29 mmol) and the solid mixture was heated under vacuum for 10 minutes. The flask was flushed with nitrogen three times and allowed to cool. DMF (0.5 mL, degassed with nitrogen) was added and the suspension was cooled to 0° C. and stirred while (R)-methyl 2-(tert-butoxycarbonyl)-3-iodopropanoate (1.82 g, 5.53 mmol) in DMF (2.8 mL) was added dropwise. The mixture was stirred for 30 minutes at 0° C. and then allowed to come to RT for 30 minutes. 1-Iodo-4-(trifluoromethyl)benzene (1.50 g, 5.53 mmol), tris(dibenzylideneacetone)dipalladium (0.101 g, 0.111 mmol), and dicyclohexylphosphino-2',6'-dimethoxy-1,1'-biphenyl (S-Phos) (0.182 g, 0.442 mmol) were added. The flask was purged with nitrogen and heated at 40° C. After 3 hours the reaction was allowed to cool and partitioned between EtOAc and an aqueous solution of ~9:1 saturated ammonium chloride/ammonium hydroxide. The aqueous layer was extracted with EtOAc and the combined organic layers were washed with water, brine, and dried over sodium sulfate. Concentration and purification by silica gel chromatography (6:1 Hexanes/EtOAc) afforded (S)-methyl 2-(tert-butoxycarbonyl)-3-(4-(trifluoromethyl)phenyl)propanoate.

Step 2: (S)-2-(tert-butoxycarbonyl)-3-(4-(trifluoromethyl)phenyl)propanoic acid (S)-Methyl 2-(tert-butoxycarbonyl)-3-(4-(trifluoromethyl)phenyl)propanoate (6.20 g, 17.9 mmol) was dissolved in THF (180 mL) and cooled to 0° C. A 0.2 M of aq. LiOH (89.3 ml, 17.9 mmol) was added dropwise and stirred 20 minutes before TLC analysis (2:1 Hexanes/EtOAc) showed no starting material. The PH of the reaction was carefully adjusted to PH=8 with 1 N HCl. The aqueous layer was washed with diethyl ether and the organics were back extracted with 1% aqueous sodium bicarbonate and the combined aqueous layers were carefully brought to a PH =4 and extracted with EtOAc. The combined organic layers were washed with brine, dried over sodium sulfate, and concentrated to afford (S)-2-(tert-butoxycarbonyl)-3-(4-(trifluoromethyl)phenyl)propanoic acid, which was used without further purification.

Example 476

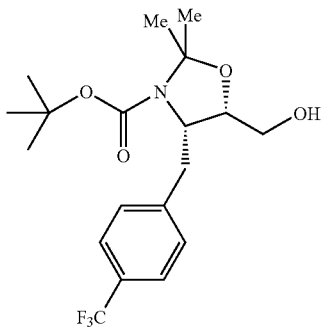

(4S,5S)-tert-butyl 4-(4-(trifluoromethyl)benzyl)-5-(hydroxymethyl)-2,2-dimethyloxazolidine-3-carboxylate The title compound was prepared according to the procedures described herein in Example 472.

Example 477

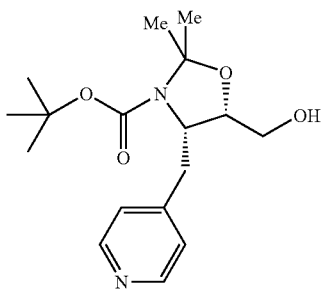

(4S,5S)-tert-butyl 5-(hydroxymethyl)-2,2-dimethyl-4-(pyridin-4-ylmethyl)oxazolidine-3-carboxylate The title compound was prepared according to the procedures described herein in Example 472.

Example 478

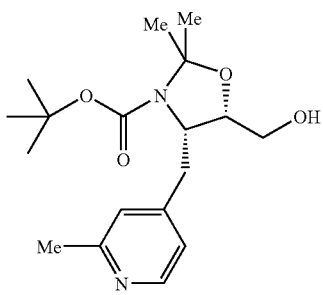

(4S,5S)-tert-butyl 5(hydroxymethyl)-2,2-dimethyl-4-((2-methylpyridin-4-yl)methyl)oxazolidine-3-carboxylate Step 1: (4S,5S)-tert-butyl 5-((tert-butyldimethylsilyloxy)methyl)-2,2-dimethyl-4-(pyridin-4-ylmethyl)oxazolidine-3-carboxylate The title compound was synthesized in manner analogous to that described in Example 472, using (4S,5S)-tert-butyl 5-(hydroxymethyl)-2,2-dimethyl-4-(pyridin-4-ylmethyl)oxazolidine-3-carboxylate in the presence of TBSCl and imidazole, and was used without further purification.

Step 2: (4S,5S)-tert-butyl 5-((tert-butyldimethylsilyloxy)methyl)-2,2-dimethyl-4-((2-methylpyridin-4-yl)methyl)oxazolidine-3-carboxylate (4S,5S)-Tert-butyl 5-((tert-butyldimethylsilyloxy)methyl)-2,2-dimethyl-4-(pyridin-4-ylmethyl)oxazolidine-3-carboxylate (0.150 g, 0.344 mmol) was dissolved in THF (3.5 mL) and cooled to 0° C. Acetyl chloride (0.0256 ml, 0.361 mmol) was added and the reaction was stirred 30 minutes before METHYLMAGNESIUM BROMIDE (0.294 ml, 0.412 mmol) was added. The reaction was stirred 1 hr. at 0° C. and then warmed to RT and quenched with saturated ammonium chloride and diluted with EtOAc and water. The layers were separated and the aqueous layer was extracted with EtOAc. The combined organic layers were washed with a 9:1 aqueous solution of saturated ammonium chloride/ammonium hydroxide, water, brine, and dried over sodium sulfate. The crude product was dissolved in isopropylacetate (4 mL) and heated to 50° C. before DDQ (0.117 g, 0.515 mmol) was added. After 30 minutes the reaction was cooled and diluted with ethyl acetate and washed twice with saturated sodium bicarbonate, once with water, brine, and dried over sodium sulfate. The mixture was passed through a plug of silica gel with 2:1 Hexanes/EtOAc and concentrated to afford the title compound, MS m/z: 451.3(100%, M+1)).

Step 3: (4S,5S)-tert-butyl 5-(hydroxymethyl)-2,2-dimethyl-4-((2-methylpyridin-4-yl)methyl)oxazolidine-3-carboxylate (4S,5S)-Tert-butyl 5-((tert-butyldimethylsilyloxy)methyl)-2,2-dimethyl-4-((2-methylpyridin-4-yl)methyl)oxazolidine-3-carboxylate (0.083 g, 0.18 mmol) was dissolved in THF (2 mL) and cooled to 0° C. Next, TBAF (0.28 ml, 0.28 mmol) was added dropwise and the reaction was stirred 1 hr. and then quenched with saturated ammonium chloride and diluted with ethyl acetate. The layers were separated and the aqueous layer was extracted with EtOAc. The combined organic layers were washed with water, brine, dried over sodium sulfate, and concentrated. Purification by column chromatography (19:1 DCM/MeOH) afforded the title compound, MS m/z: 337.2 (100%, M+1).

Example 479

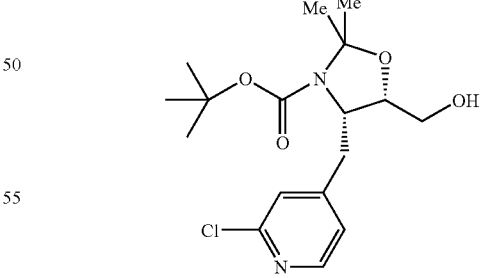

(4S,5S)-tert-butyl 4-((2-chloropyridin-4-yl)methyl)-5-(hydroxymethyl)-2,2-dimethyloxazolidine-3-carboxylate The title compound was prepared according to the procedures described herein in Example 478, from (S)-2-(tert-butoxycarbonyl)-3-(2-chloropyridin-4-yl)propanoic acid.

Example 480

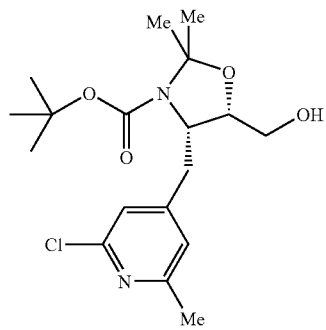

Step 1: (4S,5S)-Tert-butyl 5-((tert-butyldimethylsilyloxy)methyl)-4-((2-chloropyridin-4-yl)methyl)-2,2-dimethyloxazolidine-3-carboxylate. The title compound was synthesized in a manner analogous to Example 475, step I via (4S,5S)-tert-butyl 4-((2-chloropyridin-4-yl)methyl)-5-(hydroxymethyl)-2,2-dimethyloxazolidine-3-carboxylate in the presence of TBSCl and imidazole and was used without further purification.

Step 2: (4S,5S)-tert-butyl 5-((tert-butyldimethylsilyloxy)methyl)-4-((2-chloro-6-methylpyridin-4-yl)methyl)-2,2-dimethyloxazolidine-3-carboxylate Dimethylethanolamine (0.128 ml, 1.27 mmol) was added to anhydrous hexanes (1.4 L) and cooled to 0° C. N-BUTYL-LITHIUM (2.5 M in hexanes)(1.02 ml, 2.55 mmol) was added dropwise and stirred for 30 minutes before being cooled to −78° C. (4S,5S)-Tert-butyl 5-((tert-butyldimethylsilyloxy)methyl)-4-((2-chloropyridin-4-yl)methyl)-2,2-dimethyloxazolidine-3-carboxylate (0.200 g, 0.425 mmol) in hexanes (1 mL) was added dropwise and the solution was stirred for 1 hour at −78° C. to give a dark orange solution. MeI (0.106 ml, 1.70 mmol) in THF (3.2 mL) was added dropwise and the reaction was allowed to slowly warm to 0° C. and was quenched with saturated aqueous ammonium chloride. The reaction was diluted with ethyl acetate and water and separated. The aqueous layer was extracted with ethyl acetate and the combined organic layers were washed with water, brine, dried over sodium sulfate, and concentrated to give the titled compound which was used directly for the next step without purification.

Step 3: (4S,5S)-tert-butyl 4-((2-chloro-6-methylpyridin-4-yl)methyl)-5-(hydroxymethyl)-2,2-dimethyloxazolidine-3-carboxylate (4S,5S)-Tert-butyl 5-((tert-butyldimethylsilyloxy)methyl)-4-((2-chloro-6-methylpyridin-4-yl)methyl)-2,2-dimethyloxazolidine-3-carboxylate (0.206 g, 0.425 mmol) was dissolved in THF (4 mL) and cooled to 0° C. TBAF (0.637 ml, 0.637 mmol) was added to the mixture dropwise and the reaction was stirred 1 hr and then quenched with saturated ammonium chloride and diluted with EtOAc. The layers were separated and the aqueous layer was extracted with EtOAc. The combined organic layers were washed with water, brine, dried over sodium sulfate, and concentrated. The crude material was purified by silica column chromatography (19:1 DCM/MeOH) and then reverse phase HPLC to give the title compound. MS m/z: 371.3 (100%, M+1).

Example 481

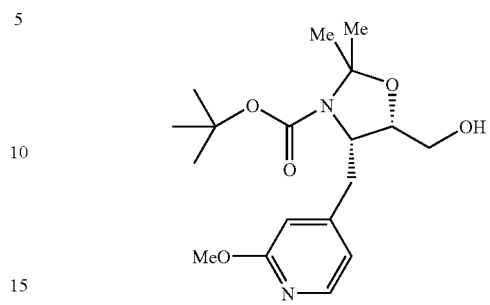

(4S,5S)-tert-butyl 5-(hydroxymethyl)-4-((2-methoxypyridin-4-yl)methyl)-2,2-dimethyloxazolidine-3-carboxylate (4S,5S)-Tert-butyl 4-((2-chloropyridin-4-yl)methyl)-5-(hydroxymethyl)-2,2-dimethyloxazolidine-3-carboxylate (0.200 g, 0.560 mmol) was dissolved in a 25% solution of SODIUM METHOXIDE (12.8 ml, 56.0 mmol) in methanol and refluxed for 12 hrs and cooled. The reaction was diluted with water and extracted with EtOAc. The combined organic layers were washed with water, brine, dried over sodium sulfate and concentrated to give (4S,5S)-tert-butyl 5-(hydroxymethyl)-4-((2-methoxypyridin-4-yl)methyl)-2,2-dimethyloxazolidine-3-carboxylate, MS m/z: 353.3 (100%, M+1).

Example 482

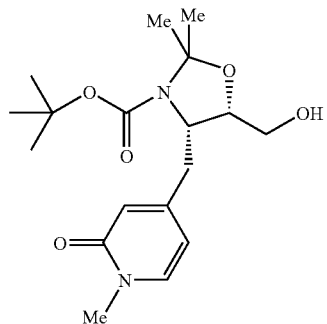

(4S,5S)-tert-butyl 5-(hydroxymethyl)-2,2-dimethyl-4-((1-methyl-2-oxo-1,2-dihydropyridin-4-yl)methyl)oxazolidine-3-carboxylate (4S,5S)-Tert-butyl 5-(hydroxymethyl)-4-((2-methoxypyridin-4-yl)methyl)-2,2-dimethyloxazolidine-3-carboxylate (0.281 g, 0.797 mmol) was refluxed in methanol (17 mL) with MeI (0.0798 ml, 1.28 mmol) for 48 hrs. Concentration and purification by silica gel chromatography (20:1 DCM/MeOH) afforded the titled compound along with recovered starting material.

Example 483

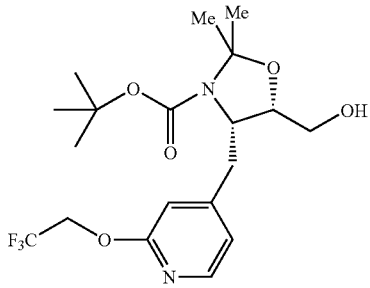

(4S,5S)-tert-butyl 5-(hydroxymethyl)-2,2-dimethyl-4-((2-(2,2,2-trifluoroethoxy)pyridin-4-yl)methyl)oxazolidine-3-carboxylate NaH (60% by weight in mineral oil) (0.672 g, 16.8 mmol) was added carefully to trifluoroethanol (20.0 ml, 276 mmol) cooled at 0° C. and then stirred at RT for 30 minutes.

The resulting solution is added to (4S,55)-tert-butyl 4-((2-chloropyridin-4-yl)methyl)-5-(hydroxymethyl)-2,2-dimethyloxazolidine-3-carboxylate (0.400 g, 1.12 mmol) dissolved in 10 mL of NMP and the resulting solution was microwaved for 30 minutes fixed at 180° C. The reaction was diluted with EtOAc and washed repeatedly with water. The combined aqueous layers were back extracted with EtOAc and the combined organic layers were washed with water, brine, dried over sodium sulfate and concentrated. The product was purified by silica gel chromatography (2:1 to 1:I Hexanes/EtOAc) to afford the title compound. MS m/z: 421.3 (100%, M+1).

Example 484

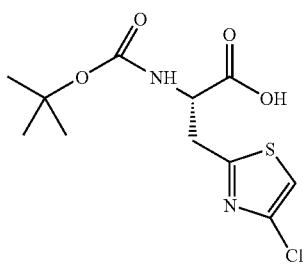

(S)-methyl 2-(tert-butoxycarbonyl)-3-(4-chlorothiazol-2-yl)propanoate

The title compound was synthesized in a manner analogous to that described Example 475, using (R)-methyl 2-(tert-butoxycarbonyl)-3-iodopropanoate and 2,4-dichlorothiazole (prepared according to Reynaud, Pierre; Robba, Max; Moreau, Robert C; New synthesis of the thiazole ring; *Bulletin de la Societe Chimique de France* (1962), 1735-8). MS m/z: 321 (23%, M+1), 265.0 (100%, M−55.1).

Example 485

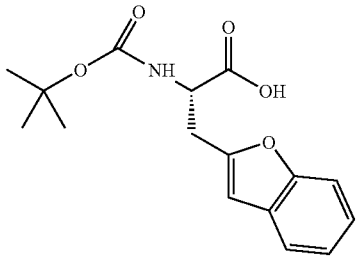

(S)-methyl 3-(benzofuran-2-yl)-2-(tert-butoxycarbonyl)propanoate

The title compound was synthesized in a manner analogous to that described Example 475, using(R)-methyl 2-(tert-butoxycarbonyl)-3-iodopropanoate and 2-bromobenzofuran. (MS m/z: 220.1 (100%, M−99).

Example 486

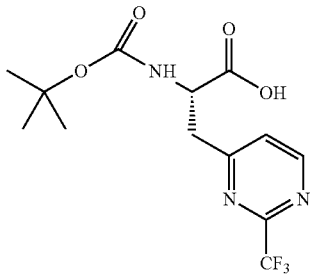

(S)-methyl 2-(tert-butoxycarbonyl)-3-(2-(trifluoromethyl)pyrimidin-4-yl)propanoate The title compound was synthesized in a manner analogous to that described Example 475, using(R)-methyl 2-(tert-butoxycarbonyl)-3-iodopropanoate and 4-chloro-2-(trifluoromethyl)pyrimidine.

Example 487

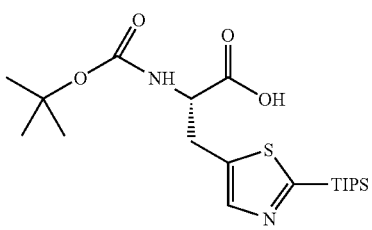

(S)-methyl 2-(tert-butoxycarbonyl)-3-(2-(triisopropylsilyl)thiazol-5-yl)propanoate The title compound was synthesized in a manner analogous to that described Example 475, using (R)-methyl 2-(tert-butoxycarbonyl)-3-iodopropanoate and 5-bromo-2-(triisopropylsilyl)thiazole (prepared according to Stangeland, Eric L.; Sammakia, Tarek, Use of Thiazoles in the Halogen Dance Reaction: Application to the Total Synthesis of WS75624 B, *Journal of Organic Chemistry* (2004), 69(7), 2381-2385.). MS m/z: 443.3 (100%, M+1).

Example 488

N-((1R,2S)-3-(((4'S)-6'-(2,2-dimethylpropyl)-3',4'-dihydrospiro[cyclobutane-1,2'-pyrano[2,3-b]pyridin-]4'-yl)amino)-2-hydroxy-1-(4pyridinylmethyl) propyl)acetamide This compound was isolated as a minor diastereomer by product following the final step in the synthesis of N-((1S,2R)-3-(((4'S)-6'-(2,2-dimethylpropyl)-3',4'-dihydro spiro [cyclobutane-1,2'-pyrano[2,3-b]pyridin]-4'-yl)amino)-2-hydroxy-1-(4-pyridinylmethyl)propyl)acetamide.

Example 489

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-oxo-1,2-dihydro-4-pyridinyl)methyl)propyl)acetamide N-((1S,2R)-3-(((4'S)-6'-(2,2-Dimethylpropyl)-3',4'-dihydrospiro[cyclobutane-1,2'-pyrano[2,3-b]pyridin]-4'-yl) amino)-2-hydroxy-1-((2-(methyloxy)-4-pyridinyl)methyl) propyl)acetamide (0.150 g, 0.302 mmol) and NaI (0.679 g, 4.53 mmol) were refluxed in HOAc (3 mL). After three hours the reaction was concentrated and dissolved in chloroform. The organic layers were washed with 1N NaOH, aqueous sodium thiosulfate, and brine. The organic layer was concentrated and purified directly by reverse-phase HPLC to afford the title product as a TFA salt. MS m/z: 483.3 (100%, M+1).

Example 490

N-((1S,2R)-1-((4-chlorophenyl)methyl)-3-(((4'S)-6'-(2-cyano-2-methylpropyl)-3',4'-dihydrospiro[cyclobutane-1,2'-pyrano[2,3-b]pyridin]-4'-yl)amino)-2-hydroxypropyl)acetamide Step 1: (S)-tert-butyl 6-bromo-2,2-spirocyclobutyl-3,4-dihydro-2H-pyrano[2,3-b]pyridin-4-ylcarbamate Triethylamine (3.74 ml, 26.8 mmol) and BOC-Anhydride (5.07 g, 23.2 mmol) were added to (S)-6-bromo-2,2-spirocyclobutyl-3,4-dihydro-2H-pyrano[2,3-b]pyridin-4-amine (4.81 g, 17.9 mmol) in DCM (50 mL) and the reaction was allowed to stir at RT until TLC analysis (20:1 DCM/MeOH) demonstrated the reaction to be complete (12 hrs). The reaction mixture was concentrated and the crude material was taken up in EtOAc, washed twice with saturated ammonium chloride, water, brine, and concentrated. The product was purified by a short column of silica gel (10:1 hexanes/EtOAC to 4:1 Hexanes/EtOAC) to afford the titled product.

Step 2: (S)-tert-butyl allyl(6-bromo-2,2-spirocyclobutyl-3,4-dihydro-2H-pyrano[2,3-b]pyridin-4-yl)carbamate (S)-Tert-butyl 6-bromo-2,2-spirocyclobutyl-3,4-dihydro-2H-pyrano[2,3-b]pyridin-4-ylcarbamate was dissolved in DMF (60 mL) and cooled to 0° C. NaH (60% by weight in mineral oil)(0.858 g, 21.4 mmol) was carefully added and the solution was allowed to stir for 40 minutes. ALLYL BROMIDE (1.62 ml, 18.8 mmol) was added and the reaction was stirred 45 minutes and then diluted with saturated ammonium chloride. Water was added and the solution was extracted with diethyl ether. The combined organic layers were washed with water, brine, dried over magnesium sulfate, and concentrated. The crude product was used without further purification. MS m/z: 409.1(100%, M).

Step 3: (S)-tert-butyl allyl(6-(hydroxymethyl)-2,2-spirocyclobutyl-3,4-dihydro-2H-pyrano[2,3-b]pyridin-4-yl)carbamate (S)-Tert-butyl allyl(6-bromo-2,2-spirocyclobutyl-3,4-dihydro-2H-pyrano[2,3-b]pyridin-4-yl)carbamate (7.02 g, 17.2 mmol) was dissolved in THF (100 mL) and cooled to −78° C. n-Butyllithium (2.5 M in hexanes) (8.23 ml, 20.6 mmol) was added dropwise to give a dark orange solution. After 30 minutes, DMF (14.5 ml, 189 mmol) was added and the solution was stirred 45 minutes before being quenched by addition of saturated ammonium chloride and water. The aqueous solution was extracted with EtOAc and the combined organic layers were washed with water, brine, dried over sodium sulfate and concentrated to afford (S)-tert-butyl allyl(6-formyl-2,2-spirocyclobutyl-3,4-dihydro-2H-pyrano[2,3-b]pyridin-4-yl)carbamate as the product which was used in the next step without further purification. MS m/z: 359.2 (100%, M+1).

The crude material was dissolved in 80 mL of methanol and cooled to 0° C. when sodium tetrahydroborate (1.62 g, 42.9 mmol) was added. After stirring 40 minutes the reaction was quenched by addition of saturated ammonium chloride and water. The aqueous solution was extracted with ethyl acetate and the combined organic layers were washed with water, brine, dried over sodium sulfate and concentrated. The product was purified by column chromatography (1:1 Hex/EtOAc to EtOAc) to give the titled compound.

Step 4: (S)-tert-butyl allyl(6-(2-cyano-2-methylpropyl)-2,2-spirocyclobutyl-3,4-dihydro-2H-pyrano[2,3-b]pyridin-4-yl)carbamate (S)-Tert-butyl allyl(6-(hydroxymethyl)-2,2-spirocyclobutyl-3,4-dihydro-2H-pyrano[2,3-b]pyridin-4-yl)carbamate (1.45 g, 4.02 mmol) in DCM (40 mL) was added to a solution of dibromotriphenylphosphorane (1.87 g, 4.43 mmol) in DCM (40 mL) at ambient temperature. After stirring 45 minutes the reaction was concentrated and the crude product, (S)-tert-butyl allyl(6-(bromomethyl)-2,2-spirocyclobutyl-3,4-dihydro-2H-pyrano[2,3-b]pyridin-4-yl)carbamate taken up in THF (40 mL). In a separate flask, diisopropylamine (3.58 ml, 25.3 mmol) was added to THF (100 mL) and the solution was cooled to −78° C. n-Butyllithium (2.5 M in hexanes)(9.65 ml, 24.1 mmol) was added and the solution was stirred 20 minutes at 0° C. Isobutyronitrile (2.17 ml, 24.1 mmol) was added and the yellow solution was stirred 30 minutes at 0° C. before the intermediate (S)-tert-butyl allyl (6-(bromomethyl)-2,2-spirocyclobutyl-3,4-dihydro-2H-pyrano[2,3-b]pyridin-4-yl)carbamate in THF (40 mL) was added dropwise. The reaction was stirred at 0° C. and after 1 hour 30 mL of a stock solution of isobutyronitrile enolate (prepared in the identical manner from the same amounts of diisopropylamine, n-butyllithium, isobutyronitrile as above in THF (70 mL)) was added to the reaction. After ten minutes, the reaction was quenched with saturated ammonium chloride and extracted with EtOAc. The combined organic layers were washed with water, brine, and dried over sodium sulfate. Concentration and purification by silica gel column (1.5:1 Hex/EtOAc) afforded the titled compound. MS m/z: 412.3 (100%, M+1).

Step 5: (S)-3-(4-amino-2,2-spirocyclobutyl-3,4-dihydro-2H-pyrano[2,3-b]pyridin-6-yl)-2,2-dimethylpropanenitrile (S)-Tert-butyl allyl(6-(2-cyano-2-methylpropyl)-2,2-spirocyclobutyl-3,4-dihydro-2H-pyrano[2,3-b]pyridin-4-yl) carbamate (0.100 g, 0.24 mmol) was stirred in DCM (2 mL) with TFA (1.0 ml, 13 mmol). After 3 hrs the reaction was concentrated. The crude product was taken up in DCM and 10% aqueous sodium carbonate and the layers were separated. The aqueous layer was extracted with DCM and the combined organic layers were washed with brine, dried over sodium sulfate and concentrated to afford (S)-3-(4-(allylamino)-2,2-spirocyclobutyl-3,4-dihydro-2H-pyrano[2,3-b]pyridin-6-yl)-2,2-dimethylpropanenitrile. The crude product was used without further purification. MS m/z: 312.2 (100%, M+1).

The crude product was dissolved in degassed (N2) DCM (2 mL) and 1,3-dimethylbarbituric acid (0.11 g, 0.73 mmol) was added. After two minutes, tetrakis(triphenylphosphine)palladium(0) (0.014 g, 0.012 mmol) was added and the reaction was stirred at 35° C. for 3 hours. The reaction was diluted with DCM and 10% aqueous sodium carbonate and the layers were separated. The aqueous layer was extracted with DCM and the combined organic layers were washed with brine, dried over sodium sulfate and concentrated. The crude product was purified by silica gel chromatography (20:1 DCM/MeOH) to afford the titled compound. m/z: 272.2 (M+1).

Step 6: N-((1S,2R)-1-((4-chlorophenyl)methyl)-3-(((4'S)-6'-(2-cyano-2-methylpropyl)-3',4'-dihydrospiro[cyclobutane-1,2'-pyrano[2,3-b]pyridin]-4'-yl)amino)-2-hydroxypropyl)acetamide The title compound was prepared by a method analogous to that described in Example 464, steps 8-10. MS Found m/z: 511.2 (M+1)

Example 491

N-((1S,2R)-((4-chlorophenyl)methyl)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-2-hydroxypropyl)acetamide Step 1: (S)-tert-butyl allyl(6-(2,2-spirocyclobutyl-3-oxopropyl)-2,2-dimethyl-3,4-dihydro-2H-pyrano[2,3-b]pyridin-4-yl)carbamate (S)-tert-butyl allyl(6-(2-cyano-2-methylpropyl)-2,2-spirocyclobutyl-3,4-dihydro-2H-pyrano[2,3-b]pyridin-4-yl)carbamate (0.708 g, 1.72 mmol) was dissolved in toluene (12 mL) and cooled to 0° C. DIBAL, 1.0 M solution in hexanes (5.08 ml, 5.08 mmol) was added dropwise and the reaction was stirred for 1 hour. The reaction was quenched with 1 N HCl and diluted with a saturated aqueous sodium potassium tartrate solution and vigorously stirred for 3 hours. The layers were separated and the aqueous layer was extracted with EtOAc and the combined organic layers were washed with water, brine, and dried over sodium sulfate. The crude product was purified by silica gel chromatography (2:1 Hexanes/EtOAc) to afford the titled compound.

Step 2: (S)-tert-butyl allyl(6-(3,3-difluoro-2,2-dimethylpropyl)-2,2-spirocyclobutyl-3,4-dihydro-2H-pyrano[2,3-b]pyridin-4-yl)carbamate (S)-Tert-butyl allyl(6-(2,2-spirocyclobutyl-3-oxopropyl)-2,2-dimethyl-3,4-dihydro-2H-pyrano[2,3-b]pyridin-4-yl)carbamate (0.196 g, 0.473 mmol) was dissolved in DCM (1.5 mL) and cooled to −78° C. DAST (0.150 ml, 1.13 mmol) was added and the reaction was slowly warmed to RT and stirred for 12 hrs. The reaction was carefully quenched with 10% aqueous sodium carbonate and diluted with DCM. The aqueous layer was extracted with DCM and the combined organic layers were washed with water, brine, and dried over sodium sulfate. The crude product was used directly for the next step without further purification.

Step 3: N-((1S,2R)-1-((4-chlorophenyl)methyl)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-2-hydroxypropyl)acetamide The title compound was prepared in a manner analogous to that described in Example 490 Step 5 and Step 6. MS Found m/z: 536.2 (M+1).

Example 492

N-((1S,2R)-,-((4-chlorophenyl)methyl)-3-(((4'S)-6'-(2,2-dimethyl-3-butyn-1-yl)-3',4'-dihydrospiro[cyclobutane-1,2'-pyrano[2,3-b]pyridin]-4'-yl)amino)-2-hydroxypropyl)acetamide Step 1: (S)-tert-butyl allyl(6-(2,2-dimethylbut-3-ynyl)-2,2-spirocyclobutyl-3,4-dihydro-2H-pyrano[2,3-b]pyridin-4-yl)carbamate Potassium carbonate (0.155 g, 1.12 mmol) was added to a solution of (S)-tert-butyl allyl(6-(2,2-spirocyclobutyl-3-oxopropyl)-2,2-dimethyl-3,4-dihydro-2H-pyrano[2,3-b]pyridin-4-yl)carbamate (0.233 g, 0.562 mmol) and Ohira's Reagent (0.130 g, 0.674 mmol) in MeOH (6 mL). After stirring 15 hrs, the reaction was diluted with 10% sodium carbonate and extracted with EtOAc. The combined organic layers were washed with water, brine, dried over sodium sulfate, and concentrated. The product obtained was taken on without further purification. MS m/z: 411.3 (M+1).

Step 2: N-((1S,2R)-1-((4-chlorophenyl)methyl)-3-(((4'S)-6'-(2,2-dimethyl-3-butyn-1-yl)-3',4'-dihydrospiro[cyclobutane-12'-pyrano[2,3-b]pyridin]-4'-yl)amino)-2-hydroxypropyl)acetamide The title compound was synthesized in analogous manner according to procedures described for Example 491, Step 3 and purified by column chromatography (20:1 DCM/MeOH). MS Found m/z: 510.2 (M+1).

Example 493

N-((1S,2R)-1-((4-chlorophenyl)methyl)-3-(((4'S)-6'-(2,2-dimethylbutyl)-3',4'-dihydrospiro[cyclobutane-1,2'-pyrano[2,3-b]pyridin]-4'-yl)amino)-2-hydroxypropyl)acetamide The compound of Example 492 (0.100 g, 0.196 mmol) was dissolved in MeOH (2 mL) and diazenedicarboxylic acid, dipotassium salt (0.762 g, 3.92 mmol) was added. HOAc (0.673 ml, 11.8 mmol) in MeOH (2 mL) was slowly added to the heterogeneous solution and the reaction was stirred. After all the acetic acid was added and the solution went from yellow to clear and upon complete reduction, the reaction was concentrated and partitioned between 1 N NaOH and DCM. The aqueous was layer was extracted with DCM and the combined organics were washed with brine and concentrated. The crude material was dissolved in a minimal amount of MeOH and directly purified by reverse phase HPLC to afford the title compound. MS 7m/z: 514.2 (M+1).

Example 494

N-((1S,2R)-3-(((4'S)-6'-(2,2-dimethylpropyl)-7'-fluoro-3',4'-dihydrospiro[cyclobutane-1,2'-pyrano[2,3-b]pyridin]-4'-yl)amino)-2-hydroxy-1-(phenylmethyl)propyl)acetamide Step 1: 2,6-difluoro-3-neopentylpyridine To a 500 mL RBF was added neopentylmagnesium chloride, 111.0M in ether (28.0 ml, 28 mmol) and an ice bath.

After cooling, zinc(II) chloride, 0.5M in THF (56.0 ml, 28 mmol) was added dropwise. The cooling bath was removed and after stirring for 45 minutes, Reactant 1 (0.26 g, 0.32 mmol) was added followed by 2,6-difluoro-3-iodopyridine (2.74 g, 8.0 mmol) in THF (10 mL), which was added dropwise. The yellow solution was then heated to 60° C. After stirring overnight the reaction was allowed to cool and sat'd. $NH_4Cl$ was added cautiously. The reaction mixture was partitioned between EtOAc/Water. The aqueous layer was extracted with EtOAc (50 mL) and the combined organic layers washed with brine and concentrated in vacuo. The crude product was adsorbed onto a plug of silica gel and chromatographed through a Redi-Sep® pre-packed silica gel column (40 g), eluting with 1% EtOAc in hexane, to provide 2,6-difluoro-3-neopentylpyridine as a colorless oil. MS m/z: 186 (M+1).

Step 2: N-((S)-2-(1-(tert-butyldimethylsilyloxy)cyclobutyl)-1-(2,6-difluoro-5-neopentlipyridin-3-yl)ethyl)-2-methylpropane-2-sulfinamide To a three-necked RBF was added 2,2,6,6-tetramethylpiperidine (0.34 ml, 2 mmol), THF (10 mL), and an ethanol/$N_2$ bath. After cooling to −78° C., butyllithium (0.70 ml, 2 mmol) was added dropwise. After stirring for several minutes, the solution was cooled to −100° C. of 2,6-difluoro-3-neopentylpyridine (0.230 g, 1 mmol) in THF (2 mL) was added dropwise. The solution was then treated with (R,E)-N-(2-(1-(tert-butyldimethylsilyloxy)cyclobutyl)ethylidene)-2-methylpropane-2-sulfinamide (0.71 g, 2 mmol) in THF (3 mL). After the addition was complete the reaction was allowed to warm to 0° C. as the liquid $N_2$ boiled off. The reaction was then quenched with water (10 mL) and extracted with EtOAc (3×20 mL). The combined organic layers were concentrated in vacuo and adsorbed onto a plug of silica gel and chromatographed through a Redi-Sep® pre-packed silica gel column (12 g), eluting with 1% to 20% EtOAc in hexane, to provide N-((S)-2-(1-(tert-butyldimethylsilyloxy)cyclobutyl)-1-(2,6-difluoro-5-neopentylpyridin-3-yl)ethyl)-2-methylpropane-2-sulfinamide (0.07 g, 11% yield). This material was used without further purification in the next step. MS m/z: 517 (M+1).

Step 3: N-((S)-7-fluoro-2,2-dimethyl-6-neopentyl-3,4-dihydro-2H-pyrano[2,3-b]pyridin-4-yl)-2-methylpropane-2-sulfinamide To a 150 mL RBF was added N-((S)-2-(1-(tert-butyldimethylsilyloxy)cyclobutyl)-1-(2,6-difluoro-5-neopentylpyridin-3-yl)ethyl)-2-methylpropane-2-sulfinamide (0.070 g, 0.14 mmol), THF (3 mL), and TBAF, 1M in THF (0.14 ml, 0.14 mmol). The reaction was stirred at RT. After 20 minutes, the reaction was eluted through a plug of silica gel with THF. The resulting filtrate was concentrated in vacuo and taken up in THF (20 mL) and treated with NaH (0.035 g, 0.88 mmol, 60% in mineral oil). The reaction was stirred at 40° C. for 16 hours. The reaction was allowed to cool to RT and quenched with sat'd $NH_4Cl$, and extracted with EtOAc (25 mL). The combined organic layers were concentrated in vacuo to give N-((S)-7-fluoro-2,2-dimethyl-6-neopentyl-3,4-dihydro-2H-pyrano[2,3-b]pyridin-4-yl)-2-methylpropane-2-sulfinamide. This material was carried forward without further purification. MS m/z: 383 (M+1).

Step 4: (S)-7-fluoro-2,2-spirocyclobutane-6-neopentyl-3,4-dihydro-2H-pyrano[2,3-b]pyridin-4-amine To a 500 mL RBF was added N-((S)-7-fluoro-2,2-dimethyl-6-neopentyl-3,4-dihydro-2H-pyrano[2,3-b]pyridin-4-yl)-2-methylpropane-2-sulfinamide (1.71 g, 4.5 mmol), dichloromethane (20 mL), and hydrogen chloride, 4.0M in dioxane (2.00 ml, 8.0 mmol). The reaction was stirred at RT. After 15 hours, the reaction was washed with sat'd $NaHCO_3$ and the organic layer concentrated in vacuo. The resulting crude product was adsorbed onto a plug of silica gel and chromatographed through a Redi-Sep® pre-packed silica gel column (12 g), eluting with 0% to 50% EtOAc in DCM to provide (S)-7-fluoro-2,2-spirocyclobutane-6-neopentyl-3,4-dihydro-2H-pyrano[2,3-b]pyridin-4-amine as a light yellow oil.

Step 5: N-((1S,2R)-3-(((4'S)-6'-(2,2-dimethylpropyl)-7'-fluoro-3',4'-dihydrospiro[cyclobutane-1 2'-pyrano[2,3-b]pyridin]-4'-yl)amino)-2-hydroxy-1-(phenylmethyl)propyl)acetamide The amine from Step 4 was used in a method analogous to that described in Example 464, steps 8-10 to give N-((1S,2R)-3-(((4'S)-6'-(2,2-dimethylpropyl)-7'-fluoro-3',4'-dihydrospiro[cyclobutane-1,2'-pyrano[2,3-b]pyridin]-4'-yl)amino)-2-hydroxy-1-(phenylmethyl)propyl)acetamide as a colorless solid. MS m/z: 484 (M+1).

Example 495

N-((1S,2R)-3-(((4'S)-6'-(1-fluoro-2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide Step 1: N-allyl-N-t-butylcarbamate-(4'S)-6'-(1-hydroxy-2,2-dimethylpropyl)-3' 4'-dihydrospiro[cyclobutane-1 2'-pyrano[2,3-b]pyridin]-4'-amine A solution of N-allyl-N-t-butylcarbamate-(4'S)-6'-(bromo)-3',4'-dihydrospiro[cyclobutane-1,2'-pyrano[2,3-b]pyridin]-4'-amine (4.12 g, 10.1 mmol) in ether (80 mL) was cooled to −78° C. and then t-butyllithium (12.5 ml, 21.3 mmol) was added and stirred for 15 minutes before the pivalaldehyde (3.80 ml, 35.0 mmol) (Note: freshly distilled) was added. After 5 minutes, LC-MS shows the starting material has been consumed. The reaction was quenched with sat'd $NH_4Cl$ and the organic layer separated. The organic layer was combined with previous trial reactions and adsorbed onto a plug of silica gel and chromatographed through a Redi-Sep® pre-packed silica gel column (120 g), eluting with 0% to 30% EtOAc in hexane, to provide N-allyl-N-t-butylcarbamate-(4'S)-6'-(1-hydroxy-2,2-dimethylpropyl)-3',4'-dihydrospiro[cyclobutane-1,2'-pyrano[2,3-b]pyridin]-4'-amine as a yellow oil. MS m/z: 417 (M+1).

Step 2: N-allyl-(4'S)-6'-(1-fluoro-2,2-dimethylpropyl)-3',4'-dihydrospiro[cyclobutane-1,2'-pyrano[2,3-b]pyridin]-4'-amine To a 250 mL RBF was added N-allyl-N-t-butylcarbamate-(4'S)-6'-(1-hydroxy-2,2-dimethylpropyl)-3',4'-dihydrospiro[cyclobutane-1,2'-pyrano[2,3-b]pyridin]-4'-amine (4.01 g, 9.6 mmol), toluene (100 mL), a dry ice bath, and after cooling for 20 minutes DAST (1.81 ml, 14 mmol) was added. After 1 hour, LC-MS shows Reactant 1 consumed. The reaction was quenched with sat'd $NH_4Cl$ (20 mL). The layers were separated and the aqueous layer extracted with EtOAc (20 mL). The combined organic layers were concentrated in vacuo to give a golden oil. The oil was taken up in MeOH (50 mL) and treated with HCl, 4M in dioxane (5.0 ml, 20 mmol). After 1.5 hours, no changes were seen by LC-MS. The reaction was treated with an additional HCl (5 mL) and heated to 60° C. After stirring for 5 hours, the solution was allowed to cool to RT. After a further 16 hours, the reaction was concentrated in vacuo to give a brown oil, which was taken up in DCM and washed with sat'd $NaHCO_3$, brine and concentrated in vacuo to give N-allyl-(4'S)-6'-(1-fluoro-2,2-dimethylpropyl)-3',4'-dihydrospiro[cyclobutane-1,2'-pyrano

[2,3-b]pyridin]-4'-amine (3.15 g) as a brown oil. MS m/z/z: 319 (M+1). The crude material was used without further purification in the next step.

Step 3: (4'S)-6'-(1-fluoro-2,2-dimethylpropyl)-3',4'-dihydrospiro[cyclobutane-1,2'-pyrano[2,3-b]pyridin]-4'-amine To a 250 mL RBF was added N-allyl-(4'S)-6'-(1-fluoro-2,2-dimethylpropyl)-3',4'-dihydrospiro[cyclobutane-1,2'-pyrano[2,3-b]pyridin]-4'-amine (3.10 g, 9.7 mmol), degassed DCM (80 mL), and 1,3-dimethylbarbituric acid (4.58 g, 29 mmol). After stirring for 5 minutes, Palladium Tetrakis (0.56 g, 0.48 mmol) was added and the solution heated to 40° C. After 4 hours, the solution was poured into a separator funnel containing 10% $Na_2CO_3$ (50 mL) and the layers separated. The organic layer was again extracted with 10% $Na_2CO_3$ (50 mL). The combined aqueous layers were back extracted with DCM (50 mL). The combined organic layers were concentrated in vacuo and adsorbed onto a plug of silica gel and chromatographed through a Redi-Sep®V pre-packed silica gel column (80 g), eluting with 50% to 80% EtOAc in hexane, to provide a mixture of product and triphenyl-phosphine oxide. The material was taken up in EtOAc and extracted with HCl (1N, 2×20 mL). The aqueous layer was then neutralized and extracted with EtOAc (2×20 mL). The combined EtOAc layers were concentrated in vacuo to give (4'S)-6'-(1-fluoro-2,2-dimethylpropyl)-3',4'-dihydrospiro[cyclobutane-1,2'-pyrano[2,3-b]pyridin]-4'-amine (1.81 g 69% for step 2 and 3) as a colorless oil. MS m/z: 279 (M+1).

Step 4: N-((1S,2R)-3-(((4'S)-6'-(1-fluoro-2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide The amine from step 3 was reacted in a manner analogous to that described in Example 464, steps 8-10, to give the title compound as a white solid. MS m/z: 502 (M+1).

Example 496

N-((1S,2R)-3-(((4'S)-6'-(cyclopropylmethyl)-3',4'-dihydrospiro[cyclobutane-1,2'-pyrano[2,3-b]pyridin]-4'-yl)amino)-1-((4-fluorophenyl)methyl)-2-hydroxypropyl)acetamide Step 1: (S)-tert-butyl 6-allyl-2,2-spirocyclobutyll-3,4-dihydro-2H-pyrano[2,3-b]pyridin-4-ylcarbamate A mixture of $Pd_2(dba)_3$ (186 mg, 0.203 mmol) tri-t-butylphosphonium tetrafluoroborate (354 mg, 1.22 mmol), cesium fluoride (3.08 g, 4.06 mmol) and (S)-tert-butyl 6-bromo-2,2-spirocyclobutyl-3,4-dihydro-2H-pyrano[2,3-b]pyridin-4-ylcarbamate in 12 mL of dioxane was purged with nitrogen for 30 minutes before being treated with allyltributylstannane (6.23 mL, 20.3 mmol). The mixture was heated to 100° C. for 10 hours at which point the reaction was allowed to cool to room temperature. The mixture was diluted with ethyl acetate (50 mL) and successively washed with saturated potassium fluoride (50 mL), water and brine. Drying over sodium sulfate and concentration provided a residue that was purified by silica gel chromatography (0-25% EtOAc in hexanes) to provide the title compound as light yellow solid. MS m/z: 331.2 (M+1).

Step 2: (S)-6-(cyclopropylmethyl)-2,2-spirocyclobutyl-3,4-dihydro-2H-pyrano[2,3-b]pyridin-4-amine A solution of diethylzinc (1.0 M in hexanes, 9.00 mL, 9.00 mmol) was cooled to −10° C. and treated with TFA (0.70 ml, 9.0 mmol) dropwise over 5 minutes. After an additional 5 minutes diiodomethane (0.70 ml, 9.0 mmol) was added, and the reaction mixture was allowed to stir for 10 minutes. The resulting suspension was treated with a solution of (S)-tert-butyl 6-allyl-2,2-spirocyclobutyl-3,4-dihydro-2H-pyrano[2,3-b]pyridin-4-ylcarbamate (0.580 g, 2.00 mmol) in 10 mL dichloromethane. The reaction mixture was allowed to stir at −10° C. for 30 minutes before being allowed to warm to RT. The suspension was quenched with MeOH and saturated sodium bicarbonate (5 mL) and was allowed to stir for an additional hour. The reaction mixture was then diluted with EtOAc (50 mL) and filtered through a short plug of silica. The filtrate was concentrated and the crude residue was resubmitted to the reaction conditions and allowed to stir at RT overnight. The reaction mixture was quenched with methanol (5 mL) and saturated sodium bicarbonate (5 mL). 6N NaOH (15 mL) was added and the reaction mixture was allowed to stir for one hour before being diluted with DCM (50 mL). The aqueous was extracted with DCM 3×50 mL and the combined organics were washed with brine, dried over magnesium sulfate and concentrated. Purification of the crude residue by reverse phase HPLC provided the title compound as a yellow oil. MS m/z: 245 (M+1).

Step 3: N-((1S,2R)-3-(((4'S)-6'-(cyclopropylmethyl)-3',4'-dihydrospiro[cyclobutane-1,2'-pyrano[2,3-b]pyridin]-4'-yl)amino)-1-((4-fluorophenyl)methyl)-2-hydroxypropyl)acetamide The title compounds made by a method analogous to that described in Example 464, steps 8-10. MS Found m/z: 468 (M+1).

Example 497

N-((1S,2R)-1-((4-Fluorophenyl)methyl)-2-hydroxy-3-(((4'S)-6'-((1-methylcyclopropyl)methyl)-3',4'-dihydrospiro[cyclobutane-1,2'-pyrano[2,3-b]pyridin]-4'-yl)amino)propyl)acetamide Step 1: (S)-tert-butyl 6-(2-methylallyl)-2,2-spirocyclobutyl-3,4-dihydro-2H-pyrano[2,3-b]pyridin-4-ylcarbamate A mixture of $Pd_2(dba)_3$ (133 mg, 0.145 mmol) tri-t-butylphosphonium tetrafluoroborate (252 mg, 0.869 mmol), cesium fluoride (1.32 g, 8.69 mmol) and (S)-tert-butyl 6-bromo-2,2-spirocyclobutyl-3,4-dihydro-2H-pyrano[2,3-b]pyridin-4-ylcarbamate in 3 mL of dioxane was purged with nitrogen for 30 minutes before being treated with tributyl(2-methylallyl)stannane (2.50 g, 7.24 mmol). The mixture was heated to 90° C. for 10 hours at which point the reaction was allowed to cool to RT and diluted with EtOAc (50 mL) and successively washed with saturated potassium fluoride (50 mL), water and brine. Drying over sodium sulfate and concentration provided a residue that was purified by silica gel chromatography (0-25% EtOAc in hexanes) to provide the title compound as light yellow solid. MS m/z: 345 (M+1).

Step 2: (S)-tert-butyl 6-((1-methylcyclopropyl)methyl)-2,2-spirocyclobutyl-3,4-dihydro-2H-pyrano[2,3-b]pyridin-4-ylcarbamate A solution of diethyl zinc (1.0 M, 35.0 mL, 35 mmol) in 20 mL hexanes was cooled to −10° C. and treated with chloroiodomethane (5.00 mL, 65 mmol). After stirring for 30 minutes at this temperature a solution of (S)-tert-butyl 6-(2-methylallyl)-2,2-spirocyclobutyl-3,4-dihydro-2H-pyrano[2,3-b]pyridin-4-ylcarbamate in 20 mL of dichloromethane was added and the reaction was allowed to warm to room temperature where it was maintained for an additional 10 hours. The reaction was quenched with methanol (10 mL) and saturated sodium bicarbonate (3 mL). The slurry was then treated with DIEA (0.80 mL, 4.00 mmol) and di-tert-butyl dicarbonate (1.0 mL, 4.0 mmol) and allowed to stir for 3 hours. The reaction was then diluted with EtOAc (25 mL) and washed successively with saturated sodium bicarbonate (30 mL), water and brine before being dried over magnesium sulfate. Concentration provided a residue that was taken up in 20 mL of DCM and added a solution of diethyl zinc (1.0 M, 35.0 mL, 35 mmol) and chloroiodomethane (5.00 mL, 65 mmol) in 20 mL hexanes at −10° C. The reaction was allowed to warm to RT where it was maintained for an additional 10 hours. The reaction was quenched with methanol (10 mL) and saturated sodium bicarbonate (3 mL). The slurry was then treated with DIEA (0.80 mL, 4.00 mmol) and di-tert-butyl dicarbonate (1.0 mL, 4.0 mmol) and allowed to stir for 3 hours. The reaction was then diluted with EtOAc (50 mL) and washed successively with saturated sodium bicarbonate (50 mL), water and brine before being dried over magnesium sulfate. Concentration and purification by silica gel chromatography (0-50% ethyl acetate in hexanes) provided the title compound as a yellow oil. MS m/z: 359 (M+1).

Step 3: (S)-6-((1-methylcyclopropyl)methyl)-2,2-spirocyclobutyl-3,4-dihydro-2H-pyrano[2,3-b]pyridin-4-amine A solution of (S)-tert-butyl 6-((1-methylcyclopropyl)methyl)-2,2-spirocyclobutyl-3,4-dihydro-2H-pyrano[2,3-b]pyridin-4-ylcarbamate (0.860 g, 2.4 mmol) and 2,6-lutidine (2.80 ml, 24.0 mmol) in 10 mL of DCM was cooled to 0° C. and treated with trimethylsilyl triflate (2.30 ml, 12.0 mmol). The reaction mixture was allowed to warm to RT and stir for 10 hours before being diluted with ethyl acetate (50 mL) and washed with saturated sodium bicarbonate (50 mL) and brine. The combined organics were dried over magnesium sulfate, concentrated and purified reverse phase HPLC to provide the title compound as a yellow oil. MS m/z: 259 (M+1).

Step 4: N-((1S,2R)-1-((4-fluorophenyl)methyl)-2-hydroxy-3-(((4'S)-6'-((1-methylcyclopropyl)methyl)-3',4'-dihydrospiro[cyclobutane-1,2'-pyrano[2,3-b]pyridin]-4'-yl)amino)propyl)acetamide The title compound was made by a method analogous to that described in Example 464, steps 8-10. MS Found m/z: 482 (M+1).

Example 498

N-((1S,2R)-3-(((4'S)-6'-(3,3-difluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide Step 1: Tert-butyl (S)-6-(2-methyl-3-oxopropyl)-2,2-spirocyclobutyl-3,4-dihydro-2H-pyrano[2,3-b]pyridin-4-ylcarbamate A solution of (S)-tert-butyl 6-bromo-2,2-spirocyclobutyl-3,4-dihydro-2H-pyrano[2,3-b]pyridin-4-ylcarbamate (1.500 g, 4.06 mmol), Pd$_2$(dba)$_3$ (0.186 g, 0.203 mmol), tri-t-butylphosphonium tetrafluoroborate (0.354 g, 1.22 mmol), 2-methylprop-2-en-1-ol (1.38 ml, 16.2 mmol), cesium fluoride (0.617 g, 4.06 mmol), and N-cyclohexyl-N-methylcyclohexanamine (5.17 ml, 24.4 mmol) in 8 mL of dioxane, was purged with nitrogen for 30 minutes. The reaction vessel was then sealed and heated to 80° C. for 10 hours. The cooled reaction mixture was quenched with saturated sodium bicarbonate (50 mL), and the aqueous layer was extracted with EtOAc 3×50 mL. The combined organics were washed with brine, dried over sodium sulfate and concentrated. Purification of the crude residue by column chromatography (0-50% EtOAc in hexanes) provided the title compound as a colorless oil. MS m/z: 361 (M+1).

Step 2: Tert-butyl (S)-6-(3,3-difluoro-2-methylpropyl)-2,2-spirocyclobutyl-3,4-dihydro-2H-pyrano[2,3-b]pyridin-4-ylcarbamate A solution of tert-butyl (S)-6-(2-methyl-3-oxopropyl)-2,2-spirocyclobutyl-3,4-dihydro-2H-pyrano[2,3-b]pyridin-4-ylcarbamate (0.270 g, 0.749 mmol) in 1.5 mL of DCM was cooled to −78° C. and treated with DAST (0.218 ml, 1.65 mmol). The reaction mixture was allowed to warm to RT and stir for 8 hours. An additional equivalent of DAST was added, and the reaction mixture was allowed to stir for 2 hours before being diluted with EtOAc (25 mL) and washed with saturated sodium bicarbonate and brine. The organics were dried over magnesium sulfate, concentrated and purified by silica gel chromatography (0-30% EtOAc in hexanes) to furnish the title compound as a yellow oil. MS m/z: 383 (M+1).

Step 3: (4S)-6-(3,3-difluoro-2-methylpropyl)-2,2-spirocyclobutyl-3,4-dihydro-2H-pyrano[2,3-b]pyridin-4-amine A solution of tert-butyl (S)-6-(3,3-difluoro-2-methylpropyl)-2,2-spirocyclobutyl-3,4-dihydro-2H-pyrano[2,3-b]pyridin-4-ylcarbamate (0.110 g, 0.3 mmol) in 2 mL of DCM was treated with HCl (4.0 M in dioxane, 1.50 ml, 6.00 mmol) and was allowed to stir at RT for 10 hours. The reaction mixture was diluted with EtOAc (50 mL) and was washed with 2N NaOH (50 mL) and brine. The organics were dried over magnesium sulfate and concentrated to provide the title compound as a yellow solid. MS m/z: 283 (M+1).

Step 4: N-((1S,2R)-3-(((4'S)-6'-(3,3-difluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide The title compound was made by a method analogous to that described in Example 464, steps 8-10. MS Found m/z: 506 (M+1).

Example 499

N-((1S,2R)-3-(((4'S)-6'-((2S)-3-fluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide; and N-((1S,2R)-3-(((4'S)-6'-((2R)-3-fluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide Step 1: Tert-butyl (S)-6-(3-(tert-butyldimethylsilyloxy)-2-methylpropyl)-2,2-spirocyclobutyl-3,4-dihydro-2H-pyrano[2,3-b]pyridin-4-ylcarbamate Tert-butyldimethyl(2-methylallyloxy)silane was treated with 9-BBN (0.5 M in diethyl ether, 53.0 ml, 26.0 mmol) and the resulting solution was purged with nitrogen for 15 minutes before being allowed to stir at RT for 10 hours. In a separate flask a solution of palladium acetate (100 mg, 0.500 mmol) and SPhos (700 mg, 2.00 mmol) in 2 mL of toluene and 2 mL of THF was purged with nitrogen for 30 minutes and allowed to stir at RT for one hour. The resulting solution was added to the organoborane, followed by potassium phosphate (4.00 g, 21.0 mmol) and a solution of (S)-tert-butyl 6-bromo-2,2-spirocyclobutyl-3,4-dihydro-2H-pyrano[2,3-b]pyridin-4-ylcarbamate (1.95 g, 5.00 mmol) in 15 mL of DMF. The reaction mixture was purged with nitrogen for 15 minutes and heated to 90° C. for 3 hours at which point it was cooled to RT, diluted with EtOAc (50 mL) and filtered through a plug of celite. The filtrate was washed with water, brine, and the organics were dried over sodium sulfate and concentrated. Purification of the crude residue by column chromatography (0-25% EtOAc in hexanes) provided the title compound, contaminated with starting olefin, as a colorless oil.

Step 2: Tert-butyl (S)-6-(3-hydroxy-2-methylpropyl)-2,2-spirocyclobutyl-3,4-dihydro-2H-pyrano[2,3-b]pyridin-4-yl-carbamate A solution of tert-butyl (S)-6-(3-(tert-butyldimethylsilyloxy)-2-methylpropyl)-2,2-spirocyclobutyl-3,4-dihydro-2H-pyrano[2,3-b]pyridin-4-ylcarbamate (2.80 g, 6 mmol) in 20 mL of DCM was treated with tetrabutyl ammonium fluoride (TBAF; 1.0 M in THF, 29.0 ml, 29.0 mmol) and allowed to stir at RT for 3 hours. The reaction mixture was concentrated to reduce the volume by half and it was allowed to stir for an additional hour at which point it was concentrated and the crude residue was purified by column chromatography to furnish the title compound as a white solid. MS m/z: 363 (M+1).

Step 3: 3-((S)-4-(tert-butoxycarbonyl)-2,2-spirocyclobutyl-3,4-dihydro-2H-pyrano[2,3-b]pyridin-6-yl)-2-methylpropyl methanesulfonate A solution of tert-butyl (S)-6-(3-hydroxy-2-methylpropyl)-2,2-spirocyclobutyl-3,4-dihydro-2H-pyrano[2,3-b]pyridin-4-ylcarbamate (0.350 g, 0.97 mmol) in 5 mL of DCM was treated with DIEA (0.340 ml, 1.90 mmol) cooled to 0° C. and exposed to methane sulfonyl chloride (0.082 ml, 1.10 mmol). The reaction mixture was allowed to warm to RT and was maintained at this temperature for one hour before being diluted with EtOAc (50 mL), washed with water and brine and dried over sodium sulfate. Concentration provided the title compound as a white solid. MS m/z: 441 (M+1).

Step 4: (4S)-6-(3-fluoro-2-methylpropyl)-2,2-spirocyclobutyl-3,4-dihydro-2H-pyrano[2,3-b]pyridin-4-amine A solution of 3-((S)-4-(tert-butoxycarbonyl)-2,2-spirocyclobutyl-3,4-dihydro-2H-pyrano[2,3-b]pyridin-6-yl)-2-methylpropyl methanesulfonate (1.200 g, 3.00 mmol) in THF (5 mL) was treated with TBAF (1.0 M in THF, 14.0 ml, 14.0 mmol) and heated to 80° C. for 10 hours. The cooled reaction mixture was diluted with EtOAc (50 mL) and was washed successively with 2N NaOH (25 mL) and brine. The organics were dried over sodium sulfate, filtered and concentrated to provide a residue that was purified by reverse phase HPLC to provide the title compound a yellow oil. MS m/z: 265 (M+1).

Step 5: N-((1S,2R)-3-(((4'S)-6'-((2S)-3-fluoro-2-methylpropyl)-3',4'-dihydrospiro[cyclobutane-12'-pyrano[2,3-b]pyridin]-4'-yl)amino)-1-((4-fluorophenyl)methyl)-2-hydroxypropyl)acetamide: and N-((1S,2R)-3-(((4'S)-6'-((2R)-3-fluoro-2-methylpropyl)-3',4'-dihydrospiro[cyclobutane-12'-pyrano[2,3-b]pyridin]-4'-yl)amino)-1-((4-fluorophenyl)methyl)-2-hydroxypropyl)acetamide The title compounds were made by a method analogous to that described in Example 464, steps 8-10. MS Found m/z: 488 (M+1).

Example 500

N-((1S,2R)-3-(((4S)-6-(2,2-dimethylpropyl)-2,2-dimethyl-1,2,3,4-tetrahydro-4-quinolinyl)amino)-1-((3-fluorophenyl)methyl)-2-hydroxypropyl)acetamide Step 1: 4-bromo-N-(2-methylbut-3-yn-2-yl)benzenamine To a solution of 4-bromobenzenamine (4.0 g, 23 mmol), TEA (4.3 ml, 31 mmol), 2.0 ml of water, copper (0.058 g, 0.91 mmol) and copper(I) chloride (0.058 g, 0.59 mmol) in diethyl ether (9.8 ml, 20 mmol) was added 3-chloro-3-methylbut-1-yne (2.0 g, 20 mmol), dropwise. After stirring overnight, the reaction mixture was transferred to a seperatory funnel containing water and diethyl ether. The aqueous layer was washed 3× with EtOAc. The organic layers were combined, dried with $MgSO_4$, filtered and concentrated. The crude oil was purified with by MPLC (100% DCM to 10% (91/10/1 DCM:MeOH:NH4OH)) to provide the product as an oil. MS m/z: 240 (M+2).

Step 2: 6-bromo-2,2-dimethyl-1,2-dihydroquinoline

To a solution of 4-bromo-N-(2-methylbut-3-yn-2-yl)benzenamine (3.30 g, 14 mmol) in toluene (14 ml, 14 mmol) was added copper(I) chloride (0.300 g, 3.0 mmol) in one portion. The reaction vessel was sealed and the resulting mixture was heated to 90 deg C. After stirring overnight, the mixture was transferred to a separatory funnel containing water and EtOAc. The aqueous layer was washed 1× with EtOAc and 3× with DCM. The organic layers were combined, dried with MgSO4, filtered and concentrated. The crude oil was purified with an MPLC (100% DCM to 10% (91/10/1 DCM:MeOH:NH4OH)) to provide the product. MS m/z: 238.

Step 3: 6-bromo-2,2-dimethyl-1 2,3,4-tetrahydroquinolin-4-ol

To a solution of 6-bromo-2,2-dimethyl-1,2-dihydroquinoline (4.50 g, 18.9 mmol) in tetrahydrofuran (37.8 ml, 18.9 mmol) was added BH3DMS (3.58 ml, 37.8 mmol) dropwise at 0 deg C. The resulting solution was allowed to warm to RT and stirred for 1 hour. The temperature was returned to 0 deg C. and sodium hydroxide (6N) (30.0 ml, 18.9 mmol) followed by Hydrogen peroxide (30.0 ml, 18.9 mmol) was slowly added to the reaction mixture. The resulting solution was stirred for 45 minutes and then transferred to a sep. funnel containing water and EtOAc. The layer were separated and the aqueous layer was subsequently washed 3× with DCM. The organic layers were dried with MgSO4, filtered and concentrated. The crude mixture was then purified with the MPLC (100% DCM to 10% 90:10:1 DCM:MeOH:$NH_4OH$) to provide the desired product. MS m/z: 257 (M+1).

Step 4 and 5: 6-bromo-2,2-dimethyl-1,2,3,4-tetrahydroquinolin-4-amine

To a solution 6-bromo-2,2-dimethyl-1,2,3,4-tetrahydroquinolin-4-ol (3.16 g, 12.3 mmol) and DPPA (1.76 ml, 8.14 mmol) in THF (41.1 ml, 12.3 mmol) at 0° C. was added DBU (1.22 ml, 8.14 mmol) dropwise. The resulting mixture was warmed to RT and stirred for 18 hours. The crude mixture was poured into a sep. funnel containing water. The aqueous layer was washed 3× with EtOAc. The organic layers were combined, dried with MgSO4 and concentrated to an oil. The crude product (2.29 g, MS m/z/z: 240 (M−N3)) was taken to the next step in the reaction sequence.

To a solution of 4-azido-6-bromo-2,2-dimethyl-1,2,3,4-tetrahydroquinoline (2.29 g, 8.15 mmol), water (6.50 ml, 361 mmol), and THF (20.4 ml, 8.15 mmol) was added triphenylphosphine (2.35 g, 8.96 mmol) in one portion. The resulting mixture was heated to 40 deg C. and stirred overnight. The crude mixture was dissolved with EtOAc and transferred to a sep. funnel containing 0.5 MHCl. The aqueous layer was washed 5×DCM. The aqueous layer was then neutralized with 6N NaOH and washed 3× with EtOAc. The organic layers were combined, dried with MgSO4, filtered and concentrated to provide the desired product. MS m/z: 239 (M−NH2).

Step 6: 2,2-dimethyl-6-neopentyl-1,2,3,4-tetrahydroquinolin-4-amine

To neopentylmagnesium chloride (1.65 ml, 1.65 mmol) was added zinc(II) chloride (2.19 ml, 1.10 mmol) dropwise—strong exotherm was observed. The resulting mixture stirred for 10 minutes. A solution of 6-bromo-2,2-dimethyl-1,2,3,4-tetrahydroquinolin-4-amine (0.0700 g, 0.274 mmol) in tetrahydrofuran (1.37 ml, 0.274 mmol) was then added followed by palladium tetrakistriphenylphosphine (0.0317 g, 0.0274 mmol). The reaction vessel was sealed and heated to 65 deg C. The reaction mixture was stirred for 6 hours. The crude mixture was filtered through a plug of celite with EtOAc and concentrated in the presence of silica gel. The crude mixture was purified with the MPLC (100% DCM to 100% 90:10:1 DCM:MeOH:NH4OH) to provide the desired product. MS m/z: 230 (M−NH2).

Step 7: Tert-butyl (2S,3R)-3-(tert-butyldimethylsilyloxy)-4-((S)-2,2-dimethyl-6-neopentyl-1,2,3,4-tetrahydroquinolin-4-ylamino)-1-(3-fluorophenyl)butan-2-ylcarbamate To a solution of tert-butyl (2S,3S)-3-(tert-butyldimethylsilyloxy)-1-(3-fluorophenyl)-4-oxobutan-2-ylcarbamate (0.148 g, 0.360 mmol) and (S)-2,2-dimethyl-6-neopentyl-1,2,3,4-tetrahydroquinolin-4-amine (0.0886 g, 0.360 mmol) in DCM (7.19 ml, 0.360 mmol) was added trimethoxymethane (0.394 ml, 3.60 mmol). The resulting solution was stirred for 1 hour at which time, sodium triacetoxyborohydride (0.229 g, 1.08 mmol) was added. The solution was then stirred for 30 minutes, quenched with saturated Rochelle's salt and stirred for an additional 20 minutes. The mixture was transferred to a sep. funnel containing DCM and H2O. The aqueous layer was washed 4x with DCM. The organic layers were combined, washed 1x with brine, dried with MgSO4, filtered and concentrated to afford the title compound. MS m/z: 642 (M+1).

Step 8: Tert-butyl (2S,3R)-4-((S)-2,2-dimethyl-6-neopentyl-1,2,3,4-tetrahydroquinolin-4-ylamino)-1-(3-fluorophenyl)-3-hydroxybutan-2-ylcarbamate To a solution of tert-butyl (2S,3R)-3-(tert-butyldimethylsilyloxy)-4-((S)-2,2-dimethyl-6-neopentyl-1,2,3,4-tetrahydroquinolin-4-ylamino)-1-(3-fluorophenyl)butan-2-ylcarbamate (0.231 g, 0.360 mmol) in DCM (1.20 ml, 0.360 mmol) was added tetrabutylammonium fluoride (1.44 ml, 1.44 mmol). The resulting solution was stirred overnight. The mixture was transferred to a sep. funnel containing EtOAc and H2O. The aqueous layer was washed 4x with EtOAc. The proganic layers were combined, dried over MgSO4, filtered and concentrated. The crude mixture was purified by the MPLC. MS m/z: 528 (M+1).

Steps 9 and 10: N-((2S,3R)-4-((S)-2,2-dimethyl-6-neopentyl-1,2,3,4-tetrahydroquinolin-4-ylamino)-1-(3-fluorophenyl)-3-hydroxybutan-2-yl)acetamide 4N HCl in MeOH (15.0 ml, 0.379 mmol) was added to tert-butyl (2S,3R)-4-((S)-2,2-dimethyl-6-neopentyl-1,2,3,4-tetrahydroquinolin-4-ylamino)-1-(3-fluorophenyl)-3-hydroxybutan-2-ylcarbamate (0.200 g, 0.379 mmol) in a RBF and the resulting solution was stirred overnight. The solution was then concentrated and the solid product was taken on to the next step.

To a solution of (2R,3S)-3-amino-1-((S)-2,2-dimethyl-6-neopentyl-1,2,3,4-tetrahydroquinolin-4-ylamino)-4-(3-fluorophenyl)butan-2-ol dihydrochloride (0.104 g, 0.379 mmol) and N-ethyl-N-isopropylpropan-2-amine (0.396 ml, 2.27 mmol) in DCM (1.52 ml, 0.379 mmol) was added 1-(1H-imidazol-1-yl)ethanone (0.0396 g, 0.360 mmol) in one portion. The resulting solution was stirred over the weekend. The crude mixture was concentrated and purified with the HPLC. Due to insufficient purity, the title compound was free based and purified with the ISCO MPLC. MS m/z: 470 (M+1).

Example 501

N-((1S,2R)-3-(((4'S)-6'-butyl-3',4'-dihydrospiro cyclobutane-1,2'-pyrano[2,3-b]pyridin]-4'-yl)amino)-1-((4-fluorophenyl)methyl)-2-hydroxypropyl)acetamide To a solution of N-((2S,3R)-4-((S)-6-bromo-2,2-spirocyclobutyl-3,4-dihydro-2H-pyrano[2,3-b]pyridin-4-ylamino)-1-(4-fluorophenyl)-3-hydroxybutan-2-yl)acetamide (0.100 g, 0.203 mmol), tri-t-butylphosphonium tetrafluoroborate (0.01 18 g, 0.0406 mmol) and butylzinc(II) bromide (2.03 ml, 1.02 mmol) in tetrahydrofuran (2.03 ml, 0.203 mmol) was added Pd(OAc)₂ (0.00456 g, 0.0203 mmol) in one portion at RT. The reaction mixture was stirred for 2.5 hours. The reaction mixture was then quenched with water and the resulting mixture was transferred to a sep. funnel. The aqueous layer was washed 3x with EtOAc. The organic layer were combined and concentrated. The crude mixture was purified with the Gilson HPLC to provide the title compound. MS m/z: 470 (M+1).

Example 502

N-((2S,3R)-1-(allyloxy)-3-hydroxy-4-(2,2-spirocyclobutyl-6-neopentyl-3,4-dihydro-2H-pyrano[2,3-b]pyridin-5-ylamino)butan-2-yl)acetamide Step 1: tert-butyl (S)-2-(allyloxy)-1-((S)-oxiran-2-yl)ethylcarbamate To a solution of tert-butyl (S)-2-hydroxy-1-((S)-oxiran-2-yl)ethylcarbamate (0.125 g, 0.6 mmol; see: Kurokawa, N.; Ohfune, Y. *Tetrahedron* 1993, 49, 6195) in toluene (6 mL), was added allyliodide 0.3 mL, 3 mmol) followed by silver(I) oxide (0.7 g, 3 mmol). The solution was stirred at 65° C. in a darkened hood for a period of 15 h. The mixture was then cooled to ambient temperature, filtered through Celite, washed with CH₂Cl₂, and conc. in vacuo. Purification on SiO₂ (10-20% EtoAc/Hexanes) gave the title compound as a yellow oil.

Step 2: (2S,3S)-4-(allyloxy)-3-(tert-butoxycarbonyl)-2-hydroxybutyl acetate

To a solution of lithium carbonate (0.10 g, 1.4 mmol) in DMF (2.5 mL), was added AcOH (0.078 mL, 1.4 mmol) and the solution stirred for a period of 5 min. To this mixture was added a solution of tert-butyl (S)-2-(allyloxy)-1-((S)-oxiran-2-yl)ethylcarbamate (0.11 g, 0.45 mmol) in DMF (2.5 mL). The mixture was heated to 110° C. overnight then cooled to ambient temperature. The cooled mixture was poured onto H₂O and 1 N citric acid (20 mL). The aqueous phase was extracted with EtOAc (3x20 mL) and the organic extracts were dried (Na₂SO₄), filtered, and conc. in vacuo to afford the title compound as a yellow oil. The crude material was used without further purification. MS m/z: 326 (M+23)

Step 3: (2S,3S)-4-(allyloxy)-3-(tert-butoxycarbonyl)-2-(tert-butyldimethylsilyloxy)butyl acetate The crude material from Step 2 (0.090 g) was dissolved in CH₂Cl₂ (3 mL) and cooled to 0° C. To the cooled solution, was added 2,6-lutidine (0.10 mL, 0.90 mmol) followed by TBSOTf (0.10 mL, 0.4 mmol). The mixture was stirred at 0° C. for 2 h then diluted with H₂O and sat'd NaHCO₃. The aqueous phase was extracted with CH₂Cl₂ (3x20 mL) and the organic extracts dried (Na₂SO₄), filtered, and conc in vacuo.

Purification on SiO$_2$ (5-20% EtOAc/Hexanes) gave the title compound as a yellow oil.

Step 4: Tert-butyl (2S,3S)-1-(allyloxy)-3-(tert-butyldimethylsilyloxy)-4-hydroxybutan-2-ylcarbamate To a solution of (2S,3S)-4-(allyloxy)-3-(tert-butoxycarbonyl)-2-(tert-butyldimethylsilyloxy)butyl acetate (0.060 g, 0.1 mmol) in MeOH (2 mL), was added K$_2$CO$_3$ (0.10 g, 0.7 mmol) and the mixture stirred at ambient temperature overnight. The mixture was then conc in vacuo and diluted with EtOAc (25 mL). The organic layer was washed with H$_2$O, brine, then dried (Na$_2$SO$_4$), filtered, and conc in vacuo. The crude material was used without further purification.

Step 5: Tert-butyl (2S,3S)-1-(allyloxy)-3-(tert-butyldimethylsilyloxy)-4-oxobutan-2-ylcarbamate The crude material from Step 4 (0.040 g) was dissolved in CH$_2$Cl$_2$ (3 mL) and treated with Dess-Martin periodinane (0.07 g, 0.2 mmol). The mixture was stirred at ambient temperature for 4 h then diluted with EtOAc (10 mL), sat'd NaHCO$_3$ (5 mL), and aqueous Na$_2$S$_2$O$_3$ (5 mL). The biphasic mixture was stirred until it was colorless. The organic layer was washed with brine, dried (Na$_2$SO$_4$), filtered, and conc in vacuo. The crude aldehyde was used without further purification.

Step 6: Tert-butyl (2S,3R)-1-(allyloxy)-3-(tert-butyldimethylsilyloxy)-4-(2,2-spirocyclobutyl-6-neopentyl-3,4-dihydro-2H-pyrano[2,3-b]pyridin-5-ylamino)butan-2-ylcarbamate To a solution of tert-butyl (2S,3S)-1-(allyloxy)-3-(tert-butyldimethylsilyloxy)-4-oxobutan-2-ylcarbamate (0.033 g) in 1,2-dichloroethane (1.0 mL), was added 2,2-spirocyclobutyl-6-neopentyl-3,4-dihydro-2H-pyrano[2,3-b]pyridin-5-amine (0.03 g, 0.1 mmol) followed by sodium triacetoxy(borohydride) (0.03 g, 0.1 mmol). The mixture was stirred overnight at ambient temperature then diluted with sat'd NaHCO$_3$ (10 mL). The mixture was extracted with EtOAc (3×25 ml), and the combined organic layers were dried (Na$_2$SO$_4$), filtered, and conc in vacuo. Purification on SiO$_2$ (1.25 to 2.5% MeOH*/CH$_2$Cl$_2$;*2.0 M NH$_3$ in MeOH) gave the title compound as a light yellow solid. MS m/z: 517 (M−Boc).

Step 7: N-((2S,3R)-1-(allyloxy)-3-hydroxy-4-(2,2-spirocyclobutyl-6-neopentyl-3,4-dihydro-2H-pyrano[2,3-b]pyridin-5-ylamino)butan-2-yl)acetamide To a solution of tert-butyl (2S,3R)-1-(allyloxy)-3-(tert-butyldimethylsilyloxy)-4-(2,2-spirocyclobutyl-6-neopentyl-3,4-dihydro-2H-pyrano[2,3-b]pyridin-5-ylamino)butan-2-ylcarbamate (0.033 g, 0.05 mmol) in 1,4-dioxane (1.0 mL), was added a solution of HCl (0.6 mL, 4 M in 1,4-dioxane). The mixture was stirred at ambient temperature for a period of 24 h then conc. in vacuo. The crude residue obtained was diluted with EtOAc (20 mL) and sat'd NaHCO$_3$ (10 mL). The resulting aqueous layer was extracted with EtOAc (2×25 mL) and the combined organic extracts were washed with brine, dried (Na$_2$SO$_4$), filtered, and conc in vacuo. The crude amino alcohol obtained was immediately dissolved in CH$_2$Cl$_2$ (1.0 mL) and treated with N,N-diisopropylethylamine (0.05 mL, 0.3 mmol) followed by N-acetyl-imidazole (0.006 g, 0.06 mmol). The mixture was stirred at ambient temperature for 15 h then conc in vacuo. Purification on SiO$_2$ (2.5% MeOH*/CH$_2$Cl$_2$; *2.0 M NH$_3$ in MeOH) gave the title compound as a white solid. MS m/z: 446 (M+1).

Example 503

N-((1S,2R)-3-(((1S)-3,3-dimethyl-7-((3S)-tetrahydro-3-furanyloxy)-1,2,3,4-tetrahydro-1-naphthalenyl)amino)-2-hydroxy-1-(phenylmethyl)propyl)acetamide Step 1. Diethyl 2-(1-(4-methoxyphenyl)-2-methylpropan-2-yl)malonate Diethylisopropylidenemalonate (6.686 ml, 34.09 mmol) was dissolved in 300 ml Et2O and cooled to −78° C. 4-Methoxybenzylmagnesium chloride (150.000 ml, 37.50 mmol) was added and stirring was continued for 5 h. The temperature was warmed up to 0° C. The reaction was hydrolyzed with 0.5 M HCl and extracted 3×EtOAc. Glass col. Chromatography (10-50% EtOAc in Hex.) provided diethyl 2-(1-(4-methoxyphenyl)-2-methylpropan-2-yl)malonate. MS m/z: 323.1 (M+1).

Step 2: 7-Methoxy-3,3-dimethyl-3,4-dihydronaphthalen-1(2H)-one contaminated with 2-chloro-7-methoxy-3,3-dimethyl-3,4-dihydronaphthalen-1(2H)-one Diethyl 2-(1-(4-methoxyphenyl)-2-methylpropan-2-yl)malonate (6.841 g, 21.22 mmol) was dissolved in 30 ml MeOH and 100 ml of 50% NaOH (aq.) was added. The mixture was refluxed for 4 h. The cooled slurry was acidified (conc. HCl) and extracted 4×EtOAc (400 ml each). The combined organic extracts were dried over MgSO4 and evaporated. The crude oil was next heated to 180° C. for 1 h (decarboxylation). The reaction mixture was dissolved in 150 ml benzene and phosphorus pentachloride (6.000 g, 28.81 mmol) was added. The mixture was refluxed for 45 min and cooled to 0° C. Stannic chloride (2.483 ml, 21.22 mmol) was added and the mixture was refluxed for 1 h. The mixture was cooled to 0° C. and washed with 2.5M HCl (aq.). The organic phase was evaporated. LCMS analysis showed the formation of 2 products approx. 1:1. The products almost co-elute on silica. The product mixture was obtained by glass col. chrom. (5-25% EtOAc in Hex.): 3g of a yellow oil.

The chlorinated product was characterized by 1H NMR of a pure fraction, as was the desired title compound (MS m/z: 205.1 (M+1)).

Step 3: 7-Methoxy-3,3-dimethyl-3,4-dihydronaphthalen-1(2H)-one

The product mixture from the previous reaction was dissolved in 30 ml THF and cooled to 0° C. 30 ml Rieke Zn (5g in 100 ml THF) was added and the mixture was stirred for 2.5 h at 0° C. The reaction was hydrolyzed with 20 ml H2O and evaporated. The mixture was dissolved in 100 ml DCM and dried over MgSO4, evaporated. Glass col. Chrom. afforded 7-methoxy-3,3-dimethyl-3,4-dihydronaphthalen-1(2H)-one as a yellow oil.

Step 4: 7-Hydroxy-3,3-dimethyl-3,4-dihydronaphthalen-1(2H)-one

7-Methoxy-3,3-dimethyl-3,4-dihydronaphthalen-1(2H)-one (2.25 g, 11.0 mmol) was dissolved in 30 ml CH$_2$Cl$_2$ and cooled to −78° C. Boron tribromide (25.000 ml, 25.0 mmol) was added and the reaction was stirred for 6 h. The temperature was elevated to 0° C. during this time. The mixture was pored into ice and extracted 3×EtOAc (300 ml each). The combined organic extracts were dried over MgSO4 and evaporated. Glass col. Chrom. gave 7-hydroxy-3,3-dimethyl-3,4-dihydronaphthalen-1(2H)-one as a yellow solid. MS m/z: 191.1 (M+1).

Step 5: (S)-3,3-Dimethyl-7-(tetrahydrofuran-3-yloxy)-3,4-dihydronaphthalen-1(2H)-one 7-Hydroxy-3,3-dimethyl-3,4-dihydronaphthalen-1(2H)-one (0.95 g, 4.99 mmol) was dissolved in 30 ml DCM and triphenylphosphine (1.96 g, 7.49 mmol) and diisopropyl azodicarboxylate (1.23 ml, 6.24 mmol) and (r)-(−)-3-hydroxytetrahydrofuran (0.600 ml, 7.49 mmol) was added. The mixture was stirred over night. 0.5M HCl (aq.) was added and the mixture was extracted 3 times with EtOAc. Glass col. Chrom. (5-30% EtOAc in Hex.) provided (S)-3,3-dimethyl-7-(tetrahydrofuran-3-yloxy)-3,4-dihydronaphthalen-1(2H)-one as a yellow oil. MS m/z: 261.1 (M+1).

Step 6: N-((1S,2R)-3-(((1S)-3,3-dimethyl-7-((3S)-tetrahydro-3-furanyloxy)-1,213,4-tetrahydro-1-naphthalenyl)amino)-2-hydroxy-1-(phenylmethyl)propyl)acetamide The title compound was made from the product from step 5 by a method analogous to that described in Example 464, steps 8-10. MS Found m/z: 467.3 (M+1).

Example 504

N-((1S,2R)-((3,5-difluorophenyl)methyl)-3-(((5'S)-3'-(2,2-dimethylpropyl)-5',6'-dihydrospiro[cyclobutane-1,7'-pyrano[2,3-c]pyridazin]-5'-yl)amino)-2-hydroxypropyl)acetamide Step 1. N-(2-(1-(tert-butyldimethylsilyloxy)cyclobutyl)-1-(3-chloro-6-neopentylpyridazin-4-yl)ethyl)-2-methylpropane-2-sulfinamide 2,2,6,6-Tetramethylpiperidine (0.68 ml, 4.0 mmol) was dissolved in 120 ml THF and 1-butyllithium (1.5 ml, 3.8 mmol) was added at −78° C. drop wise. The mixture was allowed to warm to 0° C. (over a period of 5 min) and kept there for 5 min. The mixture was cooled back to −78° C. and a solution of 3-chloro-6-neopentylpyridazine (0.45 g, 2.4 mmol) in 10 ml of THF was added drop wise. Stirring was continued for 20 min and a solution of (E)-N-(2-(1-(tert-butyldimethylsilyloxy)cyclobutyl)ethylidene)-2-methylpropane-2-sulfinamide (1.450 g, 4.4 mmol) in 5 ml THF was added drop wise. Stirring was continued for 10 min and the mixture was hydrolyzed with H2O. The mixture was extracted with EtOAc (3×300 ml) dried over MgSO4 and evaporated. The crude product was used in the next step without further purification.

Step 2: (S)-7,7-Spirocyclobutyl-3-neopentyl-6,7-dihydro-5H-pyrano[2,3-c]pyridazin-5-amine N-(2-(1-(tert-Butyldimethylsilyloxy)cyclobutyl)-1-(3-chloro-6-neopentylpyridazin-4-yl)ethyl)-2-methylpropane-2-sulfinamide (0.870 g, 2 mmol) was dissolved in 20 ml of THF and tetrabutylammonium fluoride, 1.0 m in THF (0.5 ml, 2 mmol) was added at RT.

The mixture was stirred for 10 min and filtered through a plug of silica (wash with THF). The mixture was died over MgSO4 and evaporated and re-dissolved in 200 ml of THF. NaH (60%) (0.3 g, 7 mmol) was added and the mixture was heated to 66 for 3 h. The mixture was hydrolyzed with water and extracted 3 times with EtOAc (200 ml each). The crude product (MS m/z: 366.2 (M+1)) was re-dissolved in 5 ml MeOH and 15 ml 4M HCl in dioxane was added. The mixture was stirred for 1 h and evaporated and purified on the HPLC. The Product was obtained as a brown solid.

Step 3: N-((1S,2R)-1-((3,5-difluorophenyl)methyl)-3-(((5'S)-3'-(2,2-dimethylpropyl)-5',6'-dihydrospiro[cyclobutane-1 7'-pyrano[2,3-c]pyridazin]-5'-yl)amino)-2-hydroxypropyl)acetamide The title compound was made from the product from step 5 by a method analogous to that described in Example 464, steps 8-10. MS Found m/z: 503.2 (M+1).

Example 505

N-((1S,2R)-3-(((4'S)-6'-(2,2-dimethylpropyl)-3-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide; and N-((1S,2R)-3-(((1S,3R,4'S)-6'-(2,2-dimethylpropyl)-3-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide Step 1: 1,3-Ditosyloxy-2-methyl-propane 2-Methylpropane-1,3-diol (50 g, 555 mmol) was dissolved in 555 ml pyridine and cooled to 0° C. p-Toluenesulfonyl chloride (212 g, 1110 mmol) was added and stirring was continued over night. 200 ml H2O was added and the reaction was extracted with DCM (2×1L). The combined organic extracts were dried over MgSO4 and evaporated. The product was recrystallized from EtOH/Hex and the product was obtained as a white solid. MS m/z: 399.0 (M+1).

Step 2: 3-Methyl-1-(methylsulfinyl)-1-(methylthio)cyclobutane

Methylsulfinyl(methylthio)methane (29.927 g, 240.91 mmol) was dissolved in 500 ml THF and cooled to −10° C. Butyllithium (96.363 ml, 240.91 mmol) was added slowly and stirring was continued for 2 h. 1,3-Ditosyloxy-2-methyl-propane (48.000 g, 120.45 mmol) was added at −10° C. and the mixture was allowed to warm up to RT. Stirring was continued over night. 150 ml H2O was added and the mixture was extracted with DCM, dried over MgSO4 and evaporated. The crude material was filtered through a silica plug and used without further purification in the next step.

Step 3: 3-Methylcyclobutanone

Crude 3-Methyl-1-(methylsulfinyl)-1-(methylthio)cyclobutane (11.300 g, 63.371 mmol) from the previous step was dissolved in 50 ml Et2O and 20 ml conc. HCl was added. The mixture was distilled at 1 atm and 80° C.: ether comes over. Temperature was increased to 110-120° C. where the product (along with some water) was collected. This fraction was diluted with 100 ml ether, dried over MgSO4 and evaporated (carefully) to give 3-methylcyclobutanone.

Step 4: 1-Allyl-3-methylcyclobutanol

Methylcyclobutanone (3.200 g, 38.043 mmol) was dissolved in 200 ml THF and allylmagnesium bromide (190.21 ml, 190.21 mmol) was added in one portion. The mixture was stirred for 4 h at RT, hydrolyzed with water and extracted. The combined organic extracts were dried over MgSO4 and evaporated and purified via glass col. Chrom. (25-75% hex. in EtOAc). 1-Allyl-3-methylcyclobutanol (2.250 g, 46.9% yield) was obtained as a mixture of cis-trans isomers approx 4:1 (where the major compound is the one Me-cis to OH) based on NMR.

Step 5: (1-Allyl-3-methylcyclobutoxy)(tert-butyl)dimethylsilane

1-Allyl-3-methylcyclobutanol (2.25000 g, 17.8 mmol) (the 4:1 mixture of cis/trans-isomers) was dissolved in 50 ml of $CH_2Cl_2$ and DIEA (5.59 ml, 32.1 mmol) and tert-butyldimethylsilyl triflate (5.73 ml, 25.0 mmol) were added. The mixture was stirred for 2 h and hydrolyzed with water, extracted with 200 ml Et2O (3×each), dried over MgSO4 and evaporated. Glass col. chrom. (10-30% EtOAc in Hex.) provided (1-allyl-3-methylcyclobutoxy)(tert-butyl)dimethylsilane as a yellow oil. Mixture of cis/trans at the cyclobutylring (4:1)

Step 6: (E)-N-(2-(1-(tert-butyldimethylsilyloxy)-3-methylcyclobutyl)ethylidene)-2-methylpropane-2-sulfinamide (1-Allyl-3-methylcyclobutoxy)(tert-butyl)dimethylsilane (4.1000 g, 17.05 mmol) was dissolved in 150 ml of t-BuOH/H2O/THF (2/2/1) and osmium tetroxide (10.84 ml, 0.8525 mmol, 2.5 wt %) and 4-methylmorpholine oxide (2.996 g, 25.58 mmol) were added. The mixture was stirred for 6 h and the mixture was diluted with 250 ml water and extracted with EtOAc. The combined organic extracts were evaporated and re-dissolved in 150 ml of t-BuOH/H2O/THF (2/2/1). Sodium periodate (4.741 g, 22.17 mmol) was added and stirring was continued for 6 h. The mixture was filtered and diluted with 250 ml of water. The mixture was extracted with Et2O and the combined organic extracts were dried over MgSO4, evaporated and re-dissolved in 100 ml $CH_2Cl_2$. Cupric sulfate anhydrous (8.164 g, 51.15 mmol), and(r)-(+)-2-methyl-2-propanesulfinamide (4.133 g, 34.10 mmol) were added at RT and stirring was continued over night. The reaction was filtered and hydrolyzed with 30 ml water. The mixture was extracted 3×EtOAc (3×150 ml) and the combined organic extracts were dried over MgSO4 and evaporated. Glass col. chrom. (20-50% EtOAc in Hex) provided (E)-N-(2-(1-(tert-butyldimethylsilyloxy)-3-methylcyclobutyl)ethylidene)-2-methylpropane-2-sulfinamide. Mixture of cis/trans at the cyclobutylring (4:1).

Step 7: N-((S)-2-(1-(tert-butyldimethylsilyloxy)-3-methylcyclobutyl)-1-(2-fluoro-5-neopentylpyridin-3-yl)ethyl)-2-methylpropane-2-sulfinamide 2,2,6,6-Tetramethylpiperidine (2.47 ml, 14.7 mmol) was dissolved in 100 ml THF and cooled to −78° C. 1-Butyllithium (5.23 ml, 13.1 mmol, 2.5M) was added and the reaction was allowed to warm up to 0° C. for 5 min before it was cooled back to −78° C. again. At this point, a solution of 2-fluoro-5-neopentylpyridine (1.75000 g, 10.5 mmol) was added dropwise and the reaction was stirred for 1 h. Next, a solution of (E)-N-(2-(1-(tert-butyldimethylsilyloxy)-3-methylcyclobutyl)ethylidene)-2-methylpropane-2-sulfinamide (3.98 g, 11.5 mmol) in THF was added dropwise and stirring was continued for 1 h. The mixture was hydrolyzed with NH4Cl in the cold, warmed up to RT extracted with EtOAc (3×150 ml), dried over MgSO4 and evaporated. N-((S)-2-(1-(tert-Butyldimethylsilyloxy)-3-methylcyclobutyl)-1-(2-fluoro-5-neopentylpyridin-3-yl)ethyl)-2-methylpropane-2-sulfinamide (3.30 g, 61.5% yield) was obtained after glass col. Chrom. (20-70% EtOAc in Hex.). Low yield due to the formation of a minor diastereomer at the NH center (approx 30%). Mixture of cis/trans at the cyclobutylring (4:1).

Step 8: N-((1S,2R)-3-(((4'S)-6'-(2,2-Dimethylpropyl)-3-methyl-3',4'-dihydrospiro[cyclobutane-1 2'-pyrano[2,3-b]pyridin]-4'-yl)amino)-1-((4-fluorophenyl)methyl)-2-hydroxypropyl)acetamide; and N-((1S,2R)-3-(((1S,3R,4'S)-6'-(2,2-dimethylpropyl)-3-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide N-((S)-2-(1-(Tert-butyldimethylsilyloxy)-3-methylcyclobutyl)-1-(2-fluoro-5-neopentylpyridin-3-yl)ethyl)-2-methylpropane-2-sulfinamide (3.30 g, 6.435 mmol) was dissolved in 60 ml THF and tetrabutylammonium fluoride, (1.0 M in THF; 6.435 ml, 6.435 mmol) was added. The mixture was stirred for 30 min and filtered through a plug of silica (wash with THF). The solution was evaporated and redissolved in 600 ml THF. NaH (0.74 g, 32.17 mmol, 60% in mineral oil) was added and the reaction was heated up to 65° C. for 3 h. The mixture was hydrolyzed carefully with water and extracted 3 times with EtOAc (3×200 ml). The combined organic extracts were dried over MgSO4 and evaporated. The crude product was dissolved in 20 ml MeOH and 20 ml 4M HCl in dioxane was added. The reaction was stirred for 1 h, basified with NaOH (5M aq.) and extracted 4 times with 200 ml EtOAC (each). Glass col. Chrom. gave the 2 products which were submitted for separation of the diastereomers. The major isomer was identified to be the one where the 0 and the Me group are cis to each other (NOE).

Prior to separation, the title compound, a 4:1 mixture, was made by the method described in Example 464, steps 8-10. MS Found m/z: 498.2 (M+1).

Example 506

N-((1S,2R)-3-(((1S,3S,4'S)-6'-(2,2-dimethylpropyl)-3-hydroxy-3',4'-dihydrospiro[cyclobutane-1,2'-pyrano[2,3-b]pyridin]-4'-yl)amino)-1-((4-fluorophenyl)methyl)-2-hydroxypropyl)acetamide Step 1: 1-((1,3-Dibromopropan-2-yloxy)methyl)benzene
2-Benzyloxy-1,3-propanediol (15.000 g, 82.32 mmol) was dissolved in $CH_2Cl_2$ (500 ml) and carbon tetrabromide (81.90 g, 247.0 mmol) and triphenylphosphine (64.77 g, 247.0 mmol) were added. The mixture was stirred overnight and concentrated. The reaction was suspended in hexanes and filtered and evaporated to afford the title compound.

Step 2: 3-(Benzyloxy)cyclobutanone Methylsulfinyl(methylthio)methane (13 ml, 125 mmol) was dissolved in 250 ml THF and cooled to −20° C. n-Butyllithium (50 ml, 125 mmol) was added and the mixture was stirred for 3 h at −20° C. The mixture was cooled down to −78° C. and a solution of 1-((1,3-dibromopropan-2-yloxy)methyl)benzene (16.000 g, 52 mmol) was added. The reaction was stirred over night and allowed to warm up to RT. It was stirred for an additional 6h at RT, hydrolyzed with water and extracted with EtOAc. The combined organic extracts were evaporated, dissolved in ether (50 ml) and treated with conc. HCl (10 ml) for 30 min at reflux. The mixture was neutralized with NaOH (10M) and extracted with EtOAc. The combined organic extracts were dried over MgSO4 and evaporated. Glass col. Chrom. (10-50% EtOAc in Hex) gave 3-(benzyloxy)cyclobutanone as a yellow oil.

Step 3: N-((1S,2R)-3-(((1S,3S,4'S)-6'-(2,2-dimethylpropyl)-3-hydroxy-3',4'-dihydrospiro[cyclobutane-1,2'-pyrano[2,3-b]pyridin]-4'-yl)amino)-1-((4-fluorophenyl)methyl)-2-hydroxypropyl)acetamide The title compound was prepared in a manner analogous that described in Example 505. MS Found m/z: 500 (M+1).

Example 507

N-((1S,2R)-2-hydroxy-1-(phenylmethyl)-3-(((4'S)-6'-((2S)-tetrahydro-2-furanylmethyl)-3',4'-dihydrospiro[cyclobutane-1,2'-pyrano[2,3-b]pyridin]-4'-yl)amino)propyl)acetamide; and N-((1S,2R)-2-hydroxy-1-(phenylmethyl)-3-(((4'S)-6'-((2R)-tetrahydro-2-furanylmethyl)-3',4'-dihydrospiro[cyclobutane-1,2'-pyrano[2,3-b]pyridin]-4'-yl)amino)propyl)acetamide Step 1: (4S,5R)-tert-butyl 4-benzyl-2,2-dimethyl-5-(((S)-6-((tetrahydrofuran-2-yl)methyl)-2,2-spirocyclobutyl-3,4-dihydro-2H-pyrano[2,3-b]pyridin-4-ylamino)methyl)oxazolidine-3-carboxylate A solution of sodium tert-butoxide (74 mg, 769 μmol), $Pd_2(dba)_3$ (16 mg, 17 μmol) and 1-(diphenylphosphino)-2-(2-(diphenylphosphino)phenoxy)benzene (19 mg, 35 μmol) in 5 mL of THF was purged with nitrogen for 15 minutes at which point (4S,5R)-tert-butyl 4-benzyl-5-(((S)-6-bromo-2,2-spirocyclobutyl-3,4-dihydro-2H-pyrano[2,3-b]pyridin-4-ylamino)methyl)-2,2-dimethyloxazolidine-3-carboxylate (200 mg, 349 μmol) and pent-4-en-1-ol (36 μl, 349 μmol) were added. The resulting slurry was then heated at 70° C. for 8 hours. The cooled reaction mixture was diluted with EtOAc (15 mL) and poured into 10% sodium bicarbonate (25 mL). The layers were separated and the aqueous layer was extracted with ethyl acetate 3×15 mL. The combined organic layers were washed with water then brine and dried over sodium sulfate. After filtration and concentration the residue was purified by silica gel chromatography (0-100% ethyl acetate in hexanes) to provide the title compound as a yellow oil. MS ,m/z: 578.2 (M+1).

Step 2: N-((1S,2R)-2-hydroxy-1-(phenylmethyl)-3-(((4'S)-6'-((2S)-tetrahydro-2-furanylmethyl)-3',4'-dihydrospiro[cyclobutane-1 2'-pyrano[2,3-b]pyridin]-4'-yl)amino)propyl)acetamide; and N-((1S,2R)-2-hydroxy-1-(phenylmethyl)-3-(((4'S)-6'-((2R)-tetrahydro-2-furanylmethyl)-3',4'-dihydrospiro[cyclobutane-1,2'-pyrano[2,3-b]pyridin]-4'-yl)amino)propyl)acetamide The title compounds were prepared in a manner analogous that described in Example 464, steps 8-10. MS Found m/z: 480 (M+1).

Example 508

N-((1S,2R)-2-hydroxy-3-(((4'S)-6-(((2S)-2-methyltetrahydro-2-furanyl)methyl)-3',4'-dihydrospiro[cyclobutane-1,2'-pyrano[2,3-b]pyridin]-4'-yl)amino)-1-(phenylmethyl)propyl)acetamide; and N-((1S,2R)-2-hydroxy-3-(((4'S)-6'-(((2R)-2-methyltetrahydro-2-furanyl)methyl)-3',4'-dihydrospiro[cyclobutane-1,2'-pyrano[2,3-b]pyridin]-4'-yl)amino)-1-(phenylmethyl)propyl)acetamide Step 1: (4S,5R)-tert-butyl 4-benzyl-2,2-dimethyl-5-(((S)-6-((2-methyl-tetrahydrofuran-2-yl)methyl)-2,2-spirocyclobutyl-3,4-dihydro-2H-pyrano[2,3-b]pyridin-4-ylamino)methyl)oxazolidine-3-carboxylate 1-(diphenylphosphino)-2-(2-(diphenylphosphino)phenoxy)benzene (29 mg, 0.054 mmol) and Pd$_2$(dba)$_3$ (25 mg, 0.027 mmol) were combined in a sealed tube and 1 mL of THF was introduced. After stirring for 5 minutes, sodium tert-butoxide (130 mg, 1.35 mmol) was added followed by a solution of (4S,5R)-tert-butyl 4-benzyl-5-(((S)-6-bromo-2,2-spirocyclobutyl-3,4-dihydro-2H-pyrano[2,3-b]pyridin-4-ylamino)methyl)-2,2-dimethyloxazolidine-3-carboxylate (310 mg, 0.541 mmol) and 4-methylpent-4-en-1-ol (81 mg, 0.812 mmol) in 3 mL of THF. The tube was sealed and heated at 70° C. for 8 hours. The cooled reaction mixture was diluted with EtOAc (5 mL) and poured into 10% sodium bicarbonate (25 mL). The layers were separated and the aqueous layer was extracted with ethyl acetate 3×25 mL. The combined organic layers were washed with water and brine and dried over sodium sulfate. After filtration and concentration the residue was purified by silica gel chromatography (0-100% ethyl acetate in hexanes) to provide the title compound as a yellow oil. MS m/z: 592.2 (M+1).

Step 2: N-((1S,2R)-2-hydroxy-3-(((4'S)-6'-(((2S)-2-methyltetrahydro-2-furanyl)methyl)-3',4'-dihydrospiro[cyclobutane-1,2'-pyrano[2,3-b]pyridin]-4'-yl)amino)-1-(phenylmethyl)propyl)acetamide; and N-((1S,2R)-2-hydroxy-3-(((4'S)-6'-(((2R)-2-methyltetrahydro-2-furanyl)methyl)-3',4'-dihydrospiro[cyclobutane-1 2'-pyrano[2,3-b]pyridin]-4'-yl)amino)-1-(phenylmethyl)propyl)acetamide The title compounds were prepared in a manner analogous that described in Example 464, steps 8-10. MS Found m/z: 494 (M+1).

Example 509

N-((1S,2R)-3-(((2R,4S)-6-bromo-2-methyl-2-(trifluoromethyl)-3,4-dihydro-2H-chromen-4-yl)amino)-2-hydroxy-1-(phenylmethyl)propyl)acetamide; and N-((1S,2R)-3-(((2S,4S)-6-bromo-2-methyl-2-(trifluoromethyl)-3,4-dihydro-2H-chromen-4-yl)amino)-2-hydroxy-1-(phenylmethyl)propyl)acetamide Step 1: (Z)-2-(1-(benzylimino)ethyl)-4-bromophenol A mixture of 5"-bromo-2"-hydroxyacetophenone (15.0 g, 69.8 mmol) and benzylamine (7.62 ml, 69.8 mmol) in ethanol was stirred at RT for 3 h. The resulting suspension was filtered and rinsed with hexane. The crystalline solid was dried in vacuum to afford (Z)-2-(1-(benzylimino)ethyl)-4-bromophenol as a bright yellow solid. MS m/z: 304.

Step 2: (Z)-4-(benzylamino)-4-(5-bromo-2-hydroxyphenyl)-1,1,1-trifluorobut-3-en-2-one To a solution of (Z)-2-(1-(benzylimino)ethyl)-4-bromophenol (18.0 g, 59.2 mmol) in anhydrous THF was added lithium hydride (1.65 g, 207 mmol) portion wise at room temperature. The resulting mixture was heated in a oil bath (60° C.) to initialize the reaction (cool down the mixture with a ice bath). Once the reaction is slowing down, the mixture was heated at 70-75° C. for 24 h (reaction was monitored by using TLC and LCMS). At this point, there was still trace amount of SM left (MS+=304). The mixture was concentrated to dryness under vacuum. The residue was treated with 120 ml of 7% AcOH/ H2O. The precipitate that formed was filtered and rinsed with water. The solid was dried in vacuum to give (Z)-4-(benzylamino)-4-(5-bromo-2-hydroxyphenyl)-1,1,1-trifluorobut-3-en-2-one as a orange color solid. MS m/z: 400. The crude material was used without further purification in the next step.

Step 3: (Z)-N-(6-bromo-2-(trifluoromethyl)-4H-chromen-4-ylidene)(phenyl methanamine To a cooled (ice bath) EtOH (96 ml) was bubbled through hydrogen chloride gas for 30 min. (Z)-4-(benzylamino)-4-(5-bromo-2-hydroxyphenyl)-1,1,1-trifluorobut-3-en-2-one (24.0 g, 60 mmol) was then added in one portion to this solution. The reaction was stirred at RT for 36 h. The resulted mixture was diluted with 900 ml of cool water, 28% aq NH3 (96 ml) was then added. The precipitate formed was filtered and washed with water to give a brown sticky solid. The solid was dissolved in EtOAc, washed with 1N HCl and brine. The organic layer was dried over Na2SO4, filtered and concentrated. The residue was crystallized from hexane to give the title compound as a brown solid. MS m/z: 382.

Step 4: 6-bromo-2-methyl-2-(trifluoromethyl)chroman-4-one

A mixture of malonic acid (1.2 ml, 19 mmol) and (Z)-N-(6-bromo-2-(trifluoromethyl)-4H-chromen-4-ylidene)(phenyl)methanamine (6.63 g, 17 mmol) in dioxane was heated to reflux for 18 h until the reaction was completed. The mixture was cooled to RT and treated with 50% EtOH/H2O (20 ml) followed by conc. HCl (5.0 ml). The resulted mixture was left to stand at RT for 40 min, and then diluted with water (500 ml). The product was extracted with hexane (3×300 ml). The organic layers were combined, dried over Na2SO4, filtered and concentrated. The residue was purified on silica gel column (2-10% EtOAc/hexane) to afford the title compound as yellow oil. MS m/z: 310 (M+1).

Step 5: (4R)-6-bromo-2-methyl-2-(trifluoromethyl)chroman-4-ol

To a cooled (ice bath) solution of (s)-2-methyl-cbs-oxazaborolidine 1.0 M in toluene (100 µl, 100 µmol) was added borane-dimethyl sulfide 2.0 M in THF (500 µl, 1000 µmol). After stirred 15 min, a solution of 6-bromo-2-methyl-2-(trifluoromethyl)chroman-4-one (309 mg, 1000 µmol) in toluene was added drop wise. The reaction was completed after stirring 9h at 0° C. 2N HCl was added slowly to quench the reaction. The resulted mixture was extracted with EtOAc. The organic layer was washed with water and brine, dried over Na2SO4, filtered and concentrated. The residue was purified on silica gel column to afford the title compound.

Step 6:(4S)-4-azido-6-bromo-2-methyl-2-(trifluoromethyl)chroman

To a cooled (ice bath) solution of (4R)-6-bromo-2-methyl-2-(trifluoromethyl)chroman-4-ol (277 mg, 890 µmol) was added drop wise diphenylphosphoryl azide (249 µl, 1158 µmol). After stirring 20 min, 1,8-diazabicyclo(5.4.0)undec-7-ene (173 µl, 1158 µmol) was added drop wise. The reaction was stirred at the same temperature for 2 h, then stirred 15h at ambient temperature. Water was added to quench the reaction. The resulted mixture was extracted with EtOAc. The organics were washed with brine, dried over Na2SO4, filtered and concentrated. The residue was purified on a silica gel column (5-20% EtOAc/hexane) to afford the title compound. MS m/z: 308(M−N2).

Step 7: (4S)-6-bromo-2-methyl-2-(trifluoromethyl)chroman-4-amine

To a solution of (4S)-4-azido-6-bromo-2-methyl-2-(trifluoromethyl)chroman (190 mg, 565 µmol) was added triphenylphosphine (222 mg, 848 µmol). The mixture was stirred at RT for 4 h. Water (15 ml) was added and the reaction was heated at refluxing for 24 h. The resulted mixture was concentrated to dryness and extracted with CHCl3. The organic layer was dried over anhydrous Na2SO4, filtered, concentrated and dried in vacuum to afford the title compound. MS m/z: 293, 295(M−NH2).

Step 8: tert-Butyl (2S,3R)-4-((4S)-6-bromo-2-methyl-2-(trifluoromethyl)-3,4-dihydro-2H-chromen-4-ylamino)-3-hydroxy-1-phenylbutan-2-ylcarbamate A mixture of (4S)-6-bromo-2-methyl-2-(trifluoromethyl)chroman-4-amine (179 mg, 577 µmol) and tert-butyl (S)-1-((S)-oxiran-2-yl)-2-phenylethylcarbamate (198 mg, 750 µmol) in ethanol was heated at reflux for 16 h. At this point, there was still the starting amine left. An additional 1.3 eq of epoxide was added to the reaction, and continued to reflux for 6 h. The resulted mixture was concentrated and purified on Shimadzu HPLC to afford the title compound as a TFA salt. MS m/z: 573, 575.

Step 9: N-((1S,2R)-3-(((2R,4S)-6-bromo-2-methyl-2-(trifluoromethyl)-3,4-dihydro-2H-chromen-4-yl)amino)-2-hydroxy-1-(phenylmethyl)propyl)acetamide; and N-((1S,2R)-3-(((2S,4S)-6-bromo-2-methyl-2-(trifluoromethyl)-3,4-dihydro-2H-chromen-4-yl)amino)-2-hydroxy-1-(phenylmethyl)propyl)acetamide To a solution of (2R,3S)-3-amino-1-((4S)-6-bromo-2-methyl-2-(trifluoromethyl)-3,4-dihydro-2H-chromen-4-ylamino)-4-phenylbutan-2-ol dihydrochloride (160 mg, 338 mmol) in DMF was added 1-(1H-imidazol-1-yl)ethanone (37.2 mg, 338 µmol) followed by DIPEA (177 µl, 1014 µmol). The reaction was stirred at RT for 30 min, then diluted with MeOH and purified on Shimadzu HPLC to afford 43.0 mg of the title compounds as a mixture. MS m/z: 515, 517.

Example 510

N-((1S,2R)-2-hydroxy-1-(phenylmethyl)-3-(((4S)-6 (2,2,2-trifluoroethyl)-3,4-dihydrospiro[chromene-2, 1'-cyclobutan]-4-yl)amino)propyl)acetamide Step 1: 2,2,2-trifluoro-1-(4-hydroxyphenyl)ethanone To a cooled (−78° C.) solution of 2,2,2-trifluoro-4'-methoxyacetophenone (15 ml, 73 mmol) in DCM was added 1.0 M tribromoborane (73 ml, 73 mmol) drop wise. After the addition was completed, the reaction was slowly warmed to RT and stirred for overnight (15 h). At this point, reaction was completed by TLC. The product mixture was poured into ice water. The organic layer was washed with 10% aq Na2CO3, water and brine, dried over Na2SO4, filtered and concentrated. The residue was purified on silica gel column (5-40% EtOAc/hexane) to afford the title compound as a white crystalline solid. The major side product was a colorless oil with MS+=379.

Step 2: 4-(2,2,2-trifluoro-1-hydroxyethyl)phenol

To a solution of 2,2,2-trifluoro-1-(4-hydroxyphenyl)ethanone (5.0 g, 26 mmol) in dichloroethane was added zinc iodide (2.7 ml, 39 mmol) followed by sodium cyanoborohydride (10 ml, 197 mmol). The reaction was stirred at RT for 18 h. Both TLC and LCMS showed one product was formed. MS+=175 (desired mass 192—OH). The mixture was filtered through celite and rinsed with dichloromethane. The filtrate was concentrated and dried in vacuum to afford the title compound as colorless oil. MS m/z: 175(M−H2O).

Step 3: 4-(1-chloro-2,2,2-trifluoroethyl)phenol

To a cooled (ice bath) mixture of 4-(2,2,2-trifluoro-1-hydroxyethyl)phenol (4.3 g, 22 mmol) and anhydrous pyridine (1.8 ml, 22 mmol) in toluene was added thionyl chloride (SOCl2) (2.3 ml, 31 mmol) drop wise via a syringe. After stirred for 1 h at 0° C., the reaction was heated at 70° C. for 2 h. At this point, reaction did not go completion, indicated by LCMS. Heating was continued for 16 h. Reaction was quenched with ice water. The resulted mixture was diluted with EtOAc. The organic layer was washed with saturated Na2CO3, water and brine. After dried over Na2SO4, the solution was filtered and concentrated. The residue was purified on a silica gel column (5-10% EtOAc/hexane) giving the title compound as a light yellow oil. MS m/z: 21 1(M+1).

Step 4: 4-(2,2,2-trifluoroethyl)phenol

To a solution of 4-(1-chloro-2,2,2-trifluoroethyl)phenol (3.60 g, 17.1 mmol) in THF was added sodium borohydride (0.903 ml, 25.6 mmol) in one portion. The reaction was stirred at RT for 18 h, and then quenched with MeOH. The resulting mixture was concentrated and diluted with EtOAc. After washed with water and brine. The organic layer was dried over Na2SO4, filtered and concentrated. The residue was dried in vacuum to afford 4-(2,2,2-trifluoroethyl)phenol as a colorless oil. MS m/z: 175(M−1).

Step 5: 1-(2-hydroxy-5-(2,2,2-trifluoroethyl)phenyl)ethanone To a solution of 4-(2,2,2-trifluoroethyl)phenol (1.00 g, 5.68 mmol) in CH$_2$Cl$_2$ (5.0 ml) was added trifluoromethanesulfonic acid (0.0151 ml, 0.170 mmol) with stirring. A solution of acetic chloride (0.444 ml, 6.25 mmol) in Cl2Cl2 (5.0 ml) was added drop wise to the reaction. After stirred 45 min at RT, all the phenol was consumed. The product mixture was diluted with $CH_2Cl_2$, washed with saturated sodium bicarbonate. The organic layer was dried over Na2SO4, filtered and concentrated. The residue was dried in vacuum until no weight loss was observed. To the above residue was added anhydrous aluminum(III) chloride (0.757 g, 5.68 mmol). The mixture was heated at 150° C. for 1 h until all the starting material was consumed (monitored by TLC). The resulted brown gum was cooled to 0° C., diluted with diethyl ether and 1N HCl. Layers were separated. The aqueous layer was extracted with ether. The organic layers were combined, dried over Na2SO4, filtered and concentrated. The residue was purified on silica gel column (2-15% EtOAc/hexane) to afford the title compound.

Step 6: 2,2-spirocyclobutyl-6-(2,2,2-trifluoroethyl)-2,3-dihydrochromen-4-one

A solution of 1-(2-hydroxy-5-(2,2,2-trifluoroethyl)phenyl)ethanone (320 mg, 1467 µmol), cyclobutanone (617 mg, 8800 µmol), N-ethyl-N-isopropylpropan-2-amine (569 mg, 4400 µmol) and pyrrolidine (313 mg, 4400 µmol) in ACN was heated in microwave at 75° C. for 2 h. The resulted mixture was diluted with EtOAc, washed with 1N HCl, saturated Na2CO3 and brine. The organics were dried over Na2SO4, filtered and concentrated. The residue was purified on silica gel column (2-15% EtOAc/hexane) to afford the title compound.

Step 7: (R)-2,2-spirocyclobutyl-6-(2,2,2-trifluoroethyl)-3,4-dihydro-2H-chromen-4-ol The title compound was prepared according to the methods described in step 5 of Example 509. MS m/z: 255(M+1−H2O).

Step 8: (S-4-azido-2,2-spirocyclobutyl-6-(2,2,2-trifluoroethyl)-3,4-dihydro-2H-chromene The title compound was prepared according to the methods described in step 6 of Example 509. MS m/z: 270(M+1−N2).

Step 9: (S)-2,2-spirocyclobutyl-6-(2,2,2-trifluoroethyl)-3,4-dihydro-2H-chromen-4-amine The title compound was prepared according to the methods described in step 7 of Example 509. MS m/z: 255(M−NH2).

Step 10: (4R,5S)-tert-butyl5-benzyl-4-((6-(2,2,2-trifluoroethyl)-2,2-spirocyclobutyl-3,4-dihydro-2H-chromen-4-ylamino)methyl)-2,2-dimethylpyrrolidine-1-carboxylate To a stirred solution of (S)-2,2-spirocyclobutyl-6-(2,2,2-trifluoroethyl)-3,4-dihydro-2H-chromen-4-amine (40 mg, 147 µmol) in DCM was added (4S,5S)-tert-butyl 4-benzyl-5-formyl-2,2-dimethyloxazolidine-3-carboxylate (71 mg, 221 µmol) followed by trimethoxymethane (161 µl, 1475 µmol). After stirred for ½ h, sodium cyanoborohydride (46 mg, 737 µmol) was added to the reaction. After stirred 3 h at RT, most of the amine was consumed. The reaction was quenched by the addition of saturated Na2CO3 and diluted with CH2Cl2. The resulted mixture was extracted with CH2Cl2 (2×). The combined organics were washed with brine, dried over Na2SO4, filtered and concentrated. The residue was purified on silica gel column to afford the title compound. MS m/z: 575(M+1).

Step 11: N-((1S,2R)-2-hydroxy-1-(phenylmethyl)-3-(((4S)-6-(2,2,2-trifluoroethyl)-3,4-dihydrospiro[chromene-2,1'-cyclobutan]-4-yl)amino)propyl)acetamide. TFA salt The title compound was synthesized in a manner analogous to that described in Example 509, as a white solid. MS m/z: 477.2(M+1).

Example 511

N-((1S,2R)-2-hydroxy-1-(phenylmethyl)-3-(((4S)-6-(2-pyridinyl)-3,4-dihydrospiro[chromene-2,1'-cyclobutan]-4-yl)amino)propyl)acetamide. TFA salt A mixture of (2S,3R)-3-amino-1-(6-bromo-2,2-spirocyclobutyl-3,4-dihydro-2H-chromen-4-ylamino)-4-phenylbutan-2-ol dihydrochloride salt (50 mg, 106 µmol), 2-tri-n-butylstannylpyridine (58 µl, 158 µmol) and tetrakis(triphenylphosphine)palladium(0) (6 mg, 5 µmol) in dioxane was heated in a sealed tube for 15 h. The reaction was cooled to RT and filtered. The filtrate was purified on Shimadzu HPLC to afford the title compound as a colorless oil. MS m/z: 472.2(M+1).

Example 512

N-((1S,2R)-2-hydroxy-1-(phenylmethyl)-3-(((4'S)-6'-(2,2,2-trifluoroethyl)-3',4'-dihydrospiro[cyclobutane-1,2'-pyrano[2,3-b]pyridin]-4'-yl)amino)propyl)acetamide Step 1: 6-bromo-4-(tert-butyldimethylsilyloxy)-2,2-spirolcyclobutyl-3,4-dihydro-2H-pyrano(2,3-b)pyridine To a cooled (ice bath) solution 6-bromo-2,2-spirolcyclobutyl-3,4-dihydro-2H-pyrano(2,3-b)pyridine-4-ol (3.71 g, 13.7 mmol) in DCM was added TEA (3.82 ml, 27.5 mmol) followed by tert-butyldimethylsilyl trifluoromethanesulfonate (3.47 ml, 15.1 mmol). The reaction was stirred at RT for 2 h until all the alcohol was consumed. 1N HCl was added to quench the reaction. The resulted mixture was extracted with CH2Cl2. The organic layers were combined, washed with water and brine, dried over Na2SO4, filtered and concentrated. After dried in vacuum, the title compound was obtained as a yellow solid. It was carried on to the next step without further purification. MS m/z: 386.1(M+1).

Step 2: 1-(4-(tert-butyldimethylsilyloxy)-2,2-spirolcyclobutyl-3,4-dihydro-2H-pyrano(2,3-b)pyridine-6-yl)-2,2,2-trifluoroethanone To a cooled (−78° C.) solution of compound 1 from step 1 (4.20 g, 11 mmol) in THF was added slowly butyllithium, 1.6m in hexanes (7.5 ml, 12 mmol) via a syringe. After stirred for 15 min, methyl 2,2,2-trifluoroacetate (1.1 ml, 11 mmol) was added drop wise. The reaction was stirred for 15 min at the same temperature. At this time, all the starting chromen was consumed, determined by LCMS. The reaction was quenched by the addition of saturated NH4Cl (40 ml0 and EtOAc (50 ml). The mixture was then warmed to room temperature. The aqueous layer was extracted with EtOAc (50 ml). The organics were combined, dried over Na2SO4, filtered and concentrated. The residue was purified on a silica gel column giving the title compound. MS m/z: 419.8(M+18).

Step 3: 1-(4-(tert-butyldimethylsilyloxy)-2,2-spirolcyclobutyl-3,4-dihydro-2H-pyrano(2,3-b)pyridine-6-yl)-2,2,2-trifluoroethanol To a solution of compound from step 2 (3.30 g, 8.22 mmol) in EtOH was added sodium borohydride (0.333 ml, 9.45 mmol). The reaction was stirred 4h at ambient temperature. At this point, all the starting material was consumed. Water was added to quench the reaction. Solvent was removed under reduced pressure. The aqueous residue was extracted with EtOAc (3×). The organic layers were combined, dried over MgSO4, filtered and concentrated. The residue was purified over silica gel column (2-15% EtOAc/hexane) to afford the title compound as a light yellow solid. It contained two fractions. Each had the same MS, but had different retention time on TLC. MS t/z: 404.2(M+1).

Step 4: 4-(tert-butyldimethylsilyloxy)-6-(1-chloro-2,2,2-trifluoroethyl)-2,2-spirolcyclobutyl-3,4-dihydro-2H-pyrano(2, 3-b)pyridine To a cooled (ice bath) mixture of compound 3 (2.34 g, 5.8 mmol) (from step 3) and pyridine (0.47 ml, 5.8 mmol) in toluene was added drop wise thionyl dichloride (0.59 ml, 8.1 mmol) via a syringe. After the addition was completed, the reaction was stirred at RT for 30 min, and heated at 75° C. for 16 h. Reaction was cooled to RT and quenched with water. The resulted mixture was extracted with EtOAc (2×). The organic layers were combined, dried over MgSO4, filtered and concentrated. The residue was dried in vacuum to afford the title compound. It was carried to the next step without further purification. MS m/z: 422.1 (M+1).

Step 5: 4-(tert-butyldimethylsilyloxy)-6-(2,2,2-trifluoroethyl)-2,2-spirolcyclobutyl-3,4-dihydro-2H-pyrano(2,3-b)pyridine To a solution of compound from step 4 (1.78 g, 4.22 mmol) in THF was added sodium tetrahydroborate (0.239 g, 6.33 mmol) in one portion. The reaction was heated under refluxing for 15 h and all the starting chloride was consumed. After cooled to room temperature, water was added to quench the reaction. The mixture was extracted with EtOAc (3×). The organic layers were dried over MgSO4, filtered and concentrated. The residue was dried in vacuum to afford the title compound. It was carried to the next step without further purification. MS m/z: 388.2 (M+1).

Step 6: 6-(2,2,2-trifluoroethyl)-2,2-spirolcyclobutyl-3,4-dihydro-2H-pyrano(2,3-b)pyridine-4-ol To compound 5 (1.21 g, 3 mmol) (crude from step 5) was added 4 N HCl/dioxane. The reaction was stirred at room temperature until all the starting material was consumed. The mixture was concentrated and dried in vacuum to give the title compound. It was carried to the next step without further purification.

Step 7: 6-(2,2,2-trifluoroethyl)-2,2-spirolcyclobutyl-2,3-dihydropyrano(2,3-b)pyridin-4-one To a stirred solution of compound (0.82 g, 3.0 mmol)(crude from step 6) in DCM was added sodium bicarbonate (0.12 ml, 3.0 mmol) in one portion followed by Dess martin Reactant 3 (1.3 g, 3.0 mmol) Stirring was continued for 3 h at RT and 1.0 ml MeOH was added. After Stirring for an additional 30 min, the mixture was filtrated. The filtrate was treated with 4 ml of 1M NaOH and stirred for 20 min. The mixture was extracted with 20 ml DCM (2×) and the combined organic extracts were dried over MgSO4, filtered and concentrated under reduced pressure. The residue was purified on silica gel column to afford the title compound. MS m/z: 272.0 (M+1).

Step 8: (R)-2,2-spirolcyclobutyl-6-(2,2,2-trifluoroethyl)-3,4-dihydro-2H-pyrano(2,3-b)pyridin-4-ol The title compound was prepared according to the methods described in step 5 of Example 509. MS m/z: 274.1 (M+1).

Step 9: (S)-4-azido-2,2-spirolcyclobutyl-6-(2,2,2-trifluoroethyl)-3,4-dihydro-2H-pyrano(2,3-b)pyridine The title compound was prepared according to the methods described in step 6 of Example 509. MS m/z: 299.1 (M+1).

Step 10: (S)-2,2-spirolcyclobutyl-6-(2,2,2-trifluoroethyl)-3,4-dihydro-2H-pyrano(2,3-b)pyridine-4-amine To a cooled (ice bath) solution of (S)-4-azido-2,2-spirolcyclobutyl-6-(2,2,2-trifluoroethyl)-3,4-dihydro-2H-pyrano (2,3-b)pyridine (196 mg, 657 μmol) in THF was added lithium aluminum hydride (657 μl, 1314 μmol) drop wise.

After stirred 1 h at room temperature, reduction was completed. The reaction mixture was diluted with THF and quenched by the slow addition of Na2SO4 12H2O until no bubble producing. The resulted mixture was filtered and the filtrate was concentrated, and dried in vacuum to afford the title compound as colorless oil. MS m/z: 256 (M–NH$_2$), 273 (M+1).

Step 11: N-((1S,2R)-2-hydroxy-1-(phenylmethyl)-3-(((4'S)-6'-(2,2,2-trifluoroethyl)-3',4'-dihydrospiro[cyclobutane-12'-pyrano[2,3-b]pyridin]-4'-yl)amino)propyl)acetamide. TFA salt The title compound was prepared according to the methods described in steps 10 and 11 of Example 510. MS m/z: 478.1 (M+1).

Example 513

N-((1S,2R)-1-((3-fluorophenyl)methyl)-2-hydroxy-3-(((4'S)-6'-((2R)-3,3,3-trifluoro-2-methylpropyl)-3', 4'-dihydrospiro[cyclobutane-1,2'-pyrano[2,3-b]pyridin]-4'-yl)amino)propyl)acetamide; and N-((1S,2R)-1-((3-fluorophenyl)methyl)-2-hydroxy-3-(((4'S)-6'-((2S)-3,3,3-trifluoro-2-methylpropyl)-3', 4'-dihydrospiro[cyclobutane-1,2'-pyrano[2,3-b]pyridin]-4'-yl)amino)propyl)acetamide Step 1: Tert-butyl allyl((S)-2,2-spirolcyclobutyl-6-(3,3,3-trifluoro-1-hydroxy-2-methylpropyl)-3,4-dihydro-2H-pyrano (2,3-b)pyridine-4-yl)carbamate To a cooled (−78° C.) solution of (S)-tert-butyl allyl(6-bromo-2,2-spirocyclobutyl-3,4-dihydro-2H-pyrano(2,3-b) pyridine-4-yl)carbamate (8.70 g, 21 mmol) in diethylether was added tert-butyllithium (25 ml, 43 mmol) dropwise. After stirred 15 min, the fresh distilled 3,3,3-trifluoro-2-methylpropanal (5.8 ml, 53 mmol) was added. The reaction was stirred 30 min, then quenched with sat. NH4Cl. The resulted mixture was warmed to RT and extracted with EtOAc (3×). The organic layers were combined, dried over Na2SO4, filtered and concentrated. The residue was purified on silica gel column to afford the title compound as light yellow oil. MS m/z: 457 (M+1).

Step 2: Tert-butyl alkyl((S)-2,2-spirolcyclobutyl-6-(3,3,3-trifluoro-1-chloro-2-methylpropyl)-3,4-dihydro-2H-pyrano(2, 3-b)pyridine-4-yl)carbamate To a cooled (ice bath) mixture of compound 1 (1.33 g, 2.9 mmol) (from step 1) and pyridine, anhydrous (0.24 ml, 2.9 mmol) in toluene was added thionyl chloride (SOCl2) (0.30 ml, 4.1 mmol) dropwise. After the addition was completed, the mixture was warmed to RT and then heated at 45° C. for 2 h. At this point, all the Reactant 1 was consumed and the desired product was formed, determined by LCMS. The reaction was cooled to RT and quenched with water (25 ml). The layers were separated. The aqueous layer was extracted with EtOAc (2×). The organic layers were combined, washed with brine and dried over Na2SO4. After filtration, the filtrate was concentrated and purified on silica gel column (5-15% EtOAc/hexane) to provide the title compound as yellow oil. MS m/z: 475 (M+1).

Step 3: (4S)-6-(3,3,3-trifluoro-1-chloro-2-methylpropyl)-2,2 spirocyclobutyl-3,4-dihydro-2H-pyrano(2,3-b)pyridine-4-amine To compound (1.06 g, 2 mmol) from step 2 was added hydrogen chloride 4.0 m in 1,4-dioxane (2.0 ml, 9 mmol). After stirred 15 h (over night), the Boc group was removed. The resulted mixture was diluted with CH2Cl2 and neutralized with saturated Na2HCO3 (25 ml). The aqueous layer was extracted with CH2Cl2 (2×). The organic layers were combined, dried over Na2SO4, filtered and concentrated. The residue was dried in vacuum to provide a yellow oil product. MS m/z: 475.2 (M+1). The yellow oil product from above was dissolved in CH2Cl2. 1,3-dimethylpyrimidine-2,4,6(1H,3H,5H)-trione (1 g, 7 mmol) was then added. After degassed for 10 min, PalladiumTetrakis (0.1 g, 0.1 mmol) was added and the mixture was heated at 40° C. for 1.5 h under N2 atmosphere. At this point, reaction was completed, determined by LCMS. Reaction was then warmed to room temperature and quenched with 1 N HCl. The organic layer was washed with 1 N HCl (2×). The aqueous layers were combined, neutralized with sat. Na2CO3 to PH=6.5, and then extracted with $CH_2Cl_2$ (3×). The organic layers were combined, dried over Na2SO4, filtered and concentrated. The residue was dried in vacuum to provide 845 mg of the title compound as off-white foam. MS m/z: 335 (M+1).

Step 4: N-((1S,2R)-1-((3-fluorophenyl)methyl)-2-hydroxy-3-(((4'S)-6'-((2R)-3,3,3-trifluoro-2-methylpropyl)-3',4'-dihydrospiro[cyclobutane-1,2'-pyrano[2,3-b]pyridin]-4'-yl)amino)propyl)acetamide; and N-((1S,2R)-1-((3-fluorophenyl)methyl)-2-hydroxy-3-(((4'S)-6'-((2S)-3,3,3-trifluoro-2-methylpropyl)-3',4'-dihydrospiro[cyclobutane-1,2'-pyrano[2,3-b]pyridin]-4'-yl)amino)propyl)acetamide The title compounds were prepared by the method described in co-pending patent application Ser. No. 60/738,767 Example 170. MS 71/z: 524.2 (M+1).

Example 514

Ethyl 1-(2-(((1S,2R)-3-(((4S)-6bromo-3,4-dihydrospiro[chromene-2,1'-cyclobutan]-4-yl)amino)-2-hydroxy-1-(phenylmethyl)propyl)amino)-2-oxoethyl)-1H-1,2,3-triazole-4-carboxylate Step 1: 2-Azido-N-((2S,3R)-4-((S)-6-bromo-2,2-spirocyclobutylchroman-4-ylamino)-3-hydroxy-1-phenylbutan-2-yl)acetamide The (2R,3S)-3-amino-1-((S)-6-bromo-2,2-spirocyclobutylchroman-4-ylamino)-4-phenylbutan-2-ol (0.43 g, 0.99 mmol) and 2-azidoacetic acid (0.100 g, 0.99 mmol) were dissolved in dmf (6.0 mL). Hunig's Base (0.22 ml, 1.2 mmol) was added. HATU (0.38 g, 0.99 mmol) was added, and the mixture was stirred at rt for 12 h. The reaction was concentrated to remove most of the DMF. The residue was taken up in EtOAc (100 mL) and the organic layer was extracted with water (7 mL), half-saturated brine (7 mL), and saturated brine (7 mL), then was dried over sodium sulfate and concentrated. The material was purified through silica gel (70 mL) which had been deactivated with $Et_3N$ (7.5 mL) eluting with EtOAc, affording the title compound. MS m/z 514/516 (M+1).

Step 2: Ethyl 1-(2-(((1S,2R)-3-(((4S)-6-bromo-3,4-dihydrospiro[chromene-2,1'-cyclobutan]-4-yl)amino)-2-hydroxy-1-(phenylmethyl)propyl)amino)-2-oxoethyl)-1H-1,2,3-triazole-4-carboxylate In a sealable vessel, ethyl propiolate (0.0067 ml, 0.066 mmol) and 2-azido-N-((2S,3R)-4-((S)-6-bromo-2,2-spirocyclobutylchroman-4-ylamino)-3-hydroxy-1-phenylbutan-2-yl)acetamide (0.020 g, 0.039 mmol) were dissolved in dioxane (0.3 mL). The vessel was sealed and placed in an 80 deg oil bath for 12 h. The reaction was cooled, taken up in EtOAc (60 mL) and the organic layer was extracted with dilute NaHCO3 (5 mL), half-saturated brine (5 mL) and saturated brine (5 mL), then was dried over sodium sulfate and concentrated. The material was purified through silica gel (15 mL) which had been deactivated with $Et_3N$ (2 mL), eluting with 3% MeOH-EtOAc, yielding the title compound as a white solid. MS m/z 612/614 (M+1).

Example 515

N-((1S,2R)-1-((3-Bromo-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide Step 1: (3-Bromo-4-fluorophenyl)methanol
3-Bromo-4-fluorobenzaldehyde (0.300 g, 1.48 mmol) was dissolved in methanol (3 mL). Sodium borohydride (0.0671 g, 1.77 mmol) was added. After 3 h, the reaction was quenched with methanol (1 mL), and the mixture was concentrated. The residue was taken up in 2:1 EtOAc-hexane (60 mL). The organic layer was extracted with dilute $NaHCO_3$ (6 mL) then half-saturated brine (6 mL), then was dried over sodium sulfate and concentrated. The material was purified through silica gel (45 mL) using 30% to 40% EtOAc-hexane to afford the title compound.

Step 2: 2-Bromo-4-(bromomethyl)-1-fluorobenzene
(3-Bromo-4-fluorophenyl)methanol (0.264 g, 1.29 mmol) was dissolved in DCM (3 mL). The solution was cooled to 0 deg, and tribromoborane (1.0 M in DCM, 0.863 ml, 0.863 mmol) was added. The mixture was stirred at 0 deg for 1 h, then rt for 1 h. The reaction was quenched with water, and the mixture was transferred to a separatory funnel with half-saturated $NaHCO_3$ (15 mL), and the aqueous phase was extracted with DCM (3×20 mL). The organics were combined, washed with half-saturated brine (5 mL), dried over sodium sulfate and concentrated. Purification of the residue through silica gel (40 mL) using 5% EtOAc-hexane afforded the title compound.

Step 3: N-((1S,2R)-1-((3-Bromo-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide
2-Bromo-4-(bromomethyl)-1-fluorobenzene was converted to the title compound using a method analogous to that described in Examples 509 and 510.

Example 516

2-(5-(Aminomethyl)-1H-1,2,3-triazol-1-yl)-N-((1S,2R)-3-(((4S)-6-bromo-3,4-dihydrospiro[chromene-2,1'-cyclobutan]-4-yl)amino)-2-hydroxy-1-(phenylmethyl)propyl)acetamide; and 2-(4-(aminomethyl)-1H-1,2,3-triazol-1-yl)-N-((1S,2R)-3-(((4S)-6-bromo-3,4-dihydrospiro[chromene-2,1'-cyclobutan]-4-yl)amino)-2-hydroxy-1-(phenylmethyl)propyl)acetamide In a microwave vessel, 2-azido-N-((2S,3R)-4-((S)-6-bromo-2,2-spirocyclobutylchroman-4-ylamino)-3-hydroxy-1-phenylbutan-2-yl)acetamide (0.020 g, 0.039 mmol) was taken up in prop-2-yn-1-amine (0.49 ml, 7.2 mmol). The vessel was sealed and placed in a 100 deg oil bath. After 12 h, the reaction was concentrated on the rotovap. The residue was purified through silica gel (15 mL) which had been deactivated with $Et_3N$ (2.0 mL) using 5% MeOH-dichloromethane to afford the title compounds as an equal mixture of isomers. MS m/z 569/571 (M+1)

Example 517

N-((1S,2R)-((3-Cyano-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide Step 1: (S)—N-((2S,3S)-1-(3-Bromo-4-fluorophenyl)-3,4-bis(tert-butyldimethylsilyloxy)butan-2-yl)-2-methylpropane-2-sulfinamide The title compound was prepared from (S,E)-N-((S)-2,3-bis(tert-butyldimethylsilyloxy)propylidene)-2-methylpropane-2-sulfinamide and 2-bromo-4-(bromomethyl)-1-fluorobenzene using a method analogous to that described in Examples 509 and 510.

Step 2: (S)—N-((2S,3S)-3,4-Bis(tert-butyldimethylsilyloxy)-1-(3-cyano-4-fluorophenyl)butan-2-yl)-2-methylpropane-2-sulfinamide The (S)—N-((2S,3S)-1-(3-bromo-4-fluorophenyl)-3,4-bis(tert-butyldimethylsilyloxy)butan-2-yl)-2-methylpropane-2-sulfinamide (0.247 g, 0.404 mmol), Pd$_2$(dba)$_3$-CHCl$_3$ (0.209 g, 0.202 mmol) dppf (0.224 g, 0.404 mmol) and zinc cyanide (0.0522 g, 0.445 mmol) were suspended in dmf (10 mL). A condenser was affixed and the flask was placed in a 120 deg oil bath. After 14 h, flask was concentrated. The residue was taken up in EtOAc (100 mL) and water (10 mL), and the mixture was filtered through Celite. The aqueous layer was separated and the organic layer was extracted with saturated brine (10 mL), dried over sodium sulfate and concentrated. Purification of the black residue through silica gel (40 mL) using 10% to 15% EtOAc-hexane afforded the title compound. MS m/z 557 (M+1).

Step 3: N-((1S,2R)-1-((3-Cyano-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide (S)—N-((2S,3S)-3,4-bis(tert-butyldimethylsilyloxy)-1-(3-cyano-4-fluorophenyl)butan-2-yl)-2-methylpropane-2-sulfinamide was converted to the title compound using a method analogous to that described in Examples 509 and 510. MS m/z 509 (M+1).

Example 518

N-((1S,2R)-1-((3-Chloro-2,4-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide Step 1: (3-Chloro-2,4-difluorophenyl)methanol 3-Chloro-2,4-difluorobenzoic acid (5.37 g, 27.9 mmol) was dissolved in THF (20 mL) and the solution was cooled to 0 deg. Borane methylsulfide (2.0 M in THF, 55.8 ml, 112 mmol) was added. The resulting solution was warmed to rt and stirred for 14 h. The solution was cooled in an ice bath, and 10% aqueous Na$_2$CO$_3$ (7 mL) was added slowly. The material was concentrated on the rotovap to a white solid. The residue was acidified with 3M aqueous HCl (30 mL), diluted with dichloromethane (50 mL), and the mixture was filtered through Celite. The layers were separated, and the organic layer was dried over sodium sulfate and concentrated. The residue was purified through silica gel (500 mL) using 30% EtOAc-hexane, to afford the title compound.

Step 2: 1-(Bromomethyl)-3-chloro-2,4-difluorobenzene (3-chloro-2,4-difluorophenyl)methanol was converted to the title compound using the procedure described in Example 461, Step 2. $^1$H NMR in CDCl$_3$: 7.29 (m, 1H), 6.98 (td, 1H, J=8.4, 1.6), 4.48 (s, 2H).

Step 3: N-((1S,2R)-1-((3-Chloro-2,4-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide 1-(Bromomethyl)-3-chloro-2,4-difluorobenzene was converted to the title compound using a method analogous to that described in Examples 509 and 510. MS m/z 536 (M+1).

Example 519

N-((1S,2R)-1-((4-Chlorophenyl)methyl)-2-hydroxy-3-(((4'S)-6'-((1-methylethyl)oxy)-3',4'-dihydrospiro[cyclobutane-1,2'-pyrano[2,3-b]pyridin]-4'-yl)amino)propyl)acetamide Step 1: (S)-tert-Butyl 6-bromo-2,2-spirocyclobutyl-3,4-dihydro-2H-pyrano[2,3-b]pyridin-4-ylcarbamate (S)-6-bromo-2,2-spirocyclobutyl-3,4-dihydro-2H-pyrano[2,3-b]pyridin-4-amine (968 mg, 3.6 mmol), Hunig's base (0.94 mL, 5.4 mmol), and Boc anhydride (0.98 g, 4.5 mmol) were dissolved in dichloromethane (15 mL), and the mixture was stirred at rt for 14 h. The reaction was quenched with ethanolamine (0.13 mL, 2.2 mmol), diluted with 10% aqueous sodium carbonate (9 mL), and the aqueous layer was extracted with DCM (3×20 mL). The organics were combined, washed with dilute brine, dried over sodium sulfate and concentrated. The product was purified through silica gel (200 mL) using 28% EtOAc-hexane to afford the title compound. MS m/z 369/371 (M+1).

Step 2: (S)-tert-Butyl allyl(6-bromo-2,2-spirocyclobutyl-3,4-dihydro-2H-pyrano[2,3-b]pyridin-4-yl)carbamate (S)-tert-Butyl 6-bromo-2,2-spirocyclobutyl-3,4-dihydro-2H-pyrano[2,3-b]pyridin-4-ylcarbamate (1.27 g, 3.45 mmol) was dissolved in DMF (10 mL) and NaH (60%, 165 mg, 4.14 mmol) was added. The suspension was cooled to 0 deg, and allyl bromide (0.418 mL, 4.83 mmol) was added. The mixture was stirred at 0 deg for 5 h. The mixture was concentrated, diluted with 90% ether-hexane (60 mL), and the organic layer was washed with water (2×5 mL) and saturated brine (5 mL). The organic layer was dried over magnesium sulfate, filtered, and concentrated. The residue was purified through silica gel (150 mL) using 20% EtOAc-hexane to afford the title compound. MS m/z 409/411 (M+1).

Step 3: (S)-tert-Butyl allyl(6-hydroxy-2,2-spirocyclobutyl-3,4-dihydro-2H-pyrano[2,3-b]pyridin-4-yl)carbamate (S)-tert-Butyl allyl(6-bromo-2,2-spirocyclobutyl-3,4-dihydro-2H-pyrano[2,3-b]pyridin-4-yl)carbamate (1.16 g, 2.8 mmol) and triisopropylborate (3.3 mL, 14 mmol) were dissolved in THF (25 mL). The solution was cooled to −78 deg. A solution of n-butyllithium in hexane (2.5 M, 2.1 mL, 5.2 mmol) was added. The solution was stirred at −78 deg for 30 min, then warmed to 0 deg. An aqueous solution of hydrogen peroxide (30% w/w, 2.9 mL, 28 mmol) and 2.5 M aqueous NaOH (6.5 mL) was added, and the mixture were stirred for 30 min. The aqueous layer was extracted with EtOAc (3×25 mL). The organics were combined, washed with saturated brine (2×5 mL), dried over sodium sulfate and concentrated. The material was purified through silica gel (125 mL) using 50% EtOAc-hexane to afford the title compound. MS m/z 347 (M+1).

Step 4: (S)-tert-Butyl allyl(6-isopropoxy-2,2-spirocyclobutyl-3,4-dihydro-2H-pyrano[2,3-b]pyridin-4-yl)carbamate In a sealable vessel, (S)-tert-butyl allyl(6-hydroxy-2,2-spirocyclobutyl-3,4-dihydro-2H-pyrano[2,3-b]pyridin-4-yl)carbamate (180 mg, 0.52 mmol) and cetyltrimethylammonium bromide (19 mg, 0.052 mmol) were dissolved in dioxane (0.42 mL) and 3.0 M aqueous potassium hydroxide (0.866 mL, 2.6 mmol) was added. Isopropyl bromide (0.098 mL, 1.04 mmol) was added. The vessel was sealed and the reaction mixture was heated at 100 deg for 3 h. The vessel was cooled, to rt, the mixture was diluted with ether (60 mL), and the organic layer was washed with water (2×6 mL) and saturated brine (6 mL). The organic layer was dried over magnesium sulfate, filtered, and concentrated. The residue was purified through silica gel (40 mL) using 30% EtOAc-hexane to afford the title compound. MS m/z 389 (M+1).

Step 5: (S)—N-Allyl-6-isopropoxy-2,2-spirocyclobutyl-3,4-dihydro-2H-pyrano[2,3-b]pyridin-4-amine In a sealable vessel,(S)-tert-butyl allyl(6-isopropoxy-2,2-spirocyclobutyl-3,4-dihydro-2H-pyrano[2,3-b]pyridin-4-yl) carbamate (246 mg, 0.63 mmol) was dissolved in dichloromethane (3.5 mL). TFA (0.488 mL, 6.3 mmol) was added. The vessel was sealed and heated at 50 deg for 6 h. The mixture was concentrated, and the residue was neutralized with 10% aqueous sodium carbonate (8 mL). The aqueous phase was extracted with 5% MeOH-dichloromethane (60 mL). The organic layer was dried over sodium sulfate and concentrated to afford the title compound. MS m/z 289 (M+1).

Step 6: (S)-6-Isopropoxy-2,2-spirocyclobutyl-3,4-dihydro-2H-pyrano[2,3-b]pyridin-4-amine (S)—N-Allyl-6-isopropoxy-2,2-spirocyclobutyl-3,4-dihydro-2H-pyrano[2,3-b]pyridin-4-amine (181 mg, 0.63 mmol), 1,3-dimethylpyrimidine,2,4,6(1H,3H,5H)-trione (0.294 g, 1.88 mmol), Pd(PPh$_3$)$_4$ (36.3 mg, 0.031 mmol) were dissolved in dichloromethane (4 mL). The mixture was heated at 35 deg for 1.5 h. The mixture was diluted with 0.5 M aqueous sodium carbonate (8 mL) and the aqueous phase was extracted with 5% MeOH-dichloromethane (3×20 mL). The organics were combined, washed with dilute brine (5 mL), dried over sodium sulfate, and concentrated. The residue was purified through silica gel (25 mL) which had been deactivated with triethylamine (2.5 mL), eluting with 0.5% MeOH-dichloromethane to afford the title compound. MS m/z 249 (M+1).

Step 7: N-((1S,2R)-1-((4-Chlorophenyl)methyl)-2-hydroxy-3-(((4'S)-6'-((1-methylethyl)oxy)-3',4'-dihydrospiro[cyclobutane-1 2'-pyrano[2,3-b]pyridin]-4'-yl)amino)propyl)acetamide (S)-6-Isopropoxy-2,2-spirocyclobutyl-3,4-dihydro-2H-pyrano[2,3-b]pyridin-4-amine was converted to the title compound using a method analogous to that described in Examples 509 and 510. MS m/z 488 (M+1).

The following compounds are further examples of the present invention, and were made by methods described hereinabove.

TABLE 4

| Ex. No. | Compound Name | Mass Found | Cell Assay |
|---|---|---|---|
| 520 | N-((1S,2R)-1-((3,5-difluorophenyl)methyl)-2-hydroxy-3-(((4S)-6-(1-methyl-1H-1,2,3-triazol-4-yl)-3,4-dihydrospiro[chromene-2,1'-cyclobutan]-4-yl)amino)propyl)acetamide | 512 | 2.158087 |
| 521 | N-((1S,2R)-2-hydroxy-3-(((4S)-6-(1-methyl-1H-1,2,3-triazol-4-yl)-3,4-dihydrospiro[chromene-2,1'-cyclobutan]-4-yl)amino)-1-(phenylmethyl)propyl)acetamide | 476 | 10 |
| 522 | N-((1S,2R)-3-(((4S)-6-((2R)-2-fluoropropyl)-3,4-dihydrospiro[chromene-2,1'-cyclobutan]-4-yl)amino)-2-hydroxy-1-(phenylmethyl)propyl)acetamide N-((1S,2R)-3-(((4S)-6-((2S)-2-fluoropropyl)-3,4-dihydrospiro[chromene-2,1'-cyclobutan]-4-yl)amino)-2-hydroxy-1-(phenylmethyl)propyl)acetamide | 455 | 0.010493 |
| 523 | N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-(phenylmethyl)propyl)acetamide | 452 | 0.004092 |
| 524 | N-((1S,2R)-1-((3-cyanophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide | 495 | 0.002424 |
| 525 | N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-1-((3-fluorophenyl)methyl)-2-hydroxypropyl)acetamide | 488 | 0.003945 |
| 526 | N-((1S,2R)-3-(((4S)-6-bromo-2,2-dimethyl-3,4-dihydro-2H-chromen-4-yl)amino)-1-((3-cyanophenyl)methyl)-2-hydroxypropyl)acetamide | 486, 488 | 0.116235 |
| 527 | N-((1S,2R)-3-(((4S)-6-bromo-2,2-dimethyl-3,4-dihydro-2H-chromen-4-yl)amino)-1-((3-cyanophenyl)methyl)-2-hydroxypropyl)-2-(methyloxy)acetamide | 516, 518 | 0.12029 |
| 528 | N~1~-((1S,2R)-3-(((4S)-6-bromo-2,2-dimethyl-3,4-dihydro-2H-chromen-4-yl)amino)-1-((3-cyanophenyl)methyl)-2-hydroxypropyl)-N~2~,N~2~-dimethylglycinamide | 529, 531 | 1.122924 |
| 529 | N-((1S,2R)-3-(((4S)-8-bromo-6-ethyl-2,2-dimethyl-3,4-dihydro-2H-chromen-4-yl)amino)-1-((3-cyanophenyl)methyl)-2-hydroxypropyl)acetamide | 514, 516 | 0.033865 |
| 530 | N-((1S,2R)-1-((3-cyanophenyl)methyl)-3-(((1S)-3,3-dimethyl-7-(methyloxy)-4-oxo-1,2,3,4-tetrahydro-1-naphthalenyl)amino)-2-hydroxypropyl)-2-(methyloxy)acetamide N-((1S,2R)-1-((3-cyanophenyl)methyl)-3-(((1R)-3,3-dimethyl-7-(methyloxy)-4-oxo-1,2,3,4-tetrahydro-1-naphthalenyl)amino)-2-hydroxypropyl)-2-(methyloxy)acetamide | 480 | 0.220964 |

TABLE 4-continued

| Ex. No. | Compound Name | Mass Found | Cell Assay |
|---|---|---|---|
| 531 | N-((1S,2R)-1-((3-cyanophenyl)methyl)-3-(((1S)-3,3-dimethyl-7-(methyloxy)-4-oxo-1,2,3,4-tetrahydro-1-naphthalenyl)amino)-2-hydroxypropyl)acetamide N-((1S,2R)-1-((3-cyanophenyl)methyl)-3-(((1R)-3,3-dimethyl-7-(methyloxy)-4-oxo-1,2,3,4-tetrahydro-1-naphthalenyl)amino)-2-hydroxypropyl)acetamide | 450 | 0.135497 |
| 532 | N-((1S,2R)-1-((3-cyanophenyl)methyl)-3-(((4S)-6-ethyl-2,2-dimethyl-8-(4-morpholinyl)-3,4-dihydro-2H-chromen-4-yl)amino)-2-hydroxypropyl)acetamide | 521 | 0.011199 |
| 533 | N-((1S,2R)-3-(((4R)-6-ethyl-2,2-dimethyl-8-(1-pyrrolidinyl)-3,4-dihydro-2H-chromen-4-yl)amino)-2-hydroxy-1-(phenylmethyl)propyl)acetamide N-((1S,2R)-3-(((4S)-6-ethyl-2,2-dimethyl-8-(1-pyrrolidinyl)-3,4-dihydro-2H-chromen-4-yl)amino)-2-hydroxy-1-(phenylmethyl)propyl)acetamide | 480 | 0.064408 |
| 534 | N-((1S,2R)-3-(((4S)-8-(dimethylamino)-6-ethyl-2,2-dimethyl-3,4-dihydro-2H-chromen-4-yl)amino)-2-hydroxy-1-(phenylmethyl)propyl)acetamide N-((1S,2R)-3-(((4R)-8-(dimethylamino)-6-ethyl-2,2-dimethyl-3,4-dihydro-2H-chromen-4-yl)amino)-2-hydroxy-1-(phenylmethyl)propyl)acetamide | 454 | 0.022928 |
| 535 | N-((1S,2R)-3-(((4S)-6-ethyl-2,2-dimethyl-8-(methylamino)-3,4-dihydro-2H-chromen-4-yl)amino)-2-hydroxy-1-(phenylmethyl)propyl)acetamide | 440 | 0.923788 |
| 536 | N-((1S,2R)-3-(((4S)-6-(2,2-dimethylpropyl)-8-(4-morpholinyl)-3,4-dihydrospiro[chromene-2,1'-cyclobutan]-4-yl)amino)-1-((4-fluorophenyl)methyl)-2-hydroxypropyl)acetamide | 568 | 2.090331 |
| 537 | N-((1S,2R)-3-(((4S)-6-(2,2-dimethylpropyl)-8-(4-morpholinyl)-3,4-dihydrospiro[chromene-2,1'-cyclobutan]-4-yl)amino)-2-hydroxy-1-(phenylmethyl)propyl)acetamide | 550 | 1.96531 |
| 538 | N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3-methylbutyl)acetamide | 432 | 0.176659 |
| 539 | N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3-methyl-3-buten-1-yl)acetamide | 430 | 0.050267 |
| 540 | N-((1S,2R)-1-((3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | | 0.002035 |
| 541 | N-((1S,2R)-2-hydroxy-3-(((5'S)-3'-methyl-5',8'-dihydro-6'H-spiro[cyclobutane-1,7'-quinolin]-5'-yl)amino)-1-(phenylmethyl)propyl)acetamide | 408 | 0.650675 |
| 542 | N-((1S,2R)-1-((3-cyanophenyl)methyl)-2-hydroxy-3-(((5'S)-3'-methyl-5',8'-dihydro-6'H-spiro[cyclobutane-1,7'-quinolin]-5'-yl)amino)propyl)acetamide | 433 | 0.064592 |
| 543 | N-((1S,2R)-1-((3-cyanophenyl)methyl)-2-hydroxy-3-(((5S)-3,7,7-trimethyl-5,6,7,8-tetrahydro-5-quinolinyl)amino)propyl)acetamide | 421 | 0.123613 |
| 544 | N-((1S,2R)-1-((3,5-difluorophenyl)methyl)-2-hydroxy-3-(((4S)-6-(1,3-oxazol-2-yl)-3,4-dihydrospiro[chromene-2,1'-cyclobutan]-4-yl)amino)propyl)acetamide | 498 | 0.631397 |
| 545 | N-((1S,2R)-3-(((4S)-6-(2,2-dimethylpropyl)-2,2-dimethyl-3,4-dihydro-2H-pyrano[2,3-b]pyridin-4-yl)amino)-2-hydroxy-1-(phenylmethyl)propyl)acetamide | 454 | 0.004607 |
| 546 | N-((1S,2R)-3-(((4S)-6-(2,2-dimethylpropyl)-2,2-dimethyl-3,4-dihydro-2H-pyrano[2,3-b]pyridin-4-yl)amino)-1-((3-fluorophenyl)methyl)-2-hydroxypropyl)acetamide | 472 | 0.001669 |
| 547 | N-((1S,2R)-3-(((4'S)-6'-(2,2-dimethylpropyl)-3',4'-dihydrospiro[cyclopentane-1,2'-pyrano[2,3-b]pyridin]-4'-yl)amino)-1-((4-fluorophenyl)methyl)-2-hydroxypropyl)acetamide | 498 | 0.034798 |
| 548 | N-((1S,2R)-1-((3,5-difluorophenyl)methyl)-3-(((4'S)-6'-(2,2-dimethylpropyl)-3',4'-dihydrospiro[cyclopentane-1,2'-pyrano[2,3-b]pyridin]-4'-yl)amino)-2-hydroxypropyl)acetamide | 516 | 0.002832 |
| 549 | N-((1S,2R)-3-(((4'S)-6'-(2,2-dimethylpropyl)-3',4'-dihydrospiro[cyclopentane-1,2'-pyrano[2,3-b]pyridin]-4'-yl)amino)-1-((3-fluorophenyl)methyl)-2-hydroxypropyl)acetamide | 498 | 0.006927 |
| 550 | N-((1S,2R)-3-(((4'S)-6'-(2,2-dimethylpropyl)-3',4'-dihydrospiro[cyclopropane-1,2'-pyrano[2,3-b]pyridin]-4'-yl)amino)-1-((4-fluoro-3-methylphenyl)methyl)-2-hydroxypropyl)acetamide | 442 | 0.020321 |

TABLE 4-continued

| Ex. No. | Compound Name | Mass Found | Cell Assay |
|---|---|---|---|
| 551 | N-((1S,2R)-3-(((4'S)-6'-((1S)-1-fluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide N-((1S,2R)-3-(((4'S)-6'-((1R)-1-fluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 488 | 1.647171 |
| 552 | N-((1S,2R)-3-(((4'S)-6'-((1R)-1-fluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 488 | 1.260258 |
| 553 | N-((1S,2R)-3-(((4'S)-6'-((1S)-1-fluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 488 | 0.271801 |
| 554 | N-((1S,2R)-3-(((4'S)-6'-((1S)-1-fluoro-2-methylpropyl)-3',4'-dihydrospiro[cyclobutane-1,2'-pyrano[2,3-b]pyridin]-4'-yl)amino)-2-hydroxy-1-(phenylmethyl)propyl)acetamide | 488 | 2.581944 |
| 555 | N-((1S,2R)-3-(((4'S)-6'-((1S)-1-fluoro-2-methylpropyl)-3',4'-dihydrospiro[cyclobutane-1,2'-pyrano[2,3-b]pyridin]-4'-yl)amino)-1-((3-fluorophenyl)methyl)-2-hydroxypropyl)acetamide | 488 | 1.429449 |
| 556 | N-((1S,2R)-3-(((1S)-3,3-dimethyl-7-((2-(methyloxy)ethyl)amino)-4-oxo-1,2,3,4-tetrahydro-1-naphthalenyl)amino)-2-hydroxy-1-(phenylmethyl)propyl)acetamide N-((1S,2R)-3-(((1R)-3,3-dimethyl-7-((2-(methyloxy)ethyl)amino)-4-oxo-1,2,3,4-tetrahydro-1-naphthalenyl)amino)-2-hydroxy-1-(phenylmethyl)propyl)acetamide | 468 | 10 |
| 557 | N-((1S,2R)-3-(((1R)-7-(cyclopentylamino)-3,3-dimethyl-4-oxo-1,2,3,4-tetrahydro-1-naphthalenyl)amino)-2-hydroxy-1-(phenylmethyl)propyl)acetamide N-((1S,2R)-3-(((1S)-7-(cyclopentylamino)-3,3-dimethyl-4-oxo-1,2,3,4-tetrahydro-1-naphthalenyl)amino)-2-hydroxy-1-(phenylmethyl)propyl)acetamide | 478 | 0.038437 |
| 558 | N-((1S,2R)-1-((3,5-difluorophenyl)methyl)-3-(((1S)-7-(2,2-dimethylpropyl)-3,3-dimethyl-4-oxo-1,2,3,4-tetrahydro-1-naphthalenyl)amino)-2-hydroxypropyl)acetamide N-((1S,2R)-1-((3,5-difluorophenyl)methyl)-3-(((1R)-7-(2,2-dimethylpropyl)-3,3-dimethyl-4-oxo-1,2,3,4-tetrahydro-1-naphthalenyl)amino)-2-hydroxypropyl)acetamide | 501 | 0.038226 |
| 559 | N-((1S,2R)-3-(((4'S)-6'-(2,2-dimethylpropyl)-3',4'-dihydro-1'H-spiro[cyclobutane-1,2'-quinolin]-4'-yl)amino)-1-((4-fluorophenyl)methyl)-2-hydroxypropyl)acetamide | 482 | 0.104975 |
| 560 | N-((1S,2R)-1-((3,5-difluorophenyl)methyl)-3-(((4'S)-6'-(2,2-dimethylpropyl)-3',4'-dihydro-1'H-spiro[cyclobutane-1,2'-quinolin]-4'-yl)amino)-2-hydroxypropyl)acetamide | 500 | 0.011735 |
| 561 | N-((1S,2R)-3-(((4'S)-6'-(2,2-dimethylpropyl)-3',4'-dihydro-1'H-spiro[cyclobutane-1,2'-quinolin]-4'-yl)amino)-1-((3-fluorophenyl)methyl)-2-hydroxypropyl)acetamide | 482 | 0.029368 |
| 562 | N-((1S,2R)-1-((3-bromo-4-fluorophenyl)methyl)-3-(((4'S)-6'-(2,2-dimethylpropyl)-3',4'-dihydro-1'H-spiro[cyclobutane-1,2'-quinolin]-4'-yl)amino)-2-hydroxypropyl)acetamide | 561 | 0.14112 |
| 563 | N-((1S,2R)-3-(((4'S)-6'-(2,2-dimethylpropyl)-1'-oxo-3',4'-dihydro-1'H-spiro[cyclopentane-1,2'-naphthalen]-4'-yl)amino)-1-((4-fluorophenyl)methyl)-2-hydroxypropyl)acetamide | 509 | 10 |
| 564 | N-((1S,2R)-3-(((4'R)-6'-(2,2-dimethylpropyl)-1'-oxo-3',4'-dihydro-1'H-spiro[cyclopentane-1,2'-naphthalen]-4'-yl)amino)-1-((4-fluorophenyl)methyl)-2-hydroxypropyl)acetamide | 509 | 0.569059 |
| 565 | N-((1S,2R)-3-(((3S,4'S)-6'-chloro-3',4,4',5-tetrahydrospiro[furan-3,2'-pyrano[2,3-b]pyridin]-4'-yl)amino)-2-hydroxy-1-(phenylmethyl)propyl)acetamide N-((1S,2R)-3-(((3R,4'S)-6'-chloro-3',4,4',5-tetrahydrospiro[furan-3,2'-pyrano[2,3-b]pyridin]-4'-yl)amino)-2-hydroxy-1-(phenylmethyl)propyl)acetamide | 446 | 10 |
| 566 | N-((1S,2R)-3-(((4'S)-6'-ethyl-3',4'-dihydrospiro[cyclobutane-1,2'-pyrano[2,3-b]pyridin]-4'-yl)amino)-1-((3-fluorophenyl)methyl)-2-hydroxypropyl)acetamide | 442 | 0.029044 |
| 567 | N-((1S,2R)-1-((3-chloro-5-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 518 | 0.003274 |

TABLE 4-continued

| Ex. No. | Compound Name | Mass Found | Cell Assay |
|---|---|---|---|
| 568 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 484 | 0.008126 |
| 569 | N-((1S,2R)-3-(((4'S)-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide | 484 | 0.005216 |
| 570 | N-((1S,2R)-3-(((4'S)-6'-(2,2-dimethylpropyl)-3',4'-dihydrospiro[cyclobutane-1,2'-pyrano[2,3-c]pyridin]-4'-yl)amino)-1-((4-fluorophenyl)methyl)-2-hydroxypropyl)acetamide | 484 | 0.022073 |
| 571 | N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 488 | 0.080924 |
| 572 | N-((1S,2R)-3-(((4S)-6-(2,2-dimethylpropyl)-2,2-dimethyl-3,4-dihydro-2H-pyrano[2,3-b]pyridin-4-yl)amino)-1-((4-fluorophenyl)methyl)-2-hydroxypropyl)acetamide | 472 | 0.013847 |
| 573 | N-((1S,2R)-1-((3,5-difluorophenyl)methyl)-3-(((4S)-6-(2,2-dimethylpropyl)-2,2-dimethyl-3,4-dihydro-2H-pyrano[2,3-b]pyridin-4-yl)amino)-2-hydroxypropyl)acetamide | 490 | 0.003117 |
| 574 | N-((1S,2S)-3-(((4'S)-6'-(2-fluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 488 | 0.110607 |
| 575 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluoro-3-methylphenyl)methyl)-2-hydroxypropyl)acetamide | 498 | 0.004641 |
| 576 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluoro-4-methylphenyl)methyl)-2-hydroxypropyl)acetamide | 498 | 0.002151 |
| 577 | methyl ((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)carbamate | 500 | 0.060048 |
| 578 | N-((1S,2R)-1-((4-fluoro-3-methylphenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide | 502 | 0.028506 |
| 579 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((3-(methyloxy)phenyl)methyl)propyl)acetamide | 496 | 0.00461 |
| 580 | N-((1S,2R)-1-((4-chlorophenyl)methyl)-3-(((4'S)-6'-(2,2-dimethylpropyl)-3',4'-dihydrospiro[cyclopropane-1,2'-pyrano[2,3-b]pyridin]-4'-yl)amino)-2-hydroxypropyl)acetamide | 486 | 0.119905 |
| 581 | N-((1S,2R)-3-(((4'S)-6'-(2,2-dimethyl-3-(methyloxy)propyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 514 | 0.137018 |
| 582 | N-((1S,2R)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-2-hydroxy-1-(phenylmethyl)propyl)acetamide | 509 | 0.031787 |
| 583 | N-((1S,2R)-3-(((4'S)-8'-chloro-6'-(2,2-dimethylpropyl)-3',4'-dihydrospiro[cyclobutane-1,2'-pyrano[2,3-c]pyridin]-4'-yl)amino)-1-((4-fluorophenyl)methyl)-2-hydroxypropyl)acetamide | 518 | 0.112144 |
| 584 | N-((1S,2R)-3-(((4'S)-6'-(2,2-dimethylpropyl)-8'-(ethylamino)-3',4'-dihydrospiro[cyclobutane-1,2'-pyrano[2,3-c]pyridin]-4'-yl)amino)-1-((4-fluorophenyl)methyl)-2-hydroxypropyl)acetamide | 527 | 0.005288 |
| 585 | N-((1S,2R)-3-(((4'S)-6'-(2,2-dimethylpropyl)-8'-((1-methylethyl)amino)-3',4'-dihydrospiro[cyclobutane-1,2'-pyrano[2,3-c]pyridin]-4'-yl)amino)-1-((4-fluorophenyl)methyl)-2-hydroxypropyl)acetamide | 541 | 0.022345 |
| 586 | N-((1S,2R)-3-(((4'S)-8'-(cyclopropylamino)-6'-(2,2-dimethylpropyl)-3',4'-dihydrospiro[cyclobutane-1,2'-pyrano[2,3-c]pyridin]-4'-yl)amino)-1-((4-fluorophenyl)methyl)-2-hydroxypropyl)acetamide | 539 | 0.014049 |

TABLE 4-continued

| Ex. No. | Compound Name | Mass Found | Cell Assay |
|---|---|---|---|
| 587 | N-((1S,2R)-3-(((4'S)-6'-(2,2-dimethylpropyl)-8'-(tetrahydro-2H-pyran-4-ylamino)-3',4'-dihydrospiro[cyclobutane-1,2'-pyrano[2,3-c]pyridin]-4'-yl)amino)-1-((4-fluorophenyl)methyl)-2-hydroxypropyl)acetamide | 583 | 0.008485 |
| 588 | N-((1S,2R)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-1-((4-fluorophenyl)methyl)-2-hydroxypropyl)acetamide | 527 | 0.052264 |
| 589 | N-((1S,2R)-3-(((4'S)-8'-((1,1-dimethylethyl)amino)-6'-(2,2-dimethylpropyl)-3',4'-dihydrospiro[cyclobutane-1,2'-pyrano[2,3-c]pyridin]-4'-yl)amino)-1-((4-fluorophenyl)methyl)-2-hydroxypropyl)acetamide | 555 | 0.615121 |
| 590 | N-((1S,2R)-3-(((4'S)-6'-(2,2-dimethylpropyl)-8'-(methylamino)-3',4'-dihydrospiro[cyclobutane-1,2'-pyrano[2,3-c]pyridin]-4'-yl)amino)-1-((3-fluorophenyl)methyl)-2-hydroxypropyl)acetamide | 513 | 0.001406 |
| 591 | N-((1S,2R)-3-(((4'S)-6'-(2,2-dimethylpropyl)-8'-(ethylamino)-3',4'-dihydrospiro[cyclobutane-1,2'-pyrano[2,3-c]pyridin]-4'-yl)amino)-1-((3-fluorophenyl)methyl)-2-hydroxypropyl)acetamide | 527 | 0.002976 |
| 592 | N-((1S,2R)-3-(((4'S)-6'-(2,2-dimethylpropyl)-8'-(tetrahydro-2H-pyran-4-ylamino)-3',4'-dihydrospiro[cyclobutane-1,2'-pyrano[2,3-c]pyridin]-4'-yl)amino)-1-((3-fluorophenyl)methyl)-2-hydroxypropyl)acetamide | 583 | 0.003238 |
| 593 | N-((1S,2R)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide | 527 | 0.023623 |
| 594 | N-((1S,2R)-3-(((4'S)-6'-(2,2-dimethylpropyl)-8'-oxo-3',4',7',8'-tetrahydrospiro[cyclobutane-1,2'-pyrano[2,3-c]pyridin]-4'-yl)amino)-1-((3-fluorophenyl)methyl)-2-hydroxypropyl)acetamide | 500 | 0.023364 |
| 595 | N-((1S,2R)-3-(((4'R)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((4-fluorophenyl)methyl)-2-hydroxypropyl)acetamide N-((1S,2R)-3-(((4'S)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((4-fluorophenyl)methyl)-2-hydroxypropyl)acetamide | 542 | 0.607192 |
| 596 | N-((1S,2R)-3-(((4'R)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((3-fluorophenyl)methyl)-2-hydroxypropyl)acetamide N-((1S,2R)-3-(((4'S)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((3-fluorophenyl)methyl)-2-hydroxypropyl)acetamide | 542 | 0.036426 |
| 597 | N-((1S,2R)-1-((3,5-difluorophenyl)methyl)-3-(((4'R)-6'-(2,2-dimethylpropyl)-8'-((1-methylethyl)oxy)-3',4'-dihydrospiro[cyclobutane-1,2'-pyrano[2,3-c]pyridin]-4'-yl)amino)-2-hydroxypropyl)acetamide N-((1S,2R)-1-((3,5-difluorophenyl)methyl)-3-(((4'S)-6'-(2,2-dimethylpropyl)-8'-((1-methylethyl)oxy)-3',4'-dihydrospiro[cyclobutane-1,2'-pyrano[2,3-c]pyridin]-4'-yl)amino)-2-hydroxypropyl)acetamide | 560 | 0.050591 |
| 598 | N-((1S,2R)-1-((3,5-difluorophenyl)methyl)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-2-hydroxypropyl)acetamide | 545 | 0.026836 |
| 599 | N-((1S,2R)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-1-((4-(dimethylamino)phenyl)methyl)-2-hydroxypropyl)acetamide | 552 | 0.167357 |
| 600 | N-((1S,2R)-1-((4-chlorophenyl)methyl)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-2-hydroxypropyl)acetamide | 543 | 0.633888 |
| 601 | N-((1S,2R)-1-((2,3-difluorophenyl)methyl)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-2-hydroxypropyl)acetamide | 545 | 0.226574 |
| 602 | N-((1S,2R)-3-(((4'S)-8'-(cyclopropylamino)-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide | 539 | 0.002887 |

TABLE 4-continued

| Ex. No. | Compound Name | Mass Found | Cell Assay |
|---|---|---|---|
| 603 | 1,1-dimethylethyl (2-(((4'S)-4'-(((2R,3S)-3-(acetylamino)-4-(3-fluorophenyl)-2-hydroxybutyl)amino)-6'-(2,2-dimethylpropyl)-3',4'-dihydrospiro[cyclobutane-1,2'-pyrano[2,3-c]pyridin]-8'-yl)amino)ethyl)carbamate | 642 | 0.012859 |
| 604 | N-((1S,2R)-3-(((4'S)-6'-(2,2-dimethylpropyl)-8'-(3-(methyloxy)-1-azetidinyl)-3',4'-dihydrospiro[cyclobutane-1,2'-pyrano[2,3-c]pyridin]-4'-yl)amino)-1-((3-fluorophenyl)methyl)-2-hydroxypropyl)acetamide | 569 | 0.00579 |
| 605 | N-((1S,2R)-3-(((4'S)-8'-amino-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide | 499 | 0.001558 |
| 606 | N-((1S,2R)-3-(((4'S)-8'-((2-aminoethyl)amino)-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide | 542 | 0.004432 |
| 607 | N-((1S,2R)-3-(((4'R)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((4-fluorophenyl)methyl)-2-hydroxypropyl)acetamide | 542 | 0.080297 |
| 608 | N-((1S,2R)-3-(((4'S)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((4-fluorophenyl)methyl)-2-hydroxypropyl)acetamide | 542 | 0.064326 |
| 609 | N-((1S,2R)-3-(((4'R)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((3-fluorophenyl)methyl)-2-hydroxypropyl)acetamide | 542 | 0.06672 |
| 610 | N-((1S,2R)-3-(((4'S)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((3-fluorophenyl)methyl)-2-hydroxypropyl)acetamide | 542 | 0.017223 |
| 611 | N-((1S,2R)-1-((3,5-difluorophenyl)methyl)-3-(((4'R)-6'-(2,2-dimethylpropyl)-8'-((1-methylethyl)oxy)-3',4'-dihydrospiro[cyclobutane-1,2'-pyrano[2,3-c]pyridin]-4'-yl)amino)-2-hydroxypropyl)acetamide | 560 | 0.161326 |
| 612 | N-((1S,2R)-1-((3,5-difluorophenyl)methyl)-3-(((4'S)-6'-(2,2-dimethylpropyl)-8'-((1-methylethyl)oxy)-3',4'-dihydrospiro[cyclobutane-1,2'-pyrano[2,3-c]pyridin]-4'-yl)amino)-2-hydroxypropyl)acetamide | 560 | 0.024218 |
| 613 | N-((1S,2R)-3-(((4'S)-6'-(2,2-dimethylpropyl)-8'-(methyloxy)-3',4'-dihydrospiro[cyclobutane-1,2'-pyrano[2,3-c]pyridin]-4'-yl)amino)-1-((4-fluorophenyl)methyl)-2-hydroxypropyl)acetamide | 514 | 0.103038 |
| 614 | N-((1S,2R)-3-(((4'S)-6'-(2,2-dimethylpropyl)-8'-(3-(methyloxy)-1-azetidinyl)-3',4'-dihydrospiro[cyclobutane-1,2'-pyrano[2,3-c]pyridin]-4'-yl)amino)-1-((4-fluorophenyl)methyl)-2-hydroxypropyl)acetamide | 569 | 0.059045 |
| 615 | N-((1S,2R)-1-((4-fluorophenyl)methyl)-2-hydroxy-3-((((1s,3R,4'S)-3-methyl-6'-(2-methylpropyl)-3',4'-dihydrospiro[cyclobutane-1,2'-pyrano[2,3-b]pyridin]-4'-yl)amino)propyl)acetamide | 484 | 0.024809 |
| 616 | N-((1S,2R)-1-((4-fluorophenyl)methyl)-2-hydroxy-3-((((1r,3S,4'S)-3-methyl-6'-(2-methylpropyl)-3',4'-dihydrospiro[cyclobutane-1,2'-pyrano[2,3-b]pyridin]-4'-yl)amino)propyl)acetamide | 484 | 0.062677 |
| 617 | N-((1S,2R)-1-((3-fluorophenyl)methyl)-2-hydroxy-3-((((1s,3R,4'S)-3-methyl-6'-(2-methylpropyl)-3',4'-dihydrospiro[cyclobutane-1,2'-pyrano[2,3-b]pyridin]-4'-yl)amino)propyl)acetamide | 484 | 0.002985 |
| 618 | N-((1S,2R)-1-((4-chlorophenyl)methyl)-2-hydroxy-3-((((1s,3R,4'S)-3-methyl-6'-(2-methylpropyl)-3',4'-dihydrospiro[cyclobutane-1,2'-pyrano[2,3-b]pyridin]-4'-yl)amino)propyl)acetamide | 500 | 0.072183 |
| 619 | N-((1S,2R)-3-((((1S,2S,4'S)-6'-(2,2-dimethylpropyl)-2-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide | 498 | 0.032589 |
| 620 | N-((1S,2R)-1-((4-chlorophenyl)methyl)-3-((((1S,2S,4'S)-6'-(2,2-dimethylpropyl)-2-methyl-3',4'-dihydrospiro[cyclobutane-1,2'-pyrano[2,3-b]pyridin]-4'-yl)amino)-2-hydroxypropyl)acetamide | 514 | 0.062047 |
| 621 | N-((1S,2R)-3-((((1R,2R,4'S)-6'-(2,2-dimethylpropyl)-2-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide | 498 | 10 |

TABLE 4-continued

| Ex. No. | Compound Name | Mass Found | Cell Assay |
|---|---|---|---|
| 622 | N-((1S,2R)-1-((4-chlorophenyl)methyl)-3-(((1R,2R,4'S)-6'-(2,2-dimethylpropyl)-2-methyl-3',4'-dihydrospiro[cyclobutane-1,2'-pyrano[2,3-b]pyridin]-4'-yl)amino)-2-hydroxypropyl)acetamide | 514 | 10 |
| 623 | N-((1S,2R)-3-(((1S,2R,4'S)-6'-(2,2-dimethylpropyl)-2-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide | 498 | 0.038235 |
| 624 | N-((1S,2R)-1-((4-chlorophenyl)methyl)-3-(((1S,2R,4'S)-6'-(2,2-dimethylpropyl)-2-methyl-3',4'-dihydrospiro[cyclobutane-1,2'-pyrano[2,3-b]pyridin]-4'-yl)amino)-2-hydroxypropyl)acetamide | 514 | 0.061497 |
| 625 | N-((1S,2R)-3-(((1R,2S,4'S)-6'-(2,2-dimethylpropyl)-2-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide | 498 | 10 |
| 626 | N-((1S,2R)-1-((4-chlorophenyl)methyl)-3-(((1R,2S,4'S)-6'-(2,2-dimethylpropyl)-2-methyl-3',4'-dihydrospiro[cyclobutane-1,2'-pyrano[2,3-b]pyridin]-4'-yl)amino)-2-hydroxypropyl)acetamide | 514 | 10 |
| 627 | methyl ((1S,2R)-1-((4-chlorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)carbamate | 516 | 0.936069 |
| 628 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)acetamide | 514 | 0.010499 |
| 629 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-fluoroacetamide | 502 | 0.012573 |
| 630 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2,2-difluoroacetamide | 520 | 0.036373 |
| 631 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2,2,2-trifluoroacetamide | 538 | 0.05701 |
| 632 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-3,3,3-trifluoropropanamide | 552 | 0.30775 |
| 633 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-3-(methyloxy)propanamide | 528 | 0.017117 |
| 634 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(1,3-thiazol-4-ylmethyl)propyl)acetamide | 473.3 | 0.014226 |
| 635 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(4-pyridinylmethyl)propyl)acetamide | 467.3 | 0.003044 |
| 636 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-propyl-1,3-thiazol-4-yl)methyl)propyl)acetamide | 515.3 | 0.01464 |
| 637 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((5-propyl-1,3-thiazol-4-yl)methyl)propyl)acetamide | 515.3 | 0.921516 |
| 638 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(1,3-thiazol-5-ylmethyl)propyl)acetamide | 473.3 | 0.002316 |
| 639 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-methyl-1,3-thiazol-4-yl)methyl)propyl)acetamide | 487.3 | 0.023717 |
| 640 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-methyl-4-pyridinyl)methyl)propyl)acetamide | 481.3 | 0.009886 |

TABLE 4-continued

| Ex. No. | Compound Name | Mass Found | Cell Assay |
|---|---|---|---|
| 641 | N-((1S,2R)-1-((4-chloro-1,3-thiazol-2-yl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 507.3 | 0.00682 |
| 642 | N-((1S,2R)-1-((2-chloro-4-pyridinyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 501.3 | 0.003369 |
| 643 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-(methyloxy)-4-pyridinyl)methyl)propyl)acetamide | 497.4 | 0.006793 |
| 644 | N-((1S,2R)-1-((2-chloro-6-methyl-4-pyridinyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 515.3 | 0.006321 |
| 645 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-((2,2,2-trifluoroethyl)oxy)-4-pyridinyl)methyl)propyl)acetamide | 565.3 | 0.005164 |
| 646 | N-((1S,2R)-1-(1-benzofuran-2-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 506.3 | 0.052887 |
| 647 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-(trifluoromethyl)-4-pyrimidinyl)methyl)propyl)acetamide | 536.3 | 0.152163 |
| 648 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((4-(trifluoromethyl)phenyl)methyl)propyl)acetamide | 534.3 | 0.189329 |
| 649 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((1-methyl-2-oxo-1,2-dihydro-4-pyridinyl)methyl)propyl)acetamide | 497.3 | 0.030021 |
| 650 | N-((1S,2R)-3-(((4'S)-6'-(2-cyano-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 495.3 | 0.020206 |
| 651 | N-((1S,2R)-3-(((4'S)-6'-(2-cyano-2-methylpropyl)-3',4'-dihydrospiro[cyclobutane-1,2'-pyrano[2,3-b]pyridin]-4'-yl)amino)-1-((3-fluorophenyl)methyl)-2-hydroxypropyl)acetamide | 495.2 | 0.004239 |
| 652 | N-((1S,2R)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-2-hydroxy-1-(phenylmethyl)propyl)acetamide | 502.2 | 0.00784 |
| 653 | N-((1S,2R)-3-(((4S)-2-ethyl-4,7-dihydro-5H-spiro[1-benzothiophene-6,1'-cyclobutan]-4-yl)amino)-2-hydroxy-1-(phenylmethyl)propyl)acetamide | 427.2 | 0.126989 |
| 654 | N-((1S,2R)-3-(((4S)-2-(2,2-dimethylpropyl)-6,6-dimethyl-4,5,6,7-tetrahydro-1-benzothien-4-yl)amino)-2-hydroxy-1-(phenylmethyl)propyl)acetamide | 457.2 | 0.01385 |
| 655 | methyl ((1S,2R)-3-(((4S)-2-(2,2-dimethylpropyl)-6,6-dimethyl-4,5,6,7-tetrahydro-1-benzothien-4-yl)amino)-2-hydroxy-1-(phenylmethyl)propyl)carbamate | 473.2 | 0.104522 |
| 656 | N-((1S,2R)-1-((3,5-difluorophenyl)methyl)-3-(((3S,4'R)-6'-(2,2-dimethylpropyl)-3',4,4',5-tetrahydrospiro[furan-3,2'-pyrano[2,3-b]pyridin]-4'-yl)amino)-2-hydroxypropyl)acetamide N-((1S,2R)-1-((3,5-difluorophenyl)methyl)-3-(((3R,4'R)-6'-(2,2-dimethylpropyl)-3',4,4',5-tetrahydrospiro[furan-3,2'-pyrano[2,3-b]pyridin]-4'-yl)amino)-2-hydroxypropyl)acetamide | 518.2 | 0.041264 |
| 657 | N-((1S,2R)-1-((3,5-difluorophenyl)methyl)-3-(((3S,4'S)-6'-(2,2-dimethylpropyl)-3',4,4',5-tetrahydrospiro[furan-3,2'-pyrano[2,3-b]pyridin]-4'-yl)amino)-2-hydroxypropyl)acetamide N-((1S,2R)-1-((3,5-difluorophenyl)methyl)-3-(((3R,4'S)-6'-(2,2-dimethylpropyl)-3',4,4',5-tetrahydrospiro[furan-3,2'-pyrano[2,3-b]pyridin]-4'-yl)amino)-2-hydroxypropyl)acetamide | 518.2 | 0.002512 |

TABLE 4-continued

| Ex. No. | Compound Name | Mass Found | Cell Assay |
|---|---|---|---|
| 658 | N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-1-((4-fluorophenyl)methyl)-2-hydroxypropyl)acetamide N-((1S,2R)-3-(((3R,4'S)-6'-(2,2-dimethylpropyl)-3',4,4,5-tetrahydrospiro[furan-3,2'-pyrano[2,3-b]pyridin]-4'-yl)amino)-1-((4-fluorophenyl)methyl)-2-hydroxypropyl)acetamide | 500.2 | 0.020173 |
| 659 | N-((1S,2R)-1-((3,5-difluorophenyl)methyl)-3-(((4'S)-6'-(2,2-dimethylpropyl)-7'-fluoro-3',4'-dihydrospiro[cyclobutane-1,2'-pyrano[2,3-b]pyridin]-4'-yl)amino)-2-hydroxypropyl)acetamide | 520.2 | 0.006422 |
| 660 | N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-1-((3-fluorophenyl)methyl)-2-hydroxypropyl)acetamide N-((1S,2R)-3-(((3R,4'S)-6'-(2,2-dimethylpropyl)-3',4,4',5-tetrahydrospiro[furan-3,2'-pyrano[2,3-b]pyridin]-4'-yl)amino)-1-((3-fluorophenyl)methyl)-2-hydroxypropyl)acetamide | 500.2 | 0.003621 |
| 661 | N-((1S,2R)-3-(((4'S)-6'-(2,2-dimethylpropyl)-7'-fluoro-3',4'-dihydrospiro[cyclobutane-1,2'-pyrano[2,3-b]pyridin]-4'-yl)amino)-1-((3-fluorophenyl)methyl)-2-hydroxypropyl)acetamide | 502.2 | 0.010152 |
| 662 | N-((1S,2R)-3-(((4'S)-6'-(2,2-dimethylpropyl)-7'-fluoro-3',4'-dihydrospiro[cyclobutane-1,2'-pyrano[2,3-b]pyridin]-4'-yl)amino)-1-((4-fluorophenyl)methyl)-2-hydroxypropyl)acetamide | 502.2 | 0.094665 |
| 663 | N-((1S,2R)-1-((4-chlorophenyl)methyl)-3-(((3S,4'S)-6'-(2,2-dimethylpropyl)-3',4,4',5-tetrahydrospiro[furan-3,2'-pyrano[2,3-b]pyridin]-4'-yl)amino)-2-hydroxypropyl)acetamide N-((1S,2R)-1-((4-chlorophenyl)methyl)-3-(((3R,4'S)-6'-(2,2-dimethylpropyl)-3',4,4',5-tetrahydrospiro[furan-3,2'-pyrano[2,3-b]pyridin]-4'-yl)amino)-2-hydroxypropyl)acetamide | 516.2 | 0.099545 |
| 664 | N-((1S,2R)-1-((4-chlorophenyl)methyl)-3-(((3S,4'R)-6'-(2,2-dimethylpropyl)-3',4,4',5-tetrahydrospiro[furan-3,2'-pyrano[2,3-b]pyridin]-4'-yl)amino)-2-hydroxypropyl)acetamide N-((1S,2R)-1-((4-chlorophenyl)methyl)-3-(((3R,4'R)-6'-(2,2-dimethylpropyl)-3',4,4',5-tetrahydrospiro[furan-3,2'-pyrano[2,3-b]pyridin]-4'-yl)amino)-2-hydroxypropyl)acetamide | 516.2 | TBD |
| 665 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluoro-4-(methyloxy)phenyl)methyl)-2-hydroxypropyl)acetamide | 514.2 | 0.00853 |
| 666 | N-((1S,2S)-3-(((4'S)-6'-(2,2-dimethylpropyl)-3',4'-dihydrospiro[cyclobutane-1,2'-pyrano[2,3-b]pyridin]-4'-yl)amino)-1-((3-fluoro-4-(methyloxy)phenyl)methyl)-2-hydroxypropyl)acetamide | 514.2 | 0.16163 |
| 667 | N-((1S,2R)-1-((4-chlorophenyl)methyl)-3-(((4'S)-6'-(2,2-dimethylpropyl)-7'-fluoro-3',4'-dihydrospiro[cyclobutane-1,2'-pyrano[2,3-b]pyridin]-4'-yl)amino)-2-hydroxypropyl)acetamide | 518.2 | 0.384736 |
| 668 | N-((1R,2S)-3-(((4'S)-6'-(2,2-dimethylpropyl)-3',4'-dihydrospiro[cyclobutane-1,2'-pyrano[2,3-b]pyridin]-4'-yl)amino)-1-((3-fluoro-4-(trifluoromethyl)phenyl)methyl)-2-hydroxypropyl)acetamide N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluoro-4-(trifluoromethyl)phenyl)methyl)-2-hydroxypropyl)acetamide | 552.2 | 0.156196 |
| 669 | N-((1S,2R)-1-((4-chlorophenyl)methyl)-3-(((3S,4'S)-6'-(2,2-dimethylpropyl)-3',4,4',5-tetrahydrospiro[furan-3,2'-pyrano[2,3-b]pyridin]-4'-yl)amino)-2-hydroxypropyl)acetamide | 516.2 | 10 |
| 670 | N-((1S,2R)-1-((4-chlorophenyl)methyl)-3-(((3R,4'S)-6'-(2,2-dimethylpropyl)-3',4,4',5-tetrahydrospiro[furan-3,2'-pyrano[2,3-b]pyridin]-4'-yl)amino)-2-hydroxypropyl)acetamide | 516.2 | 0.051785 |
| 671 | N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-1-((4-fluorophenyl)methyl)-2-hydroxypropyl)acetamide | 500.2 | 0.020468 |

TABLE 4-continued

| Ex. No. | Compound Name | Mass Found | Cell Assay |
|---|---|---|---|
| 672 | N-((1S,2R)-3-(((3R,4'S)-6'-(2,2-dimethylpropyl)-3',4,4',5-tetrahydrospiro[furan-3,2'-pyrano[2,3-b]pyridin]-4'-yl)amino)-1-((4-fluorophenyl)methyl)-2-hydroxypropyl)acetamide | 500.2 | 0.023752 |
| 673 | N-((1S,2R)-1-((4-chlorophenyl)methyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)acetamide N-((1S,2R)-1-((4-chlorophenyl)methyl)-3-(((4'S)-6'-((1S)-1-fluoro-2,2-dimethylpropyl)-3',4'-dihydrospiro[cyclobutane-1,2'-pyrano[2,3-b]pyridin]-4'-yl)amino)-2-hydroxypropyl)acetamide | 518.2 | 0.05856 |
| 674 | N-((1S,2R)-3-(((4'S)-6'-((1S)-1-fluoro-2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 502.2 | 1.081474 |
| 675 | N-((1S,2R)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 502.2 | 0.012112 |
| 676 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluoro-3-(trifluoromethyl)phenyl)methyl)-2-hydroxypropyl)acetamide | 552.2 | 0.018142 |
| 677 | N-((1S,2R)-1-((2,3-difluorophenyl)methyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)acetamide | 520.2 | 0.008608 |
| 678 | N-((1S,2R)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)acetamide | 502.2 | 0.002069 |
| 679 | N-((1S,2R)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxy-1-(phenylmethyl)propyl)acetamide | 484.3 | 0.006045 |
| 680 | N-((1S,2R)-1-((4-chlorophenyl)methyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)acetamide | 518.2 | 0.023122 |
| 681 | N-((1S,2R)-1-((3,5-difluorophenyl)methyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)acetamide | 520.3 | 0.003463 |
| 682 | N-((1S,2R)-3-(((4'S)-6'-(cyclobutylmethyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 482.2 | 0.066452 |
| 683 | N-((1S,2R)-3-(((5R,5aS)-3-(2,2-dimethylpropyl)-5a,6,7,8-tetrahydro-5H-pyrrolo[1',2':1,5]pyrrolo[2,3-b]pyridin-5-yl)amino)-1-((4-fluorophenyl)methyl)-2-hydroxypropyl)acetamide | 469 | 0.523798 |
| 684 | N-((1S,2R)-1-((4-fluorophenyl)methyl)-2-hydroxy-3-(((4'S)-6'-(1-hydroxypentyl)-3',4'-dihydrospiro[cyclobutane-1,2'-pyrano[2,3-b]pyridin]-4'-yl)amino)propyl)acetamide | 522 | 2.86427 |
| 685 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2,4,5-trifluorophenyl)methyl)propyl)acetamide | 520 | 0.009279 |
| 686 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((3,4,5-trifluorophenyl)methyl)propyl)acetamide | 520 | 0.007068 |
| 687 | N-((1S,2R)-3-(((4'S)-6'-(cyclopropylmethyl)-3',4'-dihydrospiro[cyclobutane-1,2'-pyrano[2,3-b]pyridin]-4'-yl)amino)-1-((3,5-difluorophenyl)methyl)-2-hydroxypropyl)acetamide | 486 | 0.007837 |
| 688 | N-((1S,2R)-3-(((4R)-6-bromo-2,2-dimethyl-1,2,3,4-tetrahydro-4-quinolinyl)amino)-2-hydroxy-1-(phenylmethyl)propyl)acetamide N-((1S,2R)-3-(((4S)-6-bromo-2,2-dimethyl-1,2,3,4-tetrahydro-4-quinolinyl)amino)-2-hydroxy-1-(phenylmethyl)propyl)acetamide | 461 | 0.230897 |
| 689 | N-((1S,2R)-3-(((4R)-6-(2,2-dimethylpropyl)-2,2-dimethyl-1,2,3,4-tetrahydro-4-quinolinyl)amino)-2-hydroxy-1-(phenylmethyl)propyl)acetamide N-((1S,2R)-3-(((4S)-6-(2,2-dimethylpropyl)-2,2-dimethyl-1,2,3,4-tetrahydro-4-quinolinyl)amino)-2-hydroxy-1-(phenylmethyl)propyl)acetamide | 452 | 0.072801 |

TABLE 4-continued

| Ex. No. | Compound Name | Mass Found | Cell Assay |
|---|---|---|---|
| 690 | N-((1S,2R)-3-(((4R)-1-acetyl-6-bromo-2,2-dimethyl-1,2,3,4-tetrahydro-4-quinolinyl)amino)-2-hydroxy-1-(phenylmethyl)propyl)acetamide N-((1S,2R)-3-(((4S)-1-acetyl-6-bromo-2,2-dimethyl-1,2,3,4-tetrahydro-4-quinolinyl)amino)-2-hydroxy-1-(phenylmethyl)propyl)acetamide | 503 | 0.873045 |
| 691 | N-((1S,2R)-1-((3,5-difluorophenyl)methyl)-3-(((4'S)-6'-(2-ethylbutyl)-3',4'-dihydrospiro[cyclobutane-1,2'-pyrano[2,3-b]pyridin]-4'-yl)amino)-2-hydroxypropyl)acetamide | 516 | 0.095804 |
| 692 | N-((1S,2R)-3-(((4S)-6-(2,2-dimethylpropyl)-2,2-dimethyl-1,2,3,4-tetrahydro-4-quinolinyl)amino)-2-hydroxy-1-(phenylmethyl)propyl)acetamide | 452 | 0.030558 |
| 693 | N-((1S,2R)-1-((3,5-difluorophenyl)methyl)-3-(((4S)-6-(2,2-dimethylpropyl)-2,2-dimethyl-1,2,3,4-tetrahydro-4-quinolinyl)amino)-2-hydroxypropyl)acetamide | 488 | 0.005491 |
| 694 | N-((1S,2R)-1-((4-fluorophenyl)methyl)-2-hydroxy-3-(((4'S)-6'-propyl-3',4'-dihydrospiro[cyclobutane-1,2'-pyrano[2,3-b]pyridin]-4'-yl)amino)propyl)acetamide | 456 | 0.037222 |
| 695 | N-((1S,2R)-1-((4-fluorophenyl)methyl)-2-hydroxy-3-(((4'S)-6'-((2S)-2-methylbutyl)-3',4'-dihydrospiro[cyclobutane-1,2'-pyrano[2,3-b]pyridin]-4'-yl)amino)propyl)acetamide | 484 | 0.043378 |
| 696 | N-((1S,2R)-1-((4-fluorophenyl)methyl)-2-hydroxy-3-(((4'S)-6'-(2-methyl-1-propen-1-yl)-3',4'-dihydrospiro[cyclobutane-1,2'-pyrano[2,3-b]pyridin]-4'-yl)amino)propyl)acetamide | 468 | 0.253945 |
| 697 | N-((1S,2R)-3-(((4'S)-6'-(2,2-dimethylpropanoyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 498 | 0.276687 |
| 698 | 2-azido-N-((1S,2R)-3-(((4S)-6-bromo-3,4-dihydrospiro[chromene-2,1'-cyclobutan]-4-yl)amino)-2-hydroxy-1-(phenylmethyl)propyl)acetamide | 514.7 | 2.377589 |
| 699 | N-((1S,2R)-1-((3-cyanophenyl)methyl)-2-hydroxy-3-(((4'S)-6'-(trifluoromethyl)-3',4'-dihydrospiro[cyclobutane-1,2'-pyrano[2,3-b]pyridin]-4'-yl)amino)propyl)acetamide | 488.8 | 0.848676 |
| 700 | N-((1S,2R)-1-((3,5-difluorophenyl)methyl)-2-hydroxy-3-(((4'S)-6'-(trifluoromethyl)-3',4'-dihydrospiro[cyclobutane-1,2'-pyrano[2,3-b]pyridin]-4'-yl)amino)propyl)acetamide | 499.8 | 1.199997 |
| 701 | N-((1S,2R)-1-((3,4-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 501.9 | 0.002356 |
| 702 | N-((1S,2R)-1-((3-chlorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 499.9 | 0.001238 |
| 703 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((2-fluorophenyl)methyl)-2-hydroxypropyl)acetamide | 483.9 | 0.005085 |
| 704 | N-((1S,2R)-1-((2,4-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 502.2 | 0.018443 |
| 705 | N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3-pentyn-1-yl)acetamide | 428.2 | 0.432865 |
| 706 | N-((1S,2R)-1-((3-chloro-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 517.8 | 0.003113 |
| 707 | N-((1S,2R)-1-((4-chlorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 499.9 | 0.012555 |
| 708 | N-((1S,2R)-1-((2-chlorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 499.9 | 0.023419 |
| 709 | N-((1S,2R)-1-((3-(dimethylamino)-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 526.9 | 0.008013 |
| 710 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-(ethylamino)-4-fluorophenyl)methyl)-2-hydroxypropyl)acetamide | 526.9 | 0.004251 |

TABLE 4-continued

| Ex. No. | Compound Name | Mass Found | Cell Assay |
|---|---|---|---|
| 711 | N-((1S,2R)-1-((3,4-dichlorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 533.8 | 0.029584 |
| 712 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((4-((trifluoromethyl)oxy)phenyl)methyl)propyl)acetamide | 549.8 | 0.064957 |
| 713 | N-((1S,2R)-1-((3-chloro-4-fluorophenyl)methyl)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)acetamide | 532.2 | 0.015499 |
| 714 | N-((1S,2R)-1-((4-chlorophenyl)methyl)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)acetamide | 514.2 | 0.026711 |
| 715 | N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-4-penten-1-yl)acetamide | 429.9 | 0.040837 |
| 716 | N-((1S,2R)-1-((4-chloro-3-(trifluoromethyl)phenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 567.8 | 0.023342 |
| 717 | N-((1S)-1-((1R)-2-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-1-hydroxyethyl)-4-penten-1-yl)acetamide | 443.9 | 0.052462 |
| 718 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((3-(trifluoromethyl)phenyl)methyl)propyl)acetamide | 533.9 | 0.003985 |
| 719 | N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-((3-(trifluoromethyl)phenyl)methyl)propyl)acetamide | 519.9 | 0.009351 |
| 720 | N-((1S,2R)-1-((4-chloro-3-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 517.8 | 0.008567 |
| 721 | N-((1S,2R)-1-((4-chloro-3-(methyloxy)phenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 530.2 | 0.021395 |
| 722 | N-((1S,2R)-1-(cyclopropylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 430.2 | 0.046453 |
| 723 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-methylcyclopropyl)methyl)propyl)acetamide | 444.3 | 0.194643 |
| 724 | N-((1S,2R)-1-(cyclopropylmethyl)-3-(((4'S)-6'-(4,4-difluoro-2,2-dimethylbutyl)-3',4'-dihydrospiro[cyclobutane-1,2'-pyrano[2,3-b]pyridin]-4'-yl)amino)-2-hydroxypropyl)acetamide | 480.2 | 0.183543 |
| 725 | N-((1S,2R)-1-(cyclopropylmethyl)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)acetamide | 444.2 | 0.068761 |
| 726 | N-((1S,2R)-1-((2-((difluoromethyl)oxy)-4-pyridinyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 533.2 | 0.009724 |
| 727 | N~1~-((1S,2R)-3-(((4S)-6-bromo-3,4-dihydrospiro[chromene-2,1'-cyclobutan]-4-yl)amino)-1-((3-cyanophenyl)methyl)-2-hydroxpropyl)-N~2~,N~2~-dimethylglycinamide | 541 | 0.300311 |
| 728 | methyl (4S)-4-(((2R,3S)-4-(3-cyanophenyl)-3-((N,N-dimethylglycyl)amino)-2-hydroxybutyl)amino)-3,4-dihydrospiro[chromene-2,1'-cyclobutane]-6-carboxylate | 521 | 0.043943 |
| 729 | methyl (4S)-4-(((2R,3S)-3-(acetylamino)-4-(3-cyanophenyl)-2-hydroxybutyl)amino)-3,4-dihydrospiro[chromene-2,1'-cyclobutane]-6-carboxylate | 478 | 1.449592 |
| 730 | methyl (4S)-4-(((2R,3S)-4-(3-cyanophenyl)-2-hydroxy-3-(((methyloxy)acetyl)amino)butyl)amino)-3,4-dihydrospiro[chromene-2,1'-cyclobutane]-6-carboxylate | 508 | 1.018648 |

TABLE 4-continued

| Ex. No. | Compound Name | Mass Found | Cell Assay |
|---|---|---|---|
| 731 | N-((1S,2R)-3-(((4S)-6-ethyl-3,4-dihydrospiro[chromene-2,1'-cyclobutan]-4-yl)amino)-2-hydroxy-1-((methyloxy)methyl)propyl)acetamide | 377 | 2.52388 |
| 732 | N-((1S,2R)-3-(((4S)-6-ethyl-3,4-dihydrospiro[chromene-2,1'-cyclobutan]-4-yl)amino)-2-hydroxy-1-((propyloxy)methyl)propyl)acetamide | 405 | 3.263952 |
| 733 | N-((1S,2R)-3-(((4S)-6-ethyl-3,4-dihydrospiro[chromene-2,1'-cyclobutan]-4-yl)amino)-2-hydroxy-1-(((phenylmethyl)oxy)methyl)propyl)acetamide | 453 | 10 |
| 734 | N-((1S,2R)-3-(((4S)-6-ethyl-3,4-dihydrospiro[chromene-2,1'-cyclobutan]-4-yl)amino)-2-hydroxy-1-(1H-pyrazol-1-ylmethyl)propyl)acetamide | 413 | 5.365972 |
| 735 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(1H-pyrazol-1-ylmethyl)propyl)acetamide | 478 | 10 |
| 736 | N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3-buten-1-yl)acetamide | 416 | 0.03402 |
| 737 | N-((1S)-1-((1S)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3-buten-1-yl)acetamide | 416 | 10 |
| 738 | N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-4,4,4-trifluorobutyl)acetamide | 472 | 1.420952 |
| 739 | N-((1S,3E)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3-penten-1-yl)acetamide | 430 | 0.298128 |
| 740 | N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-2-propen-1-yl)acetamide | 402 | 3.33333 |
| 741 | N-((1S)-1-((1R)-2-(((4'S)-6'-(2-fluoro-2-methylpropyl)-3',4'-dihydrospiro[cyclobutane-1,2'-pyrano[2,3-b]pyridin]-4'-yl)amino)-1-hydroxyethyl)-3-buten-1-yl)acetamide | 420 | 0.193221 |
| 742 | N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3-hexyn-1-yl)acetamide | 442 | 0.285911 |
| 743 | N-((1S,2R)-3-(((2S,4S)-6-chloro-8-(4-morpholinyl)-3,4,4',5'-tetrahydrospiro[chromene-2,3'-furan]-4-yl)amino)-1-((3,5-difluorophenyl)methyl)-2-hydroxypropyl)acetamide N-((1S,2R)-3-(((2R,4S)-6-chloro-8-(4-morpholinyl)-3,4,4',5'-tetrahydrospiro[chromene-2,3'-furan]-4-yl)amino)-1-((3,5-difluorophenyl)methyl)-2-hydroxypropyl)acetamide | 566.1 | 0.302172 |
| 744 | N-((1S,2R)-3-(((4S)-6-(2,2-dimethylpropyl)-3,4-dihydrospiro[chromene-2,1'-cyclobutan]-4-yl)amino)-2-hydroxy-1-(phenylmethyl)propyl)-2-(1H-2-methyl-imidazol-1-yl) acetamide | 546.3 | 0.005722 |
| 745 | N-((1S,2R)-3-(((4'S)-6'-bromo-3',4'-dihydrospiro[cyclobutane-1,2'-pyrano[2,3-b]pyridin]-4'-yl)amino)-1-((3,5-difluorophenyl)methyl)-2-hydroxypropyl)acetamide | 510.0; 512.0 | 0.033121 |
| 746 | N-((1S,2R)-1-((3,5-difluorophenyl)methyl)-2-hydroxy-3-(((4'S)-6'-(1H-pyrazol-1-yl)-3',4'-dihydrospiro[cyclobutane-1,2'-pyrano[2,3-b]pyridin]-4'-yl)amino)propyl)acetamide | 498.1 | 0.214725 |
| 747 | N-((1S,2R)-1-((3,5-difluorophenyl)methyl)-2-hydroxy-3-(((4'S)-6'-(1H-imidazol-1-yl)-3',4'-dihydrospiro[cyclobutane-1,2'-pyrano[2,3-b]pyridin]-4'-yl)amino)propyl)acetamide | 498.2 | 0.497891 |
| 748 | N-((1S,2R)-1-((3,5-difluorophenyl)methyl)-2-hydroxy-3-(((4'S)-6'-(1,3-thiazol-2-yl)-3',4'-dihydrospiro[cyclobutane-1,2'-pyrano[2,3-b]pyridin]-4'-yl)amino)propyl)acetamide | 515.1 | 1.051834 |
| 749 | N-((1S,2R)-3-(((4'S)-6'-(2,2-dimethylpropyl)-3',4'-dihydrospiro[cyclobutane-1,2'-pyrano[2,3-c]pyridin]-4'-yl)amino)-2-hydroxy-1-(phenylmethyl)propyl)acetamide | 466.2 | 0.013955 |
| 750 | N-((1S,2R)-1-((3-chloro-5-fluorophenyl)methyl)-3-(((4'S)-6'-(2,2-dimethylpropyl)-3',4'-dihydrospiro[cyclobutane-1,2'-pyrano[2,3-c]pyridin]-4'-yl)amino)-2-hydroxypropyl)acetamide | 518.2 | 0.020286 |
| 751 | N-((1S,2R)-1-((3-chloro-5-fluorophenyl)methyl)-2-hydroxy-3-(((4'S)-6'-(2-hydroxy-2-methylpropyl)-3',4'-dihydrospiro[cyclobutane-1,2'-pyrano[2,3-c]pyridin]-4'-yl)amino)propyl)acetamide | 520.2 | 0.038775 |
| 752 | N-((1S,2R)-3-(((4'S)-8'-chloro-6'-(2,2-dimethylpropyl)-3',4'-dihydrospiro[cyclobutane-1,2'-pyrano[2,3-c]pyridin]-4'-yl)amino)-1-((3-chloro-5-fluorophenyl)methyl)-2-hydroxypropyl)acetamide | 552.1 | 0.042155 |

TABLE 4-continued

| Ex. No. | Compound Name | Mass Found | Cell Assay |
|---|---|---|---|
| 753 | N-((1S,2R)-3-(((4'S)-8'-chloro-6'-(2,2-dimethylpropyl)-3',4'-dihydrospiro[cyclobutane-1,2'-pyrano[2,3-c]pyridin]-4'-yl)amino)-2-hydroxy-1-(phenylmethyl)propyl)acetamide | 500.2 | 0.01375 |
| 754 | N-((1S,2R)-3-(((4'S)-6'-(2,2-dimethylpropyl)-8'-(4-morpholinyl)-3',4'-dihydrospiro[cyclobutane-1,2'-pyrano[2,3-c]pyridin]-4'-yl)amino)-2-hydroxy-1-(phenylmethyl)propyl)acetamide | 551.3 | 0.052212 |
| 755 | N-((1S,2R)-3-(((4'S)-6'-(2,2-dimethylpropyl)-8'-(1-pyrrolidinyl)-3',4'-dihydrospiro[cyclobutane-1,2'-pyrano[2,3-c]pyridin]-4'-yl)amino)-2-hydroxy-1-(phenylmethyl)propyl)acetamide | 535.3 | 0.006495 |
| 756 | N-((1S,2R)-3-(((4S)-8-(dimethylamino)-6-(2,2-dimethylpropyl)-2,2-dimethyl-3,4-dihydro-2H-pyrano[2,3-c]pyridin-4-yl)amino)-1-((3-(dimethylamino)-5-fluorophenyl)methyl)-2-hydroxypropyl)acetamide | 558.3 | 0.199655 |
| 757 | N-((1S,2R)-1-((3-chloro-5-fluorophenyl)methyl)-3-(((4S)-8-(dimethylamino)-6-(2,2-dimethylpropyl)-2,2-dimethyl-3,4-dihydro-2H-pyrano[2,3-c]pyridin-4-yl)amino)-2-hydroxypropyl)acetamide | 549.2 | 0.068949 |
| 758 | N-((1S,2R)-1-((3,4-difluorophenyl)methyl)-3-(((4S)-6-(2,2-dimethylpropyl)-2,2-dimethyl-8-(1-pyrrolidinyl)-3,4-dihydro-2H-pyrano[2,3-c]pyridin-4-yl)amino)-2-hydroxypropyl)acetamide | 559.3 | 0.040129 |
| 759 | N-((1S,2R)-1-((3-(dimethylamino)-5-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 527.3 | 0.017872 |
| 760 | N-((1S,2R)-1-((3,4-difluorophenyl)methyl)-3-(((4S)-6-(2,2-dimethylpropyl)-2,2-dimethyl-8-(methylamino)-3,4-dihydro-2H-pyrano[2,3-c]pyridin-4-yl)amino)-2-hydroxypropyl)acetamide | 519.2 | 0.011255 |
| 761 | N-((1S,2R)-3-(((4S)-8-chloro-6-(2,2-dimethylpropyl)-2,2-dimethyl-3,4-dihydro-2H-pyrano[2,3-c]pyridin-4-yl)amino)-1-((4-fluorophenyl)methyl)-2-hydroxypropyl)acetamide | 506.2 | 0.126221 |
| 762 | N-((1S,2R)-3-(((4S)-8-(dimethylamino)-6-(2,2-dimethylpropyl)-2,2-dimethyl-3,4-dihydro-2H-pyrano[2,3-c]pyridin-4-yl)amino)-1-((4-fluorophenyl)methyl)-2-hydroxypropyl)acetamide | 515.3 | 0.165675 |
| 763 | N-((1S,2R)-1-((3-bromo-5-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 562.1;564.1 | 0.006487 |
| 764 | N-((1S,2R)-1-((3,5-difluorophenyl)methyl)-3-(((4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)acetamide | 516.2 | 0.001554 |
| 765 | N-((1S,2R)-1-((3,5-difluorophenyl)methyl)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)acetamide | 516.2 | 0.001138 |
| 766 | N-((1S,2R)-3-(((4'S)-6'-(2,2-dimethylpropyl)-3-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide | 498.2 | 0.015805 |
| 767 | N-((1S,2R)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide | 498.2 | 0.005703 |
| 768 | N-((1S,2R)-1-((2,3-difluorophenyl)methyl)-3-(((1r,3S,4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)acetamide | 516 | 0.03889 |
| 769 | N-((1S,2R)-1-((2,3-difluorophenyl)methyl)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)acetamide | 516 | 0.033758 |
| 770 | N-((1S,2R)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-1-((3-fluorophenyl)methyl)-2-hydroxypropyl)acetamide | 498.2 | 0.002464 |
| 771 | N-((1S,2R)-3-(((4S)-6-(cyclopentylamino)-3,4-dihydrospiro[chromene-2,1'-cyclobutan]-4-yl)amino)-2-hydroxy-1-(phenylmethyl)propyl)acetamide | 478.3 | 0.165691 |
| 772 | N-((1S,2R)-3-(((4S)-6-((1,1-dimethylethyl)amino)-3,4-dihydrospiro[chromene-2,1'-cyclobutan]-4-yl)amino)-2-hydroxy-1-(phenylmethyl)propyl)acetamide | 466.3 | 0.980967 |

TABLE 4-continued

| Ex. No. | Compound Name | Mass Found | Cell Assay |
|---|---|---|---|
| 773 | N-((1S,2R)-3-(((4S)-6-chloro-8-(1H-imidazol-1-yl)-3,4-dihydrospiro[chromene-2,1'-cyclobutan]-4-yl)amino)-1-((3,5-difluorophenyl)methyl)-2-hydroxypropyl)acetamide | 532.2 | 0.021949 |
| 774 | N-((1S,2R)-3-(((4S)-6-bromo-3,4-dihydrospiro[chromene-2,1'-cyclobutan]-4-yl)amino)-1-((3,5-difluorophenyl)methyl)-2-hydroxypropyl)acetamide | 510.2 | 0.088192 |
| 775 | N-((1S,2R)-3-(((4S)-8-(1H-benzimidazol-1-yl)-6-chloro-3,4-dihydrospiro[chromene-2,1'-cyclobutan]-4-yl)amino)-1-((3,5-difluorophenyl)methyl)-2-hydroxypropyl)acetamide | 582.2 | 0.212243 |
| 776 | N-((1S,2R)-3-(((4S)-6-chloro-8-(1H-pyrazol-1-yl)-3,4-dihydrospiro[chromene-2,1'-cyclobutan]-4-yl)amino)-1-((3,5-difluorophenyl)methyl)-2-hydroxypropyl)acetamide | 532.2 | 0.124289 |
| 777 | N-((1S,2R)-1-((3,5-difluorophenyl)methyl)-2-hydroxy-3-(((4S)-6-(1H-pyrazol-1-yl)-3,4-dihydrospiro[chromene-2,1'-cyclobutan]-4-yl)amino)propyl)acetamide | 497.2 | 0.041157 |
| 778 | N-((1S,2R)-2-hydroxy-1-(phenylmethyl)-3-(((4S)-6-(2-thienyl)-3,4-dihydrospiro[chromene-2,1'-cyclobutan]-4-yl)amino)propyl)acetamide | 477.2 | 0.083329 |
| 779 | N-((1S,2R)-2-hydroxy-3-(((4S)-6-(1-(2-methylpropyl)-1H-pyrazol-3-yl)-3,4-dihydrospiro[chromene-2,1'-cyclobutan]-4-yl)amino)-1-(phenylmethyl)propyl)acetamide | 517.3 | 0.190194 |
| 780 | N-((1S,2R)-1-((3,5-difluorophenyl)methyl)-2-hydroxy-3-(((4S)-6-(1-(2-methylpropyl)-1H-pyrazol-3-yl)-3,4-dihydrospiro[chromene-2,1'-cyclobutan]-4-yl)amino)propyl)acetamide | 553.3 | 1.652355 |
| 781 | N-((1S,2S)-1-((3,5-difluorophenyl)methyl)-2-hydroxy-3-(((4S)-6-(1H-pyrazol-1-yl)-3,4-dihydrospiro[chromene-2,1'-cyclobutan]-4-yl)amino)propyl)acetamide | 497.2 | 1.158731 |
| 782 | N-((1S,2R)-1-((3,5-difluorophenyl)methyl)-2-hydroxy-3-(((4S)-6-(1H-imidazol-1-yl)-3,4-dihydrospiro[chromene-2,1'-cyclobutan]-4-yl)amino)propyl)acetamide | 497.2 | 0.081605 |
| 783 | N-((1S,2R)-2-hydroxy-3-(((4S)-6-(1-methyl-1H-pyrazol-3-yl)-3,4-dihydrospiro[chromene-2,1'-cyclobutan]-4-yl)amino)-1-(phenylmethyl)propyl)acetamide | 475.3 | 3.244922 |
| 784 | N-((1S,2R)-1-((3,5-difluorophenyl)methyl)-2-hydroxy-3-(((4S)-6-(1-methyl-1H-pyrazol-3-yl)-3,4-dihydrospiro[chromene-2,1'-cyclobutan]-4-yl)amino)propyl)acetamide | 511.3 | 1.654726 |
| 785 | N-((1S,2R)-1-((3,5-difluorophenyl)methyl)-2-hydroxy-3-(((4S)-6-(2-thienyl)-3,4-dihydrospiro[chromene-2,1'-cyclobutan]-4-yl)amino)propyl)acetamide | 513.3 | 2.967655 |
| 786 | N-((1S,2S)-3-(((4S)-6-chloro-8-(1H-pyrazol-1-yl)-3,4-dihydrospiro[chromene-2,1'-cyclobutan]-4-yl)amino)-1-((3,5-difluorophenyl)methyl)-2-hydroxypropyl)acetamide | 532.2 | 1.367329 |
| 787 | N-((1S,2R)-3-(((4S)-7-bromo-3,4-dihydrospiro[chromene-2,1'-cyclobutan]-4-yl)amino)-1-((3,5-difluorophenyl)methyl)-2-hydroxypropyl)acetamide | 510.1 | 10 |
| 788 | N-((1S,2R)-1-((3,5-difluorophenyl)methyl)-2-hydroxy-3-(((4S)-7-(1H-imidazol-1-yl)-3,4-dihydrospiro[chromene-2,1'-cyclobutan]-4-yl)amino)propyl)acetamide | 497.2 | |
| 789 | N-((4S)-4-(((2R,3S)-3-(acetylamino)-4-(3,5-difluorophenyl)-2-hydroxybutyl)amino)-3,4-dihydrospiro[chromene-2,1'-cyclobutan]-6-yl)acetamide | 488.2 | 0.017688 |
| 790 | N-((1S,2R)-1-((3,5-difluorophenyl)methyl)-2-hydroxy-3-(((4S)-6-((3R)-tetrahydro-3-furanylamino)-3,4-dihydrospiro[chromene-2,1'-cyclobutan]-4-yl)amino)propyl)acetamide | 516.3 | 0.05852 |
| 791 | N-((1S,2R)-1-((3,5-difluorophenyl)methyl)-2-hydroxy-3-(((4S)-6-(2H-1,2,3-triazol-2-yl)-3,4-dihydrospiro[chromene-2,1'-cyclobutan]-4-yl)amino)propyl)acetamide | 498.3 | 0.803182 |
| 792 | N-((1S,2R)-1-((3,5-difluorophenyl)methyl)-2-hydroxy-3-(((4S)-6-(1H-1,2,4-triazol-1-yl)-3,4-dihydrospiro[chromene-2,1'-cyclobutan]-4-yl)amino)propyl)acetamide | 498.3 | 0.137058 |
| 793 | N-((1S,2R)-1-((3,5-difluorophenyl)methyl)-2-hydroxy-3-(((4S)-6-(2-oxo-1-pyrrolidinyl)-3,4-dihydrospiro[chromene-2,1'-cyclobutan]-4-yl)amino)propyl)acetamide | 514.2 | 0.358885 |
| 794 | N-((1S,2R)-3-(((4S)-6-(2,2-dimethylpropyl)-2,2-dimethyl-3,4-dihydro-2H-pyrano[2,3-c]pyridin-4-yl)amino)-2-hydroxy-1-(phenylmethyl)propyl)acetamide | 454.3 | 0.034817 |
| 795 | N-((1S,2R)-1-((3,5-difluorophenyl)methyl)-2-hydroxy-3-(((4S)-6-(2-oxo-1-azetidinyl)-3,4-dihydrospiro[chromene-2,1'-cyclobutan]-4-yl)amino)propyl)acetamide | 500.2 | 0.255326 |
| 796 | N-((1S,2R)-1-((3-chloro-5-fluorophenyl)methyl)-3-(((4S)-6-(2,2-dimethylpropyl)-2,2-dimethyl-3,4-dihydro-2H-pyrano[2,3-c]pyridin-4-yl)amino)-2-hydroxypropyl)acetamide | 507.3 | 0.008388 |

TABLE 4-continued

| Ex. No. | Compound Name | Mass Found | Cell Assay |
|---|---|---|---|
| 797 | N-((1S,2R)-1-((3-chloro-5-fluorophenyl)methyl)-3-(((4S)-6-(2,2-dimethylpropyl)-2,2-dimethyl-3,4-dihydro-2H-pyrano[2,3-c]pyridin-4-yl)amino)-2-hydroxypropyl)propanamide | 521.3 | 0.01127 |
| 798 | N-((1S,2R)-3-(((4S)-6-(2,2-dimethylpropyl)-2,2-dimethyl-3,4-dihydro-2H-pyrano[2,3-c]pyridin-4-yl)amino)-1-((3-fluorophenyl)methyl)-2-hydroxypropyl)acetamide | 472.3 | 0.006725 |
| 799 | N-((1S,2R)-3-(((4S)-6-(2,2-dimethylpropyl)-2,2-dimethyl-3,4-dihydro-2H-pyrano[2,3-c]pyridin-4-yl)amino)-1-((4-fluorophenyl)methyl)-2-hydroxypropyl)acetamide | 472.3 | 0.045368 |
| 800 | N-((1S,2R)-1-((3,5-difluorophenyl)methyl)-3-(((4S)-6-(2,2-dimethylpropyl)-2,2-dimethyl-3,4-dihydro-2H-pyrano[2,3-c]pyridin-4-yl)amino)-2-hydroxypropyl)acetamide | 490.3 | 0.003558 |
| 801 | N-((1S,2R)-3-(((4S)-6-bromo-7-fluoro-3,4-dihydrospiro[chromene-2,1'-cyclobutan]-4-yl)amino)-1-((3,5-difluorophenyl)methyl)-2-hydroxypropyl)acetamide | 528.1 | 0.570646 |
| 802 | N-((1S,2R)-3-(((4S)-6-bromo-7-fluoro-2,2-dimethyl-3,4-dihydro-2H-chromen-4-yl)amino)-1-((3,5-difluorophenyl)methyl)-2-hydroxypropyl)acetamide | 516.1 | 0.525381 |
| 803 | N-((1S,2R)-1-((3,5-difluorophenyl)methyl)-3-(((4S)-7-fluoro-6-((3R)-tetrahydro-3-furanylamino)-3,4-dihydrospiro[chromene-2,1'-cyclobutan]-4-yl)amino)-2-hydroxypropyl)acetamide | 534.3 | 0.115798 |
| 804 | N-((1S,2R)-1-((3,5-difluorophenyl)methyl)-3-(((4S)-7-fluoro-3,4-dihydrospiro[chromene-2,1'-cyclobutan]-4-yl)amino)-2-hydroxypropyl)acetamide | 449.2 | 2.952856 |
| 805 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluoro-5-(tetrahydro-2H-pyran-4-ylamino)phenyl)methyl)-2-hydroxypropyl)acetamide | 583.4 | 0.005137 |
| 806 | N-((1S,2R)-1-((3,5-difluorophenyl)methyl)-3-(((4S)-7-fluoro-6-(tetrahydro-2H-pyran-4-ylamino)-3,4-dihydrospiro[chromene-2,1'-cyclobutan]-4-yl)amino)-2-hydroxypropyl)acetamide | 548.3 | 0.451865 |
| 807 | N-((1S,2R)-1-((3-fluorophenyl)methyl)-3-(((4S)-7-fluoro-6-(1H-pyrazol-1-yl)-3,4-dihydrospiro[chromene-2,1'-cyclobutan]-4-yl)amino)-2-hydroxypropyl)acetamide | 497.2 | 0.48859 |
| 808 | N-((1S,2R)-1-((4-fluorophenyl)methyl)-3-(((4S)-7-fluoro-6-(1H-pyrazol-1-yl)-3,4-dihydrospiro[chromene-2,1'-cyclobutan]-4-yl)amino)-2-hydroxypropyl)acetamide | 497.2 | 1.94044 |
| 809 | N-((1S,2R)-1-(cyclobutylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 444.3 | 0.078673 |
| 810 | N-((1S,2R)-1-((2-bromophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 545.2 | 0.197405 |
| 811 | N-((1S,2R)-1-((3-chloro-5-fluorophenyl)methyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)acetamide | 537.2 | |
| 812 | N-((1S,2R)-3-(((2R,4S)-1'-acetyl-6-ethyl-3,4-dihydrospiro[chromene-2,3'-pyrrolidin]-4-yl)amino)-2-hydroxy-1-(phenylmethyl)propyl)acetamide N-((1S,2R)-3-(((2S,4S)-1'-acetyl-6-ethyl-3,4-dihydrospiro[chromene-2,3'-pyrrolidin]-4-yl)amino)-2-hydroxy-1-(phenylmethyl)propyl)acetamide | | 1.948759 |
| 813 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2,4,6-trifluorophenyl)methyl)propyl)acetamide | 520 | 0.100123 |
| 814 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2,3,4-trifluorophenyl)methyl)propyl)acetamide | 520 | 0.056329 |
| 815 | N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-((2,4,6-trifluorophenyl)methyl)propyl)acetamide | 506 | 0.224171 |
| 816 | N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-((2,3,4-trifluorophenyl)methyl)propyl)acetamide | 506 | 0.137486 |
| 817 | N-((1S,2R)-1-((4-chlorophenyl)methyl)-3-(((4'S)-6'-(2,2-dimethylpropyl)-3',4'-dihydrospiro[cyclopentane-1,2'-pyrano[2,3-b]pyridin]-4'-yl)amino)-2-hydroxypropyl)acetamide | 515 | 0.131569 |

TABLE 4-continued

| Ex. No. | Compound Name | Mass Found | Cell Assay |
|---|---|---|---|
| 818 | N-((1S,2R)-1-((4-fluorophenyl)methyl)-2-hydroxy-3-(((4'S)-6'-(phenylmethyl)-3',4'-dihydrospiro[cyclobutane-1,2'-pyrano[2,3-b]pyridin]-4'-yl)amino)propyl)acetamide | 504 | 1.80048 |
| 819 | N-((1S,2R)-2-hydroxy-1-(phenylmethyl)-3-(((4S)-6-((2R)-tetrahydro-2-furanyl)-3,4-dihydrospiro[chromene-2,1'-cyclobutan]-4-yl)amino)propyl)acetamide N-((1S,2R)-2-hydroxy-1-(phenylmethyl)-3-(((4S)-6-((2S)-tetrahydro-2-furanyl)-3,4-dihydrospiro[chromene-2,1'-cyclobutan]-4-yl)amino)propyl)acetamide | 465 | 0.160704 |
| 820 | N-((1S,2R)-2-hydroxy-1-(phenylmethyl)-3-(((4'S)-6'-((2R)-tetrahydro-2-furanylmethyl)-3',4'-dihydrospiro[cyclobutane-1,2'-pyrano[2,3-b]pyridin]-4'-yl)amino)propyl)-2-(methyloxy)acetamide N-((1S,2R)-2-hydroxy-1-(phenylmethyl)-3-(((4'S)-6'-((2S)-tetrahydro-2-furanylmethyl)-3',4'-dihydrospiro[cyclobutane-1,2'-pyrano[2,3-b]pyridin]-4'-yl)amino)propyl)-2-(methyloxy)acetamide | 510 | 0.098566 |
| 821 | N-((1S,2R)-2-hydroxy-1-(phenylmethyl)-3-(((4S)-6-((2S)-tetrahydro-2-furanylmethyl)-3,4-dihydrospiro[chromene-2,1'-cyclobutan]-4-yl)amino)propyl)acetamide N-((1S,2R)-2-hydroxy-1-(phenylmethyl)-3-(((4S)-6-((2R)-tetrahydro-2-furanylmethyl)-3,4-dihydrospiro[chromene-2,1'-cyclobutan]-4-yl)amino)propyl)acetamide | 479 | 0.104947 |
| 822 | N-((1S,2R)-2-hydroxy-3-(((4S)-6-(5-hydroxypentyl)-3,4-dihydrospiro[chromene-2,1'-cyclobutan]-4-yl)amino)-1-(phenylmethyl)propyl)acetamide | 481 | 0.066235 |
| 823 | N-((2S,3R)-3-hydroxy-4-((S)-6-isopropoxy-2,2-spirocyclobutyl-chroman-4-ylamino)-1-phenylbutan-2-yl)acetamide | 453 | 0.310061 |
| 824 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-pyridinylmethyl)propyl)acetamide | 467 | 0.002325 |
| 825 | N-((1S,2R)-1-((2,3-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 502 | 0.004339 |
| 826 | N-((1S,2R)-1-((2,6-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 502 | 0.006934 |
| 827 | N-((1S,2R)-3-(((4'S)-6'-(2-fluoro-2-methylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide | 488 | 0.025843 |
| 828 | N-((1S,2R)-1-((4-chlorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide | 504 | 0.07843 |
| 829 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((1-methyl-3-piperidinyl)methyl)propyl)acetamide | 487 | 2.629707 |
| 830 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((5-fluoro-3-pyridinyl)methyl)-2-hydroxypropyl)acetamide | 485 | 0.001825 |
| 831 | N-((1S,2S)-3-(((4'S)-6'-(2,2-dimethylpropyl)-3',4'-dihydrospiro[cyclobutane-1,2'-pyrano[2,3-b]pyridin]-4'-yl)amino)-1-((5-fluoro-3-pyridinyl)methyl)-2-hydroxypropyl)acetamide | 485 | 0.166762 |
| 832 | N-((1S,2R)-1-((3,4-bis(methyloxy)phenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 526 | 0.009283 |
| 833 | N-((1S,2R)-1-((2,3-difluorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide | 506 | 0.031005 |
| 834 | N-((1S,2R)-1-((3-bromo-4-fluorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide | 566 | 0.009305 |
| 835 | N-((1S,2R)-1-((3,5-difluorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide | 506 | 0.002048 |

TABLE 4-continued

| Ex. No. | Compound Name | Mass Found | Cell Assay |
|---|---|---|---|
| 836 | N-((1S,2R)-1-((3-chloro-4-fluorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide | 522 | 0.01471 |
| 837 | N-((1S,2R)-1-((3-chloro-5-fluorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide | 522 | 0.003578 |
| 838 | N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxy-1-((3-(trifluoromethyl)phenyl)methyl)propyl)acetamide | 538 | 0.013298 |
| 839 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 510 | 0.005492 |
| 840 | N-((1S,2R)-1-(1,3-benzodioxol-5-ylmethyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide | 514 | 0.027663 |
| 841 | N-((1S,2R)-2-hydroxy-1-(phenylmethyl)-3-(((4'S)-6'-(2,2,2-trifluoroethyl)-3',4'-dihydrospiro[cyclobutane-1,2'-pyrano[2,3-b]pyridin]-4'-yl)amino)propyl)acetamide | 478.2 | 0.084821 |
| 842 | N-((1S,2R)-1-((3,4-difluorophenyl)methyl)-2-hydroxy-3-(((4'S)-6'-(2,2,2-trifluoroethyl)-3',4'-dihydrospiro[cyclobutane-1,2'-pyrano[2,3-b]pyridin]-4'-yl)amino)propyl)acetamide | 514.2 | 0.106066 |
| 843 | N-((1S,2R)-3-(((4'S)-6'-bromo-3',4'-dihydrospiro[cyclobutane-1,2'-pyrano[2,3-b]pyridin]-4'-yl)amino)-1-((4-fluorophenyl)methyl)-2-hydroxypropyl)acetamide | 512.2 | 0.503441 |
| 844 | N-((1S,2R)-1-((3-fluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide | 470.2 | 0.003627 |
| 845 | N-((1S,2R)-1-((4-fluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide | 470.2 | 0.011411 |
| 846 | N-((1S,2R)-1-((3,5-difluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide | 488.2 | 0.001722 |
| 847 | N-((1S,2R)-1-((3-chloro-5-fluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide | 504.2 | 0.004272 |
| 848 | 3-((2S,3R)-2-(acetylamino)-3-hydroxy-4-(((4'S)-6'-(2-methylpropyl)-3',4'-dihydrospiro[cyclobutane-1,2'-pyrano[2,3-b]pyridin]-4'-yl)amino)butyl)benzamide | 495.2 | 0.012834 |
| 849 | N-((1S,2R)-1-((3-cyanophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide | 477.2 | 0.001259 |
| 850 | N-((1S,2R)-1-((2,3-difluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide | 488.2 | 0.008683 |
| 851 | N-((1S,2R)-1-((3,4-difluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide | 488.2 | 0.003236 |
| 852 | N-((1S,2R)-3-(((4'S)-7'-fluoro-6'-(2-methylpropyl)-3',4'-dihydrospiro[cyclobutane-1,2'-pyrano[2,3-b]pyridin]-4'-yl)amino)-2-hydroxy-1-(phenylmethyl)propyl)acetamide | 470.2 | 0.051988 |
| 853 | N-((1S,2R)-1-((3,5-difluorophenyl)methyl)-3-(((4'S)-7'-fluoro-6'-(2-methylpropyl)-3',4'-dihydrospiro[cyclobutane-1,2'-pyrano[2,3-b]pyridin]-4'-yl)amino)-2-hydroxypropyl)acetamide | 506.2 | 0.011208 |
| 854 | N-((1S,2R)-3-(((4'S)-7'-fluoro-6'-(2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 488.2 | 0.151206 |
| 855 | N-((1S,2R)-3-(((4'S)-7'-fluoro-6'-(2-methylpropyl)-3',4'-dihydrospiro[cyclobutane-1,2'-pyrano[2,3-b]pyridin]-4'-yl)amino)-1-((3-fluorophenyl)methyl)-2-hydroxypropyl)acetamide | 488.2 | 0.025226 |
| 856 | N-((1S,2R)-1-((2,3-difluorophenyl)methyl)-3-(((4'S)-7'-fluoro-6'-(2-methylpropyl)-3',4'-dihydrospiro[cyclobutane-1,2'-pyrano[2,3-b]pyridin]-4'-yl)amino)-2-hydroxypropyl)acetamide | 506.2 | 0.205783 |
| 857 | N-((1S,2R)-1-((4-chloro-3-fluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide | 504.2 | 0.026204 |

TABLE 4-continued

| Ex. No. | Compound Name | Mass Found | Cell Assay |
|---|---|---|---|
| 858 | N-((1S,2R)-1-((4-chlorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide | 486.2 | 0.052694 |
| 859 | N-((1S,2R)-1-((4-fluorophenyl)methyl)-2-hydroxy-3-(((4'S)-6'-(1,3,3,3-tetrafluoro-2-methylpropyl)-3',4'-dihydrospiro[cyclobutane-1,2'-pyrano[2,3-b]pyridin]-4'-yl)amino)propyl)acetamide | 542.2 | 0.148464 |
| 860 | N-((1S,2R)-1-((4-chlorophenyl)methyl)-2-hydroxy-3-(((4'S)-6'-(1,3,3,3-tetrafluoro-2-methylpropyl)-3',4'-dihydrospiro[cyclobutane-1,2'-pyrano[2,3-b]pyridin]-4'-yl)amino)propyl)acetamide | 558.2 | 0.452497 |
| 861 | N-((1S,2R)-1-((3-fluorophenyl)methyl)-2-hydroxy-3-(((4'S)-6'-(1,3,3,3-tetrafluoro-2-methylpropyl)-3',4'-dihydrospiro[cyclobutane-1,2'-pyrano[2,3-b]pyridin]-4'-yl)amino)propyl)acetamide | 542.2 | 0.026399 |
| 862 | N-((1S,2R)-2-hydroxy-1-(phenylmethyl)-3-(((4'S)-6'-(1,3,3,3-tetrafluoro-2-methylpropyl)-3',4'-dihydrospiro[cyclobutane-1,2'-pyrano[2,3-b]pyridin]-4'-yl)amino)propyl)acetamide | 524.2 | 0.074055 |
| 863 | N-((1S,2R)-1-((3-fluorophenyl)methyl)-2-hydroxy-3-(((4'S)-6'-(3,3,3-trifluoro-1-hydroxy-2-methylpropyl)-3',4'-dihydrospiro[cyclobutane-1,2'-pyrano[2,3-b]pyridin]-4'-yl)amino)propyl)acetamide | 540.2 | 1.82816 |
| 864 | N-((1S,2R)-1-((4-chlorophenyl)methyl)-2-hydroxy-3-(((4'S)-6'-(3,3,3-trifluoro-1-hydroxy-2-methylpropyl)-3',4'-dihydrospiro[cyclobutane-1,2'-pyrano[2,3-b]pyridin]-4'-yl)amino)propyl)acetamide | 556.2 | 10 |
| 865 | N-((1S,2R)-2-hydroxy-1-(phenylmethyl)-3-(((4'S)-6'-(3,3,3-trifluoro-1-hydroxy-2-methylpropyl)-3',4'-dihydrospiro[cyclobutane-1,2'-pyrano[2,3-b]pyridin]-4'-yl)amino)propyl)acetamide | 522.2 | 1.931998 |
| 866 | N-((1R,2R)-1-((3-chloro-2-fluorophenyl)methyl)-3-(((4'S)-6'-(2,2-dimethylpropyl)-3',4'-dihydrospiro[cyclobutane 1,2'-pyrano[2,3-b]pyridin]-4'-yl)amino)-2-hydroxypropyl)acetamide | 518 | 10 |
| 867 | N-((1S,2R)-1-((5-chloro-2-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 518 | 0.002326 |
| 868 | N-((1S,2R)-1-((3-chloro-2-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 518 | 0.006256 |
| 869 | N-((1S,2R)-1-((3-chloro-4,5-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 536 | 0.017919 |
| 870 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2,3,6-trifluorophenyl)methyl)propyl)acetamide | 520 | 0.035578 |
| 871 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2,3,5-trifluorophenyl)methyl)propyl)acetamide | 520 | 0.002026 |
| 872 | N-((1S,2R)-1-((4-bromophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 544/546 | 0.034468 |
| 873 | methyl ((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)carbamate | 482 | 0.020588 |
| 874 | N-((1S,2R)-1-((3,5-difluorophenyl)methyl)-3-(((4'S)-6'-ethyl-3',4'-dihydrospiro[cyclobutane-1,2'-pyrano[2,3-b]pyridin]-4'-yl)amino)-2-hydroxypropyl)acetamide | 460 | 0.012128 |
| 875 | methyl ((1S,2R)-1-((3,5-difluorophenyl)methyl)-3-(((4'S)-6'-ethyl-3',4'-dihydrospiro[cyclobutane-1,2'-pyrano[2,3-b]pyridin]-4'-yl)amino)-2-hydroxypropyl)carbamate | 476 | 0.325018 |
| 876 | methyl ((1S,2R)-1-((3,5-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)carbamate | 518 | 0.010815 |
| 877 | N-((1S,2R)-3-(((4'S)-6'-(2,2-dimethylpropyl)-3',4'-dihydrospiro[cyclobutane-1,2'-pyrano[2,3-c]pyridin]-4'-yl)amino)-2-hydroxy-1-(phenylmethyl)propyl)propanamide | 480 | 0.064123 |

TABLE 4-continued

| Ex. No. | Compound Name | Mass Found | Cell Assay |
|---|---|---|---|
| 878 | N-((1S,2R)-1-((4-fluorophenyl)methyl)-2-hydroxy-3-(((4'S)-6'-(3-hydroxy-2,2-dimethylpropyl)-3',4'-dihydrospiro[cyclobutane-1,2'-pyrano[2,3-b]pyridin]-4'-yl)amino)propyl)acetamide | 500 | 0.235839 |

The present invention also provides methods for making compounds of Formulas I-III. In another embodiment of the invention, there is provided a method of making a compound of Formula I or II, the method comprising the step of reacting a compound 20

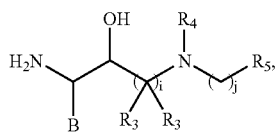

wherein i, j, A, B, $R^3$, $R^4$ and $R^5$ are as defined herein, with a compound having the structure A-W-X, wherein A and W are as defined herein and X is a leaving group, to make a compound of Formulas I or II.

In another embodiment of the invention, there is provided a method of making a compound of Formula III, the method comprising the step of reacting a compound 30

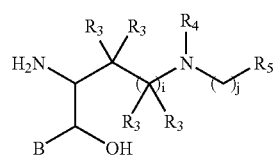

wherein i, j, B. $R^3$, $R^4$ and $R^5$ are as defined herein, with a compound having the structure A-W—X, wherein A and W are as defined herein with respect to Formula III and X is a leaving group, to make a compound of Formula III.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal such as by enzyme activity, under conditions analogous to physiological conditions. It should also be appreciated that the protecting groups should not be present in the end-products. The specialist knows, or can easily establish, which protecting groups are suitable with the reactions described herein. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary salt forms and their preparation are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., Et$_2$O and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including CH$_3$CN; halogenated hydrocarbons, including CH$_2$Cl$_2$, CHCl$_3$ and CCl$_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, H$_2$SO$_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of this invention may also be represented in multiple tautomeric forms. The compounds may also occur in cis- or trans- or E- or Z-double bond isomeric forms. The invention expressly includes all tautomeric forms of the compounds described herein.

All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen). For example, the R$^{12}$ substitutent is drawn unattached to any specific atom of ring Z$^2$, and therefore each of the n number of R$^{12}$ substitutents may be attached to any atom of Z$^2$.

The compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

Although the pharmacological properties of the compounds of the invention (Formulas I-III) vary with structural change, in general, activity possessed by compounds of Formulas I, II and III may be demonstrated both in vitro as well as in vivo. Particularly, the pharmacological properties of the compounds of this invention may be confirmed by a number of pharmacological in vitro assays. The following exemplified pharmacological assays have been carried out with the compounds according to the invention. Compounds of the invention were found to modulate BACE activity.

Biological Evaluation

The following biological assays were used to characterize the ability of compounds of the invention to regulate the cleavage of amyloid beta precursor protein, thereby reducing or inhibiting the production of amyloid beta.

In Vitro Enzymatic BACE FRET (Fluorescence Resonance Energy Transfer) Assay

Assay buffer is 0.05 M acetate, pH 4.2, 10% DMSO final, 100 uM genapol (which is a nonionic detergent, below it's Critical Micelle Concentration). Enzyme (0.2 nM) is pre-incubated for one hour with inhibitors added in 1 uL of DMSO. Then the assay is started by the addition of FRET substrate (50 nM) and incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

The compounds of Examples 1-19, 24-52, 54-74, 78-91, 93-108, 111-113, 115-137, 139, 141-142, 144-171, 173-178, 180, 182, 185-187, 190-204, 206-213, 218-247, 249-262, 264, 266-276, 278-287, 289-314, 320-327, 329-384, 386, 388, 393-418, 461-466, 468-470, 488-501, 503-510, 512 and 514-520, 522-527, 529-534, 537-562, 564-608, 610, 612-620, 623-624, 627-655, 657-663, 665-689, 691-727, 729-730, 732-734, 736, 738-739, 741-441, 443-448, 781-782, 784-787, 789-828, 830-863 and 865-878 exhibited $IC_{50}$ values of 5 µM or less in the FRET in vitro enzyme assay.

BACE Cell-Based Assay:

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 µM or 10 µM. The compounds were diluted from stock solutions in DMSO and the final DMSO concentration of the test compounds on cells was 0.1%. After 24 h of incubation with the test compounds the supernatant conditioned media was collected and the Aβ 40 levels were determined using a sandwich ELISA. The $IC_{50}$ of the compound was calculated from the percent of control or percent inhibition of Aβ 40 as a function of the concentration of the test compound.

The sandwich ELISA to detect Aβ 40 was performed in 96 well microtiter plates, which were pre-treated with goat anti-rabbit IgG (Pierce). The capture and detecting antibody pair that were used to detect Aβ 40 from cell supernatants were affinity purified pAb4O (Biosource) and biotinylated 6E10 (Signet Labs Inc.), respectively. The optimal concentration for the pAb4O antibody was 3 pg/ml in Superblock/TBS (Pierce) that was supplemented with 0.05% Tween 20 (Sigma). Optimal concentration for the detection antibody 6E10-biotinylated was 0.5 µg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Of the compounds tested, Examples 1-3, 5-7, 9-10, 16, 18-19, 24-35, 38-44, 46-52, 54-68, 70-74, 76-91, 93-108, 111-124, 126-137, 139, 141-142, 144-145, 152-171, 173-187, 190-204, 207-213, 218-223, 225-247, 249, 251-252, 254-281, 291-294, 296-299, 301-314, 315-317, 320-335, 337, 341-343, 345-349, 352-382, 384, 386, 388, 393-418, 461-466, 468-470, 488-501, 503-510, 512 and 514-519 exhibited activities with $IC_{50}$ values of 5 µM or less in the cell-based assay. In addition, the cell based assay data for each of Examples 520-876 is provided in Table 4. The majority of those Examples exhibited activities with $IC_{50}$ values of 5 µM or less in the cell-based assay.

Indications

Accordingly, compounds of the invention are useful for, but not limited to, the prevention or treatment of beta-secretase related diseases, including Alzheimer's disease. The compounds of the invention have the ability to modulate the formation of amyloid beta, and reduce the formation and deposition of plaque on the brain. In one embodiment of the invention, there is provided a method of treating a disorder related to a beta-secretase enzyme in a subject, the method comprising administering to the subject an effective dosage amount of a compound of Formulas I, II or III. In another embodiment, there is provided a method of reducing production of amyloid beta, and of reducing plaque formation. In yet another embodiment, there is provided a method of treating Alzheimer's disease.

Accordingly, the compounds of the invention would be useful in therapy as CNS agents in treating neurological disorders and related conditions.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients, adjuvants and the like (collectively referred to herein as "carrier" materials) as described herein, and, if desired, other active ingredients. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Accordingly, in yet another embodiment of the present invention, there is provided a method of manufacturing a medicament, the method comprising combining an amount of a compound according to Formulas I, II or III with a pharmaceutically acceptable carrier to manufacture the medicament.

In yet another embodiment, there is provided a method of manufacturing a medicament for the treatment of Alzheimer's disease, the method comprising combining an amount of a compound according to Formulas I, II or III with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known to influence the formation and/or deposition of amyloid beta, otherwise responsible for the formation of plaque on the brain.

If formulated as a fixed dose, such combination products employ the compounds of this invention within the accepted dosage ranges. Compounds of Formulas I, II and III may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula I:

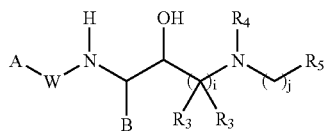

I or a stereoisomer, tautomer, or pharmaceutically acceptable salt, thereof, wherein A is $C_{1-10}$-alkyl, $C_{2-10}$-alkenyl, $C_{2-10}$-alkynyl, $R^1$-$C_{1-10}$-alkyl-, $R^1$-$C_{2-10}$-alkenyl- or $R^1$-$C_{2-10}$-alkynyl-, wherein 1,2 or 3 carbon atoms of (1) said $C_1$-$C_{10}$alkyl, $C_1$-$C_{10}$ alkenyl, $C_1$-$C_{10}$ alkynyl or (2) said $C_{1-10}$-alkyl, $C_{2-10}$-alkenyl, $C_{2-10}$-alkynyl of $R^1$-$C_{1-10}$-alkyl-, $R^1$-$C_{2-10}$-alkenyl- or $R^1$-$C_{2-10}$-alkynyl-, is optionally replaced with a heteroatom selected from O, S, S(O), S(O)$_2$ and N, and optionally substituted independently with one or more substituents of $R^9$; and $R^1$ is a fully saturated or a partially or fully unsaturated 3-8 membered monocyclic, 6-12 membered bicyclic, or 7-14 membered tricyclic ring system, said ring system formed of carbon atoms and optionally including 1-3 heteroatoms if monocyclic, 1-6 heteroatoms if bicyclic, or 1-9 heteroatoms if tricyclic, said heteroatoms selected from O, N, or S, wherein said ring system is substituted independently with one or more substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

W is —C(=O)—, or —S(=O)—$_b$, wherein b is 1 or 2;

B is $R^2$—$(CR^{2a}R^{2a})_h$—, wherein $R^2$ is phenyl optionally substituted independently with 1-5 substituents of $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

each $R^{2a}$, independently, is H; and h is 1;

i is 1;

j is 0,1 or 2;

each $R^3$, independently, is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^4$ is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^5$ is

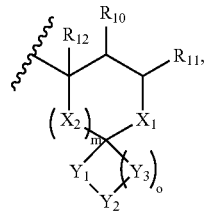

-continued

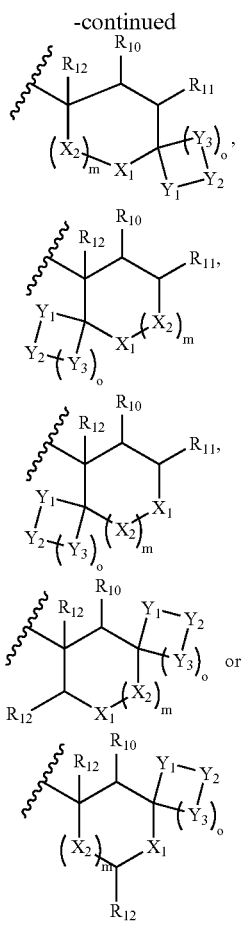

wherein X$^1$ is;
each X$^2$, independently, is CR$^{12}$R$^{12}$;
each of Y$^1$, Y$^2$ and Y$^3$, independently, is CR$^{12}$R$^{12}$, O or S;
m is 1; and
o is 0, 1, 2, 3, 4 or 5;
provided that (a) no more than two of Y$^1$, Y$^2$ and Y$^3$ is O or S and (b) when o is 0, then each of Y$^1$ and Y$^2$ is CR$^{12}$R$^{12}$;
R$^7$ is H, C$_{1-10}$-alkyl, C$_{2-10}$-alkenyl, C$_{2-10}$-alkynyl, C$_{3-10}$-cycloalkyl or C$_{4-10}$-cycloalkenyl, each of the C$_{1-10}$-alkyl, C$_{2-10}$-alkenyl, C$_{2-10}$-alkynyl, C$_{3-10}$-cycloalkyl and C$_{4-10}$-cycloalkenyl optionally comprising 1-4 heteroatoms selected from N, O and S and optionally substituted with 1-5 substituents of NR$^8$R$^9$, NR$^9$R$^9$, OR$^8$, SR$^8$, OR$^9$, SR$^9$, C(O)R$^8$, OC(O)R$^8$, COOR$^8$, C(O)R$^9$, OC(O)R$^9$, COOR$^9$, C(O)NR$^8$R$^9$, C(O)NR$^9$R$^9$, NR$^9$C(O)R$^8$, NR$^9$C(O)R$^9$, NR$^9$C(O)NR$^8$R$^9$, NR$^9$C(O)NR$^9$R$^9$, NR$^9$(COOR$^8$), NR$^9$(COOR$^9$), OC(O)NR$^8$R$^9$, OC(O)NR$^9$R$^9$, S(O)$_2$R$^8$, S(O)$_2$NR$^8$R$^9$, S(O)$_2$R$^9$, S(O)$_2$NR$^9$R$^9$, NR$^9$S(O)$_2$NR$^8$R$^9$, NR$^9$S(O)$_2$NR$^9$R$^9$, NR$^9$S(O)$_2$R$^8$, NR$^9$S(O)$_2$R$^9$, R$^8$ or R$^9$;
R$^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of R$^9$, oxo, NR$^9$R$^9$, OR$^9$; SR$^9$, C(O)R$^9$ or a partially or fully saturated or unsaturated 5-6 membered ring of carbon atoms optionally including 1-3 heteroatoms selected from O, N, or S, and optionally substituted independently with 1-5 substituents of R$^9$;
R$^9$ is H, halo, haloalkyl, CN, OH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C$_{1-10}$-alkylamino-, C$_{1-10}$-dialkylamino-, C$_{1-10}$-thioalkoxyl, benzyl or phenyl;
R$^{10}$ is H, halo, haloalkyl, CN, OH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C$_{1-10}$-alkylamino-, C$_{1-10}$-dialkylamino-, C$_{1-10}$-thioalkoxyl, benzyl or phenyl;
R$^{11}$ is H halo, haloalkyl, CN, OH, NO$_2$, NH$_2$, acetyl, C$_{1-10}$-alkyl, C$_{2-10}$-alkenyl, C$_{2-10}$-alkynyl, C$_{3-10}$ cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C$_{1-10}$-alkylamino-, C$_{1-10}$-dialkylamino-, C$_{1-10}$-thioalkoxyl, benzyl or phenyl;

alternatively, $R^{10}$ and $R^{11}$ taken together with the carbon or nitrogen atoms to which they are attached form a partially or fully saturated or unsaturated 5-6 membered second ring of carbon atoms optionally including 1-3 heteroatoms selected from O, N, or S, the second ring optionally substituted independently with 1-5 substitutents of $R^{12}$, $R^{13}$, $R^{14}$ or $R^{15}$ and optionally fused to a 4-7 membered third ring, the third ring formed of carbon atoms optionally including 1-3 heteroatoms selected from O, N, or S, and optionally substituted independently with 1-5 substitutents of $R^{12}$, $R^{13}$, $R^{14}$ or $R^{15}$;

$R^{12}$ is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl, phenyl or $R^{14}$;

$R^{13}$ is $NR^{14}R^{15}$, $NR^{15}R^{15}$, $OR^{14}$, $SR^{14}$, $OR^{15}$, $SR^{15}$, $C(O)R^{14}$, $OC(O)R^{14}$, $COOR^{14}$, $C(O)R^{15}$, $OC(O)R^{15}$, $COOR^{15}C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^{15}$; and $R^{15}$ is H, halo, haloalkyl, CN, OH, $NO_2$, $NH_2$, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, phenyl, $C_{1-10}$-alkylamino-, $C_{1-10}$-dialkylamino-, $C_{1-10}$-thioalkoxyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl or phenyl.

2. The compound of claim 1 wherein A is $C_{1-6}$-alkyl, $C_{2-6}$-alkenyl, $C_{2-6}$-alkynyl, $R^1$—O—$C_{1-6}$-alkyl-, $R^1$—S—$C_{1-6}$-alkyl-, $R^1$—S(O)$_2$—$C_{1-6}$-alkyl-, $R^1$—NH—$C_{1-6}$-alkyl-, $R^1$—O—$C_{1-6}$-alkenyl-, $R^1$—S—$C_{2-6}$-alkenyl-, $R^1$—S(O)$_2$—$C_{2-6}$-alkenyl-, $R^1$—NH—$C_{2-6}$-alkenyl-, $R^1$—O—$C_{1-6}$-alkynyl-, $R^1$—S—$C_{1-6}$-alkynyl-, $R^1$—S(O)$_2$—$C_{1-6}$-alkynyl-, $R^1$—NH—$C_{1-6}$-alkynyl-, $R^1$—$C_{1-6}$-alkyl-O—$C_{1-6}$-alkyl-, $R^1$—$C_{1-6}$-alkyl-S—$C_{1-6}$-alkyl-, $R^1$—$C_{1-6}$-alkyl-S(O)$_2$—$C_{1-6}$-alkyl-, $R^1$—$C_{1-6}$-alkyl-NH—$C_{1-6}$-alkyl-, $R^1$—$C_{1-6}$-alkyl-O—$C_{1-6}$-alkenyl-, $R^1$—$C_{1-6}$-alkyl-S—$C_{2-6}$-alkenyl-, $R^1$—$C_{1-6}$-alkyl-S(O)$_2$—$C_{2-6}$-alkenyl-, $R^1$—$C_{1-6}$-alkyl-NH—$C_{2-6}$-alkenyl-, $R^1$—$C_{1-6}$-alkyl-O—$C_{1-6}$alkynyl-, $R^1$—$C_{1-6}$-alkyl-S—$C_{1-6}$-alkynyl-, $R^1$—$C_{1-6}$-alkyl-S(O)$_2$—$C_{1-6}$alkynyl- or $R^1$—$C_{1-6}$-alkyl-NH—$C_{1-6}$-alkynyl-.

3. The compound of claim 1 wherein A is $C_{1-6}$-alkyl, $C_{2-6}$alkenyl, $C_{2-6}$-alkynyl, $C_{1-6}$alkyl-O—$C_{1-3}$-alkyl-, $C_{1-6}$-alkyl-S—$C_{1-3}$-alkyl-, $C_{1-6}$-alkyl-S(O)$_2$—$C_{1-3}$-alkyl-, $C_{1-6}$-alkyl-NH—$C_{1-3}$-alkyl, di-($C_{1-6}$-alkyl)-N—$C_{1-3}$-alkyl, $C_{2-6}$-alkenyl-O—$C_{1-3}$-alkyl-, $C_{2-6}$-alkenyl-S—$C_{1-3}$-alkyl-, $C_{2-6}$-alkenyl -S(O)$_2$—$C_{1-3}$-alkyl-, $C_{2-6}$-alkenyl-NH—$C_{1-3}$-alkyl- or $C_{2-6}$-alkynyl-NH—$C_{1-3}$-alkyl-, wherein the alkyl, alkenyl or alkynyl moiety of each is optionally substituted with 1-5 substituents of $R^9$.

4. The compound of claim 1 wherein
each $R^3$, independently, is H, haloalkyl, CN, $C_{1-10}$alkyl, $C_{2-10}$-alkenyl or $C_{2-10}$-alkynyl;
$R^4$ is H or $C_{1-10}$-alkyl;
h is 1;
i is 1; and
j is 0.

5. The compound of claim 4 wherein $R^5$ is

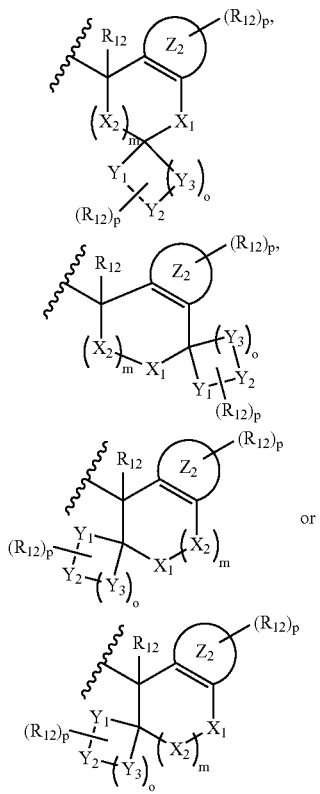

or wherein

Z² taken together with the carbon atoms to which it is attached is a partially or fully unsaturated 5-8 membered monocyclic ring, said ring formed of carbon atoms optionally including 1-3 heteroatoms if monocyclic, 1-6 heteroatoms if bicyclic, or 1-9 heteroatoms if tricyclic, said heteroatoms selected from O, N, or S, provided that (a) no more than two of $Y^1$, $Y^2$ and $Y^3$ is O or S and (b) when o is 0, then each of $Y^1$ and $Y^2$ is $CR^{12}R^{12}$; and p is 0, 1, 2, 3, 4 or 5.

6. The compound of claim 5 wherein $Z^2$ is a phenyl, pyridine, pyrimidine, triazine, pyridazine, pyrazine, pyridone, pyrrole, imidazole, pyrazole, triazole, thiophene, thiazole, thiadiazole, isothiazole, furan, oxazole, oxadiazole or isoxazole ring.

7. The compound of claim 1 wherein i is 1;

j is 0;

A is $C_{1-6}$-alkyl, $C_{2-6}$alkenyl, $C_{2-6}$-alkynyl, $C_{1-6}$alkyl-O—$C_{1-3}$-alkyl-, $C_{1-6}$-alkyl-S—$C_{1-3}$-alkyl-, $C_{1-6}$-alkyl-S(O)$_2$—$C_{1-3}$-alkyl-, $C_{1-6}$-alkyl-NH—$C_{1-3}$-alkyl, di-($C_{1-6}$-alkyl)-N—$C_{1-3}$-alkyl, $C_{2-6}$-alkenyl-O—$C_{1-3}$-alkyl-, $C_{2-6}$-alkenyl-S—$C_{1-3}$-alkyl-, $C_{2-6}$-alkenyl-S(O)$_2$—$C_{1-3}$-alkyl-, $C_{2-6}$-alkenyl-NH—$C_{1-3}$-alkyl- or $C_{2-6}$-alkynyl-NH—$C_{1-3}$-alkyl-, wherein the alkyl, alkenyl or alkynyl moiety of each is optionally substituted with 1-5 substituents of $R^9$;

W is —C(=O)—;

B is $R^2$—$(CR^{2a}R^{2a})_h$—, wherein h is 1 and $R^2$ is phenyl, optionally substituted with 1-5 substituents as defined in claim 1;

each $R^3$, independently, is H, haloalkyl, CN, $C_{1-10}$-alkyl, $C_{2-10}$-alkenyl or $C_{2-10}$-alkynyl;

$R^4$ is H, CN or $C_{1-10}$-alkyl;

$R^5$ is

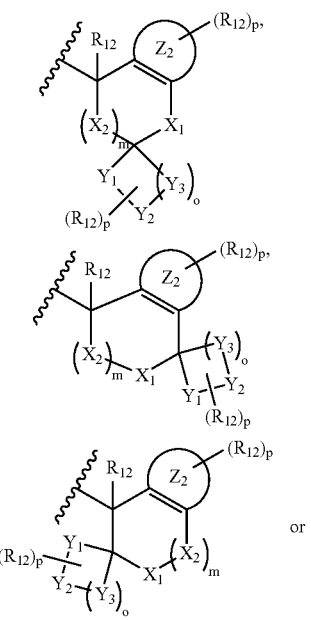

or

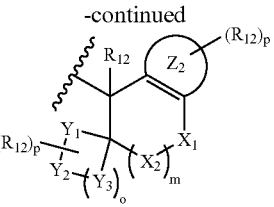

wherein m, o, $R^{12}$, $X^2$, $Y^1$, $Y^2$ and $Y^3$ are as defined in claim 1;

$X^1$ is O;

$Z^2$ is a phenyl, pyridine, pyrimidine, triazine, pyridazine, pyrazine, pyridone, pyrrole, imidazole, pyrazole, triazole, thiophene, thiazole, thiadiazole, isothiazole, furan, oxazole, oxadiazole or isoxazole ring; and p is 0, 1, 2, 3, 4 or 5;

$R^7$ is H, $C_{1-10}$-alkyl or $C_{2-10}$-alkenyl, each of the $C_{1-10}$-alkyl, or $C_{2-10}$-alkenyl optionally substituted with 1-3 substituents of $R^9$;

$R^8$ is a ring system selected from phenyl, pyridyl, pyrimidinyl, triazinyl, quinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl and cycloheptyl, said ring system optionally substituted independently with 1-3 substituents of $R^9$, oxo, $NR^9R^9$, $OR^9$, $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-7}$-cycloalkyl, $C_{4-7}$-cycloalkenyl, $C_{1-10}$-alkylamino-, $C_{1-10}$-dialkylamino-, $C_{1-10}$-alkoxyl, $C_{1-10}$-thioalkoxyl; and $R^{12}$ is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopently, hexyl, cyclohexyl, $C_{1-10}$-alkylamino-, $C_{1-10}$-dialkylamino-, $C_{1-10}$-thioalkoxyl, benzyl or phenyl.

8. The compound of claim 7 wherein $R^5$ is

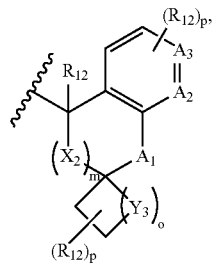

wherein m is 0 or 1;

o is 1 or 2;

p is 0, 1, 2 or 3;

$A^1$ is CH, C(=O), O or $NR^{12}$;

each of $A^1$ and $A^2$, independently, is $CR^{12}$ or N, provided that no more than one of $A^1$ and $A^2$ is N;

$X^2$ is CH;

$Y^3$ is $CR^{12}$ or O; and each $R^{12}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a ring selected from phenyl, pyridyl, pyrimidinyl, triazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, oxazolyl, oxadiazolyl, isoxazolyl, isothiazolyl, oxazolinyl, isoxazolinyl, thiazolinyl, pyrrolidinyl, pyrazolinyl, morpholinyl, piperidinyl, piperazinyl, pyranyl, dioxozinyl, cyclopropyl, cyclobutyl, azetidinyl, cyclopentyl, cyclohexyl and cycloheptyl, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopently, hexyl, cyclohexyl, $C_{1-10}$-alkylamino-, $C_{1-10}$-dialkylamino-, $C_{1-10}$-thioalkoxyl, benzyl or phenyl.

9. A compound, or a pharmaceutically acceptable salt thereof, selected from:

N-((1S,2R)-2-hydroxy-1-(phenylmethyl)-3-(((4S)-2,6,6-trimethyl-4,5,6,7-tetrahydro-1-benzofuran-4yl)amino) propyl)acetamide;

N-((1S,2R)-3-(((4S)-2-ethyl-6,6-dimethyl-4,5,6,7-tetrahydro-1-benzothien-4yl)amino)-2-hydroxy-1-(phenylmethyl)propyl)-2-(2-oxo-1-pyrrolidinyl)acetamide;

'N-((1S,2R)-3-(((4S)-6-bromo-2,2-dimethyl-3,4-dihydro-2H-chromen-4-yl)amino)-1-((3-cyanophenyl)methyl)-2-hydroxypropyl)acetamide;

'N-((1S,2R)-3-(((4S)-6-bromo-2,2-dimethyl-3,4-dihydro-2H-chromen-4-yl)amino)-1-((3-cyanophenyl)methyl)-2-hydroxypropyl)-2-(methyloxy)acetamide;

'N~1~-((1S,2R)-3-(((4S)-6-bromo-2,2-dimethyl-3,4-dihydro-2H-chromen-4-yl)amino)-1-((3-cyanophenyl) methyl)-2-hydroxypropyl)-N~2~,N~2~-dimethylglycinamide;

'N-((1S,2R)-3-(((4S)-8-bromo-6-ethyl-2,2-dimethyl-3,4-dihydro-2H-chromen-4-yl)amino)-1-((3-cyanophenyl) methyl)-2-hydroxypropyl)acetamide;

'N-((1S,2R)-1-((3-cyanophenyl)methyl)-3-(((1S)-3,3-dimethyl-7-(methyloxy)-4-oxo-1,2,3,4-tetrahydro-1-naphthalenyl)amino)-2-hydroxypropyl)-2-(methyloxy) acetamide;

N-((1S,2R)-1-((3-cyanophenyl)methyl)-3-(((1R)-3,3-dimethyl-7-(methyloxy)-4-oxo-1,2,3,4-tetrahydro-1-naphthalenyl)amino)-2-hydroxypropyl)-2-(methyloxy) acetamide;

'N-((1S,2R)-1-((3-cyanophenyl)methyl)-3-(((1S)-3,3-dimethyl-7-(methyloxy)-4-oxo-1,2,3,4-tetrahydro-1-naphthalenyl)amino)-2-hydroxypropyl)acetamide;

N-((1S,2R)-1-((3-cyanophenyl)methyl)-3-(((1R)-3,3-dimethyl-7-(methyloxy)-4-oxo-1,2,3,4-tetrahydro-1-naphthalenyl)amino)-2-hydroxypropyl)acetamide;

'N-((1S,2R)-1-((3-cyanophenyl)methyl)-3-(((4S)-6-ethyl-2,2-dimethyl-8-(4-morpholinyl)-3,4-dihydro-2H-chromen-4-yl)amino)-2-hydroxypropyl)acetamide;

'N-((1S,2R)-3-(((4R)-6-ethyl-2,2-dimethyl-8-(1-pyrrolidinyl)-3,4-dihydro-2H-chromen-4-yl)amino)-2-hydroxy-1-(phenylmethyl)propyl)acetamide;

N-((1S,2R)-3-(((4S)-6-ethyl-2,2-dimethyl-8-(1-pyrrolidinyl)-3,4-dihydro-2H-chromen-4-yl)amino)-2-hydroxy-1-(phenylmethyl)propyl)acetamide;

'N-((1S,2R)-3-(((4S)-8-(dimethylamino)-6-ethyl-2,2-dimethyl-3,4-dihydro-2H-chromen-4-yl)amino)-2-hydroxy-1-(phenylmethyl)propyl)acetamide;

N-((1S,2R)-3-(((4R)-8-(dimethylamino)-6-ethyl-2,2-dimethyl-3,4-dihydro-2H-chromen-4-yl)amino)-2-hydroxy-1-(phenylmethyl)propyl)acetamide;

'N-((1S,2R)-3-(((4S)-6-ethyl-2,2-dimethyl-8-(methylamino)-3,4-dihydro-2H-chromen-4-yl)amino)-2-hydroxy-1-(phenylmethyl)propyl)acetamide;

'N-((1S,2R)-1-((3-cyanophenyl)methyl)-2-hydroxy-3-(((5S)-3,7,7-trimethyl-5,6,7,8-tetrahydro-5-quinolinyl) amino)propyl)acetamide;

'N-((1S,2R)-3-(((4S)-6-(2,2-dimethylpropyl)-2,2-dimethyl-3,4-dihydro-2H-pyrano[2,3-b]-pyridin-4-yl) amino)-2-hydroxy-1-(phenylmethyl)propyl)acetamide;

'N-((1S,2R)-3-(((4S)-6-(2,2-dimethylpropyl)-2,2-dimethyl-3,4-dihydro-2H-pyrano[2,3-b]-pyridin-4-yl) amino)-1-((3-fluorophenyl)methyl)-2-hydroxypropyl) acetamide;

'N-((1S,2R)-3-(((1S)-3,3-dimethyl-7-((2-(methyloxy) ethyl)amino)-4-oxo-1,2,3,4-tetrahydro-1-naphthalenyl) amino)-2-hydroxy-1-(phenylmethyl)propyl)acetamide;

N-((1S,2R)-3-(((1R)-3,3-dimethyl-7-((2-(methyloxy) ethyl)amino)-4-oxo-1,2,3,4-tetrahydro-1-naphthalenyl) amino)-2-hydroxy-1-(phenylmethyl)propyl)acetamide;

'N-((1S,2R)-3-(((1R)-7-(cyclopentylamino)-3,3-dimethyl-4-oxo-1,2,3,4-tetrahydro-1-naphthalenyl)amino)-2-hydroxy-1-(phenylmethyl)propyl)acetamide;

N-((1S,2R)-3-(((1S)-7-(cyclopentylamino)-3,3-dimethyl-4-oxo-1,2,3,4-tetrahydro-1-naphthalenyl)amino)-2-hydroxy-1-(phenylmethyl)propyl)acetamide;

'N-((1S,2R)-1-((3,5-difluorophenyl)methyl)-3-(((1S)-7-(2,2-dimethylpropyl)-3,3-dimethyl-4-oxo-1,2,3,4-tetrahydro-1-naphthalenyl)amino)-2-hydroxypropyl)acetamide;

N-((1S,2R)-1-((3,5-difluorophenyl)methyl)-3-(((1R)-7-(2,2-dimethylpropyl)-3,3-dimethyl-4-oxo-1,2,3,4-tetrahydro-1-naphthalenyl)amino)-2-hydroxypropyl)acetamide;

'N-((1S,2R)-3-(((4S)-6-((2,2-dimethylpropyl)-2,2-dimethyl-3,4-dihydro-2H-pyrano[2,3-b]pyridin-4-yl)amino)-1-((4-fluorophenyl)methyl)-2-hydroxypropyl)acetamide;

N-((1S,2R)-1-((3,5-difluorophenyl)methyl)-3-(((4S)-6-(2,2-dimethylpropyl)-2,2-dimethyl-3,4-dihydro-2H-pyrano[2,3-b]pyridin-4-yl)amino)-2-hydroxypropyl)acetamide;

'N-((1S,2R)-3-(((4S)-2-(2,2-dimethylpropyl)-6,6-dimethyl-4,5,6,7-tetrahydro-1-benzothien-4-yl)amino)-2-hydroxy-1-(phenylmethyl)propyl)acetamide;

'methyl((1S,2R)-3-(((4S)-2-(2,2-dimethylpropyl)-6,6-dimethyl-4,5,6,7-tetrahydro-1-benzothien-4-yl)amino)-2-hydroxy-1-(phenylmethyl)propyl)carbamate;

'N-((1S,2R)-3-(((4R)-6-bromo-2,2-dimethyl-1,2,3,4-tetrahydro-4-quinolinyl)amino)-2-hydroxy-1-(phenylmethyl)propyl)acetamide;

N-((1S,2R)-3-(((4S)-6-bromo-2,2-dimethyl-1,2,3,4-tetrahydro-4-quinolinyl)amino)-2-hydroxy-1-(phenylmethyl)propyl)acetamide;

'N-((1S,2R)-3-(((4R)-6-(2,2-dimethylpropyl)-2,2-dimethyl-1,2,3,4-tetrahydro-4-quinolinyl)amino)-2-hydroxy-1-(phenylmethyl)propyl)acetamide;

N-((1S,2R)-3-(((4S)-6-(2,2-dimethylpropyl)-2,2-dimethyl-1,2,3,4-tetrahydro-4-quinolinyl)amino)-2-hydroxy-1-(phenymethyl)propyl)acetamide;

'N-((1S,2R)-3-(((4R)-1-acetyl-6-bromo-2,2-dimethyl-1,2,3,4-tetrahydro-4-quinolinyl)amino)-2-hydroxy-1-(phenylmethyl)propyl)acetamide;

N-((1S,2R)-3-(((4S)-1-acetyl-6-bromo-2,2-dimethyl-1,2,3,4-tetrahydro-4-quinolinyl)amino)-2-hydroxy-1-(phenylmethyl)propyl)acetamide;

N-((1S,2R)-3-(((4S)-6-(2,2-dimethylpropyl)-2,2-dimethyl-1,2,3,4-tetrahydro-4-quinolinyl)amino)-2-hydroxy-1-(phenylmethyl)propyl)acetamide;

'N-((1S,2R)-1-((3,5-difluorophenyl)methyl)-3-(((4S)-6-(2,2-dimethylpropyl)-2,2-dimethyl-1,2,3,4-tetrahydro-4-quinolinyl)amino)-2-hydroxypropyl acetamide;

'N-((1S,2R)-3-(((4S)-6-(2,2-dimethylpropyl)-2,2-dimethyl-1,2,3,4-tetrahydro-4-quinolinyl)amino)-1-((3-fluorophenyl)methyl)-2-hydroxypropyl)acetamide;

'N-((1S,2R)-3-(((4S)-6-(2,2-dimethylpropyl)-2,2-dimethyl-1,2,3,4-tetrahydro-4-quinolinyl)amino)-1-((4-fluorophenyl)methyl)-2-hydroxypropyl)acetamide;

'N-((1S,2R)-3-(((1S)-3,3-dimethyl-7-((3S)-tetrahydro-3-furanyloxy)-1,2,3,4-tetrahydro-1-naphthalenyl)amino)-2-hydroxy-1-(phenylmethyl)propyl)acetamide;

'N-((1S,2R)-3-(((4S)-8-(dimethylamino)-6-(2,2-dimethylpropyl)-2,2-dimethyl-3,4-dihydro-2H-pyrano[2,3-c]pyridin-4-yl)amino)-1-((3-(dimethylamino)-5-fluorophenyl)methyl)-2-hydroxypropyl)acetamide;

'N-((1S,2R)-1-((3-chloro-5-fluorophenyl)methyl)-3-(((4S)-8-(dimethylamino)-6-(2,2-dimethylpropyl)-2,2-dimethyl-3,4-dihydro-2H-pyrano[2,3-c]pyridin-4-yl)amino)-2-hydroxypropyl)acetamide;

'N-((1S,2R)-1-((3,4-difluorophenyl)methyl)-3-(((4S)-6-(2,2-dimethylpropyl)-2,2-dimethyl-8-(1-pyrrolidinyl)-3,4-dihydro-2H-pyrano[2,3-c]pyridin-4-yl)amino)-2-hydroxypropyl)acetamide;

'N-((1S,2R)-1-((3,4-difluorophenyl)methyl)-3-(((4S)-6-(2,2-dimethylpropyl)-2,2-dimethyl-8-(methylamino)-3,4-dihydro-2H-pyrano[2,3-c]pyridin-4-yl)amino)-2-hydroxypropyl)acetamide;

'N-((1S,2R)-3-(((4S)-8-chloro-6-(2,2-dimethylpropyl)-2,2-dimethyl-3,4-dihydro-2H-pyrano[2,3-c]pyridin-4-yl)amino)-1-((4-fluorophenyl)methyl)-2-hydroxypropyl)acetamide;

'N-((1S,2R)-3-(((4S)-8-(dimethylamino)-6-(2,2-dimethylpropyl)-2,2-dimethyl-3,4-dihydro-2H-pyrano[2,3-c]pyridin-4-yl)amino)-1-((4-fluorophenyl)methyl)-2-hydroxypropyl)acetamide;

'N-((1S,2R)-3-(((4S)-6-(2,2-dimethylpropyl)-2,2-dimethyl-3,4-dihydro-2H-pyrano[2,3-c]pyridin-4-yl)amino)-2-hydroxy-1-(phenylmethyl)propyl)acetamide;

'N-((1S,2R)-1-((3-chloro-5-fluorophenyl)methyl)-3-(((4S)-6-(2,2-dimethylpropyl)-2,2-dimethyl-3,4-dihydro-2H-pyrano[2,3-c]pyridin-4-yl)amino)-2-hydroxypropyl)acetamide;

'N-((1S,2R)-1-((3-chloro-5-fluorophenyl)methyl)-3-(((4S)-6-(2,2-dimethylpropyl)-2,2-dimethyl-3,4-dihydro-2H-pyrano[2,3-c]pyridin-4-yl)amino)-2-hydroxypropyl)propanamide;

'N-((1S,2R)-3-(((4S)-6-(2,2-dimethylpropyl)-2,2-dimethyl-3,4-dihydro-2H-pyrano[2,3-c]pyridin-4-yl)amino)-1-((3-fluorophenyl)methyl)-2-hydroxypropyl)acetamide;

'N-((1S,2R)-3-(((4S)-6-(2,2-dimethylpropyl)-2,2-dimethyl-3,4-dihydro-2H-pyrano[2,3-c]pyridin-4-yl)amino)-1-((4-fluorophenyl)methyl)-2-hydroxypropyl)acetamide;

'N-((1S,2R)-1-((3,5-difluorophenyl)methyl)-3-(((4S)-6-(2,2-dimethylpropyl)-2,2-dimethyl-3,4-dihydro-2H-pyrano[2,3-c]pyridin-4-yl)amino)-2-hydroxypropyl)acetamide;

'N-((1S,2R)-3-(((4S)-6-bromo-7-fluoro-2,2-dimethyl-3,4-dihydro-2H-chromen-4-yl)amino)-1-((3,5-difluorophenyl)methyl)-2-hydroxypropyl)acetamide;

N-((2S,3R)-3-hydroxy-4-((S)-6-isopropoxy-2,2-spirocyclobutyl-chroman-4-ylamino)-1-phenylbutan-2-yl)acetamide;

'N-((1S,2R)-3-(((2R,4S)-6-bromo-2-methyl-2-(trifluoromethyl)-3,4-dihydro-2H-chromen-4-yl)amino)-2-hydroxy-1-(phenylmethyl)propyl)acetamide; and N-((1S,2R)-3-(((2S,4S)-6-bromo-2-methyl-2-(trifluoromethyl)-3,4-dihydro-2H-chromen-4-yl)amino)-2-hydroxy-1-(phenylmethyl)propyl)acetamide.

10. A compound, or a pharmaceutically acceptable salt thereof, selected from:

N-((2S,3R)-4-(S)-2,2-spirocyclobutylchroman-4-ylamino)-3-hydroxy-1-phenylbutan-2-yl)acetamide;

N-((2S,3R)-4((S)-6-ethyl-2,2-spirocyclopentylchroman-4-ylamino)-3-hydroxy-1-phenylbutan-2-yl)acetamide. TFA salt;

N-((2S,3R)-4((S)-6-ethyl-2,2-spirocyclobutylchroman-4-ylamino)-3-hydroxy-1-phenylbutan-2-yl)-2-(pyridin-4-yl)acetamide.TFA salt;

N-((1S,2R)-3-(4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)-2-(5-methyl-1H-pyrazol-1-yl)acetamide;

Methyl(2S,3R)-3-hydroxy-4-((S)-6-neopentyl-2,2-spirocyclobutyl-3,4-dihydro-2H-pyrano[2,3-b]pyridin-4-ylamino)-1-phenylbutan-2-ylcarbamate;

Ethyl(2S,3R)-4-((S)-6-ethyl-2,2-spirocyclobutyl-chroman-4-ylamino)-3-hydroxy-1-phenylbutan-2-ylcarbamate;

N-((2S,3R)-4-((S)-6-ethyl-2,2-spirocyclobutylchroman-4-ylamino)-3-hydroxy-1-phenylbutan-2-yl)pent-4-ynamide;

3-cyclopentyl-N-((2S,3R)-4-((S)-6-ethyl-2,2-spirocyclobutylchroman-4-ylamino)-3-hydroxy-1-phenylbutan-2-yl)propanamide;

N-((2S,3R)-4-((S)-6-ethyl-2,2-spirocyclobutylchroman-4-ylamino)-3-hydroxy-1-phenylbutan-2-yl)propionamide;

N-((2S,3R)-4-((S)-6-ethyl-2,2-spirocyclobutylchroman-4-ylamino)-3-hydroxy-1-phenylbutan-2-yl)-2-methoxyacetamide;

2-(1,3-benzothiazol-2-yloxy)-N-((1S,2R)-3-(((4S)-6-ethyl-3,4-dihydrospiro[chromene-2,1'-cyclobutan]-4-yl)amino)-2-hydroxy-1-(phenylmethyl)propyl)acetamide;

N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(2-oxo-1,3-oxazolidin-3-yl)acetamide;

N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(1H-pyrrolo[2,3-b]pyridin-1-yl)acetamide;

N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-(2-oxo-1,3-oxazolidin-3-yl)acetamide;

N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-(methyloxy)acetamide;

N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)acetamide;

N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-(phenyloxy)acetamide;

(3S)-N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-1-cyclobutyl-5-oxo-3-pyrrolidinecarboxamide;

N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)propanamide;

N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-((cyclopropylmethyl)oxy)acetamide;

N-((1S,2R)-1-((3-cyanophenyl)methyl)-3-(((2S,4S)-6-ethyl-3,4,4',5'-tetrahydrospiro[chromene-2,3'-furan]-4-yl)amino)-2-hydroxypropyl)-2-(methyloxy)acetamide;

N-((1S,2R)-1-((3,5-difluorophenyl)methyl)-3-(((2S,4S)-6-ethyl-3,4,4',5'-tetrahydrospiro[chromene-2,3'-furan]-4-yl)amino)-2-hydroxypropyl)acetamide;

N-((1S,2R)-1-((3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

2-((3-chloro-2-methylphenyl)thio)-N-((1S,2R)-3-(((4S)-6-ethyl-3,4-dihydrospiro[chromene-2,1'-cyclobutan]-4-yl)amino)-2-hydroxy-1-(phenylmethyl)propyl)acetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)-2-(1-oxo-1,3-dihydro-2H-isoindol-2-yl)acetamide;

N-((1S,2R)-3-(((4'S)-6'-(2,2-dimethylpropyl)-3',4,4',5-tetrahydrospiro[furan-3,2'-pyrano[2,3-b]pyridin]-4'-yl)amino)-2-hydroxy-1-(phenylmethyl)propyl)-2-(1-oxo-1,3-dihydro-2H-isoindol-2-yl)acetamide;

N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-2-hydroxy-1-(phenylmethyl)propyl)-2-(methyloxy)acetamide;

N-((1S,2R)-3-(4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)-2-(3-methyl-5-isoxazolyl)acetamide;

N-((1S,2R)-3-(((4S)-6-ethyl-7-fluoro-3,4-dihydrospiro-2,2-spirocyclobutyl[chromene-2,1'-cyclobutan]-4-yl)amino)-2-hydroxy-1-(phenylmethyl)propyl)-2-(2-oxo-1-pyrrolidinyl)acetamide;

N-((1S,2R)-3-(((4S)-6-ethyl-3,4-dihydrospiro-2,2-spirocyclobutyl[chromene-2,1'-cyclobutan]-4-yl)amino)-2-hydroxy-1-(phenylmethyl)propyl)-2-(2-pyrazinyloxy)acetamide;

N-((1S,2R)-1-((3-cyanophenyl)methyl)-3-(((4S)-6-ethyl-3,4-dihydrospiro-2,2-spirocyclobutyl[chromene-2,1'-cyclobutan]-4-yl)amino)-2-hydroxypropyl)-2-(2-pyrimidinyloxy)acetamide;

N-((1S,2R)-3-(((4S)-6-ethyl-3,4-dihydrospiro[chromene-2,1'-cyclopentan]-4-yl)amino)-2-hydroxy-1-(phenylmethyl)propyl)-2-((5R)-2-(3-methylbutyl)-2,3,4,5-tetrahydro-1H-2-benzazepin-5-yl)acetamide;

N-((1S,2R)-3-(((4S)-6-bromo-3,4-dihydrospiro[chromene-2,1'-cyclobutan]-4-yl)amino)-2-hydroxy-1-(phenylmethyl)propyl)-2-(1H-1,2,3-triazol-4-yl)acetamide;

N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(4-propyl-1H-1,2,3-triazol-1-yl)acetamide;

N-((1S,2R)-1-(3-cyanophenyl)methyl)-3-(((4'S)-6'-ethyl-3',4'-dihydrospiro[cyclobutane-1,2'-pyrano[2,3-b]pyridin]-4'-yl)amino)-2-hydroxypropyl)-2-(methyloxy)acetamide;

N-((1S,2R)-2-hydroxy-3-(((4'S)-6'-(3-methylbutyl)-3',4'-dihydrospiro[cyclobutane-1,2'-pyrano[2,3-b]pyridin]-4'-yl)amino)-1-(phenylmethyl)propyl)-2-(methyloxy)acetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)-2-(2-methyl-1,3-thiazol-4-yl)acetamide;

2-(3,5-dimethyl-4-isoxazolyl)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)acetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)-2-(1H-1,2,4-triazol-1-yl)acetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)-2-(2H-1,2,3-triazol-2-yl)acetamide;

N-((1S,2R)-3-(((4S)-6-chloro-8-(4-morpholinyl)-3,4-dihydrospiro[chromene-2,1'-cyclobutan]-4-yl)amino)-1-((3-cyanophenyl)methyl)-2-hydroxypropyl)acetamide;

(E)-N-((2S,3R)-4-((S)-6-ethyl-2,2-spirocyclopentylchroman-4-ylamino)-3-hydroxy-1-phenylbutan-2-yl)-3-(pyridin-2-yl)acrylamide;

N-((1S,2R)-3-(((4S)-6-ethyl-3,4-dihydrospiro[chromene-2,1'-cyclobutan]-4-yl)amino)-2-hydroxy-1-((3-(2-propen-1-yl)phenyl)methyl)propyl)-6-heptenamide;

N-((1S,2R)-1-((1-acetyl-3-piperidinyl)methyl)-3-(((4S)-6-ethyl-3,4-dihydrospiro[chromene-2,1'-cyclobutan]-4-yl)amino)-2-hydroxypropyl)acetamide;

N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(1-oxo-1,3-dihydro-2H-isoindo1-2-yl)acetamide;

3-(1H-benzimidazol-1-yl)-N-((1S,2R)-3-(((4S)-6-ethyl-3,4-dihydrospiro[chromene-2,1'-cyclobutan]-4-yl)amino)-2-hydroxy-1-(phenylmethyl)propyl)-2-methylpropanamide;

(2E)-3-(4-bromo-2-furanyl)-N-((1S,2R)-3-(((4S)-6-ethyl-3,4-dihydrospiro[chromene-2,1'-cyclobutan]-4-yl)amino)-2-hydroxy-1-(phenylmethyl)propyl)-2-propenamide;

N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(1-phthalazinylthio)acetamide;

N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(2-thienylthio)propanamide;

'N-((1S,2R)-1-((3,5-difluorophenyl)methyl)-2-hydroxy-3-(((4S)-6-(1-methyl-1H-1,2,3-triazol-4-yl)-3,4-dihydro spiro[chromene-2,1'-cyclobutan]-4-yl)amino)propyl)acetamide;

'N-((1S,2R)-2-hydroxy-3-(((4S)-6-(1-methyl-1H-1,2,3-triazol-4-yl)-3,4-dihydrospiro[chromene-2,1'-cyclobutan]-4-yl)amino)-1-(phenylmethyl)propyl)acetamide;

'N-((1S,2R)-3-(((4S)-6-(2-fluoro-2-methylpropyl)-3,4-dihydrospiro[chromene-2,1'-cyclobutan]-4-yl)amino)-2-hydroxy-1-(phenylmethyl)propyl)acetamide;

'N-((1S,2R)-3-(((4S)-6-((2R)-2-fluoropropyl)-3,4-dihydrospiro[chromene-2,1'-cyclobutan]-4-yl)amino)-2-hydroxy-1-(phenylmethyl)propyl)acetamide;

'N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxy-1-(phenylmethyl)propyl)acetamide;

'N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxy-1-(phenylmethyl)propyl)acetamide;

'N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-(phenylmethyl)propyl)acetamide;

'N-((1S,2R)-1-((3-cyanophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-1-((3-fluorophenyl)methyl)-2-hydroxypropyl)acetamide;

'N-((1S,2R)-3-(((4S)-6-(2,2-dimethylpropyl)-8-(4-morpholinyl)-3,4-dihydrospiro[chromene-2,1'-cyclobutan]-4-yl)amino)-1-((4-fluorophenyl)methyl)-2-hydroxypropyl)acetamide;

'N-((1S,2R)-3-(((4S)-6-(2,2-dimethylpropyl)-8-(4-morpholinyl)-3,4-dihydrospiro[chromene-2,1'-cyclobutan]-4-yl)amino)-2-hydroxy-1-(phenylmethyl)propyl)acetamide;

'N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3-methylbutyl)acetamide;

'N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3-methyl-3-buten-1-yl)acetamide;

'N-((1S,2R)-1-((3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-2-hydroxy-3-(((5'S)-3'-methyl-5',8'-dihydro-6'H-spiro[cyclobutane-1,7'-quinolin]-5'-yl)amino)-1-(phenylmethyl)propyl)acetamide;

'N-((1S,2R)-1-((3-cyanophenyl)methyl)-2-hydroxy-3-(((5'S)-3'-methyl-5',8'-dihydro-6'H-spiro[cyclobutane-1,7'-quinolin]-5'-yl)amino)propyl)acetamide;

'N-((1S,2R)-1-((3,5-difluorophenyl)methyl)-2-hydroxy-3-(((4S)-6-(1,3-oxazol-2-yl)-3,4-dihydrospiro[chromene-2,1'-cyclobutan]-4-yl)amino)propyl)acetamide;

'N-((1S,2R)-3-(((4'S)-6'-(2,2-dimethylpropyl)-3',4'-dihydrospiro[cyclopentane-1,2'-pyrano[2,3-b]pyridin]-4'-yl)amino)-1-(4-fluorophenyl)methyl)-2-hydroxypropyl)acetamide;

'N-((1S,2R)-1-((3,5-difluorophenyl)methyl)-3-(((4'S)-6'-(2,2-dimethylpropyl)-3',4'-dihydrospiro[cyclopentane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3',4'-dihydrospiro[cyclopentane-1,2'-pyrano[2,3-b]pyridin]-4'-yl)amino)-1-((3-fluorophenyl)methyl)-2-hydroxypropyl)acetamide;

'N-((1S,2R)-3-(((4'S)-6'-(2,2-dimethylpropyl)-3',4'-dihydrospiro[cyclopropane-1,2'-pyrano[2,3-b]pyridin]-4'-yl)amino)-1-((4-fluoro-3-methylphenyl)methyl)-2-hydroxypropyl)acetamide;

'N-((1S,2R)-3-(((4'S)-6'-(2,2-dimethylpropyl)-3',4'-dihydrospiro[cyclopent-3-ene-1,2'-pyrano[2,3-b]pyridin]-4'-yl)amino)-1-((4-fluorophenyl)methyl)-2-hydroxypropyl)acetamide;

'N-((1S,2R)-3-(((4'S)-6'-((1S)-1-fluoro-2-methylpropyl)-3',4'-dihydrospiro[cyclobutane-1,2'-pyrano[2,3-b]pyridin]-4'-yl)amino)-1((4-fluorophenyl)methyl)-2-hydroxypropyl)acetamide;

N-((1S,2R)-3-(((4'S)-6'-((1R)-1-fluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-3-(((4'S)-6'-((1R)-1-fluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-3-(((4'S)-6'-((1S)-1-fluoro-2-methylpropyl)-3',4'-dihydrospiro[cyclobutane-1,2'-pyrano[2,3-1)]pyridin]-4'-yl)amino)-1-((4-fluorophenyl)methyl)-2-hydroxypropyl)acetamide;

'N-((1S,2R)-3-(((4'S)-6'-((1S)-1-fluoro-2-methylpropyl)-3',4'-dihydrospiro[cyclobutane-1,2'-pyrano[2,3-b]pyridin]-4'-yl)amino)-2-hydroxy-1-(phenylmethyl)propyl)acetamide;

'N-((1S,2R)-3-(((4'S)-6'-((1S)-1-fluoro-2-methylpropyl)-3',4'-dihydrospiro[cyclobutane-1,2'-pyrano[2,3-1)]pyridin]-4'-yl)amino)-1-((3-fluorophenyl)methyl)-2-hydroxypropyl)acetamide;

'N-((1S,2R)-3-(((4'S)-6'-(2,2-dimethylpropyl)-3',4'-dihydro-1'H-spiro[cyclobutane-1,2'-quinolin]-4'-yl)amino)-1-((4-fluorophenyl)methyl)-2-hydroxypropyl)acetamide;

'N-((1S,2R)-1-((3,5-difluorophenyl)methyl)-3-(((4'S)-6'-(2,2-dimethylpropyl)-3',4'-dihydro-1'H-spiro[cyclobutane-1,2'-quinolin]-4'-yl)amino)-2-hydroxypropyl)acetamide;

'N-((1S,2R)-3-(((4'S)-6'-(2,2-dimethylpropyl)-3',4'-dihydro-1'H-spiro[cyclobutane-1,2'-quinolin]-4'-yl)amino)-1-((3-fluorophenyl)methyl)-2-hydroxypropyl)acetamide;

'N-((1S,2R)-1-((3-bromo-4-fluorophenyl)methyl)-3-(((4'S)-6'-(2,2-dimethylpropyl)-3',4'-dihydro-1'H-spiro[cyclobutane-1,2'-quinolin]-4'-yl)amino)-2-hydroxypropyl)acetamide;

'N-((1S,2R)-3-(((4'S)-6'-(2,2-dimethylpropyl)-1'-oxo-3',4'-dihydro-1'H-spiro[cyclopentane-1,2'-naphthalen]-4'-yl)amino)-1-((4-fluorophenyl)methyl)-2-hydroxypropyl)acetamide;

'N-((1S,2R)-3-(((4'R)-6'-(2,2-dimethylpropyl)-1'-oxo-3',4'-dihydro-1'H-spiro[cyclopentane-1,2'-naphthalen]-4'-yl)amino)-1-((4-fluorophenyl)methyl)-2-hydroxypropyl)acetamide;

'N-((1S,2R)-3-(((3S,4'S)-6'-chloro-3',4,4',5-tetrahydrospiro[furan-3,2'-pyrano[2,3-b]pyridin]-4'-yl)amino)-2-hydroxy-1-(phenylmethyl)propyl)acetamide;

N-((1S,2R)-3-(((3R,4'S)-6'-chloro-3',4,4',5-tetrahydrospiro[furan-3,2'-pyrano[2,3-b]pyridin]-4'-yl)amino)-2-hydroxy-1-(phenylmethyl)propyl)acetamide;

'N-((1S,2R)-3-(((4'S)-6'-ethyl-3',4'-dihydrospiro[cyclobutane-1,2'-pyrano[2,3-b]pyridin]-4'-yl)amino)-1-((3-fluorophenyl)methyl)-2-hydroxypropyl)acetamide;

'N-((1S,2R)-1-((3-chloro-5-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-c]pyridin]-4'-yl)amino)-1-((4-fluorophenyl)methyl)-2-hydroxypropyl)acetamide;

'N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2S)-3-(((4'S)-6'-(2-fluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluoro-3-methylphenyl)methyl)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluoro-4-methylphenyl)methyl)-2-hydroxypropyl)acetamide;

'methyl ((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)carbamate;

'N-((1S,2R)-3-(((4'S)-6'-(2,2-dimethylpropyl)-3',4'-dihydrospiro[cyclopropane-1,2'-pyrano[2,3-b]pyridin]-4'-yl)amino)-1-((4-fluorophenyl)methyl)-2-hydroxypropyl)acetamide;

'N-((1S,2R)-1-((4-fluoro-3-methylphenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((3-(methyloxy)phenyl)methyl)propyl)acetamide;

'N-((1S,2R)-1-((4-chlorophenyl)methyl)-3-(((4'S)-6'-(2,2-dimethylpropyl)-3',4'-dihydrospiro[cyclopropane-1,2'-pyrano[2,3-b]pyridin]-4'-yl)amino)-2-hydroxypropyl)acetamide;

'N-((1S,2R)-3-(((4'S)-6'-(2,2-dimethyl-3-(methyloxy)propyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-2-hydroxy-1-(phenylmethyl)propyl)acetamide;

'N-((1S,2R)-3-(((4'S)-6'-(2,2-dimethylpropyl)-8'-(methylamino)-3',4'-dihydrospiro[cyclobutane-1,2'-pyrano[2,3-c]pyridin]-4'-yl)amino)-1-((4-fluorophenyl)methyl)-2-hydroxypropyl)acetamide;

N-((1S,2R)-3-(((4'S)-8'-chloro-6'-(2,2-dimethylpropyl)-3',4'-dihydrospiro[cyclobutane-1,2'-pyrano[2,3-c]pyridin]-4'-yl)amino)-1-((4-fluorophenyl)methyl)-2-hydroxypropyl)acetamide;

'N-((1S,2R)-3-(((4'S)-6'-(2,2-dimethylpropyl)-8'-(ethylamino)-3',4'-dihydrospiro[cyclobutane-1,2'-pyrano[2,3-c]pyridin]-4'-yl)amino)-1-((4-fluorophenyl)methyl)-2-hydroxypropyl)acetamide;

'N-((1S,2R)-3-(((4'S)-6'-(2,2-dimethylpropyl)-8'-((1-methylethyl)amino)-3',4'-dihydrospiro[cyclobutane-1,2'-pyrano[2,3-c]pyridin]-4'-yl)amino)-1-((4-fluorophenyl)methyl)-2-hydroxypropyl)acetamide;

'N-((1S,2R)-3-(((4'S)-8'-(cyclopropylamino)-6'-(2,2-dimethylpropyl)-3',4'-dihydrospiro[cyclobutane-1,2'-pyrano[2,3-c]pyridin]-4'-yl)amino)-1-((4-fluorophenyl)methyl)-2-hydroxypropyl)acetamide;

'N-((1S,2R)-3-(((4'S)-6'-(2,2-dimethylpropyl)-8'-(tetrahydro-2H-pyran-4-ylamino)-3',4'-dihydrospiro[cyclobutane-1,2'-pyrano[2,3-c]pyridin]-4'-yl)amino)-1-((4-fluorophenyl)methyl)-2-hydroxypropyl)acetamide;

'N-((1S,2R)-3-(((4'S)-8'-chloro-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide;

'N-((1S,2R)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-1-((4-fluorophenyl)methyl)-2-hydroxypropyl)acetamide;

'N-((1S,2R)-3-(((4'S)-8'-((1,1-dimethylethyl)amino)-6'-(2,2-dimethylpropyl)-3',4'-dihydrospiro[cyclobutane-1,2'-pyrano[2,3-c]pyridin]-4'-yl)amino)-1-((4-fluorophenyl)methyl)-2-hydroxypropyl)acetamide;

'N-((1S,2R)-3-(((4'S)-6'-(2,2-dimethylpropyl)-8'-(methylamino)-3',4'-dihydrospiro[cyclobutane-1,2'-pyrano[2,3-c]pyridin]-4'-yl)amino)-1-((3-fluorophenyl)methyl)-2-hydroxypropyl)acetamide;

'N-((1S,2R)-3-(((4'S)-6'-(2,2-dimethylpropyl)-8'-(ethylamino)-3',4'-dihydrospiro[cyclobutane-1,2'-pyrano[2, 3-c]pyridin]-4'-yl)amino)-1-((3-fluorophenyl)methyl)-2-hydroxypropyl)acetamide;

'N-((1S,2R)-3-(((4'S)-6'-(2,2-dimethylpropyl)-8'-(tetrahydro-2H-pyran-4-ylamino)-3',4'-dihydrospiro[cyclobutane-1,2'-pyrano[2,3-c]pyridin]-4'-yl)amino)-1-((3-fluorophenyl)methyl)-2-hydroxypropyl)acetamide;

'N-((1S,2R)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide;

N-((1S,2R)-3-(((4'S)-6'-(2,2-dimethylpropyl)-8'-oxo-3',4',7',8'-tetrahydrospiro[cyclobutane-1,2'-pyrano[2,3-c]pyridin]-4'-yl)amino)-1-((3-fluorophenyl)methyl)-2-hydroxypropyl)acetamide;

'N-((1S,2R)-3-(((4'R)-6'-(2,2-dimethylpropyl)-8-((1-methylethyl)oxy)-3',4'-dihydrospiro[cyclobutane-1,2'-pyrano[2,3-c]pyridin]-4'-yl)amino)-1-((4-fluorophenyl)methyl)-2-hydroxypropyl)acetamide;

N-((1S,2R)-3-(((4'S)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((4-fluorophenyl)methyl)-2-hydroxypropyl)acetamide;

'N-((1S,2R)-3-(((4'R)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((3-fluorophenyl)methyl)-2-hydroxypropyl)acetamide;

N-((1S,2R)-3-(((4'S)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((3-fluorophenyl)methyl)-2-hydroxypropyl)acetamide;

'N-((1S,2R)-1-((3,5-difluorophenyl)methyl)-3-(((4'R)-6'-(2,2-dimethylpropyl)-8'-((1-methylethyl)oxy)-3',4'-dihydrospiro[cyclobutane-1,2'-pyrano[2,3-c]pyridin]-4'-yl)amino)-2-hydroxypropyl)acetamide;

N-((1S,2R)-1-((3,5-difluorophenyl)methyl)-3-(((4'S)-6'-(2,2-dimethylpropyl)-8'-((1-methylethyl)oxy)-3',4'-dihydrospiro[cyclobutane-1,2'-pyrano[2,3-c]pyridin]-4'-yl)amino)-2-hydroxypropyl)acetamide;

'N-((1S,2R)-1-((3,5-difluorophenyl)methyl)-3-(((4'S)-8'-(dimethylamino)-6'-(2,2-dimethylpropy1)-3',4'-dihydrospiro[cyclobutane-1,2'-pyrano[2,3-c]pyridin]-4'-yl)amino)-2-hydroxypropyl)acetamide;

'N-((1S,2R)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-1-((4-(dimethylamino)phenyl)methyl)-2-hydroxypropyl)ac etamide;

'N-((1S,2R)-1-((4-chlorophenyl)methyl)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-2-hydroxypropyl)acetamide;

'N-((1S,2R)-1-((2,3-difluorophenyl)methyl)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-2-hydroxypropyl)acetamide;

'N-((1S,2R)-3-(((4'S)-8'-(cyclopropylamino)-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide;

'1,1-dimethylethyl(2-(((4'S)-4'-(((2R,3S)-3-(acetylamino)-4-(3-fluorophenyl)-2-hydroxybutyl)amino)-6'-(2,2-dimethylpropyl)-3',4'-dihydrospiro[cyclobutane-1,2'-pyrano[2,3-c]pyridin]-8'-yl)amino)ethyl)carbamate;

'N-((1S,2R)-3-(((4'S)-6'-(2,2-dimethylpropyl)-8'-(3-(methyloxy)-1-azetidinyl)-3',4'-dihydrospiro[cyclobutane-1,2'-pyrano[2,3-c]pyridin]-4'-yl)amino)-1-((3-fluorophenyl)methyl)-2-hydroxypropyl)acetamide;

'N-((1S,2R)-3-(((4'S)-8'-amino-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide;

'N-((1S,2R)-3-(((4'S)-8'-((2-aminoethyl)amino)-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide;

'N-((1S,2R)-3-(((4'S)-6'-(2,2-dimethylpropyl)-8'-(methyloxy)-3',4'-dihydrospiro[cyclobutane-1,2'-pyrano[2,3-c]pyridin]-4'-yl)amino)-1-((3-fluorophenyl)methyl)-2-hydroxypropyl)acetamide;

'N-((1S,2R)-3-(((4'R)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((4-fluorophenyl)methyl)-2-hydroxypropyl)acetamide;

'N-((1S,2R)-3-(((4'S)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((4-fluorophenyl)methyl)-2-hydroxypropyl)acetamide;

'N-((1S,2R)-3-(((4'R)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((3-fluorophenyl)methyl)-2-hydroxypropyl)acetamide;

'N-((1S,2R)-3-(((4'S)-6'-(2,2-dimethylpropyl)-8'-((1-methylethyl)oxy)-3',4'-dihydrospiro[cyclobutane-1,2'-pyrano[2,3-c]pyridin]-4'-yl)amino)-1-((3-fluorophenyl)methyl)-2-hydroxypropyl)acetamide;

'N-((1S,2R)-1-((3,5-difluorophenyl)methyl)-3-(((4'R)-6'-(2,2-dimethylpropyl)-8'-((1-methylethyl)oxy)-3',4'-dihydrospiro[cyclobutane-1,2'-pyrano[2,3-c]pyridin]-4'-yl)amino)-2-hydroxypropyl)acetamide;

'N-((1S,2R)-1-((3,5-difluorophenyl)methyl)-3-(((4'S)-6'-(2,2-dimethylpropyl)-8'-((1-methylethyl)oxy)-3',4'-dihydrospiro[cyclobutane-1,2'-pyrano[2,3-c]pyridin]-4'-yl)amino)-2-hydroxypropyl)acetamide;

'N-((1S,2R)-3-(((4'S)-6'-(2,2-dimethylpropyl)-8'-(methyloxy)-3',4'-dihydrospiro[cyclobutane-1,2'-pyrano[2,3-c]pyridin]-4'-yl)amino)-1-((4-fluorophenyl)methyl)-2-hydroxypropyl)acetamide;

'N-((1S,2R)-3-(((4'S)-6'-(2,2-dimethylpropyl)-8'-(3-(methyloxy)-1-azetidinyl)-3',4'-dihydrospiro[cyclobutane-1,2'-pyrano[2,3-c]pyridin]-4'-yl)amino)-1-((4-fluorophenyl)methyl)-2-hydroxypropyl)acetamide;

'N-((1S,2R)-1-((4-fluorophenyl)methyl)-2-hydroxy-3-(((1s,3R,4'S)-3-methyl-6'-(2-methylpropyl)-3',4'-dihydrospiro[cyclobutane-1,2'-pyrano[2,3-b]pyridin]-4'-yl)amino)propyl)acetamide;

'N-((1S,2R)-1-((4-fluorophenyl)methyl)-2-hydroxy-3-(((1r,3S,4'S)-3-methyl-6'-(2-methylpropyl)-3',4'-dihydrospiro[cyclobutane-1,2'-pyrano[2,3-b]pyridin]-4'-yl)amino)propyl)acetamide;

'N-((1S,2R)-1-((3-fluorophenyl)methyl)-2-hydroxy-3-(((1s,3R,4'S)-3-methyl-6'-(2-methylpropy1)-3',4'-dihydrospiro[cyclobutane-1,2'-pyrano[2,3-b]pyridin]-4'-yl)amino)propyl)acetamide;

'N-((1S,2R)-1-((4-chlorophenyl)methyl)-2-hydroxy-3-(((1s,3R,4'S)-3-methyl-6'-(2-methylpropy1)-3',4'-dihydrospiro[cyclobutane-1,2'-pyrano[2,3-b]pyridin]-4'-yl)amino)propyl)acetamide;

'N-((1S,2R)-3-(((1S,2S,4'S)-6'-(2,2-dimethylpropyl)-2-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-1-((4-chlorophenyl)methyl)-3-(((1S,2S,4'S)-6'-(2,2-dimethylpropyl)-2-methyl-3',4'-dihydrospiro

[cyclobutane-1,2'-pyrano[2,3-b]pyridin]-4'-yl)amino)-2-hydroxypropyl)acetamide;

'N-((1S,2R)-3-(((1R,2R,4'S)-6'-(2,2-dimethylpropyl)-2-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-1-((4-chlorophenyl)methyl)-3-(((1R,2R,4'S)-6'-(2,2-dimethylpropyl)-2-methyl-3',4'-dihydrospiro[cyclobutane-1,2'-pyrano[2,3-b]pyridin]-4'-yl)amino)-2-hydroxypropyl)acetamide;

'N-((1S,2R)-3-(((1S,2R,4'S)-6'-(2,2-dimethylpropyl)-2-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-1-((4-chlorophenyl)methyl)-3-(((1S,2R,4'S)-6'-(2,2-dimethylpropyl)-2-methyl-3',4'-dihydrospiro[cyclobutane-1,2'-pyrano[2,3-b]pyridin]-4'-yl)amino)-2-hydroxypropyl)acetamide;

'N-((1S,2R)-3-(((1R,2S,4'S)-6'-(2,2-dimethylpropyl)-2-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-1-((4-chlorophenyl)methyl)-3-(((1R,2S,4'S)-6'-(2,2-dimethylpropyl)-2-methyl-3',4'-dihydrospiro[cyclobutane-1,2'-pyrano[2,3-b]pyridin]-4'-yl)amino)-2-hydroxypropyl)acetamide;

'methyl((1S,2R)-1-((4-chlorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)carbamate;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-fluoroacetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2,2-difluoroacetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2,2,2-trifluoro acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-3,3,3-trifluoropropanamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-3-(methyloxy)propanamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(1,3-thiazol-4-ylmethyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(4-pyridinylmethyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-propyl-1,3-thiazol-4-yl)methyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((5-propyl-1,3-thiazol-4-yl)methyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(1,3-thiazol-5-ylmethyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-methyl-1,3-thiazol-4-yl)methyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-methyl-4-pyridinyl)methyl)propyl)acetamide;

'N-((1S,2R)-1-((4-chloro-1,3-thiazol-2-yl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((2-chloro-4-pyridinyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-(methyloxy)-4-pyridinyl)methyl)propyl)acetamide;

'N-((1S,2R)-1-((2-chloro-6-methyl-4-pyridinyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-((2,2,2-trifluoroethyl)oxy)-4-pyridinyl)methyl)propyl)acetamide;

'N-((1R,2S)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(4-pyridinylmethyl)propyl)acetamide;

'N-((1S,2R)-1-(1-benzofuran-2-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-oxo-1,2-dihydro-4-pyridinyl)methyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-(trifluoromethyl)-4-pyrimidinyl)methyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((4-(trifluoromethyl)phenyl)methyl)propyl)acetamide;

'N-((1S,2R)-1-((4-chlorophenyl)methyl)-3-(((4'S)-6'-(2-cyano-2-methylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((1-methyl-2-oxo-1,2-dihydro-4-pyridinyl)methyl)propyl)acetamide;

'N-((1S,2R)-1-((4-chlorophenyl)methyl)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1((4-chlorophenyl)methyl)-3-(((4'S)-6'-(2,2-dimethyl-3-butyn-1-yl)-3',4'-dihydrospiro[cyclobutane-1,2'-pyrano[2,3-b]pyridin]-4'-yl)amino)-2-hydroxypropyl)acetamide;

'N-((1S,2R)-1-((4-chlorophenyl)methyl)-3-(((4'S)-6'-(2,2-dimethylbutyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2-cyano-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-3-(((4'S)-6'-(2-cyano-2-methylpropyl)-3',4'-dihydrospiro[cyclobutane-1,2'-pyrano[2,3-b]pyridin]-4'-yl)amino)-1-((3-fluorophenyl)methyl)-2-hydroxypropyl)acetamide;

'N-((1S,2R)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-2-hydroxy-1-(phenylmethyl)propyl)acetamide;

'N-((1S,2R)-3-(((4S)-2-ethyl-4,7-dihydro-5H-spiro[1-benzothiophene-6,1'-cyclobutan]-4-yl)amino)-2-hydroxy-1-(phenylmethyl)propyl)acetamide;

'N-((1S,2R)-3-(((4'S)-6'-(2,2-dimethylpropyl)-7'-fluoro-3',4'-dihydrospiro[cyclobutane-1,2'-pyrano[2,3-b]pyridin]-4'-yl)amino)-2-hydroxy-1-(phenylmethyl)propyl)acetamide;

'N-((1S,2R)-1-((3,5-difluorophenyl)methyl)-3-(((3S,4'R)-6'-(2,2-dimethylpropyl)-3',4,4',5-tetrahydrospiro[furan-3,2'-pyrano[2,3-b]pyridin]-4'-yl)amino)-2-hydroxypropyl)acetamide;

N-((1S,2R)-1-((3,5-difluorophenyl)methyl)-3-(((3R,4'R)-6'-(2,2-dimethylpropyl)-3',4,4',5-tetrahydrospiro[furan-3,2'-pyrano[2,3-b]pyridin]-4'-yl)amino)-2-hydroxypropyl)acetamide;

'N-((1S,2R)-1-((3,5-difluorophenyl)methyl)-3-(((3S,4'S)-6'-(2,2-dimethylpropyl)-3',4,4',5-tetrahydrospiro[furan-3,2'-pyrano[2,3-b]pyridin]-4'-yl)amino)-2-hydroxypropyl)acetamide;

N-((1S,2R)-1-((3,5-difluorophenyl)methyl)-3-(((3R,4'S)-6'-(2,2-dimethylpropyl)-3',4,4',5-tetrahydrospiro[furan-3,2'-pyrano[2,3-b]pyridin]-4'-yl)amino)-2-hydroxypropyl)acetamide;

N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-1-((4-fluorophenyl)methyl)-2-hydroxypropyl)acetamide;

N-((1S,2R)-3-(((3R,4'S)-6'-(2,2-dimethylpropyl)-3',4,4,5-tetrahydrospiro[furan-3,2'-pyrano[2,3-b]pyridin]-4'-yl)amino)-1-((4-fluorophenyl)methyl)-2-hydroxypropyl)acetamide;

'N-((1S,2R)-1-((3,5-difluorophenyl)methyl)-3-(((4'S)-6'-(2,2-dimethylpropyl)-7'-fluoro-3',4'-dihydrospiro[cyclobutane-1,2'-pyrano[2,3-b]pyridin]-4'-yl)amino)-2-hydroxypropyl)acetamide;

'N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-1-((3-fluorophenyl)methyl)-2-hydroxypropyl)acetamide;

N-((1S,2R)-3-(((3R,4'S)-6'-(2,2-dimethylpropyl)-3',4,4',5-tetrahydrospiro[furan-3,2'-pyrano[2,3-b]pyridin]-4'-yl)amino)-1-((3-fluorophenyl)methyl)-2-hydroxypropyl)acetamide;

'N-((1S,2R)-3-(((4'S)-6'-(2,2-dimethylpropyl)-7'-fluoro-3',4'-dihydrospiro[cyclobutane-1,2'-pyrano[2,3-b]pyridin]-4'-yl)amino)-1-((3-fluorophenyl)methyl)-2-hydroxypropyl)acetamide;

'N-((1S,2R)-3-(((4'S)-6'-(2,2-dimethylpropyl)-7'-fluoro-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-1-((4-chlorophenyl)methyl)-3-(((3S,4'S)-6'-(2,2-dimethylpropyl)-3',4,4',5-tetrahydrospiro[furan-3,2'-pyrano[2,3-b]pyridin]-4'-yl)amino)-2-hydroxypropyl)acetamide;

N-((1S,2R)-1-((4-chlorophenyl)methyl)-3-(((3R,4'S)-6'-(2,2-dimethylpropyl)-3',4,4',5-tetrahydrospiro[furan-3,2'-pyrano[2,3-b]pyridin]-4'-yl)amino)-2-hydroxypropyl)acetamide;

'N-((1S,2R)-1-((4-chlorophenyl)methyl)-3-(((3S,4'R)-6'-(2,2-dimethylpropyl)-3',4,4',5-tetrahydrospiro[furan-3,2'-pyrano[2,3-b]pyridin]-4'-yl)amino)-2-hydroxypropyl)acetamide;

N-((1S,2R)-1-((4-chlorophenyl)methyl)-3-(((3R,4'R)-6'-(2,2-dimethylpropyl)-3',4,4',5-tetrahydrospiro[furan-3,2'-pyrano[2,3-b]pyridin]-4'-yl)amino)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluoro-4-(methyloxy)phenyl)methyl)-2-hydroxypropyl)acetamide;

'N-((1S,2S)-3-(((4'S)-6'-(2,2-dimethylpropyl)-3',4'-dihydrospiro[cyclobutane-1,2'-pyrano[2,3-b]pyridin]-4'-yl)amino)-1-((3-fluoro-4-(methyloxy)phenyl)methyl)-2-hydroxypropyl)acetamide;

'N-((1S,2R)-1-((4-chlorophenyl)methyl)-3-(((4'S)-6'-(2,2-dimethylpropyl)-7'-fluoro-3',4'-dihydrospiro[cyclobutane-1,2'-pyrano[2,3-b]pyridin]-4'-yl)amino)-2-hydroxypropyl)acetamide;

'N-((1R,2S)-3-(((4'S)-6'-(2,2-dimethylpropyl)-3',4'-dihydrospiro[cyclobutane-1,2'-pyrano[2,3-b]pyridin]-4'-yl)amino)-1-((3-fluoro-4-(trifluoromethyl)phenyl)methyl)-2-hydroxypropyl)acetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluoro-4-(trifluoromethyl)phenyl)methyl)-2-hydroxypropyl)acetamide;

'N-((1S,2R)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

N-((1S,2R)-3-(((4'S)-6'-((1S)-1-fluoro-2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-1-((4-chlorophenyl)methyl)-3-(((3S,4'S)-6'-(2,2-dimethylpropyl)-3',4,4',5-tetrahydrospiro[furan-3,2'-pyrano[2,3-b]pyridin]-4'-yl)amino)-2-hydroxypropyl)acetamide;

'N-((1S,2R)-1-((4-chlorophenyl)methyl)-3-(((3R,4'S)-6'-(2,2-dimethylpropyl)-3',4,4',5-tetrahydrospiro[furan-3,2'-pyrano[2,3-b]pyridin]-4'-yl)amino)-2-hydroxypropyl)acetamide;

'N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-1-((4-fluorophenyl)methyl)-2-hydroxypropyl)acetamide;

'N-((1S,2R)-3-(((3R,4'S)-6'-(2,2-dimethylpropyl)-3',4,4',5-tetrahydrospiro[furan-3,2'-pyrano[2,3-b]pyridin]-4'-yl)amino)-1-((4-fluorophenyl)methyl)-2-hydroxypropyl)acetamide;

'N-((1S,2R)-1-((4-chlorophenyl)methyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)acetamide;

N-((1S,2R)-1-((4-chlorophenyl)methyl)-3-(((4'S)-6'-((1S)-1-fluoro-2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-((1S)-1-fluoro-2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-1((4-fluorophenyl)methyl)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1((4-fluoro-3-(trifluoromethyl)phenyl)methyl)-2-hydroxypropyl)acetamide;

'N-((1S,2R)-1-((2,3-difluorophenyl)methyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-1'-(3-fluorophenyl)methyl)-2-hydroxypropyl)acetamide;

'N-((1S,2R)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxy-1-(phenylmethyl)propyl)acetamide;

'N-((1S,2R)-1-((4-chlorophenyl)methyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((3,5-difluorophenyl)methyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(cyclobutylmethyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-3-(((5R,5aS)-3-(2,2-dimethylpropyl)-5a,6,7,8-tetrahydro-5H-pyrrolo[1',2':1,5]pyrrolo[2,3-b]pyridin-5-yl)amino)-1-((4-fluorophenyl)methyl)-2-hydroxypropyl)acetamide;

'N-((1S,2R)-1-((4-fluorophenyl)methyl)-2-hydroxy-3-(((4'S)-6'-(1-hydroxypentyl)-3',4'-dihydrospiro[cyclobutane-1,2'-pyrano[2,3-b]pyridin]-4'-yl)amino)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2,4,5-trifluorophenyl)methyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((3,4,5-trifluorophenyl)methyl)propyl)acetamide;

'N-((1S,2R)-3-(((4'S)-6'-(cyclopropylmethyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-1-((4-fluorophenyl)methyl)-2-hydroxy-3-(((4'S)-6'-((1-methylcyclopropyl)methyl) -3',4'-dihydrospiro[cyclobutane-1,2'-pyrano[2,3-b]pyridin]-4'-yl)amino)propyl)acetamide;

'N-((1S,2R)-3-(((4'S)-6'-(3,3-difluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-3-(((4'S)-6'-(cyclopropylmethyl)-3',4'-dihydrospiro[cyclobutane-1,2'-pyrano[2,3-b]pyridin]-4'-yl)amino)-1-((3,5-difluorophenyl)methyl)-2-hydroxypropyl)acetamide;

'N-((1S,2R)-3-(((4'S)-6'-((2S)-3-fluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

N-((1S,2R)-3-(((4'S)-6'-((2R)-3-fluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-1-((3,5-difluorophenyl)methyl)-3-(((4'S)-6'-(2-ethylbutyl)-3',4'-dihydrospiro[cyclobutane-1,2'-pyrano[2,3-b]pyridin]-4'-yl)amino)-2-hydroxypropyl)acetamide;

'N-((1S,2R)-1((4-fluorophenyl)methyl)-2-hydroxy-3-(((4'S)-6'-propyl-3',4'-dihydrospiro[cyclobutane-1,2'-pyrano[2,3-b]pyridin]-4'-yl)amino)propyl)acetamide;

'N-((1S,2R)-1-((4-fluorophenyl)methyl)-2-hydroxy-3-(((4'S)-6'-((2S)-2-methylbutyl)-3',4'-dihydrospiro[cyclobutane-1,2'-pyrano[2,3-b]pyridin]-4'-yl)amino)propyl)acetamide;

'N-((1S,2R)-3-(((4'S)-6'-butyl-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-1-((4-fluorophenyl)methyl)-2-hydroxy-3-(((4'S)-6'-(2-methyl-1-propen-1-yl)-3',4'-dihydrospiro[cyclobutane-1,2'-pyrano[2,3-b]pyridin]-4'-yl)amino)propyl)acetamide;

'N-((1S,2R)-3-(((4'S)-6'-(2,2-dimethylpropanoyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'2-azido-N-((1S,2R)-3-(((4S)-6-bromo-3,4-dihydrospiro[chromene-2,1'-cyclobutan]-4-yl)amino) -2-hydroxy-1-(phenylmethyl)propyl)acetamide;

'N-((1S,2R)-1((3-cyanophenyl)methyl)-2-hydroxy-3-(((4'S)-6'-(trifluoromethyl)-3',4'-dihydrospiro[cyclobutane-1,2'-pyrano[2,3-b]pyridin]-4'-yl)amino)propyl)acetamide;

'N-((1S,2R)-1-((3,5-difluorophenyl)methyl)-2-hydroxy-3-(((4'S)-6'-(trifluoromethyl)-3',4'-dihydrospiro[cyclobutane-1,2'-pyrano[2,3-b]pyridin]-4'-yl)amino)propyl)acetamide;

'N-((1S,2R)-1-((3,4-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((3-chlorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((2-fluorophenyl)methyl)-2-hydroxypropyl)acetamide;

'N-((1S,2R)-1-((2,4-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3-pentyn-1-yl)acetamide;

'N-((1S,2R)-1-((3-chloro-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((4-chlorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((2-chlorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((3-(dimethylamino)-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-(ethylamino)-4-fluorophenyl)methyl)-2-hydroxypropyl)acetamide;

'N-((1S,2R)-1-((3,4-dichlorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((4-((trifluoromethyl)oxy)phenyl)methyl)propyl)acetamide;

N-((1S,2R)-1-((3-chloro-4-fluorophenyl)methyl)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)acetamide;

N-((1S,2R)-1-((4-chlorophenyl)methyl)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)acetamide;

'N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-4-penten-1-yl)acetamide;

'N-((1S,2R)-1-((4-chloro-3-(trifluoromethyl)phenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S)-1-((1R)-2-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-1-hydroxyethyl)-4-penten-1-yl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((3-(trifluoromethyl)phenyl)methyl)propyl)acetamide;

'N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-((3-(trifluoromethyl)phenyl)methyl)propyl)acetamide;

'N-((1S,2R)-1-((4-chloro-3-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((4-chloro-3-(methyloxy)phenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-(cyclopropylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-methylcyclopropyl)methyl)propyl)acetamide;

'N-((1S,2R)-1-(cyclopropylmethyl)-3-(((4'S)-6'-(4,4-difluoro-2,2-dimethylbutyl)-3',4'-dihydrospiro[cyclobutane-1,2'-pyrano[2,3-b]pyridin]-4'-yl)amino)-2-hydroxypropyl)acetamide;

'N-((1S,2R)-1-(cyclopropylmethyl)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)acetamide;

'N-((1S,2R)-1-((2-((difluoromethyl)oxy)-4-pyridinyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N~1~-((1S,2R)-3-(((4S)-6-bromo-3,4-dihydrospiro[chromene-2,1'-cyclobutan]-4-yl)amino)-1-((3-cyanophenyl)methyl)-2-hydroxypropyl)-N~2~,N~2~-dimethylglycinamide;

'methyl(4S)-4-(((2R,3S)-4-(3-cyanophenyl)-3-((N,N-dimethylglycyl)amino)-2-hydroxybutyl)amino)-3,4-dihydrospiro[chromene-2,1'-cyclobutane]-6-carb oxylate;

'methyl(4S)-4-(((2R,3S)-3-(acetylamino)-4-(3-cyanophenyl)-2-hydroxybutyl)amino)-3,4-dihydrospiro[chromene-2,1'-cyclobutane]-6-carb oxylate;

'methyl(4S)-4-(((2R,3S)-4-(3-cyanophenyl)-2-hydroxy-3-(((methyloxy)acetyl)amino)butyl)amino)-3,4-dihydrospiro[chromene-2,1'-cyclobutane]-6-carboxylate;

'N-((1S,2R)-3-(((4S)-6-ethyl-3,4-dihydrospiro[chromene-2,1'-cyclobutan]-4-yl)amino)-2-hydroxy-1-((methyloxy)methyl)propyl)acetamide;

'N-((1S,2R)-3-(((4S)-6-ethyl-3,4-dihydrospiro[chromene-2,1'-cyclobutan]-4-yl)amino)-2-hydroxy-1-((propyloxy)methyl)propyl)acetamide;

'N-((1S,2R)-3-(((4S)-6-ethyl-3,4-dihydrospiro[chromene-2,1'-cyclobutan]-4-yl)amino)-2-hydroxy-1-(((phenylmethyl)oxy)methyl)propyl)acetamide;

'N-((1S,2R)-3-(((4S)-6-ethyl-3,4-dihydrospiro[chromene-2,1'-cyclobutan]-4-yl)amino)-2-hydroxy-1-(1H-pyrazol-1-ylmethyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(1H-pyrazol-1-ylmethyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-propen-1-yloxy)methyl)propyl)acetamide;

'N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3-buten-1-yl)acetamide;

'N-((1S)-1-((1S)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3-buten-1-yl)acetamide;

'N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-4,4,4-trifluorobutyl)acetamide;

'N-((1S,3E)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3-penten-1-yl)acetamide;

'N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-2-propen-1-yl)acetamide;

'N-((1S)-1-((1R)-2-(((4'S)-6'-(2-fluoro-2-methylpropyl)-3',4'-dihydrospiro[cyclobutane-1,2'-pyrano[2,3-b]pyridin]-4'-yl)amino)-1-hydroxyethyl)-3-buten-1-yl)acetamide;

'N-((1S)-1-((1R)-2-(((4'S)-6'-(2,2-dimethylpropyl)-3',4'-dihydrospiro[cyclobutane-1,2'-pyrano[2,3-b]pyridin]-4'-yl)amino)-1-hydroxyethyl)-3-hexyn-1-yl)acetamide;

'N-((1S,2R)-3-(((2S,4S)-6-chloro-8-(4-morpholinyl)-3,4,4',5'-tetrahydrospiro[chromene-2,3'-furan]-4-yl)amino)-1-((3,5-difluorophenyl)methyl)-2-hydroxypropyl)acetamide;

N-((1S,2R)-3-(((2R,4S)-6-chloro-8-(4-morpholinyl)-3,4,4',5'-tetrahydrospiro[chromene-2,3'-furan]-4-yl)amino)-1-((3,5-difluorophenyl)methyl)-2-hydroxypropyl)acetamide;

N-((1S,2R)-3-(((4S)-6-(2,2-dimethylpropyl)-3,4-dihydrospiro[chromene-2,1'-cyclobutan]-4-yl)amino)-2-hydroxy-1-(phenylmethyl)propyl)-2-(1H-2-methyl-imidazol-1-yl)acetamide;

'N-((1S,2R)-3-(((4'S)-6'-bromo-3',4'-dihydrospiro[cyclobutane-1,2'-pyrano[2,3-b]pyridin]-4'-yl)amino)-1-((3,5-difluorophenyl)methyl)-2-hydroxypropyl)acetamide;

'N-((1S,2R)-1-((3,5-difluorophenyl)methyl)-2-hydroxy-3-(((4'S)-6'-(1H-pyrazol-1-yl)-3',4'-dihydrospiro[cyclobutane-1,2'-pyrano[2,3-b]pyridin]-4'-yl)amino)propyl)acetamide;

'N-((1S,2R)-1-((3,5-difluorophenyl)methyl)-2-hydroxy-3-(((4'S)-6'-(1H-imidazol-1-yl)-3',4'-dihydrospiro[cyclobutane-1,2'-pyrano[2,3-b]pyridin]-4'-yl)amino)propyl)acetamide;

'N-((1S,2R)-1-((3,5-difluorophenyl)methyl)-2-hydroxy-3-(((4'S)-6'-(1,3-thiazol-2-yl)-3',4'-dihydrospiro[cyclobutane-1,2'-pyrano[2,3-b]pyridin]-4'-yl)amino)propyl)acetamide;

'N-((1S,2R)-3-(((4'S)-6'-(2,2-dimethylpropyl)-3',4'-dihydrospiro[cyclobutane-1,2'-pyrano[2,3-c]pyridin]-4'-yl)amino)-2-hydroxy-1-(phenylmethyl)propyl)acetamide;

'N-((1S,2R)-1-((3-chloro-5-fluorophenyl)methyl)-3-(((4'S)-6'-(2,2-dimethylpropyl)-3',4'-dihydrospiro[cyclobutane-1,2'-pyrano[2,3-c]pyridin]-4'-yl)amino)-2-hydroxypropyl)acetamide;

'N-((1S,2R)-1-((3-chloro-5-fluorophenyl)methyl)-2-hydroxy-3-(((4'S)-6'-(2-hydroxy-2-methylpropyl)-3',4'-dihydrospiro[cyclobutane-1,2'-pyrano[2,3-c]pyridin]-4'-yl)amino)propyl)acetamide;

'N-((1S,2R)-3-(((4'S)-8'-chloro-6'-(2,2-dimethylpropyl)-3',4'-dihydrospiro[cyclobutane-1,2'-pyrano[2,3-c]pyridin]-4'-yl)amino)-1-((3-chloro-5-fluorophenyl)methyl)-2-hydroxypropyl)acetamide;

'N-((1S,2R)-3-(((4'S)-8'-chloro-6'-(2,2-dimethylpropyl)-3',4'-dihydrospiro[cyclobutane-1,2'-pyrano[2,3-c]pyridin]-4'-yl)amino)-2-hydroxy-1-(phenylmethyl)propyl)acetamide;

'N-((1S,2R)-1-((3,5-difluorophenyl)methyl)-3-(((5'S)-3'-(2,2-dimethylpropyl)-5',6'-dihydrospiro[cyclobutane-1,7'-pyrano[2,3-c]pyridazin]-5'-yl)amino)-2-hydroxypropyl)acetamide;

'N-((1S,2R)-3-(((4'S)-6'-(2,2-dimethylpropyl)-8'-(4-morpholinyl)-3',4'-dihydrospiro[cyclobutane-1,2'-pyrano[2,3-c]pyridin]-4'-yl)amino)-2-hydroxy-1-(phenylmethyl)propyl)acetamide;

'N-((1S,2R)-3-(((4'S)-6'-(2,2-dimethylpropyl)-8'-(1-pyrrolidinyl)-3',4'-dihydrospiro[cyclobutane-1,2'-pyrano[2,3-c]pyridin]-4'-yl)amino)-2-hydroxy-1-(phenylmethyl)propyl)acetamide;

'N-((1S,2R)-1-((3-(dimethylamino)-5-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((3-bromo-5-fluorophenyl)methyl)-3-(((4'S)-6'-(2,2-dimethylpropyl)-3',4'-dihydro spiro[cyclobutane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3-methyl-3',4'-dihydrospiro[cyclobutane-1,2'-pyrano[2,3-b]pyridin]-4'-yl)amino)-1((4-fluorophenyl)methyl)-2-hydroxypropyl)acetamide;

N-((1S,2R)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-1-((3,5-difluorophenyl)methyl)-3-(((4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)acetamide;

'N-((1S,2R)-1-((3,5-difluorophenyl)methyl)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-1-((2,3-difluorophenyl)methyl)-3-(((1r,3S,4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)acetamide;

'N-((1S,2R)-1-((2,3-difluorophenyl)methyl)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)acetamide;

'N-((1S,2R)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-1-((3-fluorophenyl)methyl)-2-hydroxypropyl)acetamide;

'N-((1S,2R)-3-(((1s,3S,4'S)-6'-(2,2-dimethylpropyl)-3-hydroxy-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-3-(((4S)-6-(cyclopentylamino)-3,4-dihydrospiro[chromene-2,1'-cyclobutan]-4-yl)amino)-2-hydroxy-1-(phenylmethyl)propyl)acetamide;

'N-((1S,2R)-3-(((4S)-6-((1,1-dimethylethyl)amino)-3,4-dihydrospiro[chromene-2,1'-cyclobutan]-4-yl)amino)-2-hydroxy-1-(phenylmethyl)propyl)acetamide;

'N-((1S,2R)-3-(((4S)-6-chloro-8-(1H-imidazol-1-yl)-3,4-dihydrospiro[chromene-2,1'-cyclobutan]-4-yl)amino)-1-((3,5-difluorophenyl)methyl)-2-hydroxypropyl)acetamide;

'N-((1S,2R)-3-(((4S)-6-bromo-3,4-dihydrospiro[chromene-2,1'-cyclobutan]-4-yl)amino)-1-((3,5-difluorophenyl)methyl)-2-hydroxypropyl)acetamide;

'N-((1S,2R)-3-(((4S)-8-(1H-benzimidazol-1-yl)-6-chloro-3,4-dihydrospiro[chromene-2,1'-cyclobutan]-4-yl)amino)-1-((3,5-difluorophenyl)methyl)-2-hydroxypropyl)acetamide;

'N-((1S,2R)-3-(((4S)-6-chloro-8-(1H-pyrazol-1-yl)-3,4-dihydrospiro[chromene-2,1'-cyclobutan]-4-yl)amino)-1-((3,5-difluorophenyl)methyl)-2-hydroxypropyl)acetamide;

'N-((1S,2R)-1-((3,5-difluorophenyl)methyl)-2-hydroxy-3-(((4S)-6-(1H-pyrazol-1-yl)-3,4-dihydrospiro[chromene-2,1'-cyclobutan]-4-yl)amino)propyl)acetamide;

'N-((1S,2R)-2-hydroxy-1-(phenylmethyl)-3-(((4S)-6-(2-thienyl)-3,4-dihydrospiro[chromene-2,1'-cyclobutan]-4-yl)amino)propyl)acetamide;

'N-((1S,2R)-2-hydroxy-3-(((4S)-6-(1-(2-methylpropyl)-1H-pyrazol-3-yl)-3,4-dihydrospiro[chromene-2,1'-cyclobutan]-4-yl)amino)-1-(phenylmethyl)propyl)acetamide;

'N-((1S,2R)-1-((3,5-difluorophenyl)methyl)-2-hydroxy-3-(((4S)-6-(1-(2-methylpropyl)-1H-pyrazol-3-yl)-3,4-dihydrospiro[chromene-2,1'-cyclobutan]-4-yl)amino)propyl)acetamide;

'N-((1S,2S)-1-((3,5-difluorophenyl)methyl)-2-hydroxy-3-(((4S)-6-(1H-pyrazol-1-yl)-3,4-dihydrospiro[chromene-2,1'-cyclobutan]-4-yl)amino)propyl)acetamide;

'N-((1S,2R)-1-((3,5-difluorophenyl)methyl)-2-hydroxy-3-(((4S)-6-(1H-imidazol-1-yl)-3,4-dihydrospiro[chromene-2,1'-cyclobutan]-4-yl)amino)propyl)acetamide;

'N-((1S,2R)-2-hydroxy-3-(((4S)-6-(1-methyl-1H-pyrazol-3-yl)-3,4-dihydrospiro[chromene-2,1'-cyclobutan]-4-yl)amino)-1-(phenylmethyl)propyl)acetamide;

'N-((1S,2R)-1-((3,5-difluorophenyl)methyl)-2-hydroxy-3-(((4S)-6-(1-methyl-1H-pyrazol-3-yl)-3,4-dihydrospiro[chromene-2,1'-cyclobutan]-4-yl)amino)propyl)acetamide;

'N-((1S,2R)-1-((3,5-difluorophenyl)methyl)-2-hydroxy-3-(((4S)-6-(2-thienyl)-3,4-dihydrospiro[chromene-2,1'-cyclobutan]-4-yl)amino)propyl)acetamide;

'N-((1S,2S)-3-(((4S)-6-chloro-8-(1H-pyrazol-1-yl)-3,4-dihydrospiro[chromene-2,1'-cyclobutan]-4-yl)amino)-1-((3,5-difluorophenyl)methyl)-2-hydroxypropyl)acetamide;

'N-((1S,2R)-3-(((4S)-7-bromo-3,4-dihydrospiro[chromene-2,1'-cyclobutan]-4-yl)amino)-1-((3,5-difluorophenyl)methyl)-2-hydroxypropyl)acetamide;

'N-((1S,2R)-1-((3,5-difluorophenyl)methyl)-2-hydroxy-3-(((4S)-7-(1H-imidazol-1-yl)-3,4-dihydrospiro[chromene-2,1'-cyclobutan]-4-yl)amino)propyl)acetamide;

'N-((4S)-4-(((2R,3S)-3-(acetylamino)-4-(3,5-difluorophenyl)-2-hydroxybutyl)amino)-3,4-dihydrospiro[chromene-2,1'-cyclobutan]-6-yl)acetamide;

'N-((1S,2R)-1-((3,5-difluorophenyl)methyl)-2-hydroxy-3-(((4S)-6-((3R)-tetrahydro-3-furanylamino)-3,4-dihydrospiro[chromene-2,1'-cyclobutan]-4-yl)amino)propyl)acetamide;

'N-((1S,2R)-1-((3,5-difluorophenyl)methyl)-2-hydroxy-3-(((4S)-6-(2H-1,2,3-triazol-2-yl)-3,4-dihydrospiro[chromene-2,1'-cyclobutan]-4-yl)amino)propyl)acetamide;

'N-((1S,2R)-1-((3,5-difluorophenyl)methyl)-2-hydroxy-3-(((4S)-6-(1H-1,2,4-triazol-1-yl)-3,4-dihydrospiro[chromene-2,1'-cyclobutan]-4-yl)amino)propyl)acetamide;

'N-((1S,2R)-1-((3,5-difluorophenyl)methyl)-2-hydroxy-3-(((4S)-6-(2-oxo-1-pyrrolidinyl)-3,4-dihydrospiro[chromene-2,1'-cyclobutan]-4-yl)amino)propyl)acetamide;

'N-((1S,2R)-1-((3,5-difluorophenyl)methyl)-2-hydroxy-3-(((4S)-6-(2-oxo-1-azetidinyl)-3,4-dihydrospiro[chromene-2,1'-cyclobutan]-4-yl)amino)propyl)acetamide;

'N-((1S,2R)-3-(((4S)-6-bromo-7-fluoro-3,4-dihydrospiro[chromene-2,1'-cyclobutan]-4-yl)amino)-1-((3,5-difluorophenyl)methyl)-2-hydroxypropyl)acetamide;

'N-((1S,2R)-1-((3,5-difluorophenyl)methyl)-3-(((4S)-7-fluoro-6-((3R)-tetrahydro-3-furanylamino)-3,4-dihydrospiro[chromene-2,1'-cyclobutan]-4-yl)amino)-2-hydroxypropyl)acetamide;

'N-((1S,2R)-1-((3,5-difluorophenyl)methyl)-3-(((4S)-7-fluoro-3,4-dihydrospiro[chromene-2,1'-cyclobutan]-4-yl)amino)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluoro-5-(tetrahydro-2H-pyran-4-ylamino)phenyl)methyl)-2-hydroxypropyl)acetamide;

'N-((1S,2R)-1-((3,5-difluorophenyl)methyl)-3-(((4S)-7-fluoro-6-(tetrahydro-2H-pyran-4-ylamino)-3,4-dihydrospiro[chromene-2,1'-cyclobutan]-4-yl)amino)-2-hydroxypropyl)acetamide;

'N-((1S,2R)-1-((3-fluorophenyl)methyl)-3-(((4S)-7-fluoro-6-(1H-pyrazol-1-yl)-3,4-dihydrospiro[chromene-2,1'-cyclobutan]-4-yl)amino)-2-hydroxypropyl)acetamide;

'N-((1S,2R)-1-((4-fluorophenyl)methyl)-3-(((4S)-7-fluoro-6-(1H-pyrazol-1-yl)-3,4-dihydrospiro[chromene-2,1'-cyclobutan]-4-yl)amino)-2-hydroxypropyl)acetamide;

'N-((1S,2R)-1-(cyclobutylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1((2-bromophenyl)methyl)-3(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((3-chloro-5-fluorophenyl)methyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(1-azatricyclo[6.2.2.0~2,7~]dodeca-2,4,6-trien-8-ylamino)-2-hydroxy-1-(phenylmethyl)propyl)acetamide;

'N-((1S,2R)-3-(((2R,4S)-1'-acetyl -6-ethyl-3,4-dihydrospiro[chromene-2,3'-pyrrolidin]-4-yl)amino)-2-hydroxy-1-(phenylmethyl)propyl)acetamide;

N-((1S,2R)-3-(((2S,4S)-1'-acetyl-6-ethyl-3,4-dihydrospiro[chromene-2,3'-pyrrolidin]-4-yl)amino)-2-hydroxy-1-(phenylmethyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2,4,6-trifluorophenyl)methyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2,3,4-trifluorophenyl)methyl)propyl)acetamide;

'N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-((2,4,6-trifluorophenyl)methyl)propyl)acetamide;

'N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-((2,3,4-trifluorophenyl)methyl)propyl)acetamide;

'N-((1S,2R)-1((4-chlorophenyl)methyl)-3-(((4'S)-6'-(2,2-dimethylpropyl)-3',4'-dihydrospiro[cyclopentane-1,2'-pyrano[2,3-b]pyridin]-4'-yl)amino)-2-hydroxypropyl)acetamide;

'N-((1S,2R)-1-((4-fluorophenyl)methyl)-2-hydroxy-3-(((4'S)-6'-(phenylmethyl)-3',4'-dihydrospiro[cyclobutane-1,2'-pyrano[2,3-b]pyridin]-4'-yl)amino)propyl)acetamide;

'N-((1S,2R)-2-hydroxy-1-(phenylmethyl)-3-(((4S)-6-((2R)-tetrahydro-2-furanyl)-3,4-dihydrospiro[chromene-2,1'-cyclobutan]-4-yl)amino)propyl)acetamide;

N-((1S,2R)-2-hydroxy-1-(phenylmethyl)-3-(((4S)-6-((2S)-tetrahydro-2-furanyl)-3,4-dihydrospiro[chromene-2,1'-cyclobutan]-4-yl)amino)propyl)acetamide;

'N-((1S,2R)-2-hydroxy-1-(phenylmethyl)-3-(((4'S)-6'-((2S)-tetrahydro-2-furanylmethyl)-3',4'-dihydrospiro[cyclobutane-1,2'-pyrano[2,3-b]pyridin]-4'-yl)amino)propyl)acetamide;

N-((1S,2R)-2-hydroxy-1-(phenylmethyl)-3-(((4'S)-6'-((2R)-tetrahydro-2-furanylmethyl)-3',4'-dihydrospiro[cyclobutane-1,2'-pyrano[2,3-b]pyridin]-4'-yl)amino)propyl)acetamide;

'N-((1S,2R)-2-hydroxy-1-(phenylmethyl)-3-(((4'S)-6'-((2R)-tetrahydro-2-furanylmethyl)-3',4'-dihydrospiro[cyclobutane-1,2'-pyrano[2,3-b]pyridin]-4'-yl)amino)propyl)-2-(methyloxy)acetamide;

N-((1S,2R)-2-hydroxy-1-(phenylmethyl)-3-(((4'S)-6'-((2S)-tetrahydro-2-furanylmethyl)-3',4'-dihydrospiro[cyclobutane-1,2'-pyrano[2,3-b]pyridin]-4'-yl)amino)propyl)-2-(methyloxy)acetamide;

'N-((1S,2R)-2-hydroxy-1-(phenylmethyl)-3-(((4S)-6-((2S)-tetrahydro-2-furanylmethyl)-3,4-dihydrospiro[chromene-2,1'-cyclobutan]-4-yl)amino)propyl)acetamide;

N-((1S,2R)-2-hydroxy-1-(phenylmethyl)-3-(((4S)-6-((2R)-tetrahydro-2-furanylmethyl)-3,4-dihydrospiro[chromene-2,1'-cyclobutan]-4-yl)amino)propyl)acetamide;

'N-((1S,2R)-2-hydroxy-3-(((4S)-6-(5-hydroxypentyl)-3,4-dihydrospiro[chromene-2,1'-cyclobutan]-4-yl)amino)-1-(phenylmethyl)propyl)acetamide;

'N-((1S,2R)-2-hydroxy-3-(((4'S)-6'-(((2S)-2-methyltetrahydro-2-furanyl)methyl)-3',4'-dihydrospiro[cyclobutane-1,2'-pyrano[2,3-b]pyridin]-4'-yl)amino)-1-(phenylmethyl)propyl)acetamide;

N-((1S,2R)-2-hydroxy-3-(((4'S)-6'-(((2R)-2-methyltetrahydro-2-furanyl)methyl)-3',4'-dihydrospiro[cyclobutane-1,2'-pyrano[2,3-b]pyridin]-4'-yl)amino)-1-(phenylmethyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-pyridinylmethyl)propyl)acetamide;

'N-((1S,2R)-1-((2,3-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((2,6-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2-fluoro-2-methylpropyl)-3',4'-dihydrospiro[cyclobutane-1,2'-pyrano[2,3-c]pyridin]-4'-yl)amino)-1-((3-fluorophenyl)methyl)-2-hydroxypropyl)acetamide;

'N-((1S,2R)-1-((4-chlorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((1-methyl-3-piperidinyl)methyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((5-fluoro-3-pyridinyl)methyl)-2-hydroxypropyl)acetamide;

'N-((1S,2S)-3-(((4'S)-6'-(2,2-dimethylpropyl)-3',4'-dihydrospiro[cyclobutane-1,2'-pyrano[2,3-b]pyridin]-4'-yl)amino)-1-((5-fluoro-3-pyridinyl)methyl)-2-hydroxypropyl)acetamide;

'N-((1S,2R)-1-((4-fluorophenyl)methyl)-2-hydroxy-3-(((4'S)-6'-((trimethylsilyl)methyl)-3',4'-dihydrospiro[cyclobutane-1,2'-pyrano[2,3-b]pyridin]-4'-yl)amino)propyl)acetamide;

'N-((1S,2R)-1-((3,4-bis(methyloxy)phenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((3-fluorophenyl)methyl)-2-hydroxy-3-(((4'S)-6'-((trimethylsilyl)methyl)-3',4'-dihydrospiro[cyclobutane-1,2'-pyrano[2,3-b]pyridin]-4'-yl)amino)propyl)acetamide;

'N-((1S,2R)-1-((2,3-difluorophenyl)methyl)-2-hydroxy-3-(((4'S)-6'-((trimethylsilyl)methyl)-3',4'-dihydrospiro[cyclobutane-1,2'-pyrano[2,3-b]pyridin]-4'-yl)amino)propyl)acetamide;

'N-((1S,2R)-1-((2,3-difluorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((3-bromo-4-fluorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((3,5-difluorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((3-chloro-4-fluorophenyl)methyl)-3-(((4'S)-6'-(2-fluoro-2-methylpropyl)-3',4'-dihydrospiro

[cyclobutane-1,2'-pyrano[2,3-b]pyridin]-4'-yl)amino)-2-hydroxypropyl)acetamide;

'N-((1S,2R)-1-((3-chloro-5-fluorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxy-1-((3-(trifluoromethyl)phenyl)methyl)propyl)acetamide;

'N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-(1,3-benzodioxol-5-ylmethyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide;

'N-((1S,2R)-2-hydroxy-1-(phenylmethyl)-3-(((4S)-6-(2,2,2-trifluoroethyl)-3,4-dihydrospiro[chromene-2,1'-cyclobutan]-4-yl)amino)propyl)acetamide;

'N-((1S,2R)-2-hydroxy-1-(phenylmethyl)-3-(((4S)-6-(2-pyridinyl)-3,4-dihydrospiro[chromene-2,1'-cyclobutan]-4-yl)amino)propyl)acetamide;

'N-((1S,2R)-2-hydroxy-1-(phenylmethyl)-3-(((4'S)-6'-(2,2,2-trifluoroethyl)-3',4'-dihydrospiro[cyclobutane-1,2'-pyrano[2,3-b]pyridin]-4'-yl)amino)propyl)acetamide;

'N-((1S,2R)-1-((3,4-difluorophenyl)methyl)-2-hydroxy-3-(((4'S)-6'-(2,2,2-trifluoroethyl)-3',4'-dihydrospiro[cyclobutane-1,2'-pyrano[2,3-b]pyridin]-4'-yl)amino)propyl)acetamide;

'N-((1S,2R)-1-((3-fluorophenyl)methyl)-2-hydroxy-3-(((4'S)-6'-(2,2,2-trifluoroethyl)-3',4'-dihydrospiro[cyclobutane-1,2'-pyrano[2,3-b]pyridin]-4'-yl)amino)propyl)acetamide;

'N-((1S,2R)-3-(((4'S)-6'-bromo-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-1-((3-fluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide;

'N-((1S,2R)-1-((4-fluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide;

'N-((1S,2R)-1-((3,5-difluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide;

'N-((1S,2R)-1-((3-chloro-5-fluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide;

'3-((2S,3R)-2-(acetylamino)-3-hydroxy-4-(((4'S)-6'-(2-methylpropyl-3',4'-dihydrospiro[cyclobutane-1,2'-pyrano[2,3-b]pyridin]-4'-yl)amino)butyl)benzamide;

'N-((1S,2R)-1-((3-cyanophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide;

'N-((1S,2R)-1((2,3-difluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)acetamide;

'N-((1S,2R)-1-((3,4-difluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide;

'N-((1S,2R)-3-(((4'S)-7'-fluoro-6'-(2-methylpropyl)-3',4'-dihydrospiro[cyclobutane-1,2'-pyrano[2,3-b]pyridin]-4'-yl)amino)-2-hydroxy-1-(phenylmethyl)propyl)acetamide;

'N-((1S,2R)-1-((3,5-difluorophenyl)methyl)-3-(((4'S)-7'-fluoro-6'-(2-methylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-7'-fluoro-6'-(2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide;

'N-((1S,2R)-3-(((4'S)-7'-fluoro-6'-(2-methylpropyl)-3',4'-dihydrospiro[cyclobutane-1,2'-pyrano[2,3-b]pyridin]-4'-yl)amino)-1-((3-fluorophenyl)methyl)-2-hydroxypropyl)acetamide;

'N-((1S,2R)-1-((2,3-difluorophenyl)methyl)-3-(((4'S)-7'-fluoro-6'-(2-methylpropy1)-3',4'-dihydrospiro[cyclobutane-1,2'-pyrano[2,3-b]pyridin]-4'-yl)amino)-2-hydroxypropyl)acetamide;

'N-((1S,2R)-1-((4-chloro-3-fluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide;

'N-((1S,2R)-1-((4-chlorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide;

'N-((1S,2R)-1-((4-fluorophenyl)methyl)-2-hydroxy-3-(((4'S)-6'-(1,3,3,3-tetrafluoro-2-methylpropyl)-3',4'-dihydrospiro[cyclobutane-1,2'-pyrano[2,3-b]pyridin]-4'-yl)amino)propyl)acetamide;

'N-((1S,2R)-1-((4-chlorophenyl)methyl)-2-hydroxy-3-(((4'S)-6'-(1,3,3,3-tetrafluoro-2-methylpropyl)-3',4'-dihydrospiro[cyclobutane-1,2'-pyrano[2,3-b]pyridin]-4'-yl)amino)propyl)acetamide;

'N-((1S,2R)-1-((3-fluorophenyl)methyl)-2-hydroxy-3-(((4'S)-6'-(1,3,3,3-tetrafluoro-2-methylpropyl)-3',4'-dihydrospiro[cyclobutane-1,2'-pyrano[2,3-b]pyridin]-4'-yl)amino)propyl)acetamide;

'N-((1S,2R)-2-hydroxy-1-(phenylmethyl)-3-(((4'S)-6'-(1,3,3,3-tetrafluoro-2-methylpropyl)-3',4'-dihydrospiro[cyclobutane-1,2'-pyrano[2,3-b]pyridin]-4'-yl)amino)propyl)acetamide;

'N-((1S,2R)-1-((3-fluorophenyl)methyl)-2-hydroxy-3-(((4'S)-6'-(3,3,3-trifluoro-1-hydroxy-2-methylpropyl)-3',4'-dihydrospiro[cyclobutane-1,2'-pyrano[2,3-b]pyridin]-4'-yl)amino)propyl)acetamide;

'N-((1S,2R)-1-((4-chlorophenyl)methyl)-2-hydroxy-3-(((4'S)-6'-(3,3,3-trifluoro-1-hydroxy-2-methylpropyl)-3',4'-dihydrospiro[cyclobutane-1,2'-pyrano[2,3-b]pyridin]-4'-yl)amino)propyl)acetamide;

'N-((1S,2R)-2-hydroxy-1-(phenylmethyl)-3(((4'S)-6'-(3,3,3-trifluoro-1-hydroxy-2-methylpropyl)-3',4'-dihydrospiro[cyclobutane-1,2'-pyrano[2,3-b]pyridin]-4'-yl)amino)propyl)acetamide;

'N-((1S,2R)-1-((3-fluorophenyl)methyl)-2-hydroxy-3-(((4'S)-6'-((2R)-3,3,3-trifluoro-2-methylpropyl)-3',4'-dihydrospiro[cyclobutane-1,2'-pyrano[2,3-b]pyridin]-4'-yl)amino)propyl)acetamide;

N-((1S,2R)-1-((3-fluorophenyl)methyl)-2-hydroxy-3-(((4'S)-6'-((2S)-3,3,3-trifluoro-2-methylpropyl)-3',4'- dihydrospiro[cyclobutane-1,2'-pyrano[2,3-b]pyridin]-4'-yl)amino)propyl)acetamide;

'ethyl 1-(2-(((1S,2R)-3-(((4S)-6-bromo-3,4-dihydrospiro[chromene-2,1'-cyclobutan]-4-yl)amino)-2-hydroxy-1-(phenylmethyl)propyl)amino)-2-oxoethyl)-1H-1,2,3-triazole-4-carboxylate;

'N-((1S,2R)-1-((3-bromo-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'2-(5-(aminomethyl)-1H-1,2,3-triazol-1-yl)-N-((1S,2R)-3-(((4S)-6-bromo-3,4-dihydrospiro[chromene-2,1'-cyclobutan]-4-yl)amino)-2-hydroxy-1-(phenylmethyl)propyl)acetamide;

'N-((1R,2R)-1-((3-chloro-2-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((5-chloro-2-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((3-chloro-2-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((3-chloro-2,4-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((3-chloro-4,5-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2,3,6-trifluorophenyl)methyl)propyl)acetamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2,3,5-trifluorophenyl)methyl)propyl)acetamide;

'N-((1S,2R)-1((4-bromophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

'N-((1S,2R)-1-((4-chlorophenyl)methyl)-2-hydroxy-3-(((4'S)-6'-((1-methylethyl)oxy)-3',4'-dihydrospiro[cyclobutane-1,2'-pyrano[2,3-b]pyridin]-4'-yl)amino)propyl)acetamide;

'methyl ((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)carbamate;

'N-((1S,2R)-1((3,5-difluorophenyl)methyl)-3-(((4'S)-6'-ethyl-3',4'-dihydro spiro[cyclobutane-1,2'-pyrano[2,3-b]pyridin]-4'-yl)amino)-2-hydroxypropyl)acetamide;

'methyl ((1S,2R)-1-((3,5-difluorophenyl)methyl)-3-(((4'S)-6'-ethyl-3',4'-dihydrospiro[cyclobutane-1,2'-pyrano[2,3-b]pyridin]-4'-yl)amino)-2-hydroxypropyl)carbamate;

'methyl ((1S,2R)-1-((3,5-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)carbamate; and 'N-((1S,2R)-3-(((4'S)-6'-(2,2-dimethylpropyl)-3',4'-dihydrospiro[cyclobutane-1,2'-pyrano[2,3-c]pyridin]-4'-yl)amino)-2-hydroxy-1-(phenylmethyl)propyl)propanamide; and 'N-((1S,2R)-1-((4-fluorophenyl)methyl)-2-hydroxy-3-(((4'S)-6'-(3-hydroxy-2,2-dimethylpropyl)-3',4'-dihydrospiro[cyclobutane-1,2'-pyrano[2,3-b]pyridin]-4'-yl)amino)propyl)acetamide.

11. A pharmaceutical composition comprising a pharmaceutically acceptable carrier and a compound according to claim 1.

12. A pharmaceutical composition comprising a pharmaceutically acceptable carrier and a compound according to claim 8.

13. A method of treating Alzheimer's disease in a subject, the method comprising administering to the subject an effective dosage amount of a compound according to claim 1.

14. A method of treating Alzheimer's disease in a subject, the method comprising administering to the subject an effective dosage amount of a compound according to claim 8.

15. A method of making a compound of claim 1, the method comprising the step of
reacting a compound 20

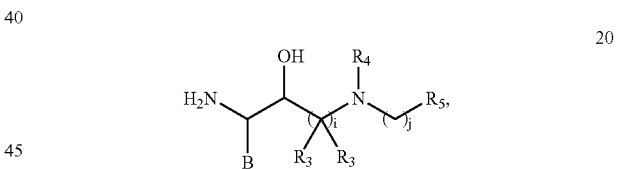

wherein i, j, A, B, $R^3$, $R^4$ and $R^5$ are as defined in claim 1, with a compound having the structure A-W-X, wherein A and W are as defined in claim 1 and X is a leaving group, to make a compound of claim 1.

* * * * *